US006984627B1

(12) United States Patent
Antonsson et al.

(10) Patent No.: US 6,984,627 B1
(45) Date of Patent: *Jan. 10, 2006

(54) PEPTIDE DERIVATIVES

(75) Inventors: Karl Thomas Antonsson, Lindome (SE); Ruth Elvy Bylund, Västra Frölunda (SE); Nils David Gustafsson, Kullavik (SE); Nils Olov Ingemar Nilsson, Fjärås (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,403

(22) Filed: May 8, 2000

Related U.S. Application Data

(63) Continuation of application No. 09/398,826, filed on Sep. 17, 1999, now abandoned, which is a continuation of application No. 08/382,036, filed as application No. PCT/SE94/00535 on Jun. 2, 1994, now abandoned.

(30) Foreign Application Priority Data

Jun. 3, 1993 (SE) .............................................. 9301916

(51) Int. Cl.
A61K 38/00 (2006.01)
A01N 43/40 (2006.01)

(52) U.S. Cl. .......................... 514/19; 514/18; 514/315; 514/326

(58) Field of Classification Search .................. 514/18, 514/19, 315, 326; 530/331; 560/24–35, 168–169; 562/126, 439
See application file for complete search history.

(56) References Cited

U.S. PATENT DOCUMENTS

| 4,346,078 A | 8/1982 | Bajusz et al. |
| 4,568,636 A | 2/1986 | Svendsen |
| 4,703,036 A | 10/1987 | Bajusz et al. |
| 4,977,168 A | 12/1990 | Bernat et al. |
| 5,037,819 A | 8/1991 | Han |
| 5,110,812 A | 5/1992 | Han |
| 5,187,157 A | 2/1993 | Kettner et al. |
| 5,260,307 A | 11/1993 | Ackermann et al. |
| 5,273,982 A | 12/1993 | Alig et al. |
| 5,583,146 A | 12/1996 | Kimball et al. |
| 5,614,499 A | 3/1997 | Bylund et al. |
| 5,705,487 A | 1/1998 | Schacht et al. |
| 5,707,966 A | 1/1998 | Schacht et al. |
| 5,710,130 A | 1/1998 | Schacht et al. |
| 5,726,159 A | 3/1998 | Schacht et al. |
| 5,744,487 A | 4/1998 | Ohshima et al. |
| 5,783,563 A | * 7/1998 | Antonsson et al. ............ 514/9 |
| 5,795,896 A | * 8/1998 | Lofroth et al. .............. 514/256 |
| 5,830,865 A | * 11/1998 | Stjernfelt et al. .............. 514/8 |
| 5,856,307 A | * 1/1999 | Antonsson et al. ............ 514/18 |
| 5,880,136 A | * 3/1999 | Duggan et al. .............. 514/317 |
| 5,939,392 A | * 8/1999 | Antonsson et al. ............ 514/18 |
| 5,965,692 A | * 10/1999 | Gustafsson et al. ......... 530/300 |
| 6,262,028 B1 | * 7/2001 | Antonsson et al. ........... 514/19 |

FOREIGN PATENT DOCUMENTS

| EP | 0074787 | 3/1983 |
| EP | 0 074 787 | 3/1983 |
| EP | 0 192 135 | 3/1986 |
| EP | 0192135 | 3/1986 |
| EP | 0 185 390 A3 | 6/1986 |
| EP | 0 195 212 | 9/1986 |
| EP | 0 235 692 | 9/1987 |
| EP | 0235692 | 9/1987 |
| EP | 0 236 163 | 9/1987 |
| EP | 0 293 881 | 6/1988 |
| EP | 0 362 002 | 4/1990 |
| EP | 0 364 344 | 4/1990 |
| EP | 0479489 | 9/1991 |
| EP | 0 468 231 | 1/1992 |
| EP | 0471651 | 2/1992 |
| EP | 0 478 362 A2 | 4/1992 |
| EP | 0 513 543 A1 | 11/1992 |
| EP | 0 513 543 | 11/1992 |
| EP | 0 526 877 A2 | 2/1993 |
| EP | 0 530 167 A1 | 3/1993 |
| EP | 0 530 167 | 3/1993 |
| EP | 0530167 | 3/1993 |
| EP | 0 542 525 | 5/1993 |
| EP | 0 542 525 A2 | 5/1993 |
| EP | 0 559 046 A1 | 9/1993 |
| EP | 0 641 779 A1 | 3/1995 |
| EP | 0 648 780 A1 | 4/1995 |
| EP | 0 669 317 A1 | 8/1995 |
| GB | 2085444 | 4/1982 |
| GB | 2 085 444 | 4/1982 |
| GB | 2 161 801 A | 1/1986 |
| WO | 9204371 | 3/1992 |
| WO | 9 204 371 | 3/1992 |
| WO | 9208709 | 3/1992 |
| WO | 9207869 | 5/1992 |
| WO | WO 93/11152 | 6/1993 |
| WO | WO 93/18060 | 9/1993 |

OTHER PUBLICATIONS

Honour et al. , British Journal of Experimental Pathology (1977) vol. 58, No. 5, pp. 474–477.*

(Continued)

Primary Examiner—Bennett Celsa
(74) Attorney, Agent, or Firm—Nixon & Vanderhye

(57) ABSTRACT

Pharmaceutical preparation containing an effective amount of acetylsalicylic acid and a compound of Formula I.

$$A^1 - A^2 - NH - (CH_2)_n - B$$

wherein $A^1$, $A^2$, n and B are as defined in the specification, which is either the compound as such, or a stereoisomer thereof, and which may be in the form of a physiologically acceptable salt, in association with a pharmaceutical carrier. The combinations are suitable for use in inhibiting thrombin, or in the treatment or prophylaxis of thrombosis or hypercoagulability in patients in need thereof.

57 Claims, No Drawings

OTHER PUBLICATIONS

Biosis Abstract No. 1978:223366 to Honour et al. Br. J. Exp. Pathol. (1977) vol. 58 (5) pp. 474–477.*

Stewart et al: "Solid Phase Peptide Synthesis," Pierce Chemical Company, pp. 18–20 (with appendix).

Bajusz: "Interaction of Trypsin–like Enzymes With Small Inhibitors," pp. 277–298, *Symposia Biologica Hungarica 25* (1984).

Jackson et al, "Pharmacological Assessment of the Antithrombotic Activity . . . " J. of Pharm. Exp. Ther.261: 546–552, 1992.

Knabb et al, "In Vivo Characterization of a New Synthetic Thrombin Inhibitor," Thrombosis and Haemostasis, 67(1): 56–59, 1992.

Bajusz et al, "Inhibition of Thrombin with H– and Boc–D–Phe–Pro–Agm," Chem. Abs. 99:205609W, 1983.

Klement et al, "The Effect of Thrombin Inhibitors on Tissue Plasminogen . . . " Thrombosis and Haemostasis, 68(1): 64–68, 1992.

Marki et all, "The Anticoagulant and Antithrombotic Properties of Hirudins . . . " Thrombosis and Haemostasis, 64(3): 344–348, 1990.

Broersma et al, "The Effect of Thrombin Inhibition in a Rat . . . ," Thrombosis Research, 64: 405–412, 1991.

Persson et al, Thorax, 47: 993–1000, 1992.

Salomonson et al, Am. Rev. Resp. Dis. 146:1535–1542, 1992.

Markwardt et al, Biochem. Pharm. 23: 2247–2256, 1974.

Malek et al, "Palladium–catalyzed synthesis of Cinnamylamides," J. Org. Chem. 47(27): 5395–5397, 1982.

Malek, et al, Chem. Abs. 98:16353, 1983.

Chung et al, J. Organic Chem. 1: 270–275.

Glusa et al, "The influence of benzamidine . . . ," Thrombosis et Diathesis Haemorrhagica 31:172–178, 1974.

Anderson and Lok, J. Organic Chem. 37:3953, 1972.

Fareed et al, Ann, N.Y. Acad. Sci. 370: 765–784, 1981.

Geratz, J.D., "Inhibition of thrombin, plasmin . . . " Thrombosis et Diathesis Halmorrhagica 23(3), 486–499 (1970).

Stewart et al, "Solid Phase Peptide Synthesis," Pierce Chemical Company, pp. 18–20 (with appendix).

Bajusz, "Interaction of Trypsin–like Enzymes with Small Inhibitors," pp. 277–298, Symposia Biologica Hungarica 25 (1984).

Jackson et al, "Pharmacological Assessment of the Antithrombotic . . . " J. of Pharm. Exp. Ther.261: 546–552, 1992.

Knabb et al, "In Vivo Characterization of a New Synthetic . . . " Thrombosis and Haemostasis, vol. 67 No. 1, pp. 56–59 (1992).

Bajusz et al, "Inhibition of Thrombin with H– and Boc–D–Phe–Pro–Agm," Chem. Abs. 99: 205609W (1983).

Klement et al, "The Effect of Thrombin Inhibitors on Tissue Plasminogen . . . ," Thrombosis and Haemostasis, vol. 68, No. 1, pp. 64–68 (1992).

Marki et al, "The Anticoagulant and Antithrombotic . . . ," Thrombosis and Haemostasis, vol. 64, No. 3, pp. 344–348 (1990).

Broersma et al, "The Effect of Thrombin Inhibition in a Rat Arterial . . . ," Thrombosis Research, vol. 64, pp. 405–412 (1991).

Persson et al, Thorax, vol. 47, pp. 993–1000 (1992).

Salomonson et al, Am. Rev. Resp. Dis., vol. 146, 1535–1542 (1992).

Markwardt et al, Biochem. Pharm., vol. 23, pp. 2247–2256 (1974).

Malek et al, "Palladium–catalyzed synthesis" J. Org. Chem., vol. 47, No. 27, 5395–5397 (1982).

Malek et al, Chem. Abs. 98: 16353 (1983).

Chung et al, J. Organic Chem. vol. 1, pp. 270–275.

Glusa et al, "The influence of benzamidine derivatives . . . ," Thrombosis et Diathesis Haemorrhagica, vol. 31, pp. 172–178 (1974).

Anderson and Lok, J. Organic Chem., vol. 37, p. 3953 (1972).

Fareed et al, Ann. N.Y. Acad. Sci., vol. 370, pp. 765–784 (1981).

Geratz, J.D., "Inhibition of thrombin, plasmin and plasminogen compounds," Thrombosis et Diathesis Halmorrhagica, vol. 23, No. 3, pp. 486–499 (1970).

Claeson, G.; "Synthetic Peptides and Peptidomimetics as Substrates and Inhibitors of Thrombin and Other Proteases in the Blood Coagulation System"; *Blood Coagulation and Fibrinolysis*; vol. 5; pp 411–436 (1994).

Blomback, B., et al; "Synthetic Peptides and Aticoagulant and Vasodilating Activity", *Clin. Lab. Invest.*; vol. 24, Suppl. pp. 107–59 (1969).

Abdel–Wahab, A.A.; "Modern Friedel–Crafts Chemistry. XI. Cyclization of Aryl Haloalkyl Sulfones, Arylsulfonylacyl Chlorides and Their Corresponding Sulfides"; *Phosphorous and Suflur*, vol. 19; pp. 31–44 (1984).

Stephan, D., et al; "Effect of Tertatolol and of Its Metabolites and Structural Analogues in Isolated Perfused Rat Kidney Vasculature";*Journal of Cardiovascular Pharmacology*; vol. 16 pp. 338–346 (1990).

Ofosu, F.A., et al; "Inhibition of Factor X and Factor V Activation by Dermatan Sulfate and a Pentasaccharide with High affinity for Antithrombin III in Human Plasma"; *Eur. J. Biochem* ; vol. 193; pp. 485–493 (1990).

* cited by examiner

PEPTIDE DERIVATIVES

This application is a continuation of Ser. No. 09/398,826, filed Sep. 17, 1999, now abandoned, which is a continuation of Ser. No. 08/382,036, filed Aug. 19, 1994, now abandoned, which is a 371 of PCT/SE94/00535 filed Jun. 2, 1994, the entire content of which is hereby incorporated by reference in this application.

This invention relates to new competitive inhibitors of trypsin-like serine proteases, especially thrombin and kininogenases such as kallikrein, their synthesis, pharmaceutical compositions containing the compounds as active ingredients, and the use of the compounds as thrombin inhibitors and anticoagulants and as antiinflammatory inhibitors, respectively.

The invention also relates to novel use of compounds as starting materials in synthesis of a serine protease inhibitor. Furthermore the invention relates to a novel structural fragments in serine protease inhibitors.

BACKGROUND

Blood coagulation is the key process involved in both haemostasis (i.e. prevention of blood loss from a damaged vessel) and thrombosis (i.e. the pathological occlusion of a blood vessel by a blood clot). Coagulation is the result of a complex series of enzymatic reactions, where one of the final steps is conversion of the proenzyme prothrombin to the active enzyme thrombin.

Thrombin plays a central role in coagulation. It activates platelets, it converts fibrinogen into fibrin monomers, which polymerise spontaneously into filaments, and it activates factor XIII, which in turn crosslinks the polymer to insoluble fibrin. Thrombin further activates factor V and factor VIII in a positive feedback reaction. Inhibitors of thrombin are therefore expected to be effective anticoagulants by inhibition of platelets, fibrin formation and fibrin stabilization. By inhibiting the positive feedback mechanism they are expected to excert inhibition early in the chain of events leading to coagulation and thrombosis.

Kininogenases are serine proteases that act on kininogens to produce kinins (bradykinin, kallidin, and Met-Lys-bradykinin). Plasma kallikrein, tissue kallikrein, and mast cell tryptase represent important kininogenases.

Kinins (bradykinin, kallidin) are generally involved in inflammation. For example, the active inflammation process is associated with increased permeability of the blood vessels resulting in extravasation of plasma into the tissue. The ensuing plasma exudate contains all the protein systems of circulating blood. The plasma-derived kininogens inevitably will be interacting with different kallikreins, forming kinins continually as long as the active plasma exudation process is ongoing. Plasma exudation occurs independent of the mechanisms that are involved in the inflammation, whether it is allergy, infection or other factors (Persson et al., Editorial, Thorax, 1992, 47:993–1000). Plasma exudation is thus a feature of many diseases including asthma, rhinitis, common cold, and inflammatory bowel diseases. Particulary in allergy mast cell tryptase will be released (Salomonsson et al., Am. Rev. Respir. Dis., 1992, 146:1535–1542) to contribute to kinin formation and other pathogenic events in asthma, rhinitis, and intestinal diseases.

The kinins are biologically highly active substances with smooth muscle effects, sectretory effects, neurogenic effects, and actions that may perpetuate inflammatory processes including activation of phospholipase $A_2$ and increasing vascular permeability. The latter action potentially induces a vicious circle with kinins providing for the generation of more kinins etc.

Tissue kallikrein cleaves primarily low molecular weight kininogen to produce kallidin and plasma kallikrein preferably releases bradykinin from high molecular weight kininogen.

PRIOR ART

Inhibitors of thrombin based on the amino acid sequence around the cleavage site for the fibrinogen Aα chain were first reported by Blombäck et al. in J. Clin. Lab. Invest. 24, suppl 107, 59, (1969), who suggested the sequence Phe-Val-Arg (P9-P2-P1, herein referred to as the P3-P2-P1 sequence) to be the best inhibitor.

In U.S. Pat. No. 4,346,078 has S. Bajusz et al. described the thrombin inhibitor H-DPhe-Pro-Agm, a dipeptidyl derivative with an aminoalkyl guanidine in the P1-position.

Inhibitors of thrombin based on peptide derivatives with a cyclic aminoalkyl guanidine, e.g. 3-aminomethyl-1-amidinopiperidine, in the P1-position have been disclosed in EP-A2-0,468,231.

In EP-A2-0,185,390 has S. Bajusz et. al. disclosed that replacing the agmatine with an arginine aldehyde gave a thrombin inhibitor which had much higher potency.

Inhibitors of kallikrein based on the amino acid sequence around the cleavage site Arg-Ser have been reported earlier.

The arginine chloromethyl ketones H-DPro-Phe-Arg-$CH_2Cl$ and H-D Phe-Phe-Arg-$CH_2Cl$ were reported as plasma kallikrein inhibitors by Kettner and Shaw in Biochemistry 1978, 17:4778–4784 and Meth. Enzym. 1981, 80:826–842.

Likewise, esters and amides containing the H-DPro-Phe-Arg sequence were reported by Fareed et al. in Ann. N.Y. Acad. Sci. 1981, 370:765–784 to be plasma kallikrein inhibitors.

Inhibitors of serine proteases that are based on electrophilic ketones instead of aldehydes in the P1-position are described in the following patent documents:

EP-A2-0,195,212 describing peptidyl α-keto esters and amides, EP-A1-0,362,002 describing fluoroalkylamide ketones and EP-A2-0,364,344 describing α,β,δ-triketo compounds possessing different peptidase inhibiting properties.

Inhibitors of trypsin-like serine proteases, such as thrombin and kallikrein, based on C-terminal boronic acid derivatives of arginine and isothiouronium analogues thereof have been revealed in EP-A2-0,293,881.

WO 92/04371 describing kininogenase inhibitors, e.g. kallikrein inhibitors based on derivatives of arginine.

EP-A1-0,530,167 describing α-alkoxy ketone derivatives of arginine as thrombin inhibitors.

DISCLOSURE OF THE INVENTION

An object of the present invention is to provide novel and potent trypsine-like serine protease inhibitors, especially anticoagulantia and antiinflammatory compounds with competitive inhibitory activity towards their enzyme i.e. causing reversible inhibition. More specifically anticoagulants for prophylaxis and treatment of thromboembolic diseases such as venous thrombosis, pulmonary embolism, arterial thrombosis, in particular myocardial infarction and cerebral thrombosis, general hypercoagulable states and local hypercoagulable states, e.g. following angioplasty and coronary bypass operations, and other situations where thrombin is believed to play a role, e.g. Alzheimers disease, as well as inhibition of kininogenases for treatment of inflammatory disorders e.g. asthma, rhinitis, urticaria, inflammatory bowel disease, and arthritis. A further object is to obtain thrombin inhibitors which are orally bioavailable and selective in inhibiting thrombin over other serine proteases. A further object of the invention is to obtain kininogenase inhibitors which can be given orally, rectally, topically e.g. dermally, or via the inhalation route.

Compounds

According to the invention it has been found that compounds of the general Formula I, either as such or in the form of physiologically acceptable salts, and including stereoisomers, are potent inhibitors of serine proteases, especially thrombin and kininogenases such as kallikrein:

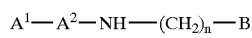

Formula I wherein:
$A^1$ represents a structural fragment of Formula IIa, IIb, IIc, IId or IIe;

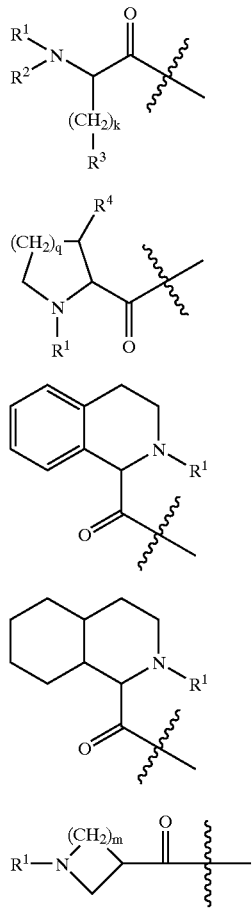

IIa

IIb

IIc

IId

IIe wherein:
k is an integer 0, 1, 2, 3 or 4;
m is an integer 0, 2, 3 or 4;
q is an integer 0, 1, 2 or 3;
$R^1$ represents H, an alkyl group having 1 to 4 carbon atoms, or $R^{11}$OOC-alkyl-, where the alkyl group has 1 to 4 carbon atoms and is possibly substituted in the position which is alpha to the carbonyl group, and the alpha substituent is a group $R^{17}$—$(CH_2)_p$—, wherein p is 0, 1 or 2 and $R^{17}$ is methyl, phenyl, OH, COOR$^{12}$, CONHR$^{12}$, where $R^{12}$ is H or an alkyl group having 1 to 4 carbon atoms, and $R^{11}$ is H or an alkyl group having 1 to 6 carbon atoms, or $R^1$ represents Ph(4-COOR$^{12}$)—CH$_2$—, where $R^{12}$ is as defined above, or $R^1$ represents $R^{13}$—NH—CO-alkyl-, where the alkyl group has 1 to 4 carbon atoms and is possibly substituted alpha to the carbonyl with an alkyl group having 1 to 4 carbon atoms and where $R^{13}$ is H or an alkyl group having 1 to 4 carbon atoms or —CH$_2$COOR$^{12}$, where $R^{12}$ is as defined above, or $R^1$ represents $R^{12}$OOC—CH$_2$—OOC-alkyl-, where the alkyl group has 1 to 4 carbon atoms and is possibly substituted alpha to the carbonyl with an alkyl group having 1 to 4 carbon atoms and where $R^{12}$ is as defined above, or $R^1$ represents $R^{14}$SO$_2$—, Ph(4-COOR$^{12}$)—SO$_2$—, Ph(3-COOR$^{12}$)—SO$_2$—, Ph(2-COOR$^{12}$)—O$_2$—, where $R^{12}$ is as defined above and $R^{14}$ is an alkyl group having 1–4 carbon atoms, or $R^1$ represents —CO—$R^{15}$, wherein R's is an alkyl group having 1–4 carbon atoms, or $R^1$ represents —CO—OR$^{15}$, where $R^{15}$ is as defined above, or $R^1$ represent —CO—(CH$_2$)$_p$—COOR$^{12}$, where $R^{12}$ is as defined above and p is an interger 0, 1 or 2, or $R^1$ represents —CH$_2$PO(OR$^{16}$)$_2$, —CH$_2$SO$_3$H or —CH$_2$-(5-(1H)-tetrazolyl), where $R^{16}$ is, individually at each occurrence, H, methyl or ethyl;

$R^2$ represents H or an alkyl group having 1 to 4 carbon atoms or $R^{21}$OOC-alkyl-, where the alkyl group has 1 to 4 carbon atoms and, where $R^{21}$ is H or an alkyl group having 1 to 4 carbon atoms;

$R^3$ represents an alkyl group having 1–4 carbon atoms, and the alkyl group may or may not carry one or more flourine atoms, or $R^3$ represents a cyclopentyl, cyclohexyl- or a phenyl group which may or may not be substituted with an alkyl group having 1 to 4 carbon atoms, or $R^3$ represents a phenyl group substituted with a OR$^{31}$ group, where $R^{31}$ is H or an alkyl group having 1 to 4 carbon atoms and k is 0, 1, or $R^3$ represents a 1-naphthyl or 2-naphthyl group and k is 0, 1, or $R^3$ represent a cis- or trans-decalin group and k is 0, 1, or $R^3$ represents 4-pyridyl, 3-pyrrolidyl or 3-indolyl which may or may not be substituted with a OR$^{31}$ group, where $R^{31}$ is as defined above and k is 0, 1, or $R^3$ represents Si(Me)$_3$ or CH(R$^{32}$)$_2$, wherein $R^{32}$ is a cyclohexyl- or a phenyl group;

$R^4$ represents H, an alkyl group having 1 to 4 carbon atoms, a cyclohexyl- or a phenyl group;

$A^2$ represents a structural fragment of Formula IIIa, IIIb or IIIc

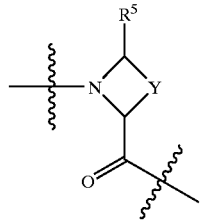

IIIa

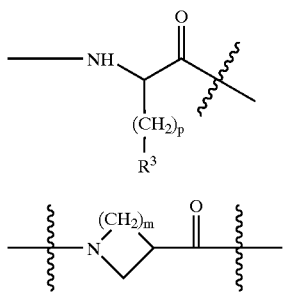

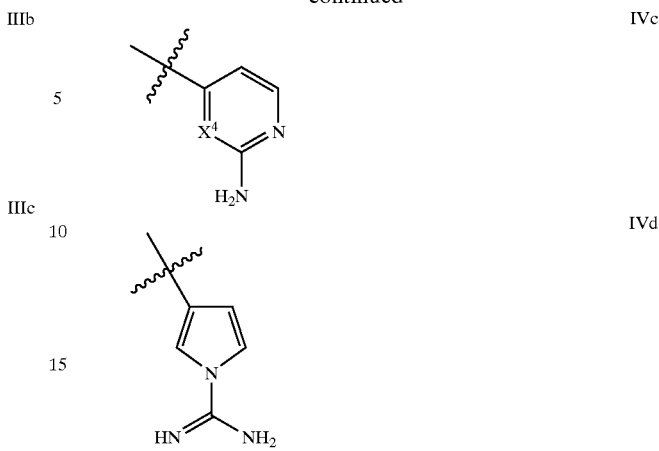

wherein:

p is an interger 0, 1 or 2;

m is an integer 1, 2, 3 or 4;

Y represents a methylene group, or

Y represents an ethylene group and the resulting 5-membered ring may or may not carry one or two fluorine atoms, a hydroxy group or an oxo group in position 4, or may or may not be unsaturated, or Y represents —CH$_2$—O—, —CH$_2$—S—, —CH$_2$—SO—, with the heteroatom functionality in position 4, or Y represents a n-propylene group and the resulting 6-membered ring may or may not carry in position 5 one fluorine atom, a hydroxy group or an oxo group, carry two fluorine atoms in one of positions 4 or 5 or be unsaturated in position 4 and 5, or carry in position 4 an alkyl group with 1 to 4 carbon atoms, or Y represents —CH$_2$—O—CH$_2$—, —CH$_2$—S—CH$_2$—, —CH$_2$—SO—CH$_2$—, or Y represent —CH$_2$—CH$_2$—CH$_2$—CH$_2$—;

R$^3$ is as defined above;

R$^5$ represents H or an alkyl group having 1 to 4 carbon atoms, or

R$^5$ represents —(CH$_2$)$_n$—COOR$^{51}$, where p is 0, 1 or 2 and R$^{51}$ is H or an alkyl group having 1 to 4 carbon atoms;

n is an integer 0, 1, 2, 3 or 4;

B represents a structural fragment of Formula IVa, IVb, IVc or IVd

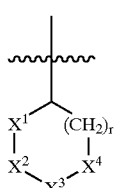

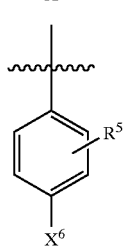

wherein:

r is an interger 0 or 1;

X$^1$ represent CH$_2$, NH or is absent;

X$^2$ represents CH$_2$, NH or C=NH;

X$^3$ represents NH, C=NH, N—C(NH)—NH$_2$, CH—C(NH)—NH$_2$, CH—NH—C(NH)—NH$_2$ or CH—CH$_2$—C(NH)—NH$_2$;

X$^4$ represents CH$_2$ or NH;

Preferred combinations of X$^1$, X$^2$, X$^3$, 4 and r are

X$^1$, X$^2$ and X$^4$ are CH$_2$, X$^3$ is CH—C(NH)—NH$_2$ and r is 0, 1, or,

X$^1$, X$^2$ and X$^4$ are CH$_2$, X$^3$ is N—C(NH)—NH$_2$ and r is 0, 1, or

X$^1$ and X$^3$ are NH, X$^2$ is C—NH, X$^4$ is CH$_2$ and r is 0, 1, or

X$^1$ and X$^4$ are CH$_2$, X$^2$ is C=NH, X$^3$ is NH and r is 0, 1, or

X$^1$ is CH$_2$, X$^2$ and X$^4$ are NH, X$^3$ is C=NH and r is 1, or

X$^1$, X$^2$ and X$^4$ are CH$_2$, X$^3$ is CH—NH—C(NH)—NH$_2$ and r is 0, 1, or X$^1$ is absent, X$^2$ and X$^4$ are CH$_2$, X$^3$ is CH—C(NH)—NH$_2$ and r is 0, or X$^1$ is absent, X$^2$ and X$^4$ are CH$_2$, X$^3$ is N—C(NH)—NH$_2$ and r is 0;

Particularly preferred combinations of X$^1$, X$^2$, X$^3$, X$^4$ and r are

X$^1$, X$^2$ and X$^4$ are CH$_2$. X$^3$ is CH—C(NH)—NH$_2$ and r is 1;

X$^1$, X$^2$ and X$^4$ are CH$_2$, X$^3$ is N—C(NH)—NH$_2$ and r is 0 or

X$^1$ is absent, X$^2$ and X$^4$ are CH$_2$, X$^3$ is N—C(NH)—NH$_2$ and r is 0;

X$^1$ and X$^3$ are NH, X$^2$ is C=NH, X$^4$ is CH$_2$ and r is 1;

X$^5$ represents C(NH)—NH$_2$ or NH—C(NH)—NH$_2$;

R$^6$ is H or an alkyl group having 1–4 carbon atoms;

X$^6$ represents CH or N;

Compounds of Formula I having S-configuration on the A$^2$ amino acid are preferred ones, of those compounds also having R-configuration on the A$^1$ amino acid are particularly preferred ones.

In the present context the term "an alkyl group having 1 to 4 carbon atoms" may be straight or branched unless specified otherwise. An alkyl group having 1 to 4 carbon atoms may be methyl, ethyl, n-propyl, i-propyl, n-butyl, i-butyl, s-butyl and t-butyl.

In the present context the term "an alkyl group having 1 to 6 carbon atoms" may be straigh or branched unless specified otherwise. An alkyl group having 1 to 6 carbon atoms may be methyl, ethyl, n-propyl, i-propyl, n-butyl, i-butyl, s-butyl, t-butyl, n-pentyl, i-pentyl, t-pentyl, neopentyl, n-hexyl or i-hexyl. When unsaturation is referred to, a carbon-carbon double bond is intended.

The wavy lines on the carbon atom in the carbonyl group in formulas IIa, IIb, IIc, IId, IIe, IIIa, IIIb, IIIc, on the nitrogen atom in formulas IIIa, IIIb, IIIc and on the carbon atom in the ring system in formulas IVa, IVb, IVc, IVd signify the bond position of the fragment.

Abbreviations are listed at the end of this specification.

According to the invention it has been found that compounds of the general Formula Ia, either as such or in the form of physiologically acceptable salts, and including stereoisomers, are potent inhibitors of thrombin:

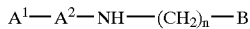

Ia wherein:
$A^1$ represents a structural fragment of Formula IIa, IIb, IIc or IId, preferably IIa or IIb;
wherein:
k is an integer 0, 1, 2, 3 or 4, preferably 0, 1;
q is an integer 0, 1, 2 or 3, preferably 1;
$R^1$ represents H, an alkyl group having 1 to 4 carbon atoms, $R^{11}$OOC-alkyl-, where the alkyl group has 1 to 4 carbon atoms and is possibly substituted in the position which is alpha to the carbonyl group, and the alpha substituent is a group $R^{17}$—$(CH_2)_n$—, wherein p is 0, 1 or 2 and $R^{17}$ is methyl, phenyl, OH, COOR$^{12}$, CONHR$^{12}$, where $R^{12}$ is H or an alkyl group having 1 to 4 carbon atoms, and $R^{11}$ is H or an alkyl group having 1 to 6 carbon atoms, or
$R^1$ represents Ph(4-COOR$^{12}$)—CH$_2$—, where $R^{12}$ is as defined above, or
$R^1$ represents $R^{13}$—NH—CO-alkyl-, where the alkyl group has 1 to 4 carbon atoms and is possibly substituted alpha to the carbonyl with an alkyl group having 1 to 4 carbon atoms and where $R^{13}$ is H or an alkyl group having 1 to 4 carbon atoms or —CH$_2$COOR$^{12}$ where $R^{12}$ is as defined above, or
$R^1$ represents $R^{12}$OOC—CH$_2$—OOC-alkyl-, where the alkyl group has 1 to 4 carbon atoms and is possibly substituted alpha to the carbonyl with an alkyl group having 1 to 4 carbon atoms and where $R^{12}$ is as defined above, or
$R^1$ represents $R^{14}$SO$_2$—, Ph(4-COOR$^{12}$)—SO$_2$—, Ph(3-COOR$^{12}$)—SO$_2$—, Ph(2-COOR$^{12}$)—SO$_2$— where $R^{12}$ is as defined above and $R^{14}$ is an alkylgroup having 1–4 carbon atoms, or
$R^1$ represents —CO—$R^{15}$, wherein $R^{15}$ is an alkyl group having 1–4 carbon atoms, or
$R^1$ represents —CO—OR$^{15}$, where $R^{15}$ is as defined above, or
$R^1$ represent —CO—(CH$_2$)$_p$—COOR$^{12}$, where $R^{12}$ is as defined above and p is an interger 0, 1 or 2, or
$R^1$ represents —CH$_2$PO(OR$^{16}$)$_2$, —CH$_2$SO$_3$H or —CH$_2$-(5-(1H)-tetrazolyl), where $R^{16}$ is, individually at each occurrence, H, methyl or ethyl;
Preferably $R^1$ represents $R^{11}$OOC-alkyl-, where the alkyl group has 1 to 4 carbon atoms and $R^{11}$ is H.
$R^2$ represents H or an alkyl group having 1 to 4 carbon atoms, or $R^{21}$OOC-alkyl-, where the alkyl group has 1 to 4 carbon atoms and $R^{21}$ is H or an alkyl group having 1 to 4 carbon atoms;
$R^3$ represents an alkyl group having 1–4 carbon atoms, and the alkyl group may or may not carry one or more fluorine atoms, or
$R^3$ represents a cyclopentyl, cyclohexyl- or a phenyl group which may or may not be substituted with an alkyl group having 1 to 4 carbon atoms, or
$R^3$ represents a 1-naphthyl or 2-naphthyl group and k is 0, 1, or
$R^3$ represent a cis- or trans-decalin group and k is 0, 1, or
$R^3$ represents Si(Me)$_3$ or CH(R$^{32}$)$_{21}$ wherein $R^{32}$ is a cyclohexyl- or phenyl group;
$R^4$ represents an alkyl group having 1 to 4 carbon atoms, a cyclohexyl or a phenyl group, preferably a cyclohexyl or a phenyl group;
$A^2$ represents a structural fragment of Formula IIIa, IIIb or IIIc, preferably IIIa;
wherein:
p is an interger 0, 1 or 2;
m is an integer 1, 2, 3 or 4, preferably 2, 3;
Y represents a methylene group, or
Y represents an ethylene group and the resulting 5-membered ring may or may not carry one or two fluorine atoms, a hydroxy group or an oxo group in position 4, or may or may not be unsaturated, or
Y represents —CH$_2$—O—, —CH$_2$—S—, —CH$_2$—SO—, with the heteroatom functionality in position 4, or
Y represents a n-propylene group and the resulting 6-membered ring may or may not carry in position 5 one fluorine atom, a hydroxy group or an oxo group, carry two fluorine atoms in one of positions 4 or 5 or be unsaturated in position 4 and 5, or carry in position 4 an alkyl group with 1 to 4 carbon atoms, or
Y represents —CH$_2$—O—CH$_2$—, —CH$_2$—S—CH$_2$—, —CH$_2$—SO—CH$_2$—, or
Y represent —CH$_2$—CH$_2$—CH$_2$—CH$_2$—;
$R^3$ represents an alkyl group having 1–4 carbon atoms, or
$R^3$ represents a Si(Me)$_3$ group;
$R^5$ represents H or an alkyl group having 1 to 4 carbon atoms, preferably H or a methylgroup, or
$R^5$ represents —(CH$_2$)$_p$—COOR$^{51}$, where p is 0, 1 or 2 and $R^{51}$ is H or an alkyl group having 1 to 4 carbon atoms, preferably p is 0 and $R^{51}$ is H;
n is an integer 0, 1, 2, 3 or 4, preferably 1, 2, 3;
B represents a structural fragment of Formula IVa, IVb, IVc or IVd, preferably IVa or IVb
wherein:
$X^1$, $X^2$, $X^3$, $X^4$, $X^5$ and $X^6$ are as defined above;
r is an integer 0 or 1;
$R^6$ is H or an alkyl group having 1–4 carbon atoms, preferably H;
preferred combinations of $X^1$, $X^2$, $X^3$, $X^4$ and r are
$X^1$, $X^2$ and $X^4$ are CH$_2$, $X^3$ is CH—C(NH)—NH$_2$ and r is 0 or 1, or
$X^1$, $X^2$ and $X^4$ are CH$_2$, $X^3$ is N—C(NH)—NH$_2$ and r is 0 or 1, or
$X^1$ and $X^3$ are NH, $X^2$ is C=NH, $X^4$ is CH$_2$ and r is 0 or 1, or
$X^1$ and $X^4$ are CH$_2$', $X^2$ is C=NH, $X^3$ is NH and r is 0 or 1, or
$X^1$ is CH$_2$' $X^2$ and $X^4$ are NH, $X^3$ is C=NH and r is 1, or
$X^1$, $X^2$ and $X^4$ are CH$_2$, $X^3$ is CH—NH—C(NH)—NH$_2$ and r=0 or 1, or
or $X^1$ is absent, $X^2$ and $X^4$ are CH$_2$, $X^3$ is CH—C(NH)—NH$_2$ and r is 0,
or $X^1$ is absent, $X^2$ and $X^4$ are CH$_2$, $X^3$ is N—C(NH)—NH$_2$ and r is 0;
Particularly preferred combinations of $X^1$, $X^2$, $X^3$, $X^4$ and r are
$X^1$ is absent, $X^2$ and $X^4$ are CH$_2$, $X^3$ is N—C(NH)—NH$_2$ and r is 0, or $X^1$, $X^2$ and $X^4$ are $CH_2$, $X^3$ is CH—C(NH)—$NH_2$ and r=1, or $X^1$, $X^2$ and $X^4$ are $CH_2$, $X^3$ is N—C(NH)—$NH_2$ and r=0 or 1, or $X^1$ and $X^3$ are NH, $X^2$ is C=NH, $X^4$ is $CH_2$ r is 1;

$X^5$ represents C(NH)—$NH_2$ or NH—C(NH)—$NH_2$, preferably C(NH)—$NH_2$;

$X^6$ represents CH or N;

According to a preferred embodiment the invention relates to compounds of Formula Ia, wherein:

$A^1$ represents a structural fragment of Formula IIa, wherein:

k is 0 or 1;

$R^1$ represents $R^{11}$OOC-alkyl-, where the alkyl group has 1 to 4 carbon atoms, particularly methylene, ethylene and $R^{11}$ is H;

$R^2$ represents H;

$R^3$ represents a cyclohexyl group;

$A^2$ represents a structural fragment of Formula IIIa, wherein:

Y represents a methylene group, an ethylene group, or a n-propylene group and the resulting 6-membered ring may or may not carry in position 4 an alkyl group with 1 to 4 carbon atoms, preferably Y represents methylene, ethylene;

$R^5$ represents H;

B represents a structural fragment of formula IVa wherein:

$X^1$ is absent, $X^2$ and $X^4$ are $CH_2$, $X^3$ is N—C(NH)—$NH_2$, r is 0 and n is 1 or 2;

$X^1$, and $X^3$ are NH, $X^2$ is C=NH, $X^4$ is $CH_2$, r is 1 and n is 2, or $X^1$, $X^2$ and $X^4$ are $CH_2$, $X^3$ is CH—C(NH)—$NH_2$, r is 1 and n is 1, or $X^1$, $X^2$ and $X^4$ are $CH_2$, $X^3$ is N—C(NH)—$NH_2$, r is 0 or 1 and n is 1 or 2, or More particularly preferred are compounds wherein B represents a structural fragment for formula IVb wherein: $X^5$ represents C(NH)—$NH_2$, $R^6$ is H, and n=1

Preferred compounds of the invention are:

HOOC—$CH_2$—(R)Cgl-Aze-Pab
HOOC—$CH_2$—$CH_2$—(R)Cgl-Aze-Pab
HOOC—$CH_2$—(R)Cgl-Pro-Pab
HOOC—$CH_2$—$CH_2$—(R)Cgl-Pro-Pab
(HOOC—$CH_2$)$_2$—(R)Cgl-Pro-Pab
H—(R)Cgl-Pic-Pab
HOOC—$CH_2$—(R,S)CH(COOH)—(R)Cgl-Pic-Pab
H—(R)Cha-Aze-Pab
HOOC—$CH_2$—(R)Cha-Aze-Pab
HOOC—$CH_2$—(R,S)CH(COOH)—(R)Cha-Aze-Pab
HOOC—$CH_2$—(R or S)CH(COOH)—(R)Cha-Aze-Pab/a
HOOC—$CH_2$—(R or S)CH(COOH)—(R)Cha-Aze-Pab/b
HOOC—$CH_2$—$CH_2$—(R)Cha-Aze-Pab
HOOC—$CH_2$—NH—CO—$CH_2$—(R)Cha-Aze-Pab
H—(R)Cha-Pro-Pab
HOOC—$CH_2$—(R)Cha-Pro-Pab
HOOC—$CH_2$—(Me)(R)Cha-Pro-Pab
HOOC—$CH_2$—$CH_2$—(R)Cha-Pro-Pab
HOOC—$CH_2$—$CH_2$-(Me)(R)Cha-Pro-Pab
HOOC—$CH_2$—(R or S)CH(COOH)—(R)Cha-Pro-Pab/a
HOOC—$CH_2$—(R or S)CH(COOH)—(R)Cha-Pro-Pab/b
HOOC—$CH_2$—NH—CO—$CH_2$—(R)Cha-Pro-Pab
EtOOC—$CH_2$—$CH_2$—$CH_2$—(R)Cha-Pro-Pab
Ph (4-COOH)—$SO_2$—(R)Cha-Pro-Pab
H—(R)Cha-Pic-Pab
HOOC—$CH_2$—(R)Cha-Pic-Pab
HOOC—$CH_2$—(R or S)CH(COOH)—(R)Cha-Pic-Pab/a
HOOC—$CH_2$—(R or S)CH(COOH)—(R)Cha-Pic-Pab/b
HOOC—$CH_2$—$CH_2$—(R) cha-Pic-Pab
HOOC—CO—(R)Cha-Pic-Pab
HOOC—$CH_2$—CO—(R) cha-Pic-Pab
Me—OOC—$CH_2$—CO—(R)Cha-Pic-Pab
$H_2$N—CO—$CH_2$—(R)Cha-Pic-Pab
Boc-(R)Cha-Pic-Pab
Ac—(R)Cha-Pic-Pab
Me—$SO_2$—(R)Cha-Pic-Pab
H—(R)Cha-(R,S)betaPic-Pab
HOOC—$CH_2$—$CH_2$—(R)Cha-(R,S) betapic-Pab
HOOC—$CH_2$—(R)Cha-Val-Pab
HOOC—$CH_2$—$CH_2$—(R)Cha-Val-Pab
H—(R)Hoc-Aze-Pab
HOOC—$CH_2$—$CH_2$—(R)Hoc-Aze-Pab
HOOC—$CH_2$—(R,S)CH(COOH)—(R)Hoc-Pro-Pab
HOOC—$CH_2$—(R)Hoc-Pic-Pab
(HOOC—$CH_2$)$_2$—(R)Hoc-Pic-Pab
HOOC—$CH_2$—(R)Pro(3-(S)Ph)-Pro-Pab
HOOC—$CH_2$—$CH_2$—(R)Pro(3-(S)Ph)-Pro-Pab
HOOC—$CH_2$—$CH_2$—(R)Tic-Pro-Pab
HOOC—$CH_2$—$CH_2$—(R)Cgl-Aze-Pig
HOOC—$CH_2$—(R)Cgl-Pro-Pig
H—(R)Cha-Aze-Pig
HOOC—$CH_2$—(R)Cgl-Aze-Pac
H—(R)Cha-Pro-Pac
H—(R)Cgl-Ile-Pab
H—(R)Cgl-Aze-Pab
HOOC—(R,S)CH(Me)—(R)Cha-Pro-Pab
MeOOC—$CH_2$—(R)Cgl-Aze-Pab
EtOOC—$CH_2$—(R)Cgl-Aze-Pab
$^n$BuOOC—$CH_2$—(R)Cgl-Aze-Pab
$^n$HexOOC—$CH_2$—(R)Cgl-Aze-Pab
H—(R)Cgl-Pro-Pac
HOOC—$CH_2$—(R)Cha-Pro-Pac
HOOC—$CH_2$—$CH_2$—(R)Cgl-Pro-Pac
HOOC—$CH_2$—$CH_2$—(R)Cha-Aze-Pac
HOOC—$CH_2$—(R)cha-Aze-Pig
HOOC—$CH_2$—(R)Cha-Pro-Pig
HOOC—$CH_2$—$CH_2$—(R)Cha-Pro-Pig
(HOOC—$CH_2$)$_2$—(R)Cgl-Pro-Pig
HOOC—$CH_2$—$CH_2$(HOOC—$CH_2$)—(R)Cha-Pro-Pig
HOOC—$CH_2$—(R)Cgl-Aze-(R,S)Itp
HOOC—$CH_2$—(R)Cha-Aze-(R,S)Itp
H—(R)Cha-Pic-(R,S)Itp
HOOC—$CH_2$—(R)Cha-Pic-(R,S)Itp
H—(R)Cgl-Pro-(R,S)Hig
HOOC—$CH_2$—(R)Cgl-Pro-(R,S)Hig
H—(R)Cha-Pro-(R,S)Hig
H—(R)Cgl-Aze-Rig
HOOC—$CH_{12}$—(R)Cgl-Aze-Rig
HOOC—$CH_2$—(R)Cha-Pro-Rig
HOOC—$CH_2$—$CH_2$—(R)Cha-Aze-Rig
HOOC—$CH_2$—(R)Cha-Pro-(S)Itp
H—(R)Cha-Pro-(R,S)Nig
H—(R)Cha-Pro-Mig
H—(R)Cha-Pro-Dig
H—(R)Cha-Aze-Dig At present the particularly preferred compounds of formula Ia is HOOC—$CH_2$—(R)Cgl-Aze-Pab
HOOC—$CH_2$—$CH_2$—(R)Cha-Aze-Pab
HOOC—$CH_2$—(R)Cha-Pro-Pab
HOOC—$CH_2$—$CH_2$—(R)Cha-Pro-Pab
HOOC—$CH_2$—(R)Cha-Pic-Pab
HOOC—$CH_2$—(R)Cgl-Pro-Pig
EtOOC—$CH_2$—(R)Cgl-Aze-Pab
HOOC—$CH_2$—(R)Cha-Pro-Pac HOOC—CH$_2$—(R)Cha-Pro-Pig In the above tables of compounds, the letters /a and /b refer to a substantially pure stereoisomer at the carbon atom noted "R or S". The stereoisomer can be identified for each compound with reference to the experimental part herein. "R,S" refers to a mixture of stereoisomers.

According to the invention it has been found that compounds of the general Formula Ib, either as such or in the form of physiologically acceptable salts, and including stereoisomers, are potent inhibitors of kininogenases:

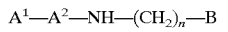   Ib wherein:
A$^1$ represents a structural fragment of formula IIa, IIb or IIe, preferably IIa or IIb;
wherein:
k is an integer 0, 1, 2, 3 or 4, preferably 0, 1;
q is an integer 0, 1, 2, or 3, preferably 1;
R$^1$ represents H, an alkyl group having 1 to 4 carbon atoms, or R$^{11}$OOC-alkyl-, where the alkyl group has 1 to 4 carbon atoms and is possibly substituted in the position which is alpha to the carbonyl group, and the alpha substituent is a group R$^{17}$—(CH$_2$)$_p$—, wherein p is 0, 1 or 2 and R$^{17}$ is methyl, phenyl, OH, COOR$^{12}$, CONHR$^{12}$, where R$^{12}$ is H or an alkyl group having 1 to 4 carbon atoms, and R$^{11}$ is H or an alkyl group having 1 to 6 carbon atoms, or
R$^1$ represents Ph(4-COOR$^2$)—CH$_2$—, where R$^{12}$ is H or an alkyl group having 1 to 4 carbon atoms, or
R$^1$ represents R$^{13}$—NH—CO-alkyl-, where the alkyl group has 1 to 4 carbon atoms and is possibly substituted alpha to the carbonyl with an alkyl group having 1 to 4 carbon atoms and where R$^{13}$ is H or an alkyl group having 1 to 4 carbon atoms or —CH$_2$COOR$^{12}$ where R$^{12}$ is as defined above, or
R$^1$ represents R$^{12}$OOC—CH$_2$—OOC-alkyl-, where the alkyl group has 1 to 4 carbon atoms and is possibly substituted alpha to the carbonyl with an alkyl group having 1 to 4 carbon atoms and where R$^{12}$ is as defined above, or
R$^1$ represents R$^{14}$SO$_2$—, Ph(4-COOR$^{12}$)—SO$_2$—, Ph(3-COOR$^{12}$)—SO$_2$, Ph(2-COOR$^{12}$)—SO$_2$—, where R$^{12}$ is as defined above and R$^{14}$ is an alkylgroup having 1–4 carbon atoms, or
R$^1$ represents —CO—R$^{15}$, wherein R$^{15}$ is an alkyl group having 1–4 carbon atoms, or
R$^1$ represents —CO—OR$^{15}$, where R's is as defined above, or
R$^1$ represent —CO—(CH$_2$)$_n$—COOR$^{12}$, where R$^{12}$ is as defined above and p is 0, 1 or 2, or
R$^1$ represents —CH$_2$PO(OR$^{16}$)$_2$, —CH$_2$SO$_3$H or —CH$_2$-(5-(1H)-tetrazolyl), where R$^{16}$ is, individually at each occurrence, H, methyl or ethyl;
R$^2$ represents H or an alkyl group having 1 to 4 carbon atoms or R$^{21}$OOC-alkyl-, where the alkyl group has 1 to 4 carbon atoms and R$^{21}$ is H or an alkyl group having 1 to 4 carbon atoms;
R$^3$ represents an alkyl group having 1–4 carbon atoms, and the alkyl group may or may not carry one or more fluorine atoms, or
R$^3$ represents a cyclopentyl, cyclohexyl- or a phenyl group which may or may not be substituted with an alkyl group having 1 to 4 carbon atoms, or
R$^3$ represents a phenyl group substituted with a OR$^{31}$ group, where R$^{31}$ is H or an alkyl group having 1 to 4 carbon atoms and k is 0, 1, or
R$^3$ represents a 1-naphthyl or 1-naphthyl group and k is 0, 1, or
R$^3$ represent a cis- or trans-decalin group and k is 0,1, or
R$^3$ represents 4-pyridyl, 3-pyrrolidyl or 3-indolyl which may or may not be substituted with a OR$^{31}$ group, where R$^{31}$ is as defined above and k is 0, 1, or
R$^3$ represents Si(Me)$_3$ or CH(R$^{32}$)$_2$, wherein R$^{32}$ is a cyclohexyl- or phenyl group;
R$^4$ represents H, an alkyl group having 1 to carbon atoms, a cyclohexyl or a phenyl group, preferably H;
A$^2$ represents a structural fragment of formula IIIb or IIIc, preferably IIIb
wherein:
p is an integer 0, 1 or 2;
m is an integer 1, 2, 3, or 4, preferably 2, 3;
R$^3$ is as defined above;
n is an integer 0, 1, 2, 3 or 4, preferably 1,2,3;
B represents a structural fragment of Formula IVa, IVb, IVc or IVd, preferably IVa or IVb;
wherein:
X$^1$, X$^2$, X$^3$, X$^4$ are as defined above;
R$^6$ is H or an alkyl group having 1–4 carbon atoms, preferably H or a methyl group;
r is an integer 0 or 1;
preferred combinations of X$^1$, X$^2$, X$^3$ and X$^4$ are
X$^1$, X$^2$ and X$^4$ are CH$_2$, X$^3$ is CH—C(NH)—NH$_2$ and r is 0 or 1, or
X$^1$, X$^2$ and X$^4$ are CH$_2$, X$^3$ is N—C(NH)—NH$_2$ and r is 0 or 1, or
X$^1$ and X$^3$ are NH, X$^2$ is C=NH, X$^4$ is CH$_2$ and r is 0 or 1, or
X$^1$ and X$^4$ are CH$_2$, X$^2$ is C=NH, X$^3$ is NH and r is 0 or 1, or
X$^1$ is CH$_2$, X$^2$ and X$^4$ are NH, X$^3$ is C=NH and r is 1, or
X$^1$, X$^2$ and X$^4$ are CH$_2$, X$^3$ is CH—NH—C(NH)—NH$_2$ and r is 0 or 1,
or X$^1$ is absent, X$^2$ and X$^4$ are CH$_2$, X$^3$ is CH—C(NH)—NH$_2$ and r is 0, or
X$^1$ is absent, X$^2$ and X$^4$ are CH$_2$, X$^3$ is N—C(NH)—NH$_2$ and r is 0;
particularly preferred combinations of X$^1$, X$^2$, X$^3$ and X$^4$ are
X$^1$, X$^2$ and X$^4$ are CH$_2$, X$^3$ is CH—C(NH)—NH$_2$ and r is 1 or,
X$^1$, X$^2$ and X$^4$ are CH$_2$, X$^3$ is N—C(NH)—NH$_2$ and r is 1;
X$^5$ represents C(NH)—NH$_2$ or NH—C(NH)—NH$_2$, preferably C(NH)—NH$_2$;
X$^6$ represents CH or N.
Preferred compound of the invention are:
H—(R)Pro-Phe-Pab
HOOC—CH$_2$—(R)Pro-Phe-Pab
H—(R)Phe-Phe-Pab
HOOC—CO—(R)Phe-Phe-Pab
HOOC—CH$_2$—(R)Phe-Phe-Pab
H—(R)Cha-Phe-Pab
HOOC—CH$_2$—(R)Cha-Phe-Pab
H—(R)Phe-Cha-Pab
HOOC—CH$_2$—(R)Phe-Cha-Pab
H—(R)Cha-Cha-Pab
HOOC—CH$_2$—(R)Cha-Cha-Pab Furthermore, it has been found that compounds of the general Formula V, either as such or in the form of physiologically acceptable salts, and including stereoisomers, are potent inhibitors of serine proteases, especially thrombin and kininogenases such as kallikrein after oral or parenteral administration:

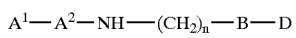

Formula V wherein:
A¹ represents a structural fragment of Formula IIa, IIb, IIc, IId or IIe;

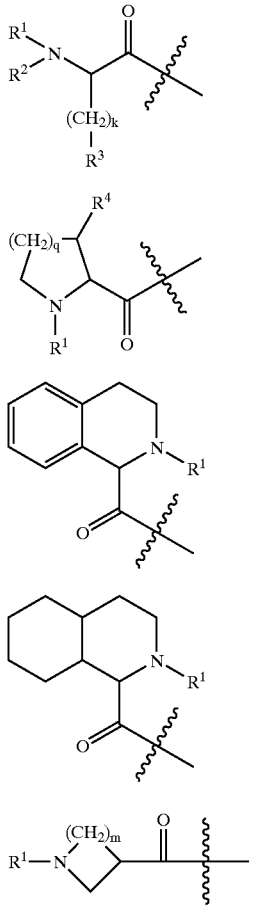

wherein:
k is an integer 0, 1, 2, 3 or 4;
m is an integer 1, 2, 3 or 4;
q is an integer 0, 1, 2 or 3;
$R^1$ represents $R^{11}OOC$-alkyl-, where the alkyl group has 1 to 4 carbon atoms and is possibly substituted in the position which is alpha to the carbonyl group, and the alpha substituent is a group $R^{17}$—$(CH_2)_p$— wherein p is 0, 1 or 2 and $R^{17}$ is $COOR^{12}$, $CONHR^{12}$, where $R^{12}$ is H or an alkyl group having 1 to 4 carbon atoms or a benzyl group, and $R^{11}$ is H or an alkyl group having 1 to 6 carbon atoms, or a benzyl group, or
$R^1$ represents $Ph(4-COOR^{12})$—$CH_2$—, where $R^{12}$ is as defined above, or
$R^1$ represents $R^{13}$—NH—CO-alkyl-, where the alkyl group has 1 to 4 carbon atoms and is possibly substituted alpha to the carbonyl with an alkyl group having 1 to 4 carbon atoms and where $R^{13}$ is H or an alkyl group having 1 to 4 carbon atoms or —$CH_2COOR^{12}$, where $R^{12}$ is as defined above, or
$R^1$ represents $R^{12}OOC$—$CH_2$—OOC-alkyl-, where the alkyl group has 1 to 4 carbon atoms and is possibly substituted alpha to the carbonyl with an alkyl group having 1 to 4 carbon atoms and where $R^{12}$ is as defined above, or $R^1$ represents $R^{14}SO_2$—, $Ph(4-COOR^{12})$—$SO_2$—, $Ph(3-COOR^{12})$—$SO_2$—, $Ph(2-COOR^{12})$—$SO_2$—, where $R^{12}$ is as defined above and $R^{14}$ is an alkyl group having 1–4 carbon atoms, or
$R^1$ represents —CO—$R^{15}$ is wherein $R^{15}$ is an alkyl group having 1–4 carbon atoms, or
$R^1$ represents —CO—$OR^{15}$, where $R^{15}$ is as defined above, or
$R^1$ represent —CO—$(CH_2)$—$COOR^{12}$, where $R^{12}$ is as defined above and p is an interger 0, 1 or 2, or
$R^2$ represents H or an alkyl group having 1 to 4 carbon atoms or $R^{21}OOC$-alkyl-, where the alkyl group has 1 to 4 carbon atoms and, where $R^{21}$ is H, an alkyl group having 1 to 4 carbon atoms or a benzyl group;
$R^3$ represents an alkyl group having 1–4 carbon atoms, and the alkyl group may or may not carry one or more flourine atoms, or
$R^3$ represents a cyclopentyl, cyclohexyl- or a phenyl group which may or may not be substituted with an alkyl group having 1 to 4 carbon atoms, or
$R^3$ represents a phenyl group substituted with a $OR^{31}$ group, where $R^{31}$ is H or an alkyl group having 1 to 4 carbon atoms and k is 0, 1, or
$R^3$ represents a 1-naphthyl or 2-naphthyl group and k is 0, 1, or
$R^3$ represent a cis- or trans-decalin group and k is 0, 1, or
$R^3$ represents 4-pyridyl, 3-pyrrolidyl or 3-indolyl which may or may not be substituted with a $OR^{31}$ group, where $R^{31}$ is as defined above and k is 0, 1, or
$R^3$ represents $Si(Me)_3$ or $CH(R^{32})_{21}$ wherein $R^{32}$ is a cyclohexyl- or a phenyl group;
$R^4$ represents H, an alkyl group having 1 to 4 carbon atoms, a cyclohexyl- or a phenyl group;
$A^2$, B and n are defined as described under Formula I above;
D is Z or $(Z)_21$ wherein Z represents a benzyloxycarbonyl group.
The benzyloxycarbonyl group (Z or $(Z)_2$) will bind to the amidino- or guanidino nitrogens present in B.
Preferred and particularly preferred combinations are the same as described for Formula I above.
Furthermore, it has been found that compounds of the general Formula Va, either as such or in the form of physiologically acceptable salts, and including stereoisomers, are potent inhibitors of thrombin after oral or parenteral administration:

Formula Va wherein:
$A^1$ represents a structural fragment of Formula IIa, IIb, IIc or IId, preferably IIa or IIb;
wherein:
k is an integer 0, 1, 2, 3 or 4, preferably 0, 1;
q is an integer 0, 1, 2 or 3, preferably 1;
$R^1$ represents $R^{11}OOC$-alkyl-, where the alkyl group has 1 to 4 carbon atoms and is possibly substituted in the position which is alpha to the carbonyl group, and the alpha substituent is a group $R^{17}$-$(CH_2)_n$—, wherein p is 0, 1 or 2 and $R^{17}$ is $COOR^{12}$, $CONHR^{12}$; where $R^{12}$ is H, an alkyl group having 1 to 4 carbon atoms or a benzyl group, and $R^{11}$ is H or an alkyl group having 1 to 6 carbon atoms, or a benzyl group, or
$R^1$ represents $Ph(4-COOR^{12})$—$CH_2$—, where $R^{12}$ is as defined above, or
$R^1$ represents $R^{13}$—NH—CO-alkyl-, where the alkyl group has 1 to 4 carbon atoms and is possibly substituted alpha to the carbonyl with an alkyl group having 1 to 4 carbon atoms and where $R^{13}$ is H or an alkyl group having 1 to 4 carbon atoms or —$CH_2COOR^{12}$ where $R^{12}$ is as defined above, or $R^1$ represents $R^{12}OOC$—$CH_2$—OOC-alkyl-, where the alkyl group has 1 to 4 carbon atoms and is possibly substituted alpha to the carbonyl with an alkyl group having 1 to 4 carbon atoms and where $R^{12}$ is as defined above, or $R^1$ represents $R^{14}SO_2$—, Ph(4-$COOR^{12}$)—$SO_2$—, Ph(3-$COOR^{12}$)—$SO_2$—, Ph(2-$COOR^{12}$)—$SO_2$— where $R^{12}$ is as defined above and $R^{14}$ is an alkylgroup having 1–4 carbon atoms, or $R^1$ represents —CO—$R^{15}$, wherein R's is an alkyl group having 1–4 carbon atoms, or $R^1$ represents —CO—$OR^{15}$, where $R^{15}$ is as defined above, or $R^1$ represent —CO—$(CH_2)_p$—$COOR^{12}$, where $R^{12}$ is as defined above and p is an interger 0, 1 or 2, or Preferably $R^1$ represents $R^{11}OOC$-alkyl-, where the alkyl group has 1 to 4 carbon atoms and $R^{11}$ is as defined above.

$R^2$ represents H or an alkyl group having 1 to 4 carbon atoms, or $R^{21}OOC$-alkyl-, where the alkyl group has 1 to 4 carbon atoms and $R^{21}$ is H or an alkyl group having 1 to 4 carbon atoms or a benzyl group;

$R^3$ represents an alkyl group having 1–4 carbon atoms, and the alkyl group may or may not carry one or more fluorine atoms, or $R^3$ represents a cyclopentyl, cyclohexyl- or a phenyl group which may or may not be substituted with an alkyl group having 1 to 4 carbon atoms, or $R^3$ represents a 1-naphthyl or 2-naphthyl group and k is 0, 1, or $R^3$ represent a cis- or trans-decalin group and k is 0, 1, or $R^3$ represents $Si(Me)_3$ or $CH(R^{32})_2 1$ wherein $R^{32}$ is a cyclohexyl- or phenyl group;

$R^4$ represents an alkyl group having 1 to 4 carbon atoms, a cyclohexyl or a phenyl group, preferably a cyclohexyl or a phenyl group;

$A^2$, B and n are defined as described under Formula Ia above;

D is Z or $(Z)_2$;

Z represents a benzyloxycarbonyl group.

Preferred integers, groups or combinations and particularly preferred combinations are the same as described for Formula Ia above but $R^{11}$ is H, an alkyl group having 1 to 6 carbon atoms or a benzyl group.

Preferred compounds having Formula Va are:
BnOOC—$CH_2$—(R)Cgl-Aze-Pab(Z)
BnOOC—$CH_2$—$CH_2$—(R)Cgl-Aze-Pab (Z)
BnOOC—$CH_2$—(R)Cgl-Pro-Pab(Z)
BnOOC—$CH_2$—$CH_2$—(R)Cgl-Pro-Pab (Z)
BnOOC—$CH_2)_2$—(R)Cgl-Pro-Pab (Z)
BnOOC—$CH_2$—(R,S)CH(COOBn)-(R)Cgl-Pic-Pab (Z)
BnOOC—$CH_2$—(R)Cha-Aze-Pab(Z)
BnOOC—$CH_2$—(R,S)CH(COOBn)—(R)Cha-Aze-Pab(Z)
BnOOC—$CH_2$—(R or S)CH(COOBn)—(R)Cha-Aze-Pab (Z)/a
BnOOC—$CH_2$—(R or S)CH(COOBn)—(R)Cha-Aze-Pab (Z)/b
BnOOC—$CH_2$—$CH_2$—(R)Cha-Aze-Pab(Z)
BnOOC—$CH_2$—NH—CO—$CH_2$—(R)Cha-Aze-Pab(Z)
BnOOC—$CH_2$—(R)Cha-Pro-Pab(Z)
BnOOC—$CH_2$—(Me)(R)cha-Pro-Pab(Z)
BnOOC—$CH_2$—$CH_2$—(R)Cha-Pro-Pab(Z)
BnOOC—$CH_2$—$CH_2$-(Me)(R)Cha-Pro-Pab(Z)
BnOOC—$CH_2$—(R,S)CH(COOBn)—(R)Cha-Pro-Pab(Z)
BnOOC—$CH_2$—NH—CO—$CH_2$—(R)Cha-Pro-Pab(Z)
Ph(4-COOH)—$SO_2$—(R)Cha-Pro-Pab(Z)
Boc-(R)Cha-Pic-Pab(Z)
BnOOC—$CH_2$—(R)Cha-Pic-Pab(Z)
BnOOC—$CH_2$—(R,S)CH(COOBn)—(R)Cha-Pic-Pab(Z)
BnOOC—$CH_2$—$CH_2$—(R)Cha-Pic-Pab(Z)
EtOOC—CO—(R)Cha-Pic-Pab(Z)
MeOOC—$CH_2$—CO—(R)Cha-Pic-Pab(Z)
$H_2N$—CO—$CH_2$—(R)Cha-Pic-Pab(Z)
Ac—(R)Cha-Pic-Pab(Z)
Me—$SO_2$—(R)Cha-Pic-Pab(Z)
BnOOC—$CH_2$—(R)Cha-Val-Pab(Z)
BnOOC—$CH_2$—$CH_2$—(R)Cha-(R,S)Val-Pab(Z)
BnOOC—$CH_2$—$CH_2$—(R)Hoc-Aze-Pab(Z)
BnOOC—$CH_2$—(R,S)CH(COOBn)-(R)Hoc-Pro-Pab (Z)
BnOOC—$CH_2$—(R)Hoc-Pic-Pab(Z)
(BnOOC—$CH_2$) 2-(R)Hoc-Pic-Pab (Z)
BnOOC—$CH_2$—(R)Pro(3-(S)Ph)-Pro-Pab(Z)
BnOOC—$CH_2$—$CH_2$—(R)Pro(3-(S)Ph)-Pro-Pab(Z)
BnOOC—$CH_2$—$CH_2$—(R)Tic-Pro-Pab(Z)
BnOOC—$CH_2$—$CH_2$—(R)Cgl-Aze-Pig$(Z)_2$
BnOOC—$CH_2$—(R)Cgl-Pro-Pig(Z) 2
BnOOC—$CH_2$—(R)Cgl-Aze-Pac(Z)
BnOOC—(R,S)CH(Me)—(R)Cha-Pro-Pab(Z)
MeOOC—$CH_2$—(R)Cgl-Aze-Pab(Z)
EtOOC—$CH_2$—(R)Cgl-Aze-Pab(Z)
"BuOOC—$CH_2$—(R)Cgl-Aze-Pab(Z)
"HexOOC—$CH_2$—(R)Cgl-Aze-Pab(Z)
BnOOC—$CH_2$—(R)Cha-Pro-Pac(Z)
BnOOC—$CH_2$—$CH_2$—(R)Cgl-Pro-Pac(Z)
BnOOC—$CH_2$—$CH_2$—(R)Cha-Aze-Pac(Z)
BnOOC—$CH_2$—(R)Cha-Aze-Pig(Z)
BnOOC—$CH_2$—(R)Cha-Pro-Pig(Z)
BnOOC—$CH_2$—$CH_2$—(R)Cha-Pro-Pig(Z)
(BnOOC—$CH_2)_2$—(R)Cgl-Pro-Pig(Z)
BnOOC—$CH_2$—$CH_2$ (BnOOC—$CH_2$)—(R)Cha-Pro-Pig (Z)
BnOOC—$CH_2$—(R)Cha-Pic-(R,S)Itp (Z)
BnOOC—$CH_2$—(R)Cgl-Pro-(R,S)Hig(Z)
BnOOC—$CH_2$—(R)Cgl-Aze-Rig(Z)
BnOOC—$CH_2$—(R)Cha-Pro-Rig(Z)
BnOOC—$CH_2$—$CH_2$—(R)Cha-Aze-Rig(Z)

Particularly preferred compounds are:
BnOOC—$CH_2$—(R)Cgl-Aze-Pab(z)
BnOOC—$CH_2$—(R)Cha-Pro-Pab(Z)
BnOOC—CH—(R)Cha-Pic-Pab(Z)
BnOOC—$CH_2$—(R)Cgl-Pro-Pig$(Z)_2$
EtOOC—$CH_2$—(R)Cgl-Aze-Pab(Z)
BnOOC—$CH_2$—(R)Cha-Pro-Pac(Z)
Bn OOC—$CH_2$—(R)Cha-Pro-Pig(Z)

Furthermore, it has been found that compounds of the general Formula Vb, either as such or in the form of physiologically acceptable salts, and including stereoisomers, are potent inhibitors of kallikrein after oral or parenteral administration:

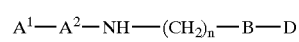

Formula Vb wherein:
$A^1$ represents a structural fragment of formula IIa, IIb or IIe, preferably IIa or IIb; wherein:
k is an integer 0, 1, 2, 3 or 4, preferably 0, 1;
q is an integer 0, 1, 2, or 3, preferably 1;
$R^1$ represents $R^{11}OOC$-alkyl-, where the alkyl group has 1 to 4 carbon atoms and is possibly substituted in the position which is alpha to the carbonyl group, and the alpha substituent is a group R$^{17}$—(CH$_2$)$_n$—, wherein p is 0, 1 or 2 and R$^{17}$ is COOR$^{12}$, CONHR$^{12}$, where R$^{11}$ is H or an alkyl group having 1 to 4 carbon atoms, and R$^{11}$ is H or an alkyl group having 1 to 6 carbon atoms, or a benzyl group, or R$^1$ represents Ph(4-COOR$^{12}$)—CH$_2$—, where R$^{12}$ is as defined above, or R$^1$ represents R$^{13}$—NH—CO-alkyl-, where the alkyl group has 1 to 4 carbon atoms and is possibly substituted alpha to the carbonyl with an alkyl group having 1 to 4 carbon atoms and where R$^{13}$ is H or an alkyl group having 1 to 4 carbon atoms or —CH$_2$COOR$^{12}$ where R$^{12}$ is as defined above, or R$^1$ represents R$^{12}$OOC—CH$_2$—OOC-alkyl-, where the alkyl group has 1 to 4 carbon atoms and is possibly substituted alpha to the carbonyl with an alkyl group having 1 to 4 carbon atoms and where R$^{12}$ is as defined above, or R$^1$ represents R$^{14}$SO$_2$—, Ph(4-COOR$^{12}$)—SO$_2$—, Ph(3-COOR$^{12}$)—SO$_2$, Ph(2-COOR$^{12}$)—SO$_2$—, where R$^{12}$ is as defined above and R$^{14}$ is an alkylgroup having 1–4 carbon atoms, or R$^1$ represents —CO—R$^{15}$, wherein R$^{15}$ is an alkyl group having 1–4 carbon atoms, or R$^1$ represents —CO—OR$^{15}$, where R$^{15}$ is as defined above, or R$^1$ represent —CO—(CH$_2$)$_p$—COOR$^{12}$, where R$^{12}$ is as defined above and p is 0, 1 or 2, or R$^2$ represents H or an alkyl group having 1 to 4 carbon atoms or R$^{21}$OOC-alkyl-, where the alkyl group has 1 to 4 carbon atoms and R$^{21}$ is H, an alkyl group having 1 to 4 carbon atoms or a benzyl group;

R$^3$ represents an alkyl group having 1–4 carbon atoms, and the alkyl group may or may not carry one or more fluorine atoms, or R$^3$ represents a cyclopentyl, cyclohexyl- or a phenyl group which may or may not be substituted with an alkyl group having 1 to 4 carbon atoms, or R$^3$ represents a phenyl group substituted with a OR$^{31}$ group, where R$^{31}$ is H or an alkyl group having 1 to 4 carbon atoms and k is 0, 1, or R$^3$ represents a 1-naphthyl or 1-naphthyl group and k is 0, 1, or R$^3$ represent a cis- or trans-decalin group and k is 0,1, or R$^3$ represents 4-pyridyl, 3-pyrrolidyl or 3-indolyl which may or may not be substituted with a OR$^{31}$ group, where R$^{31}$ is as defined above and k is 0, 1, or R$^3$ represents Si(Me)$_3$ or CH(R$^{32}$)$_2$, wherein R$^{32}$ is a cyclohexyl- or phenyl group;

R$^4$ represents H, an alkyl group having 1 to carbon atoms, a cyclohexyl or a phenyl group, preferably H;

A$^2$, B and n are defined as described under Formula Ib above;

D represents Z or (Z)$_2$.

Preferred integers, groups or combinations and particularly preferred combinations are the same as described in Formula Ib above but R$^{11}$ is H, an alkyl group having 1 to 6 carbon atoms or a benzyl group.

Preferred compounds having Formula Vb are:
Boc-(R)Pro-Phe-Pab(Z)
BnOOC—CH$_2$—(R)Pro-Phe-Pab(Z)
Boc-(R)Phe-Phe-Pab(Z)
MeOOC—CO—(R)Phe-Phe-Pab(Z)
BnOOC—CH$_2$—(R)Phe-Phe-Pab(Z)

In a further embodiment the invention relates to novel use of a compound of the formula:

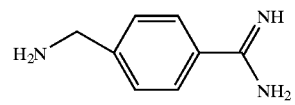

as a starting material in synthesis of a peptidic serine protease inhibitor, and in particular in synthesis of peptidic thrombin inhibitors or kininogenases inhibitors. It can be used as such or having the amidino group either mono- or diprotected at the nitrogens with a protective group such as benzyloxy carbonyl. Protection of the amidino derivatives is carried out by methods known in the art for amidino compounds. This compound is named "1-amidino-4-aminomethylbenzene" or "H-Pab" herein. The compound has been previously disclosed in inter alia Biochem. Pharm. vol 23, p. 2247–2256.

The structural fragment of the formula

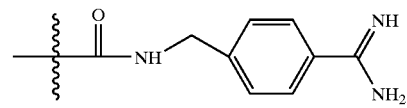

has however not been previously disclosed as a structural element in a pharmaceutically active compound, especially a peptic compound. The fragment renders a serine protease inhibitor, and in particular a thrombin inhibitor or kininogenases inhibitor valuable.

In a further embodiment the invention relates to novel use of a compound of the formula:

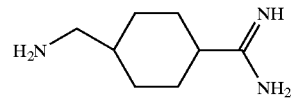

as a starting material in synthesis of a thrombin inhibitor. The compound may have the amidino group either mono- or diprotected at the nitrogens with a protective group such as benzyloxy carbonyl. Protection of the amidino derivatives is carried out by methods known in the art for amidino compounds. This compound is named "1-amidino-4-aminomethyl cyclohexane" or "H-Pac" herein.

The compound has been previously disclosed in DE 2748295.

The structural fragment of the formula

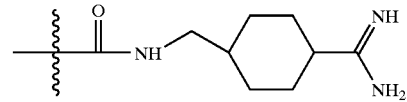

has however not been previously disclosed as a structural element in a thrombin inhibitor valuable.

In a further embodiment the invention relates to a novel compound of the formula:

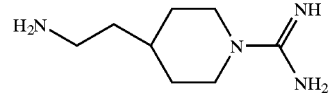

and the use of said compound as a starting material in synthesis of a serine protease inhibitor, especially a thrombin inhibitor or kininogenase inhibitor. The compound may have the amidino group either mono- or diprotected at the nitrogens with a protective group such as benzyloxy carbonyl. Protection of the amidino derivatives is carried out by methods known in the art for amidno compounds. This compound is named "4-aminoethyl-1-amidino piperidine" or "H—Rig" herein.

The structural fragment of the formula has however not been previously disclosed as a structural element in a pharmaceutically active compound, especially a peptic compound. The fragment renders a serine protease inhibitor, and in particular a thrombin inhibitor or kininogenases inhibitor varuable.

In a further embodiment the invention relates to a novel compound of the formula:

and the use of said compound as a starting material in synthesis of a serine protease inhibitor especially a thrombin inhibitor or kininogenase inhibitor. The compound may have the amidino group either mono- or diprotected at the nitrogens with a protective group such as benzyloxy carbonyl. Protection of the amidino derivatives is carried out by methods known in the art for amidino compounds. This compound is named "1,3-diaza-2-imino-4-aminoethyl cyclohexane" or "H-Itp" herein.

The structural fragment of the formula has however not been previously disclosed as a strucural element in a pharmaceutically active compound, especially a peptic compound. The fragment renders a serine protease inhibitor, and in particular a thrombin inhibitor or kiniogenases inhibitor varuable.

In a further embodiment the invention relates to novel compounds of the formula:

where n is 1 or 2
s is 0 ro 1,
and the use of said compounds as a starting material in synthesis of serine protease inhibitors, especially thrombin inhibitors or kininogenases inhibitors. The compound may have the amidino group either mono- or diprotected at the nitrogens with a protective group such as benzyloxy carbonyl. Protection of the amidino derivatives is carried out by methods known in the art for amidino compounds. These compounds are named:

1-amidino-3-aminomethylpyrrolidine or "H-Nig" when n is 1 and s is 1
1-amidino-3-aminoethyl pyrrolidine or "H-Hig" when n is 2 and s is 1
3-aminomethyl-1-amidino azetidine or "H-Mig" when n is 1 and s is 0
3-aminoethyl-1-amidino azetidine or "H-Dig" when n is 2 and s is 0

The structural fragment of the formula has however not been previously disclosed as a structural element in a pharmaceutically active compound, especially a peptic compound. The fragment renders a serine protease inhibitor, and in particular a thrombin inhibitor or kininogenases inhibitor valuable.

A further embodiment of the invention are the novel compounds having the amidino group mono- or di-protected at the nitrogens with a benzyloxy carbonyl group, examples of such compounds are 4-aminomethyl-1-(N-benzyloxycarbonylamidino)benzene (H-Pab(Z)),
4-aminomethyl-1-(N,N'-di(benzyloxycarbonyl)amidino) benzene (H-Pab(Z)$_2$),
4-aminomethyl-1-(N-benzyloxycarbonylamidino) cyclohexane (H-Pac(Z)),
4-aminomethyl-1-(N,N'-di(benzyloxycarbonyl)amidino) cyclohexane (H-Pac(Z)$_2$),
4-aminoethyl-1-(N-benzyloxy-carbonylamidino piperidine (H—Rig(Z)),
4-aminoethyl-1-N,N'-di(benzyloxycarbonyl)amidino piperidine (H—Rig(Z)$_2$),
(3RS)-1-(N-benzyloxycarbonylamidino)-3-aminomethyl pyrrolidine (H-Nig(Z)),
(3RS)-1-(N,N'-di(benzyloxycarbonyl)amidino)-3-aminomethylpyrrolidine (H-Nig(Z)$_2$),
(3RS)-1-(N-benzyloxycarbonylamidino)-3-aminoethyl pyrrolidine (H-Hig(Z)),
(3RS)-1-(N,N'-di(benzyloxycarbonyl)amidino)-3-aminoethyl pyrrolidine (H-Hig(Z)$_2$),
3-aminomethyl-1-(N-benzyloxycarbonylamidino) azetidine (H-Mig(Z)),
3-aminomethyl-1-(N,N'-di(benzyloxycarbonyl)amidino) azetidine (H-Mig(Z)$_2$),
3-aminoethyl-1-(N-benzyloxycarbonylamidino) azetidine (H-Dig(Z)),
3-aminoethyl-1-(N,N'-di(benzyloxycarbonyl)amidino) azetidine (H-Dig(Z)$_2$)

Said compounds are used as starting materials in the preparation of the claimed peptide derivatives of formulas I, Ia, Ib, V, Va and Vb.

Medical and Pharmaceutical Use

The invention also provides compositions and methods for the treatment, in a human or animal organism, of conditions where inhibition of thrombin is required and of physiologically disorders especially inflammatory diseases.

The thrombin inhibiting compounds of the invention are expected to be useful in particular in animals including man in treatment or prophylaxis of thrombosis and hypercoagulability in blood and tissues. They are furthermore expected to be useful in situations where there is an undesirable excess of the thrombin without signs of hypercoagulability, for example as in Alzheimers disease and pancreatitis. Disease states in which these compounds have a potential utility, in treatment and/or prophylaxis, include venous thrombosis and pulmonary embolism, arterial thrombosis, such as in myocardial infarction, unstable angina, thrombosis-based stroke and peripheral arterial thrombosis and systemic embolism usually from the atrium during arterial fibrillation or from the left ventricule after transmural myocardial infarction. Further, these compounds have expected utility in prophylaxis of atherosclerotic diseases such as coronary arterial disease, cerebral arterial disease and peripheral arterial disease. Further, these compounds are expected to have synergistic antithrombotic effects when combined with any antithrombotic agent with a different mechanism of action, such as the antiplatelet agent acetylsalicylic acid. Further, these compounds are expected to be useful together with thrombolytics in thrombotic diseases, in particular myocardial infarction. Further, these compounds have expected utility in prophylaxis for re-occlusion after thrombolysis, percutaneous trans-luminal angioplasty (PTCA) and coronary bypass operations. Further, these compounds have expected utility in prevention of re-thrombosis after microsurgery and vascular surgery in general. Further, these compounds have expected utility in treatment and prophylaxis of disseminated intravascular coagulation caused by bacteria, multiple trauma, intoxication or any other mechanism. Further, these compounds are expected to be useful in anticoagulant treatment when blood is in contact with foreign surfaces in the body such as vascular grafts, vasculars stemts, vascular catheters, mechanical and biological prosthetic or any other medical device. Further, these compounds have expected utility in anticoagulant treatment when blood is in contact with medical devices outside the body such as during cardiovascular surgery using or heart-lung machine or in haemodialysis.

A further expected utility of the anticoagulant compounds of the invention are in rinsing of catheters and mechanical devises used in patients in vivo, and as anticoagulants for preservation of blood, plasma and other blood products in vitro.

The antiinflammatory inhibiting compounds of the invention are expected to be useful in particular in animals including man in treatment or prophylaxis of inflammatory diseases such as asthma, rhinitis, pancreatitis, uticaria, inflammatory bowel diseases, and arthritis. An effective amount of kininogenase inhibiting compounds with or without a physiologically acceptable carrier or diluent can be used solely or in combination with other therapeutic agents.

The compounds inhibit the activity of kallikreins assessed with chromogenic substrates according to known procedures. The anti-inflammatory actions of the present compounds can for example be studied by their inhibition of allergen-induced exudative inflammatory processes in airway mucosa or gut mucosa.

Pharmaceutical Preparations

The compounds of the invention will normally be administered orally, rectally, dermally, nasally, tracheally, bronchially, parenterally or via inhalation route, in the form of pharmaceutical preparations comprising the active ingredient either as a free base or a pharmaceutical acceptable non-toxic organic or inorganic acid addition salt, e.g. the hydrochloride, hydrobromide, sulphate, hydrosulphate, nitrate, lactate, acetate, citrate, bensoate, succinate, tartrate, trifluoroacetate and the like in a pharmaceutically acceptable dosage form. Depending upon the disorder and patient to be treated and the route of administration, the compositions may be administered at varying doses.

The dosage form may be a solid, semisolid or liquid preparation prepared by per se known techniques. Usually the active substance will constitute between 0.1 and 99% by weight of the preparation, more specifically between 0.1 and 50% by weight for preparations intended for parenteral administration and between 0.2 and 75% by weight for preparations suitable for oral administration.

Suitable daily doses of the compounds of the invention in therapeutical treatment of humans are about 0.001–100 mg/kg body weight at peroral administration and 0.001–50 mg/kg body weight at parenteral administration.

Preparation

A further objective of the invention is the mode of preparation of the compounds. The compounds of Formula I and V may be prepared by processes comprise coupling of an N-terminally protected dipeptide or aminoacid, when a N-terminally amino acid is used a second aminoacid is added afterwards using standard methods to a compound

$H_2N-(CH_2)_n-X$ wherein n is an integer 0, 1, 2, 3 or 4, X is B or B-D where B is as defined in formula I and D is as defined in formula V as such or having the guanidino or amidino nitrogens either mono or diprotected with an amin protecting group such as a benzyloxy carbonyl-, tert-butyloxy carbonyl- or p-toluenesulphonyl-group or X is a group transferable into B followed by removal of the protectary group(s) or deprotection of the N-terminal nitrogen followed by alkylation of the N-terminal nitrogen and if desired deprotection by known methods and if desired forming a physiologically acceptable salt, and in those cases where the reaction results in a mixture of stereoisomers, these are optionally separated by standard chromatographic or re-crystallisation techniques, and if desired a single stereoisomer is isolated.

In more detail the compounds of Formula I or V may be prepared by either of the following methods:

Method Ia

Coupling of an N-terminally protected dipeptide, selected from $A^1$ and $A^2$ in Formulas I or V and prepared by standard peptide coupling, with a compound

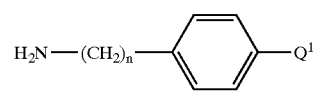

using standard peptide coupling, shown in the formula

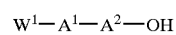

$W^1-A^1-A^2-OH$

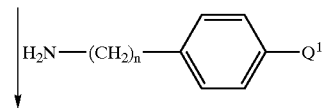

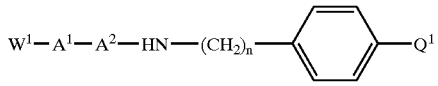

wherein n is as defined in Formula I $W^1$ is an N-teminal amino protecting group such as tert-butyloxy carbonyl and benzyloxy carbonyl and and $Q^1$ is —C(NH)—$NH_2$, —C($NW^2$)—NH—$W^2$, —C(NH)—NH—$W^2$, —NH—C(NH)—$NH_2$, —NH—C(NH)—NH—$W^2$, —N($W^2$)—C(NH)—NH—$W^2$ or —NH—C($NW^2$)—NH—$W^2$, where $W^2$ is an amine protecting group such as tert-butyloxy carbonyl or benzyloxy carbonyl, or $Q^1$ is —CN, —CO—$NH_2$ or —CS—$NH_2$, where the group is subsequently transferred into a amidino group (e.g giving $Q^1$=—C(NH)—$NH_2$) by methods known in the art or $Q^1$ is $NH_2$ or NH—$W^2$, where $W^2$ is as defined above, where the amino group is subsequently transferred into a guanidino group (giving $Q^1$=—NH—C(NH)—$NH_2$), after deprotection of the $W^2$-group when $Q^1$ is —NH—$W^2$ ($W^2$ in this case must be orthogonal to $W^1$), by methods known in the art.

The final compounds can be made in any of the following ways, depending on the nature of the $Q^1$-group used: Removal of the protecting group(s) (when $Q^1$=—C(NH)—$NH_2$, —C($NW^2$)—NH—$W^2$, —C(NH)—NH—$W^2$, —NH—C(NH)—$NH_2$, —NH—C(NH)—NH—$W^2$, —N($W^2$)—C(NH)—NH—$W^2$ or —NH—C($NW^2$)—NH—$W^2$), or a selective deprotection of the $W^1$-group (e.g when $Q^1$=—C($NW^2$)—NH—$W^2$, —C(NH)—NH—$W^2$, —NH—C(NH)—H—$W^2$, —N($W^2$)—C(NH)—NH—$W^2$ or —NH—C($NW^2$)—NH—$W^2$ ($W^2$ in this case must be orthogonal to $W^1$) followed by alkylation of the N-terminal nitrogen by methods known in the art and if desired deprotection by known methods.

Method Ib

Coupling of an N-terminally protected amino acid, selected from $A^2$ in Formulas I or V and prepared by standard methods, with a compound of formula

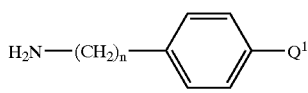

using standard peptide coupling, shown in the formula

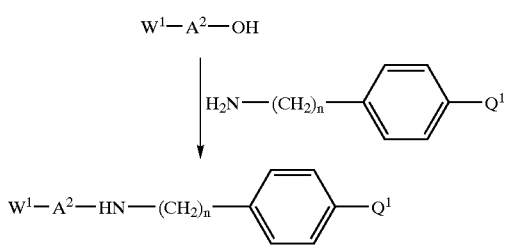

wherein n, $W^1$, and $Q^1$ are as defined above followed by deprotection of the $W^1$-group and coupling with the N-terminal amino acid, in a protected form, leading to the protected peptide described in Method Ia. The synthesis to the final peptides is then continued according to Method Ia.

Method IIa

Coupling of an N-terminally protected dipeptide, selected from $A^1$ and $A^2$ in Formulas I or V and prepared by standard peptide coupling, with a compound

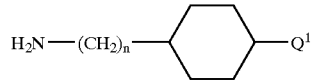

using standard peptide coupling, shown in the formula

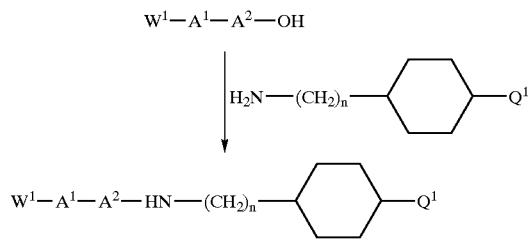

wherein n is as defined in Formula I, $W^1$ is an N-teminal amino protecting group such as tertbutyloxy carbonyl and benzyloxy carbonyl and and $Q^1$ is —C(NH)—$NH_2$, —C($NW^2$)—NH—$W^2$, —C(NH)—NH—$W^2$, —NH—C(NH)—$NH_2$, —NH—C(NH)—NH—$W^1$—N($W^2$)—C(NH)—NH—$W^2$ or —NH—C($W^2$)—NH—$W^2$ where $W^2$ is an amine protecting group such as tert-butyloxy carbonyl or benzyloxy carbonyl, or $Q^1$ is —CN, —CO—$NH_2$ or —CS—$NH_2$, where the group is subsequently transferred into a amidino group (e.g giving $Q^1$=—C(NH)—$NH_2$) by methods known in the art or $Q^1$ is $NH_2$ or NH—$W^2$, where $W^2$ is as defined above, where the amino group is subsequently transferred into a guanidino group (giving $Q^1$=—NH—C(NH)—$NH_2$), after deprotection of the $W^2$-group when $Q^1$ is —NH—$W^2$ ($W^2$ in this case must be orthogonal to $W^1$) by methods known in the art.

The final compounds can be made in any of the following ways, depending on the nature of the $Q^1$-group used: Removal of the protecting group(s) (when $Q^1$=—C(NH)—$NH_2$, —C($NW^2$)—NH—$W^2$, —C(NH)—NH—$W^2$, —NH—C(NH)—$NH_2$, —NH—C(NH)—NH—$W^2$, —N($W^2$)—C(NH)—NH—$W^2$ or —NH—C($NW^2$)—NH—$W^2$), or a selective deprotection of the $W^1$-group (e.g when $Q^1$=—C($NW^2$)—NH—$W^2$, —C(NH)—NH—$W^2$, —NH—C(NH)—NH—$W^2$, —N($W^2$)—C(NH)—NH—$W^2$ or —NH—C($NW^2$)—NH—$W^2$ ($W^2$ in this case must be orthogonal to $W^1$) followed by alkylation of the N-terminal nitrogen by methods known in the art and if desired deprotection by known methods.

Method IIb

Coupling of an N-terminally protected amino acid, =elected from $A^2$ in Formulas I or V and prepared by standard methods, with a compound of formula

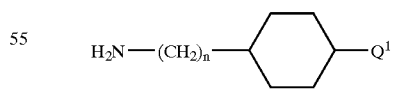

using standard peptide coupling, shown in the formula

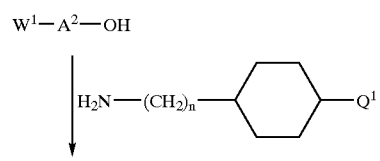

-continued

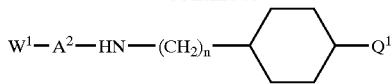

wherein n, $W^1$ and $Q^1$ are as defined above followed by deprotection of the $W^1$-group and coupling with the N-terminal amino acid, in a protected form, leading to the protected peptide described in Method IIa. The synthesis to the final peptides is then continued according to Method IIa.

Method IIIa

Coupling of an N-terminally protected dipeptide, selected from $A^1$ and $A^2$ in Formulas I or V and prepared by standard peptide coupling, with a compound

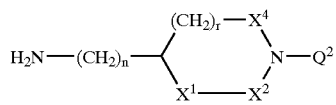

using standard peptide coupling, shown in the formula

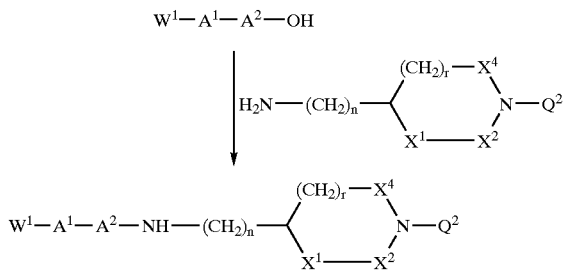

wherein n is as defined in Formula I and r is 0.1 when $X^1$, $X^2$ and $X^4$ are $CH_2$ or r is 0 when $X^2$ and $X^4$ are $CH_2$ and $X^1$ is absbent, $W^1$ is an N-teminal amino protecting group such as tert-butyloxy carbonyl and benzyloxy carbonyl and and $Q^2$ is —C(NH)—$NH_2$, —C($NW^2$)—NH—$W^2$, or —C(NH)—NH—$W^2$, where $W^2$ is an amine protecting group such as tert-butyloxy carbonyl or benzyloxy carbonyl, or $Q^2$ is equal to $W^2$ where the amino group, after deprotection of the $W^2$ group ($W^2$ in this case must be orthogonal to $W^1$), is subsequently transferred into a guanidino group using a unprotected, N-protected or N,N'-diprotected guanidation reagent by methods known in the art (giving $Q^2$=—C(NH)—$NH_2$, —C($NW^2$)—NH—$W^2$ or —C(NH)—NH—$W^2$).

The final compounds can be made in any of the following ways, depending on the nature of the $Q^2$-group used: Removal of the protecting group(s) (when $Q^2$=—C(NH)—$NH_2$, —C($NW^2$)—NH—$W^2$ or —C(NH)—NH—$W^2$), or a selective deprotection of the $W^1$-group (e.g when $Q^2$=—C($NW^2$)—NH—$W^2$, —C(NH)—NH—$W^2$, $W^2$ in this case must be orthogonal to $W^1$) followed by alkylation of the N-terminal nitrogen by methods known in the art and if desired deprotection known methods.

Method IIIb

Coupling of an N-terminally protected amino acid, selected from $A^2$ in Formulas I or V and prepared by standard methods, with a compound of formula

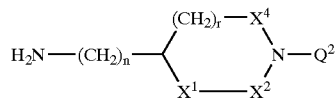

using standard peptide coupling, shown in the formula

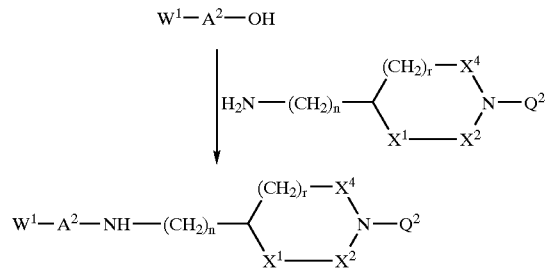

wherein n, r, $X^1$, $X^2$ and $X^4$ $W^1$, and $Q^2$ are as defined above followed by deprotection of the $W^1$-group and coupling with the N-terminal amino acid, in a protected form, leading to the protected peptide described in Method IIIa. The synthesis to the final peptides is then continued according to Method IIIa.

Method IVa

Coupling of an N-terminally protected dipeptide, selected from $A^1$ and $A^2$ in Formulas I or V and prepared by standard peptide coupling, with a compound

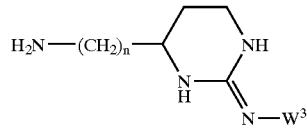

using standard peptide coupling, shown in the formula

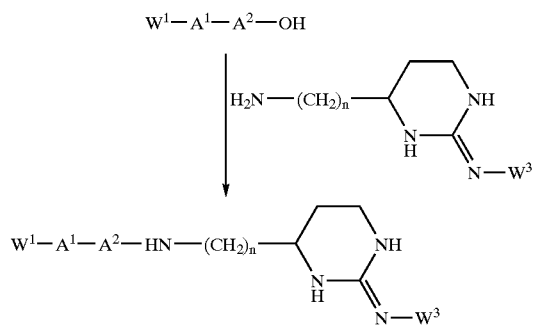

wherein n is as defined in Formula I, $W^1$ is an N-terminal amino protecting group such as tert-butyloxy carbonyl or benzyloxy carbonyl and $W^3$ is H or an amino protecting group such as aryl sulfonyl, benzyloxy carbonyl or tert-butyloxy carbonyl. The final compounds can be made in any of the following ways: Removal of the protecting group(s), or a selective deprotection of the $W^1$-group ($W^1$ must be orthogonal to $W^3$) followed by alkylation of the N-terminal nitrogen and if desired deprotection.

Method IVb

Coupling of an N-terminally protected amino acid, selected from $A^2$ in Formulas I or V and prepared by standard methods, with a compound of formula

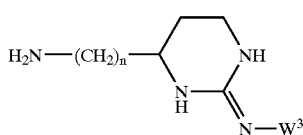

using standard peptide coupling, shown in the formula

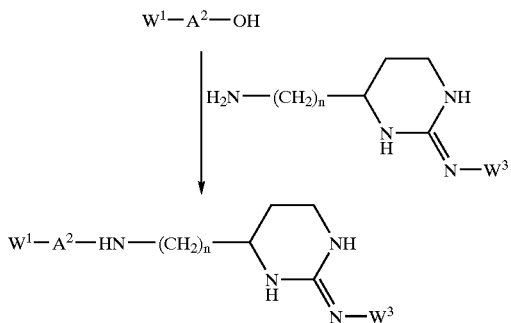

wherein n, $W^1$, and $W^3$ are as defined above followed by deprotection of the $W^1$-group ($W^1$ must be orthogonal to $W^3$) and coupoing with the N-terminal amino acid, in a protected form, leading to the protected peptide described in Method IVa. The synthesis to the final peptides is then continued according to Method IVa.

DETAILED DESCRIPTION OF THE INVENTION

The following description is illustrative of aspects of the invention.
Experimental Part
General experimental Procedures.

Mass spectra were recorded on a Finnigan MAT TSQ 700 triple quadropole mass spectrometer equipped with an electrospray interface.

The $^1$H NMR and $^{13}$C NMR measurements were performed on BRUKER AC-P 300 and BRUKER AM 500 spectrometers, the former operating at a $^1$H frequency of 500.14 MHz and a $^{13}$C frequency of 125.76 MHz and the latter at $^1$H and $^{13}$C frequency of 300.13 MHz and 75.46 MHz respectively.

The samples were about 10–50 mg dissolved in 0.6 ml of either of the following solvents; $CDCl_3$ (isotopic purity>99.8%), $CD_3OD$ (isotopic purity>99.95%), $D_2O$ (isotopic purity>99.98%) or $DMSO-d_6$ (isotopic purity>99.8%). All solvents where purchased from Dr. Glaser A G, Basel.

The $^1$H and $^{13}$C chemical shift values in $CDCl_3$ and $CD_3OD$ are relative to tetramethylsilane as an external standard. The $^1$H chemical shifts in $D_2O$ are relative to the sodium salt of 3-(trimethylsilyl)-$d_4$-propanoic acid and the $^{13}$C chemical shifts in $D_2O$ are referenced relative to 1,4-dioxane (67.3 ppm), both as external standard. Calibrating with an external standard may in some cases cause minor shift differences compared to an internal standard, however, the difference in $^1$H chemical shift is less than 0.02 ppm and in $^{13}$C less than 0.1 ppm.

The $^1$H NMR spectrum of peptide sequences containing a proline or a "proline like" residue frequently exhibits two sets of resonances. This corresponds to the existence of two contributing conformers with respect to the rotation around the amide bond, where proline is the N-part of the amide bond. The conformers are named cis and trans. In our compounds the sequences (R)Cha-Aze-, (R)Cha-Pro- and (R)Cha-Pic- often give rise to a cis-trans equilibrium with one conformer as the preponderant conformer (>90%). In those cases only the $^1$H chemical shifts of the major rotamer is reported. Only in the cases where the signals of the minor rotamer are clearly resolved they are reported in the NMR documentation. The same criterium is valid for the NH-signals in $CDCl_3$, only in the cases where the signals are clearly resolved they are reported in the NMR-documentation. This implies that the number of protons reported for some of the intermediates are less than the number of protons expected from the chemical formula.

Thin-Layer Chromatography was carried out on commercial Merck Silicagel $60F_{254}$ coated glass or aluminium plates. Visualisation was by a combination of UV-light, followed by spraying with a solution prepared by mixing 372 ml of EtOH(95%), 13.8 ml of concentrated $H_2SO_4$, 4.2 ml of concentrated acetic acid and 10.2 ml of p-methoxy benzaldehyde or phosphomolybdic acid reagent (5–10 w.t % in EtOH(95%)) and heating.

Flash chromatography was carried out on Merck Silica gel 60 (40–63 mm, 230–400 mesh) under pressure of air.

Reversed phase high-performance liquid chromatography (in the Examples referred to as RPLC) was performed on a Waters M-590 instrument equipped with three reverse phase Kromasil 100,C8 columns (Eka-Nobel) having different dimensions for analytical (4.6 mm×250 mm), semipreparative (1"×250 mm) and preparative (2"×500 mm) chromatography detecting at 226 nm.

Freeze-drying was done on a Leybold-Heraeus, model Lyovac GT 2, apparatus.
Preparation of Starting Materials
Boc-(R)Pgl-OH
Prepared in the same way as described for Boc-(R)Cha-OH (vide infra) from H—(R)Pgl-OH.
Boc-(R)Cha-OH To a solution of H—(R)Cha-OH, 21.55 g (125.8 mmol), in 130 ml 1 M NaOH and 65 ml THF was added 30 g (137.5 mmol) of $(Boc)_2O$ and the mixture was stirred for 4.5 h at room temperature. The THF was evaporated and an additional 150 ml of water was added. The alkaline aqueous phase was washed twice with EtOAc, then acidified with 2 M $KHSO_4$ and extracted with 3×150 ml of EtOAc. The combined organic phase was washed with water, brine and dried ($Na_2SO_4$). Evaporation of the solvent afforded 30.9 g (90.5%) of the title compound as a white solid.
Boc-(R)Hop-OH Prepared by the same procedure as described for Boc-(R) Cha-OH starting from H—(R)Hop-OH.

$^1$H-NMR (300 MHz, $CDCl_3$): δ 1.45 (s, 9H), 2.00 (m, 1H), 2.22 (m, 1H), 2.75 (bt, 2H), 4.36 (bs, 1H), 5.05 (bs, 1H), 7.15–7.33 (m, 5H).

4-(tert-butyloxycarbonylaminomethyl)pyridin

To a solution of 10.81 g (100 mmol) 4-aminomethyl pyridine in 100 ml THF was added 24 g (110 mmol) $Boc_2O$ dissolved in 70 ml THF at 10° C. for 20 minutes. The solution was allowed to reach room temperature and stirred for 4 h (a precipitate was formed during the reaction and the slurry became red). The solvent was removed and the residue was dissolved in EtOAc and filtered through silica gel. Evaporation of the solvent gave the title compound as a red oil which crystallized on standing. The crude product was used without further purification.

$^1$H-NMR (300 MHz, $CDCl_3$): δ 1.45 (s, 9H), 4.32 (d, 2H), 5.05 (bs, 1H(NH)), 7.2 (d, 2H), 8.55 (d, 2H).

4-aminomethyl-1-(N-benzyloxycarbonylamidino)-benzene (H-Pab(Z))

(i) 4-cyanobenzyl azide

A solution of 20.23 g (0.31 mol) sodium azide in 50 ml water was added to 49.15 g (251 mmol) 4-cyanobenzyl bromide in 200 ml DMF at ambient temperature. An exothermic reaction took place and after 1.5 h the reaction mixture was diluted with 200 ml toluene (caution: In order to avoid separation of potentially explosive azide compounds it is adviceable to add the toluene to the rection mixture before addition of the water) and 500 ml water. The aqueous phase was extracted with an additional 2×50 ml toluene. The combined organic extracts were washed with 2×50 ml water and brine and finally dried (MgSO$_4$) and filtered. The solution was used as such in the next step.

$^1$H-NMR (300 MHz, CDCl$_3$); δ 4.4 (s, 2H), 7.4 (d, 2H), 7.7 (d, 2H)

(ii) 4-amidino benzyl azide

Hydrogen chloride was bubbled into a mixture of 250 ml absolute ethanol and the solution from step (i) (approximatly 200 ml) above at −5° C. until saturation. Storage at 8° C. for 24 h and evaporation of most of the solvent followed by precipitation by addition of anhydrous ether gave white crystals which were isolated by filtration and dissolved in 1.8 l of alcoholic ammonia. After 48 h most of the solvent was removed and 200 ml 3.75 M NaOH solution was added whereupon 4-amidino benzyl azide precipitated as colourless crystals. The crystals were isolated by filtration. At this point the yield of 4-amidino benzyl azide was 22.5 g (total 51%).
Ethylimidatobenzyl azide hydrochloride:

$^1$H-NMR (500 MHz, CD$_3$OD); δ 1.6 (t, 3H), 4.5 (s, 2H), 4.65 (q, 2H), 4.8 (br s, 2H), 7.6 (d, 2H), 8.1 (d, 2H)
4-amidino benzyl azide:

$^1$H-NMR (500 MHz, CDCl$_3$); δ 4.3 (s, 2H), 5.7 (br s, 3H), 7.3 (d, 2H), 7.6 (d, 2H).

$^{13}$C-NMR (125 MHz, CDCl$_3$): amidine carbon: δ 165.5.

(iii) 4-(benzyloxycarbonylamidino)benzyl azide

The crystals from (ii) above were dissolved in 500 ml methylene chloride and the resulting solution was dried (K$_2$CO$_3$), filtered and 27 ml (194 mmol) triethyl amine was added. 25 ml Benzyl chloroformate was slowly added to the stirred solution while the reaction mixture was cooled in an ice bath. After 30 minutes an additional 2 ml benzyl chloroformate was added and stirring was continued for another 30 minutes. Subsequently, water was added and the aqueous phase was adjusted to pH 7 with 2M HCl. The organic phase was dried (MgSO$_4$) and the solvent was removed in vacuo. 4-(benzyloxycarbonylamidino)benzyl azide was finally isolated as colorless crystals from ether/methylene chloride/hexane.

$^1$H-NMR (500 MHz, CDCl$_3$); δ 4.4 (s, 2H), 5.3 (s, 2H), 6.3–7.0 (br s, 1H), 7.3–7.4 (m, 5H), 7.5 (d, 2H), 7.9 (d, 2H), 9.3–9.6 (br s, 1H).

$^{13}$C-NMR (125 MHz, CDCl$_3$): amidine carbon: δ 167.5.

(iv) 4-aminomethyl-1-(N-benzyloxycarbonylamidino)-benzene (H-Pab(Z))

26.3 g (100 mmol) triphenylphosphine was added at room temperature to the 4-(benzyloxycarbonylamidino)benzyl azide from (iii) above dissolved in 160 ml THF. After 16 h an additional 6.6 g (25 mmol) triphenylphosphine was added and the solution was allowed to stand for 4 h before removal of the solvent in vacuo. The residue was dissolved in methylene chloride and extracted with 2M HCl. The aqueous phase was washed with methylene chloride and ether and was subsequently made alcaline with 3.75M sodium hydroxide solution. Extraction with methylene chloride followed by drying (K$_2$CO$_3$) and removal of the solvent in vacuo gave 20 g (The total yield starting from cyanobenzyl bromide is 28%) of a yellow oil which solidified on standing.

$^1$H-NMR (500 MHz, CDCl$_3$); δ 1.2–2.2 (br s, 2H), 3.8 (s, 2H), 5.2 (s, 2H), 7.2–7.35 (m, 5H), 7.4 (d, 2H), 7.8 (d, 2H), 9.1–9.6 (br s, 1H).

$^{13}$C-NMR (125 MHz, CDCl$_3$): amidine and carbonyl carbons: δ 164.6 and 168.17.

H-Pig(Z)$_2$ (i) 4-(tert-butyloxycarbonyl-aminomethyl)piperidine

To a solution of 17.7 g 4-tert-butyloxycarbonylaminomethyl pyridine in 125 ml MeOH was added 2 g of 5% Rh/Al$_2$O$_3$ and the mixture was hydrogenated at 0.34 MPa over night. $^1$H-NMR showed that the hydrogenation was incomplete. Therefore, the catalyst was filtered off and the solvent removed in vaccuo and the residue was dissolved in 100 ml acetic acid, 2 g of 5% Rh/Al$_2$O$_3$ was added and the mixture was hydrogenated for 4 days at 0.34 MPa. The catalyst was filtered off and most of the acetic acid was removed in vaccuo. After addition of 50 ml water to the residue the mixture was made alkaline with 5 M NaOH and the water phase was extracted with 1×200+1×100 ml CH$_2$Cl$_2$. The combined organic phase was washed with 25 ml water and dried (MgSO$_4$). Evaporation of the solvent gave a 17.2 g of a brownish oil which was dissolved in 50 ml of diethyl ether. Addition of 200 ml pentane gave a precipitate which was filtered off to give 7.7 g of a brown powder. Evaporation of the mother liqour gave 7 g of a white oil. The brown powder was dissolved in 100 ml EtOAc and the organic phase was washed with 1×50 ml+1×25 ml 1 M KHSO$_4$ The combined acidic phase was made alkaline with 2 M NaOH and extracted with 1×200+1×75 ml EtOAc. The combined organic phase was dried and evaporated to give 5.2 g of the title compound as a white powder.

Treatment of the white oil obtained from the mother liqour above in the same way afforded an additional 3.4 g of the product. Total yield 40%.

$^1$H-NMR (500 MHz, CDCL$_3$, mixture of two rotamers, 3:1): major rotamer: δ 1.11 (dq, 2H), 1.44 (s, 9H), 1.49–1.60 (m, 1H), 1.63–1.70 (m, 2H), 2.58 (dt, 2H), 2.93–3.03 (m, 2H), 3.07 (m, 2H), 4.75 (bs, 1H(NH)).

Resolved signals arising from the minor rotamer appear at δ 1.21 (dq) and 1.91 (dt).

(ii) Boc-Pig(Z)$_2$

To a solution of 2 g (9.33 mmol) 4-(tert-butyloxycarbonyl-aminomethyl) piperidine in 60 ml CH$_3$CN was added 3.34 g (9.33 mmol) of N,N'-(dibenzyloxy-carbonyl)methylisothiourea and the mixture was stirred at 60° C. for 22 h. The solvent was evaporated and the residue was dissolved in EtOAc. The organic phase was washed with 2×20 ml 1 M KHSO$_{41}$ 1×20 ml water, 1×20 ml brine and dried (MgSO$_4$). Evaporation of the solvent followed by flash chromatography using pethroleum ether/EtOAc (1/1) as eluent afforded 2.43 g (50%) of the desired product.

$^1$H-NMR (500 MHz, CDCl$_3$): Some signals, especially in the piperidine ring, are selectively broadend due to an intramolecular exchange process. This is especially pronounced for the 2- and 6-CH$_2$ groups of the piperidine ring, which exhibit a broad peak ranging from 3.7 to 4.5 ppm.

δ 1.19–1.31 (m, 2H), 1.43 (s, 9H), 1.63–1.80 (m, 3H), 2.66–3.05 (m, 4H), 3.7–4.5 (bs, 2H), 4.65 (bt, 1H(NH)), 5.13 (s, 4H), 7.2–7.4 (m, 10H), 10.5 (bs, 1H(NH)).

(iii) H-Pig(Z)$_2$

A solution of 163 mg (0.31 mmol) Boc-Pig(Z)$_2$ in 5 ml EtOAc saturated with HCl(g) was stirred at ambient temperatur for 3 h and 20 minutes. The solvent was evaporated and the residue was dissolved in 30 ml CH$_2$Cl$_2$. The organic phase was washed with 5 ml 2 M NaOH, 1×5 ml water, 1×5 ml brine and dried (MgSO$_4$). Evaporation of the solvent afforded 100 mg (76%) of the title compound.

$^1$H-NMR (500 MHz, CDCl$_3$): Some signals, especially in the piperidin ring, are selectively broadend due to an intramolecular exchange process. This is especially pronounced for the 2- and 6-CH$_2$ groups of the piperidine ring, which exhibit a broad peak ranging from 3.7 to 4.5 ppm.

δ 1.18–1.37 (m, 2H), 1.46–1.63 (m, 1H), 1.68–1.83 (m, 2H), 2.57 (d, 2H), 2.86–3.03 (m, 2H), 3.7–4.5 (bs, 2H), 5.13 (s, 4H), 7.2–7.4 (m, 10H).

4-aminomethyl-1-(N-benzyloxy carbonylamidino)-cyclohexane (H-Pac(Z)×2HCl)

(i) N-[N-4-(benzyloxycarbonyl)amidino benzyl]tert-butyl carbamate 1.466 g (6.7 mmol) (Boc)$_2$O was added to a stirred ice cold solution of 1.81 g (6.4 mmol) 4-(benzyloxycarbonyl)amidino benzyl amine and 1 ml (7.1 mmol) triethyl amine in 25 ml methylene chloride. After 20 minutes more methylene chloride was added and the mixture was washed with 5% acetic acid and 10% sodium carbonate solution. Drying (magnesium sulphate) and removal of the solvent in vauo left a residue which could be crystallised from methylene chloride/hexane. The yield was 1.66 g (68%).

(ii) N-[N-4-amidino benzyl]tert-butyl carbamate

A mixture of 1.60 g (4.2 mmol) N-[4-(benzyloxycarbonyl)amidino benzyl]tert-butyl carbamate, 5 ml acetic acid, and 160 mg 10% palladium on charcoal in 50 ml ethanol was sirred in an atmosphere of hydrogen for 2 h. The catalyst was removed by filtration through celite and the solvent was removed in vacuo to give the acetate of the title compound in quantitative yield.

(iii) N-[4-amidino cyclohexyl methyl]tert-butyl carbamate 17 mmol of the acetate of N-[4-amidino benzyl]tert-butyl carbamate was hydrogenated in 100 ml metanol in the presence of 863 mg 5% rhodium on alumina at 3.4 MPa for 20 h. The catalyst was removed by filtration and the solvent was removed in vacuo. The residue was dissolved in water and the solution was made basic with sodium hydroxide. Subsequent extraction with methylene chloride, drying of the combined organic phases (potassium carbonate) and removal of the solvent in vacuo gave 3.8 g (87%) of the title compound.

(iv) N-[N-4-(benzyloxycarbonyl)amidino cyclohexyl methyl]tert-butyl carbamate 1.25 ml (8.8 mmol)benzyl chloroformate was added at 0° C. to a stirred solution of 2.04 g (8 mmol) N-[4-amidino cyclohexyl]tert-butyl carbamate, 1.23 ml (8.8 mmol) triethyl amine, and 197 mg DMAP in 40 ml methylene chloride. After 10 minutes the reaction mixture was diluted with methylene chloride and extracted with water, dilute acetic acid, and sodium hydrogen carbonate solution. The organic phase was applied on a column of silica and subsequent elution with methylene chloride containing increasing amounts of ethyl acetate yielded 2.49 g (80%) of the title compound.

(v) 4-aminomethyl-1-(N-benzyloxy carbonylamidino)-cyclohexane (H-Pac(Z)×2HCl)

Hydrogen chloride was passed through a solution of 2 g (5.1 mmol) N-[4-(benzyloxycarbonyl)amidino cyclohexyl methyl]tert-butyl carbamate in 40 ml ethyl acetate. After 10 minutes methanol was added and upon removal of some of the solvent in vacuo the dihydrochloride of title compound crystallised.

4-aminomethyl-1-(N-benzyloxy carbonylamidino) piperidine (H-Pig(Z)×HCl)

(i) 4-(N-tert-butyloxycarbonylaminomethyl)-1-(N-benzyloxycarbon ylamidino)piperidine (Boc-Pig(Z))

7.8 g (36.4 mmole) of 4-(N-tert-butyloxycarbonylaminomethyl) piperidine and 8.98 g (40 mmole) of N-benzyloxycarbonyl-S-methylisothiourea was mixed in 25 mL ethanol. The mixture was heated at 60–70° C. for six hours and left at roomtemperature for two days. The solvent was evaporated and the residue was dissolved in CH$_2$Cl$_2$. The organic layer was washed twice with 0.3 M KHSO$_4$ and once with brine. The combined organic layer was dried (Na$_2$SO$_4$), filtered and evaporated. The crude product was purified by flash chromatography using a stepwise gradient of CH$_2$Cl$_2$/MeOH (100/0, 97/3, 95/5, 90/10) as eluent to yield 5.22 g (37%) of the title product.

(ii) H-Pig(Z)×HCl (4-aminomethyl-1-(N-benzyloxy carbonylamidino)piperidine 5.22 g (13.5 mmole) of Boc-Pig(Z) was dissolved in 100 mL ethyl acetate saturated with HCl(g). The mixture was allowed to stand for one hour and then evaporated. The residue was dissolved in water and washed with a mixture of diethylether and ethyl acetate. The water layer was freeze-dried to yield 4.0 g (91%) of the title compound.

$^1$H-NMR (D$_2$O, 300 MHz): δ 1.40–1.60 (m, 2H), 2.05 (bd, 2H), 2.19 (m, 1H), 3.07 (d, 2H), 3.34 (bt, 2H), 4.08 (bd, 2H), 5.40 (s, 2H), 7.5–7.63 (m, 5H)

MS m/z 291 (M$^+$+1)

4-Aminoethyl-1-benzyloxycarbonylamidino piperidine (H—Rig(Z))

(i) 1-Benzyloxycarbonylamidino-4-hydroxyethyl piperidine

A mixture of 6.2 g (0.028 mol) of 4-hydroxyethyl piperidine and 3.6 g (0.028 mol) of N-benzyloxycarbonyl-S-methyl isothiourea in 50 ml of acetonitrile was refluxed overnight. Evaporation and flash chromatography on silica gel with ethyl acetate gave 3.5 g (41%) of the title compound.

$^1$H-NMR (300 MHz, CDCl$_3$): δ 1.1–1.85 (m, 7H), 2.83 (bt, 2H), 4.70 (bt, 2H), 4.18 (bd, 2H), 5.12 (s, 2H), 6.9–7.2 (m, 2H), 7.2–7.5 (m, 5H).

(ii) 1-Benzyloxycarbonylamidino-4-mesyloxyethyl piperidine

To an ice cooled solution of 3.50 g (0.0115 mol) of 1-benzyloxy-carbonylamidino-4-hydroxyethyl piperidine, 1.15 g (0.0115 mol) of triethyl amine in 40 ml of methylene chloride and 10 ml of tetrahydrofurane was added dropwise 1.30 g (0.115 mol) of mesyl chloride.

The reaction mixture was allowed to stir for 1 h. The mixture was poured into water and the organic layer was kept. The aqueous layer was extracted with methylene chloride and the combined organic layers were washed with water, dried (Na$_2$SO$_4$) and evaporated. The product was used without further purification in the next step. Yield: 4.4 q (100%).

$^1$H NMR (500 MHz, CDCl$_3$) d 1.15–1.3 (m, 2H), 1.65–1.8 (m, 5H), 2.84 (bt, 2H), 3.01 (s, 3H), 4.20 (bd, 2H), 4.27 (t, 2H), 5.12 (s, 2H), 7.1–7.5 (m, 7H).

(iii) 4-Azidoethyl-1-benzyloxycarbonylamidino piperidine

In 100 ml of dimethylformamide was dissolved 4.4 g (0.0115 mol) of crude 1-benzyloxycarbonylamidino-4-mesyloxyethyl piperidine and 4.5 g (0.069 Mol) of sodium azide was added. The mixture was heated at 100° C. for 2.5 h. It was then poured into water and extracted with ethyl acetate three times. The combined organic phase was washed with water, dried (Na$_2$SO$_4$) and evaporated. The residue was flash chromatographed on silica gel using ethyl acetate/heptane 1/1 as eluent. Yield: 3.0 g (79%).

$^1$H-NMR (500 MHz, CDCl$_3$) δ 1.20 (dq, 2H), 1.5–1.8 (m, 5H), 2.85 (dt, 2H), 3.35 (t, 2H), 4.22 (bd, 2H), 5.13 (s, 2H), 6.9–7.2 (b, 2H), 7.2–7.45 (m, 5H).

(iv) 4-Aminoethyl-1-benzyloxycarbonylamidino piperidine (H—Rig(Z))

To 30 ml of water was added 0.40 g of 10% Pd/C. Sodium borohydride, 1.0 g (0.031 mol), was dissolved in 30 ml of water and was added carefully to the stirred and ice-cooled slurry of Pd/C and water. 4-Azidoethyl-1-benzyloxycarbonylamidino piperidine, 2.9 g (8.8 mmol), was dissolved in 80 ml of tetrahydrofurane and this solution was added dropwise to the ice-cooled aqueous slurry above. After 4 h of stirring at room temperature the mixture was ice-cooled again and 30 ml of 2 M HCl was added. The mixture was filtered through celite and the celite was rinsed with additional water. The tetrahydrofuran was evaporated and the aqueous phase was washed with ethyl acetate. The aqueous phase was made alkaline with 2 M NaOH and extracted with methylene chloride three times. The combined organic phase was washed with water, dried (Na$_2$SO$_4$) and evaporated. The product was used in the following step without further purification.

$^1$H-NMR (500 MHz, CDCl$_3$) δ 1.1–1.5 (m, 6H), 1.55–1.65 (m, 1H), 1.73 (bd, 2H), 2.72 (b, 2H), 2.81 (dt, 2H), 4.20 (bd, 2H), 5.12 (s, 2H), 6.9–7.2 (b, 2H), 7.2–7.5 (m, 5H).

(3RS)-1-(N-benzyloxycarbonylamidino)-3-aminomethyl pyrrolidine(H—(R,S)Nig(z))

(i) (3RS)-3-hydroxymethylpyrrolidine 16.4 g (0.0857 mole) (3RS)-1-benzyl-3-hydroxymethyl pyrrolidine (See H—(R,S)Hig(Z) (i) vide supra) was mixed with 1.6 g Pd/C (10%), 5 ml water and 150 ml ethanol and the mixture was hydrogenated at 0.26 MPa over night. After filtration through hyflo and evaporation of the solvent the $^1$H-NMR showed that the reaction was not completed. Continued hydrogenation at 0.26 MPa over 1.6 g Pd/C (10%) in 5 ml water/150 ml ethanol for three days completed the reduction. Filtration through hyflo and evaporation of the solvent gave the product in a quantitative yield.

(ii) (3RS)-1-(N-benzyloxycarbonylamidino)-3-hydroxymethylpyrrolidine 1.01 g (0.01 mole) (3RS)-3-hydroxymethylpyrrolidine and 2.29 g (0.011 mole) N-benzyloxycarbonyl-O-methylisourea was dissolved (the amine not very soluble) in toluene and heated to 60° C. for three hours followed by stirring at room temperature over night. The mixture was evaporated and the $^1$H-NMR showed that the reaction was not completed. The mixture was therefore dissolved in 15 ml acetonitrile and heated to 60° C. for three hours followed by stirring at room temperature over night. The solvebt was evaporated and the mixture was dissolved in CH$_2$Cl$_2$, washed once with water, dried (Na$_2$SO$_4$), filtered and evaporated. The crude product was purified by flash chromatography using CH$_2$Cl$_2$/MeOH 95/5 as eluent to yield 0.70 g (25%) of the product.

MS m/z 278 (M$^+$+1)

(iii) (3RS)-1-(N-benzyloxycarbonylamidino)-3-mesyloxymethyl pyrrolidine 0.7 g (2.53 mmole) (3RS)-1-(N-benzyloxycarbonylamidino)-3-hydroxymethylpyrrolidine and 0.70 ml (5.05 mmole) triethylamine was dissolved in 15 ml diethyl ether/CH$_2$Cl$_2$ 1/1 and the mixture was cooled to 0° C. 0.25 ml (3.29 mole) methanesulphonyl chloride in 3 ml diethyl ether was slowly added and the reaction mixture was stirred at 0° C. for three hours. The solvent was evaporated and the residue was dissolved in ethyl acetate and extracted with a 0.3 M KHSO$_4$-solution. The water layer was washed once with CH$_2$Cl$_2$ The water layer was made neutral with 10M NaOH-solution and extracted twice with CH$_2$Cl$_2$. The combined organic layer was dried (Na$_2$SO$_4$), filtered and evaporated to yield 0.450 g (50%) of the title compound.

(iv) (3RS)-1-(N-benzyloxycarbonylamidino)-3-azidomethyl pyrrolidine 0.450 g (1.27 mmole) (3RS)-1-(N-benzyloxycarbonylamidino)-3-mesyloxymethyl pyrrolidine and 0.124 g (1.9 mmole) of sodium azide were dissolved in 10 ml dimethylformamide and heated to 60° C. for four hours followed by stirring at room temperature over night. Water was added and the mixture was extracted twice with toluene/ethyl acetate 2/1. The combined organic layer was dried (Na$_2$SO$_4$), filtered and evaporated. The crude product was purified by flash chromatography using CH$_2$Cl$_2$/MeOH 95/5 as eluent to yield 0.262 g (68%) of the product.

MS m/z 303 (M$^+$+1)

(v) (3RS)-1-(N-benzyloxycarbonylamidino)-3-aminomethyl pyrrolidine (H—(R,S)Nig(Z))

32 mg Pd/C (10%) and 2.6 ml H$_2$O was mixed and a gentle stream of nitrogen was passed. 98 mg NaBH$_4$ in 2.6 ml H$_2$O was added folowed by a slow addition of 262 mg (0.87 mmole) (3RS)-1-(N-benzyloxycarbonylamidino)-3-mesyloxymethyl pyrrolidine dissolved in 7 ml MeOH. The mixture was allowed to stand for one hour. 5 ml 1M HCl was added and the mixture was filtered through hyflo. The organic solvent was evaporated under reduced pressurea and the remaining water layer was washed once with ethyl acetate, made alkaline with NaOH-solution and extracted several times with CH$_2$Cl$_2$. The combined organic layer was dried (Na$_2$SO$_4$), filtered and evaporated to yield 130 mg (54%) of the product.

MS M/z 277 (M$^+$+1)

(3RS)-1-(N-benzyloxycarbonylamidino)-3-aminoethyl pyrrolidine (H—(R,S)Hig(z))

(i) (3RS)-1-benzyl-3-hydroxymethylpyrrolidine 25.2 g (0.1063 mole) (3RS)-1-bensyl-2-oxo-4-methoxycarbonyl pyrrolidine was slowly added to a slurry of 6.22 g lithium aluminium hydride in 160 ml diethyl ether under an argon-atmosphere. The mixture was stirred over night and then heated to reflux for one hour. The reaction mixture was cooled to room temperature and 0.2 g of $Na_2SO_4 \times 10H_2O$ was added followed by a slow addition of, in that order, 6 ml water, 18 ml 3.75 M NaOH-solution and 6 ml water. The slurry was dried from excess of water with $Na_2SO_4$/cellite, filtered and evaporated to give (20.3 g) of the product.

$^1$H-NMR (CDCl$_3$, 300 MHz): δ 1.64–1.77 (m, 1H), 1.93–2.07 (m, 1H), 2.27–2.40 (m, 2H), 2.51 (dd, 1H), 2.62 (dd, 1H), 2.82 (m, 1H), 3.52 (dd, 1H), 3.59 (s, 2H), 3.67 (dd, 1H), 7.15–7.40 (m, 5H)

(ii) (3RS)-1-benzyl-3-chloromethyl pyrrolidine

To a refluxing solution of 15.3 g (0.08 mole) (3RS)-1-benzyl-3-hydroxymethylpyrrolidine in 220 ml CHCl$_3$ was slowly added a solution of 330 ml thionyl chloride in 60 ml CHCl$_3$, and the reflux was continued for one hour. The mixture was evaporated and the residue was dissolved in water.

The water layer was washed with ethyl acetate and then made alkaline with 0.2 M NaOH-solution. The water layer was extracted three times with ethyl acetate and the combined organic layer was dried (Na$_2$SO$_4$), filtered and evaporated to give the product in a quantitative yield (16.8 g).

$^1$H-NMR (CDCl$_3$, 300 MHz): δ 1.55 (m, 1H), 2.05 (m, 1H), 2.38 (dd, 1H), 2.48–2.64 (m, 3H; thereof 2.58 (t, 2H))), 2.73 (dd, 1H), 3.51 (d, 2H), 3.60 (s, 2H), 7.2–7.4 (m, 5H)

(iii) (3RS)-1-benzyl-3-cyanomethyl pyrrolidine 16.8 q (0.08 mole) (3RS)-1-benzyl-3-chloromethyl pyrrolidine and 5.88 g (0.12 mole) of sodium cyanide was dissolved in 250 ml dimethyl sulfoxide. The mixture was stirred at 60° C. for two days and at room temperature for one week. Water was added and the mixture was extracted three times with ethyl acetate. The combined organic layer was washed with brine, dried (Na$_2$SO$_4$), filtered and evaporated to yield 14.7 g (92%) of the product.

$^1$H-NMR (CDCl$_3$, 500 MHz): δ 1.55 (m, 1H), 2.13 (m, 1H), 2.35 (dd, 1H), 2.42 (t, 2H), 2.44–2.59 (m, 2H), 2.65 (m, 1H), 2.73 (dd, 1H), 3.61 (s, 2H), 7.2–7.4 (m, 5H)

(iv) (3RS)-1-benzyl-3-aminoethyl pyrrolidine 14.7 g (0.0734 mole) (3RS)-1-benzyl-3-cyanomethyl pyrrolidine dissolved in 220 ml diethyl ether was slowly added to a slurry of 2.94 g of lithium aluminium hydride in 74 ml diethyl ether under an argon atmosphere. The mixture was stirred over night, and 6 ml water, 18 ml 3.75 M NaOH-solution and 6 ml water was added to the mixture. The slurry was dried from excess of water with Na$_2$SO$_4$/cellite, filtered by suction and evaporated to yield 14.84 g (99%) of the product.

$^1$H-NMR (CDCl$_3$, 300 MHz): δ 1.41 (m, 1H), 1.51 (q, 2H), 1.90–2.10 (m, 2H; thereof 2.05 (dd, 1H))), 2.18 (m, 1H), 2.43 (m, 1H), 2.55–2.73 (m, 3H), 2.80 (apparent t, 1H), 3.58 (apparent d, 2H), 7.15–7.4 (m, 5H)

(v) (3RS)-1-benzyl-3-(N-tert-butyloxycarbonylaminoethyl) pyrrolidine

To a mixture of 14.84 g (0.0726 mole) (3RS)-1-benzyl-3-aminoethyl pyrrolidine, 72.6 ml 1M NaOH-solution, 76 ml water and 145 ml THF was added 17.44 g (0.08 mole) di-tert-butyl dicarbonate and the mixture was stirred over night. The solution was concentrated and extracted three times with ethyl acetate. The combined organic layer was washed with brine, dried (Na$_2$SO$_4$), filtered and evaporated. The crude product was purified by flash chromatography using a stepwise gradient of CH$_2$Cl$_2$/MeOH (95/5, 90/10) as eluent to yield 14.69 g (80%) of the product.

$^1$H-NMR (CDCl$_3$, 300 MHz): δ 1.25–1.65 (m, 12H; thereof 1.40 (s, 9H)), 1.90–2.25 (m, 3H), 2.46 (m, 1H), 2.67 (m, 1H), 2.80 (apparent t, 1H), 3.09 (m, 2H), 3.59 (s, 2H), 4.60 (bs, NH), 7.15–7.35 (m, 5H)

(vi) (3RS)-3-(N-tert-butyloxycarbonylaminoethyl) pyrrolidine 3.1 q (0.01 mol) (3RS)-1-benzyl-3-(N-tert-butyloxycarbonylaminoethyl) pyrrolidine was hydrogenated at 0.28 MPa over 0.6 g of Pearlman's catalyst (Pd(OH)$_2$) in 40 ml ethanol (95%) over night. After filtration of the catalyst through cellite and evaporation of the solvent $^1$H-NMR showed that the reaction was not completed. Therefore 0.6 g of Pearlman's catalyst was added in 40 ml ethanol (95%) once more and the mixture was treated under H$_2$-atmosphere at 0.28 MPa over night. Filtration through cellite and evaporation of the solvent gave the product in a quantitative yield (2.18 g).

MS m/z 214 (M+)

(vii) (3RS)-1-(N-benzyloxycarbonylamidino)-3-aminoethyl pyrrolidine (H—(R,S)Hig(Z))

2.18 g (0.0102 mmole) (3RS)-3-(N-tert-butyloxycarbonylaminoethyl) pyrrolidine and 2.81 g (0.0125 mole) N-benzyloxycarbonyl-S-methylisothiourea was dissolved in 30 ml toluene and heated to 60–70° C. for eight hours followed by stirring at room temperature for one day. 0.3 M KHSO$_4$-solution was added and the water layer was washed with a mixture of the toluene and ethyl acetate and left for 2 days under which time the Boc group was removed. The acidic water phase was made alkaline and extracted four times with CH$_2$Cl$_2$ The combined organic layer was dried (Na$_2$SO$_4$), filtered and evaporated to yield 2.0 g (51%) of the title compound.

$^1$H-NMR (CDCl$_3$,330 K, 300 MHz): δ 1.45–1.7 (m, 3H), 2.07 (m, 1H), 2.26 (m, 1H), 2.74 (t, 2H), 3.00 (apparent t, 1H), 3.33 (apparent q, 1H), 3.45–3.80 (m, 2H), 5.12 (s, 2H), 6.72 (bs, 2 NH), 7.15–7.45 (m, 5H)

(4RS)-1,3-diaza-2-tosylimino-4-aminoethyl cyclohexane (H—(R,S)Itp (Ts))

(i) (4RS)-1,3-diaza-2-tosylimino-4-carboxy cyclohexane

Prepared using the same method as described in Journal of Org. Chem., p. 46, 1971.

(ii) (4RS)-1,3-diaza-2-tosylimino-4-hydroxymethyl cyclohexane 12.9 g (345 mmol) LiAlH$_4$ was carefully added to a cold slurry (ice bath temperature) of 9.9 g (33 mmol) of (4RS)-1,3-diaza-2-tosylimino-4-carboxy cyclohexane in 330 mL dry THF. The reaction was stirred at room temperature over night. The reaction mixture was worked up according to Fieser & Fieser, e.g by adding 12.9 g water, 38.7 g 3.75 M NaOH, 12.9 g water, Na$_2$SO$_4$, CH$_2$Cl$_2$ and celite to the mixture, and filtered. Evaporation of the solvent gave 7.0 g (75%) of the desired product.

MS m/z 284 (M$^+$+1)

(iii) (4RS)-1,3-diaza-2-tosylimino-4-mesyloxymethyl cyclohexane 2.9 mL MsCl (37.1 mmol) was added carefully to a cold (ice bath temperature) slurry of 7.0 g (24.7 mmol) of (4RS)-1,3-diaza-2-tosylimino-4-hydroxymethyl cyclohexane in 6.9 mL (49.4 mmol) triethylamine and 125 mL $CH_2Cl_2$. Water was added after 1 h 15 min and the organic phase was separated, dried ($Na_2SO_4$), filtered and evaporated to give the title compound in quantitative yield.

MS m/z 362 ($M^+$+1))

(iv) (4RS)-1,3-diaza-2-tosylimino-4-cyanomethyl cyclohexane 8.9 g (24.7 mmol) of (4RS)-1,3-diaza-2-tosylimino-4-mesyloxymethyl cyclohexane and 1.3 g (27.2 mmol) NaCN was dissolved in 75 mL DMSO. After stirring at 40° C. for 60 hours an additional amount of 0.31 g (6 mmol) NaCN was added and the solution was stirred at 65° C. for three hours. 150 mL water was added and crystals precipitated out of the solution. They where filtered off and dried to give 5.4 g (75%) of the desired product.

MS m/Z 293 ($M^+$+1)

(4RS)-1,3-diaza-2-tosylimino-4-aminoethyl cyclohexane (H—(R,S)Itp(Ts))

935 mg $LiAlH_4$ was added carefully to a cooled (ice bath temperature) slurry of 2.4 g (8.2 mmol) of (4RS)-1,3-diaza-2-tosylimino-4-cyanomethyl cyclohexane in 90 mL THF. After stirring for 2 hours 1 g $H_2O$, 3 g 3.75M NaOH, 1 g $H_2O$, $Na_2SO_4$, celite and $CH_2Cl_2$ was added. The mixture was filtered and the solvent removed in vacuo to give 2.2 g (90%) of the desired product.

$^1H$ NMR (500 MHz, MeOD); δ 1.52–1.71 (m, 3H), 1.88–1.96 (m, 1H), 2.37 (s, 3H), 2.64–2.73 (m, 2H), 3.2–3.4 (m, 2H, partially overlapping with the solventsignal), 3.44–3.53 (m, 1H), 7.28 (d, 2H), 7.71 (d, 2H)

(4S)-1,3-diaza-2-tosylimino-4-aminoethyl cyclohexane (H—(S)Itp(Ts))

Prepared in the same way as described for H—(R,S)Itp (Ts) starting from optically pure 2,4-diaminobutyric acid.

$^1H$ NMR (300.13 MHz, $CDCl_3$); δ 0.97–1.15 (s broad, 1H), 1.48–1.69 (m, 3H), 1.84–1.95 (m, 1H), 2.37 (s, 3H), 2.68–2.82 (m, 1H), 2.86–2.98 (m, 1H), 3.22–3.44 (m, 2H), 3.45–3.58 (m, 1H), 7.19 (d, 2H), 7.72 (d, 2H)

$^{13}C$ NMR (300.13 MHz, $CDCl_3$); δ guanidinecarbon 154.05

H-Aze-OEtxHCl

Prepared in the same way as described for H-Pic-OEtx HCl from H-Aze-OH (vide infra).

H-Aze-OMexHCl

Prepared according to the procedure described by Seebach D. et. al. in Liebigs Ann. Chem., p. 687, 1990.

H-Pab(Z)xKCl

Prepared by adding 1 mole equivalent of 5 M HCl in iso-propanol to a solution of crude H-Pab(Z) in EtOH (about 1 g/10 ml) where upon H-Pab(Z)xHCl immedeately precipitates out of the solution. After filtration the precipitate was washed 2 times with cold EtOH and dried to give the title compound in almost quantitative yield.

H-Pic-OEtxHCl

L-Pipecolinic acid, 4.0 g (0.031 mol), was slurried in 100 ml of abs. ethanol and HCl (g) was carefully bubbled through until a clear solution was obtained. It was cooled in an ice bath and 17 ml of thionyl chloride was added dropwise over 15 min. The ice bath was removed and the mixture was refluxed for 2.5 h. The solvent was evaporated and the product was obtained as its hydrochloride salt in a quantitative yield.

$^1H$-NMR (300 MHz, $D_2O$): δ 1.33 (t, 3H), 1.8–2.1 (m, 5H), 2.3–2.5 (m, 1H), 3.1–3.3 (m, 1H), 3.5–3.7 (m, 1H), 4.14 (dd, 1H), 4.44 (q, 2H).

H—(R,S)betaPic-OMexHCl

A mixture of 2.0 g (15.5 mmol) nipecotic acid in 8 ml methanol was cooled in an ice-bath and 2.76 g (23.2 mmol) thionyl chloride was added. The mixture was stirred at room temperature for 20 hours. The solvent was evaporated and the residue was dissolved in a small amount of methanol, diethylether was added and H—(R,S)betaPic-OMexHCl precipitated as white crystals. The crystals 2.57 g (92%) were isolated by filtration.

Doc-(R)Cgl-OH

Boc-(R)-Pgl-OH, 32.6 g (0.13 mol), was dissolved in 300 ml of methanol and 5 g of $Rh/Al_2O_3$ was added. The solution was hydrogenated at 5.2 to 2.8 MPa for 3 days. After filtration and evaporation of the solvent NMR showed the presence of about 25% of the methyl ester is of the title compound. The crude material was dissolved in 500 ml of THF and 300 ml of water and 20 g of LioH were added. The mixture was stirred overnight and the THF was evaporated. The remaining water phase was acidified with $KHSO_4$ and extracted three times with ethyl acetate. The combined organic layer was washed with water, dried ($Na_2SO_4$) and evaporated to give 28.3 g (83%) of the desired product.

$^1H$-NMR (300 MHz, $CDCl_3$): δ 0.9–1.7 (m, 20H), 4.0–4.2 (m, 1H), 5.2 (d, 1H).

Boc-(R)Cgl-OSu

To an ice-cold solution of 2.01 g (7.81 mmol) of Boc-(R)Cgl-OH and 1.83 g (15.6 mmol) of HOSu in 25 ml of $CH_3CN$ was added 1.69 g (8.2 mmol) of DCC and the reaction was allowed to reach room temperature. After stirring for 3 days the precipitated DCU was filtered off and the solvent evaporated. The residue was dissolved in EtOAc and the organic phase was washed with $H_2O$, $KHSO_4$, $NaHCO_3$, brine and dried($Na_2SO_4$). Evaporation of the solvent gave the title compound in quantitative yield.

Boc-(R)Cha-OSu

Boc-(R)Cha-OH (1 eq.), HOSu (1.1 eq) and DCC or CME-CDI (1.1 eq) were dissolved in acetonitrile (about 2.5 ml/mmol acid) and stirred at room temperature over night. The precipitate formed during the reaction was filtered off, the solvent evaporated and the product dried in vacuo. (When CME-CDI was used in the reaction the residue, after evaporation of the $CH_3CN$, was dissolved in EtOAc and the organic phase washed with water and dried). Evaporation of the solvent gave the title compound.

$^1H$-NMR (500 MHz, $CDCl_3$, 2 rotamers ca: 1:1 ratio) 0.85–1.1 (m, 2H), 1.1–1.48 (m, 4H), 1.5–1.98 (m, 16H; thereof 1.55 (bs, 9H)), 2.82 (bs, 4H), 4.72 (bs, 1H, major rotamer), 4.85 (bs, 1H, minor).

Boc-(R)Hoc-OH

Boc-(R)Hop-OH (See above), 3.2 q (11.46 Mmol) was dissolved in methanol (75 ml). Rhodium on activated aluminium oxide ($Rh/Al_2O_3$), 0,5 g was added and the mixture was stirred under a hydrogen atmosphere at 0.41 MPa for 18 h. The catalyst was filtered off through hyflo and the solvent evaporated giving the product in almost quantitative yield.

$^1H$-NMR (500 MHz, $CDCl_3$): δ 0.90 (m, 2H), 1.08–1.33 (m, 6H), 1.43 (s, 9H), 1.60–1.74 (m, 6H), 1.88 (bs, 1H), 4.27 (bs, 1H).

Boc-(R)Hoc-OSu

Prepared in the same way as described for Boc-(R)Cha-OSu from Boc-(R)Hoc-OH.

Boc-(R)Pr(3-(S)Ph)—OH

Prepared according to the method described by J. Y. L Chung et al in Journal of Organic Chemistry, No 1, pp. 270–275, 1990.

Boc-(R)Cgl-Aze-OH (i) Boc-(R)Cgl-Aze-OMe

To a stirred mixture of 3.86 g (15 mmol) Boc-(R)Cgl-OH, 2.27 g (15 mmol) H-Aze-OMe×HCl and 2.75 g (22.5 mmol) DMAP in 40 mL $CH_3CN$ at 5° C. was added 3.16 g (16.5 mmol) EDC. The reaction mixture was stirred at room temperature for 48 h. The solvent was evaporated and the residue was dissolved in 150 ml EtOAc and 20 ml $H_2O$. The separated organic layer was washed with 2×20 ml 0.5 M $KHSO_4$, 2×10 ml $NaHCO_3$(saturated), 1×10 ml $H_2O$, 1×10 ml brine and dried ($MgSO_4$). Evaporation of the solvent gave 4.91 g (92%) of the title compound which was used without further purification in the next step.

$^1$H NMR (500 MHz, $CDCl_3$, 0.1 g/ml): major rotamer, 0.83–1.35 (m, 5H), 1.38 (s, 9H), 1.47–1.84 (m, 6H), 2.18–2.27 (m, 1H), 2.50–2.62 (m, 1H), 3.72 (s, 3H), 3.94–4.06 (m, 1H), 4.07–4.15 (m, 1H), 4.39–4.47 (m, 1H), 4.68 (dd, J=9.1, J=5.1, 1H), 5.09 (d, J=9.2, 1H).

Resolved peaks from minor rotamer, 2.27–2.35 (m, 1H), 3.77 (s, 3H), 3.80–3.87 (m, 1H), 3.88–3.95 (m, 1H), 4.92 (d, J=9.2, 1H), 5.21 (dd, J=9.1, J-5, 1H).

(ii) Boc-(R)Cgl-Aze-OH

The hydrolysis of Boc-(R)Cgl-Aze-OMe was carried out according to the procedure described for Boc-(R)Cha-Pic-OEt (vide infra). The product was crystallized from EtOH/acetone/water (1/1/3.95) yield 80%.

$^1$H-NMR (500 MHz, $CDCl_3$): δ 0.85–1.3 (m, 5H), 1.40 (s, 9H), 1.5–1.9 (m, 6H), 1.95–2.2 (m, 2H), 3.92 (m, 1H), 4.09 (m, 1H), 4.35 (m, 1H), 4.95 (m, 1H), 5.16 (bd, 1H).

Boc-(R)Cgl-Pic-OH (i) Boc-(R)Cgl-Pic-OMe

Pivaloyl chloride (1.0 ml, 8.1 mmol) was added to a solution of Boc-(R)Cgl-OH (2.086 g, 8.1 mmol) and triethyl amine (1.13 ml, 8.1 mmol) in toluene (25 ml) and DMF (5 ml). A mixture of H-Pic-OMe×HCl (1.46 g, 8.1 mmol) and triethyl amine (1.13 ml, 8.1 mmol) in DMF (20 ml) was subsequently added at ice bath temperature. The reaction mixture was slowly allowed to warm up to room temperature and after 24 h it was diluted with water and extracted with toluene. After washing with 0.3 M $KHSO_4$, 10% $Na_2CO_3$ and brine the solvent was removed in vacuo to give 2.52 g (81) of colorless oil which was used without further purification.

$^1$H-NMR (500 MHz, $CDCl_3$, 2 rotamers, 5:1 ratio) δ 0.8–1.8 (m, 25H), 2.25 (d, 1H), 2.75 (t, 1H, minor rotamer), 3.3 (t, 1H), 3.7 (s, 3H), 3.85 (d, 1H), 4.3 (t, 1H, minor rotamer), 4.5–4.6 (m, 1H), 5.25 (d, 1H), 5.30 (d, 1H).

(ii) Boc-(R)Cgl-Pic-OH

Prepared according to the procedure for hydrolysis of Boc-(R)Cha-Pic-OEt (vide infra) using the product from (i) above. The product was crystallized from di-isopropyl ether and hexane.

$^1$H-NMR (500 MHz, $CDCl_3$, 2 rotamers, 5:1 ratio) δ 0.8–1.8 (m, 25H), 2.3 (d, 1H), 2.8 (t, 1H, minor rotamer), 3.3 (t, 1H), 3.9 (d, 1), 4.4 (t, 1H, minor), 4.5–4.6 (m, 1H), 5.1 (s, 1H, minor rotamer), 5.3 (d, 1H), 5.40 (d, 1H).

Boc-(R)Cgl-Pro-OH 3.59 g (31.24 mmol) of L-proline was mixed with 20 ml water and 1.18 g (29.7 mmol) of sodium hydroxide. 2.8 g (7.8 mmol) of Boc-(R)Cgl-OSu in 10 ml DMF was added to the mixture. Because of solubility problem an additional 30 ml of DMF was added and the reaction mixture was stirred for three days. The solvent was evaporated and water was added. The water phase was washed with ethyl acetate, acidified with 0.3 M $KHSO_4$-solution and extracted three times with ethyl acetate. The organic phase was washed once with water and once with brine, dried ($Na_2SO_4$), filtered and evaporated to yield 2.3 g (83%) of the product.

$^1$H-NMR (300 MHz, $CDCl_3$): δ 0.89–2.17 (m, 23H), 2.37 (m, 1H), 3.55 (q, 1H), 3.90 (bs, 1H), 4.28 (t, 1H), 4.52 (bs, 1H), 5.22 (bs, 1H(NH)).

Boc-(R)Cha-Aze-OH

Prepared in the same way as described for Boc-(R)Cha-Pic-OH starting from Boc-(R)Cha-OH and H-Aze-OEt×HCl (vide infra).

Boc-(R)Cha-Pro-OH

H—(S)Pro-OH (680 mmol) was dissolved in 0.87 M sodium hydroxide (750 ml). Boc-(R)Cha-OSu (170 mmol) dissolved in DMF (375 ml) was added dropwise during 20 min. The reaction mixture was stirred at room temperature for 20 h. The mixture was acidified (2M $KHSO_4$) and extracted three times with ethyl acetate. The organic layers were combined and washed three times with water and once with brine. After drying over sodium sulphate and evaporation of the solvent, the syrupy oil was dissolved in diethyl ether, the solvent evaporated and finally the product dried in vacuo to yield Boc-(R)Cha-Pro-OH as a white powder in almost quantitative yield.

$^1$H-NMR (500 MHz, $CDCl_3$, mixture of two rotamers 9:1) δ 0.8–1.05 (m, 2H), 1.05–1-55 (m, 15H; thereof 1.5 (bs, 9H)), 1.55–1.8 (m, 5H), 1.8–2.15 (m, 3H), 2.47 (m, 1H), 3.48 (m, 1H), 3.89 (m, 1H), 4.55 (m, 2H), 5.06 (m, 1H);

Resolved signals from the minor rotamer appears at d 2.27 (m), 3.58 (m), 4.33 (m), 5.0 (m).

Boc-(Me)(R)Cha-Pro-OSu (i) Boc-(Me)(R)Cha-Pro-OH

Prepared in the same way as described above for Boc-(R)Cha-Pro-OH starting from Boc-(Me)(R)Cha-OSu and H-Pro-OH.

(ii) Boc-(Me)(R)Cha-Pro-OSu

Prepared in the same way as described for Boc-(R)Cha-OSu starting from Boc-(Me)(R)Cha-Pro-OH.

Boc-(R)Cha-Pic-OH (ia) Boc-(R)Cha-Pic-OEt

Boc-(R)Cha-OH, 6.3 g (0.023 mol), was dissolved in 150 ml of $CH_2Cl_2$. The solution was cooled in an ice bath and 6.3 g (0.047 mol) of N-hydroxybenzotriazole and 11.2 g (0.0265 mol) of CME-CDI were added. The ice bath was removed after 15 min and the reaction mixture was stirred for 4 h at room temperature. The solvent was evaporated and the residue dissolved in 150 ml of DMF and cooled in an ice bath. H-Pic-OEt×HCl, 4.1 g (0.021 mol) was added and the pH adjusted to approximately 9 by addition of N-methylmorpholine. The ice bath was removed after 15 min and the reaction mixture was stirred for 3 days. The solvent was evaporated and the residue was dissolved in ethyl acetate and washed with dilute $KHSO_4$ (aq), $NaHCO_3$ (aq) and water. The organic layer was dried ($Na_2SO_4$) and evaporated to give 7.7 g (89%) of Boc-(R)Cha-Pic-OEt which was used without further purification.

$^1$H-NMR (500 MHz, $CDCl_3$, 2 rotamers, 3:1 ratio) d 0.7 –1.0 (m, 2H), 1.1–1.9 (m, 29H; thereof 1.28 (t, 3H)), 1.45 (bs, 9H), 2.01 (bd, 1H, major rotamer), 2.31 (bd, 1H), 2.88 (bt, 1H, minor), 3.30 (bt, 1H, major), 3.80 (bd, 1H, major), 4.15–4.3 (m, 2H), 4.5–4.7 (m, 2H, minor), 4.77 (bq, 1H, major), 4.90 (bd, 1H, minor), 5.28 (bd, 1H, major), 5.33 (bd,1H, major).

(ib) Boc-(R)Cha-Pic-OMe

400 µl (3.23 mmol) of pivaloyl chloride was added to a stirred mixture of 875 mg (3.22 mmol) Boc-(R)Cha-OH and 450 µl (3.23 mmol) triethyl amine in 10 ml toluene and 2 ml DMF. A mixture of 596 mg (3.32 mmol) methyl(S)-pipecolate hydrochloride and 463 µl (3.32 mmol) triethyl amine in 5 ml DMF was added to the resulting slurry after 45 minutes. After 2 h 100 µl (0.72 mmol) triethyl amine was added and stirring was continued for another 18 h. Water and toluene was added to the reaction mixture and the organic phase was washed with 0.3 M $KHSO_4$, 10% $Na_2CO_3$ and brine. Drying ($MgSO_4$) and removal of the solvent in vacuo gave 1.16 g of the title compound.

(ii) Boc-(R)Cha-Pic-OH

Boc-(R)Cha-Pic-OEt, 5.6 g (0.014 mol), was mixed with 100 ml of THF, 100 ml of water and 7 g of LiOH. The mixture was stirred at room temperature overnight. The THF was evaporated and the aqueous solution was acidified with $KHSO_4$ (aq) and extracted three times with ethyl acetate. The combined organic phase was washed with water, dried ($Na_2SO_4$) and evaporated to give 4.9 g (94%) of Boc-(R)Cha-Pic-OH which was used without further purification. The compound can be crystallized from diisopropyl ether/hexane.

The methyl ester formed in procedure (ib) above can be hydrolysed using the same procedure as described for the ethyl ester in (ii).

$^1$H-NMR (500 MHz, $CDCl_3$, 2 rotamers, 3.5:1 ratio) δ 0.8–1.1 (m, 2H), 1.1–2.1 (m, 27H; thereof 1.43 (s, 9H, major rotamer), 1.46 (s, 9H, minor)), 2.33 (bd, 1H), 2.80 (bt, 1H, minor), 3.33 (bt, 1H, major), 3.85 (bd, 1H, major), 4.57 (bd, 1H, minor), 4.68 (m, 1H, minor), 4.77 (bq, 1H, major), 5.03 (bs, 1H, minor), 5.33 (bd, 1H, major), 5.56 (m, 1H, major).

Boc-(R)Cha-(R,S)betapic-OH (i) Boc-(R)Cha-(R,S) betaPic-OMe

Pivaloyl chloride 0.9 ml (7.3 mmol) was added to a solution of 2.0 g (7.3 mmol) Boc-(R)Cha-OH and 0.81 ml (7.3 mmol) 4-N-methyl morpholin in 20 ml acetonitrile. After stirring for 1 h and 30 minutes 1.3 g (7.3 mmol) H—(R,S)betaPic-OMe×HCl and 1.62 ml (14.6 mmol) 4-N-methyl morpholine was added and the reaction mixture was stirred for 24 h. The solvent was evaporated and the residue was dissolved in toluene and some diethyleter. After washing with 0.3 M $KHSO_4$ and $KHCO_3$-solution, and drying with $Na_2SO_4$ the solvent was removed in vacuo. Flash chromatography using heptane/ethyl acetate (7/3) as eluent gave 2.4 g (83%) of the desired product.

(ii) Boc-(R)Cha-(R,S)betaPic-OH

At room temperature 2.35 g (5.9 mmol) of Boc-(R)Cha-(R,S)betaPic-OMe was dissolved in 35 ml THF and 2.1 g of LiOH in 35 ml water was added. After stirring for 5 h the THF was removed in vacuo. The aqueous phase was acidified with 2M $KHSO_4$ and extracted with ethyl acetate, dried over $Na_2SO_4$ and evaporated to give 2.0 g (89%) of the product.

Boc-(R)Cha-Val-OH (i) Boc-(R)Cha-Val-OMe 3.1 ml (25 mmol) pivaloyl chloride was added at ambient temperature to a stirred mixture of 6.75 g (25 mmol) Boc-(R)Cha-OH and 3.5 ml (25 mmol) triethyl amine in 50 ml DMF. After 3 hours 4.16 g (25 mmol) valine methyl ester hydrochloride in 50 ml DMF and 3.5 ml triethyl amine was added. After stirring over night, a few crystals of DMAP were added and the reaction mixture was heated to 50° C. for 5 minutes. The solvent was removed in vacuo and ether and toluene was added to the residue. Washing with 0.3 N $KHSO_4$ and 10% $Na_2CO_3$ followed by drying ($MgSO_4$) and removal of the solvent in vacuo gave a residue which was subjected to flash chromatography using toluene/ethyl acetate as eluent. The yield of the title compound was 6.99 g (73%).

(ii) Boc-(R)Cha-Val-OH

A mixture of 8.73 g (23 mmol) Boc-(R)Cha-Val-OMe and 5.6 g (230 mmol) lithium hydroxide in 75 ml THF and 75 ml of water was stirred for 4 hours. The THF was removed in vacuo and the remaining solution was diluted with water and extracted with ether. Acidification with 2 M $KHSO_4$ and extraction with ethyl acetate followed by drying ($MgSO_4$) and removal of the solvent in vacuo gave 8.15 g (96%) of the title compound.

Boc-(R)Hoc-Aze-OH (i) Boc-(R)Hoc-Aze-OEt

At room temperature 1.0 g (3.5 mmol) Boc-(R)Hoc-OH and 0.95 g (7.0 mmol) HOBt was dissolved in 15 ml $CH_2Cl_2$. The solution was cooled in an ice bath and 0.77 g (4.0 mmol) of EDC was added. The ice bath was removed and the reaction mixture was stirred for 3 h at room temperature. The solvent was evaporated and the residue dissolved in 20 ml DMF. 0.58 g (3.5 mmol) H—(R)Aze-OH was added and the pH adjusted to approximately 9 by addition of N-methyl morpholine. The reaction mixture was stirred for one day. The reaction mixture was partitioned between water and toluene. The organic phase was separated and washed with 0.3 M $KHSO_4$, diluted $KHCO_3$, brine, dried with $NaSO_4$ and evaporated. Flash chromatography (1% EtOH in $CH_2Cl_2$ and heptane: EtOAc) gave 0.35 g (25%) of the desired product.

(ii) Boc-(R)Hoc-Aze-OH

At room temperature 0.65 g (1.6 mmol) Boc-(R)Hoc-Aze-OEt was dissolved in 10 ml THF and 0.59 g of LiOH in 10 ml water was added. After stirring for 24 hours 2 M $KHSO_4$ was added and the THF was removed in vacuo. The aqueous phase was then made acidic with more 2M $KHSO_4$ and extracted with ethyl acetate, dried over $Na_2SO_4$ and evaporated to give 0.5 g (85%) of the title compound.

Boc-(R)Roc-Pro-OH

Prepared in the same way as described for Boc-(R)Cha-Pro-OH from Boc-(R)Hoc-OSu.

$^1$H-NMR (500 MHz, $CDCl_3$): δ 0.80–0.94 (m, 2H), 1.05–1.36 (m, 7H), 1.36–1.48 (bs, 9H), 1.48–1.78 (m, 7H), 1.98–2.14 (m, 2H), 2.34 (m, 1H), 3.48 (m, 1H), 3.85 (m, 1H), 4.43 Cm, 1H), 4.52 (bd, 1H), 5.26 (bd, 1H), signals of a minor rotamer appears at: δ 1.92, 2.25, 3.58, 4.20 and 4.93.

Boc-(R)Hoc-Pic-OH (i) Boc-(R)Hoc-Pic-OMe

Prepared the same way as described for Boc-(R)Cha-Pic-OEt (vide supra) from Boc-(R)Hoc-OH and H-Pic-OMe×HCl.

(ii) Boc-(R)Hoc-Pic-OH

Prepared in the same way as described for Boc-(R)Cha-Pic-OH (vide supra) from Boc-(R)Hoc-Pic-OMe.

$^1$H-NMR (500 MHz, $CDCl_3$): δ 0.82–0.97 (m, 2H), 1.10–1.36 (m, 7H), 1.36–1.50 (bs, 9H), 1.50–1.82 (m, 11H), 2.35 (bd, 1H) 3.28 (bt. 1H), 3.85 (bd, 1H) 4,63 (m, 1H), 5.33 (bs, 1H), 5.44 (bd, 1H), signals of a minor rotamer appear at: δ 1.88, 2.80, 4.25, 4.55 and 4.97.

Boc-(R)Pro-Phe-OH (i) Boc-(R)Pro-Phe-OMe

To a solution of 2.0 q (9.29 mmol) Boc-(R)Pro-OH and 0.94 g (9.29 mmol) triethyl amine in 70 ml toluene/DMF (5/2) was added 1.12 g (9.29 mmol) pivaloylchloride and the reaction was stirred for 30 minutes at room temperature. The reaction was cooled to 0° C. and a mixture of 2.0 g (9.29 mmol) H-Phe-OMe and 0.94 g triethyl amine in 40 ml DMF was added and the reaction was stirred over night at room temperature. The reaction mixture was diluted with toluene and the organic phase was washed with 3×50 ml 0.3 M KHSO$_4$, 1×50 ml water and dried (Na$_2$SO$_4$). Evaporation of the solvent gave the title compound in quantitative yield which was used in the next step without further purification.
(ii) Boc-(R)Pro-Phe-OH A mixture of 4.0 g (10.6 mmol) Boc-(R)Pro-Phe-OMe and 8.93 g (21.3 mmol) LiOH×H$_2$O in 140 ml water/THF (1/1) was stirred vigorously over night at room temperature. The THF was evaporated and the water phase was made acidic with 1 M KHSO$_4$ and extracted with 3×75 ml EtOAc. The combined organic phase was washed with water and dried (Na$_2$SO$_4$). Filtration and evaporation of the solvent gave a residue which was purified by crystallization from diisopropyl ether to give 2.329 g (60%) of the title compound as a white crystalline solid.

Boc-(R)Pro(3-(S)Ph)-Pro-OH
(i) Boc-(R)Pro(3-(S)Ph)-Pro-OBn

To a mixture of 1.61 g Boc-(R)Pro(3-(S)Ph)—OH, 1.65 g H-Pro-OBn×HCl and 0.75 g HOBt in 11 mL DMF was added 0.84 mL NMM and 2.92 g CME-CDI at room temperature and the reaction mixture was stirred for three days. The solvent was evaporated and the residue was dissolved in 300 mL EtOAc. The organic phase was washed with 2×100 mL H$_2$O, 2×100 mL 1 M KHSO$_4$, 3×100 mL 1 M NaOH, 3×100 ml H$_2$O and dried (MgSO$_4$). Evaporation of the solvent gave 2.53 g of an oil which was purified by flash chromatography using CH$_2$Cl$_2$/MeOH (97/3) as eluent to give 2.11 g (88%) of the title compound.
(ii) Boc-(R)Pro(3-(S)Ph)-Pro-OH 0.94 q of Boc-(R)Pro(3-(S)Ph)-Pro-OBn was dissolved in 70 ml EtOH and hydrogenated over 0.42 g 5% Pd/C for 3.5 hours. Filtration of the catalyst and evaporation of the solvent gave the title compound as white crystals in a quantitative yield.

Boc-(R)Tic-Pro-OH

Prepared according to the procedure described by P. D. Gesellchen and R. T. Shuman in EP-0,479,489-A2.

BnOOC—CH$_2$—NH—CO—CH$_2$—Br 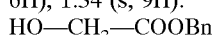

To a solution of p-TsOH×H-Gly-OBn (5 mmol) and triethyl amine (5 mmol) in 10 ml of CH$_2$Cl$_2$ was added 2-bromoacetic acid (5 mmol) dissolved in 10 ml of CH$_2$Cl$_2$ and dicyclohexyl carbodiimide (5 mmol). The mixture was stirred at room temperature over night and filtered. The organic phase was washed twice with 0.2 M KHSO$_4$, 0.2 M NaOH, brine and dried. Evaporation and flash chromatography (CH$_2$Cl$_2$/MeOH, 95/5) gave a quantitative yield of the desired compound.

$^1$H-NMR (300 MHz, CDCl$_3$): δ 3.89 (s, 2H), 4.05–4.11 (d, 2H), 5.19 (s, 2H), 7.06 (bs, 1H), 7.3–7.4 (m, 5H).

Boc-(R)Cgl-Ile-OH

Prepared in the same way as described for Boc-(R)Cgl-Pro-OH using H-Ile-OH, instead of H-Pro-OH, in 91% yield.

Boc-(R)Phe-Phe-OH
(i) Boc-(R)Phe-Phe-OMe

Boc-(R)Phe-OH (18.8 mmol; purchased from Bachem Feinchemicalien AG), Phe-OMe (20.7 mmol) and 4-dimethylaminopyridine (37.7 mmol) were dissolved in 30 mL of acetonitrile. The solution was cooled to ice-water temperature and 1-(3-dimethylaminopropyl)-3-ethylcarbodiimide hydrochloride (24.5 mmol) was added. The cooling bath was removed and the reaction mixture was stirred over night. The solvent was then removed under reduced pressure and the residue was dissolved in 50 mL of ethylacetate. Extraction of the organic phase with 50 mL aliquats of 0.5 M potassiumhydrogensulfate, 1 M sodiumbicarbonate and finally water followed by evaporation of the solvent yielded 7.5 g of Boc-(R)Phe-Phe-OMe (94%) which was used in the next step without further purification.
(ii) Boc-(R)Phe-Phe-OH Boc-(R)Phe-Phe-OMe (16.4 mmol) was dissolved in 40 mL of tetrahydrofuran and lithiumhydroxide (32.8 mmol) dissolved in 20 mL of water was added rapidly. The reaction mixture was stirred for 3.5 h after which the solvent was removed under reduced pressure. The residue was dissolved in 50 mL of ethylacetate and extracted with 50 mL of 0.5 M potassiumsulfate followed by 50 mL of water. The solvent was removed under reduced pressure yielding 8.0 g of Boc-(R)Phe-Phe-OH (quant) as an amorphous solid. $^1$H NMR (200 MHz, d-CHCl$_3$); δ 7.4–6.7 (m, 10H), 5.7–4.2 (m, 6H), 1.34 (s, 9H).

HO—CH$_2$—COOBn

Prepared according to the procedure described by Lattes A. et al in Bull. Soc. Chim. France., Noll, pp 4018–23, 1971.

Benzyl-2-(ortho-nitrobenzenesulfonyloxy)acetate(2-NO$_2$) Ph-SO$_2$—OCH$_2$—COOBn 1.66 g (10 mmol) benzylglykolate was dissolved in 25 ml CH$_2$Cl$_2$ and 25 ml diethylether. The mixture was cooled to 0° C. and 2.8 ml (20 mmol) triethylamin was added. While keeping the temperature at 0° C. 2.44 g (11 mmol) ortho-nitrobenzenesulfonylchloride was added in small portions during 15 minutes. The slurry was stirred at OC for 50 minutes and then 20 ml water and 30 ml CH$_2$Cl$_2$ were added. The phases were separated and the organic phase was washed with 20 ml 1 M HCl and 20 ml H2O, dried (Na$_2$SO$_4$), filtered and evaporated in vacuo to give 3.34 g of a residue that was subjected to flash chromatography, using heptan:EtOAc 2:1 as eluent to give 1.18 g (34%) of the title compound.

$^1$H-NMR (300 MHz, CDCl$_3$): δ 4.92 (s, 2H), 5.17 (s, 2H), 7.83 (m, 5H), 7.76 (m, 3H), 8.16 (dd, 1H).

Benzyl-2-(para-nitrobenzenesulfonyloxy)acetate(4-NO$_2$) Ph—SO$_2$—OCH$_2$—COOBn Prepared according to the same procedure as described for Benzyl-2-(ortho-nitrobenzenesulfonyloxy)acetate above. The final compound was obtained in a crystalline form after evaporation of the solvent and pure enough to use without further purification (64% yield).

$^1$H-NMR (300 MHz, CDCl$_3$): δ 4.79 (s, 2H), 5.13 (s, 2H), 7.2–7.4 (a, 5H), 8.10 (d, 2H), 8.30 (d, 2H).

TfO—CH$_2$COOMe 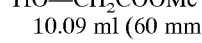

10.09 ml (60 mmol) trifluorometansulfonic anhydrid dissolved in CH$_2$Cl$_2$ was added dropwise to a mixture of 4.05 ml (50 mmol) methylglycolate and 4.04 ml (50 mmol) pyridin in CH$_2$Cl$_2$ (totally 62.5 ml) at 0° C. during 25 minutes, and thereafter stirred at 0° C. for 1H. After washing with 0.3 M KHSO$_4$ and saturated NA$_2$CO$_3$, drying (Na$_2$SO$_4$) and filtration, evaporation of the solvent in vacuo gave 9.94 g (90%) of the title compound.

TfO-CR$_2$COOEt 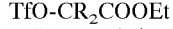

Prepared in the same way as described for TfO-CH$_2$COOMe starting with ethylglycolate.

TfO—CH$_2$COO"Bu 

Prepared in the same way as described for TfO-CH$_2$COOMe starting with butylglycolate.

TfO—CH$_2$COOBn 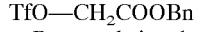

Prepared in the same way as described for TfO-CH$_2$COOMe starting with HO—CH$_2$COOBn TfO-CH$_2$COO"Hax 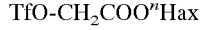

(i) HO—CH$_2$COO"Hex

To 215 mg (2.82 mmol) glycolic acid in 12.8 ml CH$_3$CN was added 719 mg (3.39 mmol) 1-hexyl iodide and 429 mg (2.82 mmol) DBU. After stirring over night and reflux for 4 h, the solvent was evaporated, ethylacetat and 1 M KHSO$_4$ was added and the phases were separated. The organic layer was washed with brine, dried (MgSO$_4$), filtered and evaporated in vacuo to give 333 mg (74%) of the product.

(ii) TfO-CH$_2$COO"Hex

Prepared in the same way as described for TfO-CH$_2$COOMe starting with HO—CH$_2$COO"Hex.

H-Mig(z) (3-aminomethyl-1-(N-benzyloxycarbonylamidino) azetidine (i) 3-aminomethyl-1-benzhydryl azetidine was Prepared According to the Literature, see A. G. Anderson, Jr., and R. Lok, *J.Org.Chem.*, 37, 3953, 1972.

(ii) 3-(N-tert-butyloxycarbonylaminomethyl)-1-benzhydryl azetidine

To 3.50 g (13.9 mmol) of 3-aminomethyl-1-benzhydryl azetidine dissolved in 45 mL THF was added a solution of 0.56 g (13.9 mmol) NaOH in 45 mL H$_2$O. The reaction mixture was cooled to 0° C. and 3.03 g (13.9 mmol) of di-tert-butyl dicarbonate was added. The cooling bath was removed after a few minutes and the mixture was stirred at roomtemperature over night. The THF was evaporated and the residue was extracted with 3×45 mL of diethyl ether. The combined organic layer was washed with brine, dried with Na$_2$SO$_4$ and filtered. Evaporation of the solvent gave 4.6 g (94%) of the title compound.

(iii) 3-(N-tert-butyloxycarbonylaminomethyl) azetidine 3.4 g (9.6 mmol) of 3-(N-tert-butyloxycarbonylaminomethyl)-1-benzhydryl azetidine was dissolved in 170 mL MeOH and hydrogenated over 0.30 g Pd(OH)$_2$ at 5 MPa over night. The catalyst was filtered off and the solvent evaporated. The crude product was purified by flash chromatography using MeOH/CH$_2$Cl$_2$, 1/9, followed by MeOH (saturated with NH$_3$ (g))/CH$_2$Cl$_{21}$ 1/9, as eluent to yield 1.2 g (67%) of the title compound.

(iv) 3-(N-tert-butyloxycarbonylaminomethyl)-1-(N-benzyloxycarbonylamidino) azetidine (Boc-Mig(Z))

0.9 g (4.8 mmol) of 3-(N-tert-butyloxycarbonylaminomethyl) azetidine and 1.3 g (6.3 mmol) of N-benzyloxycarbonyl-O-methylisourea was mixed in 6.5 mL toluene and heated to 70° C. for 72 h and then left at roomtemperature for another 72 h. Evaporation followed by flash chromatography using EtOAc followed by MeOH (saturated with NH$_3$(g))/CH$_2$Cl$_{21}$ 1/9, as eluent gave 0.67 g (38%) of the title compound as a white powder.

(v) 3-aminomethyl-1-(N-benzyloxycarbonylamidino) azetidine (H-Mig(Z))

0.67 g (1.85 mmol) of Bcc-Mig(Z) was dissolved in 10 mL of EtOAc saturated with HCl(g) and stirred for 10 min. at roomtemperature. 10 mL of a saturated solution of KOH (aq) was added dropwise. The layers were separated and the aqueous phase was extracted with 3×8 mL EtOAc. The organic layers were combined, washed with brine, dried with Na$_2$SO$_4$ and evaporated to yield 0.43 g (89%) of the title compound.

$^1$H-NMR (300 MHz, CDCl$_3$): δ 2.55–2.65 (m, 1H), 2.84 (d, 2H), 3.66 (dd, 2H) 4.03 (dd, 2H) 5.07 (s, 2H), 7.2–7.4 (m, 5H).

MS m/z 263 (M$^+$+1)

3-amino thyl-1-(N-benzyloxycarbonylamidino) azetidine (H-Dig(Z))

(i) 3-carboxylic acid-1-benzhydryl azetidine was Prepared According to the Literature, see A. G. Anderson, Jr., and R. Lok, *J.Org.Chem.*, 37, 3953, 1972.

(ii) 3-hydroxymethyl-1-benzhydryl azetidine

A solution of 8.7 g (32.5 mmol) 3-carboxylic acid-1-benzhydryl azetidine in 80 mL of dry THF was added slowly to a suspension of 4.9 g (130.2 mmol) of LiAlH$_4$ in 30 mL THF at roomtemperature. The reaction mixture was refluxed for 3.5 h. Excess hydride reagent was hydrolyzed by careful addition, with cooling, of NH$_4$Cl(aq), the gelatinous mixture was filtered and the filter cake was washed repeatedly with THF. Evaporation of the solvent gave 7.1 g (86%) of the title compound as pale yellow crystals.

(iii) 3-methanesulfonatomethyl-1-benzhydryl azetidine

To a solution of 6.62 g (26.1 mmol) 3-hydroxymethyl-1-benzhydryl azetidine in 50 mL of dry pyridine was added 4.50 g (39.2 mmol) of methanesulfonyl chloride at 0° C. The reaction mixture was stirred for 1 h. and then allowed to stand in a refrigerator over night. The reaction mixture was poured into a mixture of ice and H$_2$O. The precipitate was collected, washed with H$_2$O and dried in vacuo to yield 7.75 g (89.5%) of the title compound.

(iv) 3-cyanomethyl-1-benzhydryl azetidine

To a solution of 7.75 g (23.4 mmol) 3-methanesulfonatomethyl-1-benzhydryl azetidine in 50 mL DMF was added a solution of 3.44 g (70.0 mmol) NaCN in 10 mL H$_2$O. The mixture was heated at 65° C. for 20 h, cooled, and poured into a mixture of ice and H$_2$O. The precipitate was collected, washed with H 0 and dried in vacuo to yield 5.7 g (93%) of the title compound.

(v) 3-aminoethyl-1-benzhydryl azetidine 5.7 g (21.7 mmol) of 3-cyanomethyl-1-benzhydryl azetidine was added slowly to a suspension of 2.9 g (76.0 mmol) of LiAlH$_4$ in 80 mL of dry THF at roomtemperature. The reaction mixture was refluxed for 4 h. Excess hydride reagent was hydrolyzed by careful addition, with cooling, of NH$_4$Cl(aq), the gelatinous mixture was filtered and the filter cake was washed repeatedly with THF. The solvent was evaporated, the residue was dissolved in diethyl ether, washed with brine and dried with Na$_2$SO$_4$. Evaporation of the solvent gave 5.0 g (87%) of the title compound.

(vi) 3-(N-tert-butyloxycarbonylaminoethyl)-1-benzhydryl azetidine

The title compound was prepared from 3-aminoethyl-1-benzhydryl azetidine according the procedure for 3-(N-tert-butyloxycarbonylaminomethyl)-1-benzhydryl azetidine, in a yield of 6.5 g (95%).

(vii) 3-(N-tert-butyloxycarbonylaminoethyl) azetidine

The title compound was prepared from 3-(N-tert-butyloxycarbonylaminoethyl)-1-benzhydryl azetidine according the procedure for 3-(N-tert-butyloxycarbonylaminomethyl) azetidine, in a yield of 1.2 g (70%).

(viii) 3-(N-tert-butyloxycarbonylaminoethyl)-1-(N-benzyloxycarbony lamidino) azetidine (Boc-Dig(Z))

The title compound was prepared from 3-(N-tert-butyloxycarbonylaminoethyl) azetidine according the procedure for 3-(N-tert-butyloxycarbonylaminomethyl)-1-(N-benzyloxycarbon ylamidino) azetidine, in a yield of 0.090 g (34%).

(ix) 3-aminoethyl-1-(N-benzyloxycarbonylamidino) azetidine (H-Dig(Z))

0.589 g (1.56 mmol) of Boc-Dig(Z) was dissolved in 10 mL of EtOAc saturated with HCl(g) and stirred for 10 min. at roomtemperature. 10 mL of a saturated solution of KOH (aq) was added dropwise. The layers were separated and the aqueous phase was extracted with 3×8 mL EtOAc. The organic layers were combined, washed with brine, dried with $Na_2SO_4$ and evaporated to yield 0.415 g (96%) of the title compound.

$^1$H-NMR (500 MHz, CDCl$_3$): δ 1.60 (dt, 2H), 2.52–2.54 (m, 3H), 3.53 (bs, 2H), 4.0 (bt, 2H), 5.00 (s, 2H), 7.17–7.31 (m, 5H).

WORKING EXAMPLES

Example 1

HOOC—CH$_2$—(R)Cgl-Aze-Pab (i) Boc-(R)Cgl-Aze-Pab(Z)

To a stirred mixture of 3.40 g (10 mmol) Boc-(R)Cgl-Aze-OH (See Preparation of starting materials) and 5.13 g DMAP (42 mmol) in 120 ml CH$_3$CN was added 3.18 g H-Pab(Z)×HCl (See Preparation of starting materials). After stirring for 2 hours at room temperature the mixture was cooled to −8° C. and 2.01 g (10.5 mmol) EDC was added. The reaction was allowed to reach room temperature and the stirring was continued for an additional 47 hours. The solvent was evaporated and the residue was dissolved in 200 ml EtOAc. The organic phase was washed with 1×50 ml water, 1×50+2×25 ml 0.5 M KHSO$_4$, 2×25 ml NaHCO$_3$ (saturated), 1×50 ml water and dried. Evaporation of the solvent gave 5.21 g (86%) of the title compound.

$^1$H-NMR (500 MHz, CDCl$_3$): δ 0.8–1.9 (m, 20H; thereof 1.30 (s, 9H)), 2.35–2.6 (m, 2H), 3.74 (bt, 1H), 4.10 (m, 1H), 4.25–4.4 (m, 2H), 4.45–4.6 (m, 1H, rotamers), 4.75–5.0 (m, 1H, rotamers), 5.08 (bd, 2H), 5.15 (s, 2H), 7.15–7.35 (m, 5H), 7.41 (d, 2H), 7.77 (d, 2H), 8.21 (m, 1H).

(ii) H—(R)Cgl-Aze-Pab(Z)

To a cold (ice bath temperature) solution of 18.8 g HCl$_{(g)}$ in 195 ml EtOAc was added 4.69 g (7.743 mmol) of Boc-(R)Cgl-Aze-Pab(Z) together with 40 ml EtOAc. The reaction mixture was allowed to reach room temperature and stirred for 30 min. 140 ml Et$_2$O was added to the clear solution where upon a precipitate was formed. The reaction was left at room temperature for an additional 1 h and 40 minutes. The precipitate was filtered off, washed quickly with 150 ml Et$_2$O and dried in vaccuo. The precipitate was dissolved in 50 ml of water and made alkaline with 15 ml 2 M NaOH. The alkaline waterphase was extracted with 1×100+1×50 ml CH$_2$Cl$_2$. The combined organic phase was washed with 1×20 ml water, 1×20 ml Brine and dried (MgSO$_4$). Evaporation of the solvent gave 3.44 g (88%) of the title compound.

$^1$H-NMR (500 MHz, CDCl$_3$): δ 0.8–2.0 (m, 11H), 2.51 (m, 1H), 2.67 (m, 1H), 3.07 (d, 1H), 4.11 (m, 1H), 4.18 (m, 1H), 4.43 (dd, 1H), 4.53 (dd, 1H), 4.91 (m, 1H), 5.22 (s, 2H), 7.2–7.4 (m, 7H), 7.45 (d, 2H), 8.51 (d, 2H).

(iii) BnOOC—CH$_2$—(R)Cgl-Aze-Pab(Z)

1.13 g (2.2 mmol) H—(R)Cgl-Aze-Pab(Z), 0.9 g (2.6 mmol) benzyl-2-(orto-nitrobenzenesulfonyloxy)acetate((2-NO$_2$)Ph—SO$_2$—OCH$_2$—COOBn) (See Preparation of starting materials), 0.99 g (5.6 mmol) K$_2$CO$_3$ and 113 ml CH$_3$CN were mixed and heated in a 60° C. oilbath for 3 h. The solvent was evaporated in vacuo. EtOAc was added and the mixture was washed with water, the organic phase was extracted with 1 M KHSO$_4$ and this waterphase was washed with EtOAc. The acidic waterphase was made alcaline with 1 N NaOH to pH>8 and extracted with EtOAc. The organic phase was washed with water, dried (Na$_2$SO$_4$), filtered and evaporated in vacuo to give 1.17 g of a residue that was twice subjected to flash chromatography using first CH$_2$Cl$_2$/MeOH(NH$_3$-saturated) 95/5 and then diethylether/MeOH (NH$_3$-saturated) 9/1 as eluents to give 0.525 g (36%) of the title compound.

The alkylation was also carried out using Benzyl-2-(para-nitrobenzenesulfonyloxy)acetate((4-NO$_2$)Ph-SO$_2$—OCH$_2$—COOBn) (See Preparation of starting materials) using the same procedure as above to give the title compound in 52% yield.

$^1$H-NMR (300 MHz, CDCl$_3$): δ 0.85–2.15 (m, 1H), 2.48 (m, 1H), 2.63 (m, 1H), 2.88 (d, 1H), 3.24 (d, 1H), 3.27 (d, 1H), 3.95 (m, 1H), 4.05 (m, 1H), 4.44 (m, 1H), 4.55 (m, 1H), 4.91 (m, 1H), 5.07 (s, 2H), 5.22 (s, 2H), 7.2–7.4 (m, 10H), 7.45 (d, 2H), 7.79 (d, 2H), 8.42 (m, 1H).

(iva) HOOC—CH$_2$—(R)Cgl-Aze-Pab×2 HCl

BnOOC—CH$_2$—(R)Cgl-Aze-Pab(z), 20 mg (0.031 mmol), was dissolved in 5 ml of methanol. A few drops of chloroform and 5% Pd/C were added and the mixture was hydrogenated at atmospheric pressure for 1 h. After filtration and evaporation the product was lyophilized from water to give 11 mg (72%) of the title compound.

$^1$H-NMR (500 MHz, D$_2$O): δ 1.0–2.0 (m, 11H), 2.10 (m, 1H), 2.44 (m, 1H), 2.82 (m, 1H), 3.90 (s, 2H), 4.09 (d, 1H), 4.4–4.55 (m, 2H), 4.66 (s, 2H), 5.08 (m, 1H), 7.65 (d, 2H), 7.89 (d, 2H).

$^{13}$C-NMR (75.5 MHz, D$_2$O): amidine and carbonyl carbons: δ 167.3, 167.9, 169.9 and 172.4.

(ivb) HOOC—CH$_2$—(R)Cgl-Aze-Pab

BnOOC—CH$_2$—(R)Cgl-Aze-Pab(Z) was dissolved in EtOH (99%) and hydrogenated over 5% Pd/C at atmospheric pressure for 5 hours. Filtration of the catalyst through cellite and evaporation of the solvent gave the title compound in 97% yield.

$^1$H-NMR (500 MHz, CD$_3$OD, mixture of two rotamers): major rotamer: δ 1.00–1.12 (m, 1H), 1.13–1.34 (m, 4H), 1.55–1.70 (m, 3H), 1.73–1.85 (m, 2H), 1.94–2.02 (bd, 1H), 2.32–2.42 (m, 1H), 2.54–2.64 (m, 1H), 2.95–3.10 (AB-system plus d, 3H), 4.18–4.25 (bq, 1H), 4.28–4.32 (b, 1H), 4.43–4.60 (AB-system, 2H), 4.80–4.85 (dd, 1H), 7.48–7.54 (d,2H), 7.66–7.71 (d, 2H).

Resolved signals from the minor rotamer appears at δ 0.95 (m), 1.43 (m), 2.24 (m), 2.84 (d), 3.96 (m), 4.03 (m), 7.57 (bd), 7.78 (bd).

$^{13}$C-NMR (125 MHz, CD$_3$OD): amidine and carbonyl carbons: δ 168.0, 173.0, 176.3 and 179.0

Example 2

HOOC—CH$_2$—CH$_2$—(R)Cgl-Aze-Pab×2 HCl (i) H—(R)Cgl-Aze-Pab(Z)

Prepared in the same way as decribed in Example 1 (ii) by treating the formed hydrochloride salt with base to afford the free base.

(ii) BnOOC—CH$_2$—CH$_2$—(R)Cgl-Aze-Pab(Z)

H—(R)Cgl-Aze-Pab(Z), 0.19 g (0.38 mmol), and 70 mg (0.43 mmol) of benzyl acrylate were dissolved in 2 ml of isopropanol. The mixture was left standing for 6 days. Flash chromatography using CH$_2$Cl$_2$/THF=8/2 as eluent afforded 0.12 g (48%) of the title compound.

$^1$H NMR (500 MHz, CDCl$_3$) δ 0.8–1.9 (m, 10H), 1.95 (bd, 1H), 2.4–2.6 (m, 4H), 2.7–2.8 (m, 3H; thereof 2.79 (d, 1H)), 4.13 (m, 1H), 4.37 (dd, 1H), 4.60 (dd, 1H), 14.97 (dd, 1H), 5.09 (dd, 2H), 5.22 (s, 2H), 7.25–7.4 (m, 10H), 7.47 (d, 2H), 7.83 (d, 2H), 8.61 (bt, 1H).

(iii) HOOC—CH$_2$—CH$_2$—(R)Cgl-Aze-Pab×2 HCl

BnOOC—CH$_2$—CH$_2$—(R)Cgl-Aze-Pab(Z), 0.10 g (0.15 mmol), was dissolved in 10 ml of ethanol and hydrogenated over 5% Pd/C at atmospheric pressure for 1 h.

The solution was filtered, evaporated and the crude product was purified on RPLC using CH$_3$CN/0.1 M NH$_4$OAc (1/4). The resulting product was freeze dried, treated with an excess of conc. HCl and freeze dried again to give 31 mg of the dihydrochloride salt.

$^1$H NMR (300 MHz, D$_2$O) δ 0.8–2.1 (m, 11H), 2.38 (m, 1H), 2.7–2.9 (m, 3H), 3.2–3.4 (m, 2H), 3.98 (d, 1H), 4.35–4.55 (m, 2H), 4.60 (s, 2H), 5.04 (dd, 1H), 7.59 (d, 2H), 7.83 (d, 2H).

$^{13}$C NMR (75 MHz, D$_2$O): amidine and carbonyl carbons: δ 167.2, 167.8, 172.3 and 175.5.

Example 3
HOOC—CH$_2$—(R)Cgl-Pro-Pab×2 HCl
(i) Boc-(R)Cgl-Pro-Pab(Z)

Boc-(R)Cgl-Pro-OH (See preparation of starting materials), 2.3 g (6.49 mmol), DMAP, 2.38 g (19.47 mmol), and H-Pab(Z)(See preparation of starting materials), 1.84 g (6.49 mmol) was mixed in 30 ml acetonitrile. The mixture was cooled to −15"c and EDC, 1.31 g (6.81 mmole) was added. The temperature was allowed to reach room temperature and the mixture was stirred over night. After evaporation, the residue was dissolved in ethyl acetate and 0.3 M KHSO$_4$-solution. The acidic water phase was extracted three times with ethyl acetate. The organic phase was washed twice with a 0.3 M KHSO$_4$-solution, twice with a NaHCO$_3$-solution and once with brine, dried (Na$_2$SO$_4$), filtered and evaporated. The crude product was purified by flash chromatography on silica gel using ethyl acetate as eluent to yield 1.77 g (44%) of the product.

$^1$H-NMR (500 MHz, CDCl$_3$): δ 0.9–1.49 (m, 14H), 1.5–2.1 (m, 9H), 2.37 (bs, 1H), 3.53 (q, 1H), 3.94 (bs, 1H), 4.02 (m, 1H), 4.43 (bs, 2H), 4.65 (d, 1H), 5.09 (bs, 1H), 5.20 (s, 2H), 7.18–7.4 (m, 5H), 7.45 (d, 2H), 7.62 (bs, 1H), 7.81 (m, 2H), (ii) H—(R)Cgl-Pro-Pab(Z)

1.45 q (2.34 mmol) of Boc-(R)Cgl-Pro-Pab(Z) was dissolved in 75 ml HCl saturated ethyl acetate. The mixture was allowed to stand for 10 min at room temperature. The solvent was evaporated to yield 1.3 g of the dihydrochloride salt of the product.

$^1$H-NMR (300 MHz, D$_2$O): δ 1.0–1.45 (m, 5H), 1.58–2.2 (m, 9H), 2.3–2.5 (m, 1H), 3.75–3.90 (m, 2H), 4.25 (d, 2H), 4.5–4.66 (m, 3H), 5.49 (s, 2H), 7.45–7.7 (m, 7H), 7.87 (d, 2H)

The amine was obtained by dissolving the dihydrochloride salt in 0.1 M NaOH-solution and extracting the water phase three times with ethyl acetate. The organic phase was washed once with brine, dried (Na$_2$SO$_4$), filtered and evaporated to yield 1.19 g (97%) of the title compound.

(iii) BnOOC—CH$_2$—(R)Cgl-Pro-Pab(Z)

0.340 g (0.65 mmole) H—(R)Cgl-Pro-Pab(Z) was mixed with 0.215 g (0.65 mmole) BnOOC—CH$_2$—OTf (see preparation of starting materials), 0.299 g (2.17 mmole) K$_2$CO$_3$ in 4 ml dichloromethane and refluxed for half an hour. The reaction mixture was then stirred over night at room temperature. The reaction mixture was diluted with CH$_2$Cl$_2$ and the organic layer was washed once with water and brine, dried (Na$_2$SO$_4$), filtered and evaporated. The crude product was purified by flash chromatography using a stepwise gradient of CH$_2$Cl$_2$/MeOH (97/3 followed by 95/5) to give 299 mg of a mixture of two products according to TLC. The mixture was therefore purified further by flash chromatography using a stepwise gradient of ethyl acetate/toluene (9/1, 93/7, 95/5, 100/0) to give 46 mg (9%) of (BnOOC—CH$_2$)$_2$—(R)Cgl-Pro-Pab(Z) which eluated first from the column followed by 133 mg (31%) of the desired product BnOOC—CH$_2$—(R)Cgl-Pro-Pab(Z).

$^1$H-NMR (300 MHz, CDCl$_3$): BnOOC—CH$_2$—(R)Cgl-Pro-Pab(Z): δ 0.9–1.3 (m, 5H), 1.4–2.1 (m, 9H), 2.3–2.4 (m, 1H), 3.05 (d, 1H), 3.20–3.37 (AB-system centered at δ 3.29, 2H), 3.5–3.6 (m, 2H), 4.29–4.57 (ABX-system centered at d 4.43, 2H), 4.62 (d, 1H), 4.91 (apparent singlet, 2H), 5.19 (s, 2H), 6.75 (bs, NH), 7.1–7.5 (m, 12H), 8.7–8.8 (m, 2H+NH), 9.45 (bs, NH)

$^1$H-NMR (300 MHz, CDCl$_3$): (BnOOC—CH$_2$)$_2$—(R)Cgl-Pro-Pab(Z): δ0.68–0.9 (m, 2H), 1.0–1.3 (m, 3H), 1.43 (bd, 1H), 1.55–2.0 (m, 7H), 2.05 (bd, 1H), 2.3–2.4 (m, 1H), 3.15 (d, 1H), 3.25–3.48 (m, 2H), 3.55–3.79 (AB-system centered at d 3.67, 4H), 4.38–4.58 (ABX-system centered at d 4.48, 2H), 4.68 (d, 1H), 4.82–4.98 (AB-system centered at d 4.91, 4H), 5.19 (s, 2H), 6.66 (bs, NH), 7.1–7.5 (m, 17H), 7.75 (d, 2H), 7.80 (t, NH), 9.37 (bs, NH)

$^{13}$C-NMR (75 MHz, CDCl$_3$): amidine and carbonyl carbons: δ 164.7, 168.1, 171.5, 172.3 and 172.6

(iv) HOOC—CH$_2$—(R)Cgl-Pro-Pab×2 HCl 0.133 g (0.20 mmole) of BnOOC—CH$_2$—(R)Cgl-Pro-Pab(Z) was mixed with 0.060 g 5% Pd/C, 1 ml 1M HCl-solution and 10 ml ethanol. The mixture was treated under H$_2$-atmosphere for one hour. After filtration through hyflo and evaporation of the solvent the product in 90% yield, 93 mg, was obtained by freeze drying twice from water.

$^1$H-NMR (300 MHz, D$_2$O): δ 1.0–1.45 (m, 5H), 1.5–2.1 (m, 9H), 2.2–2.4 (m, 1H), 3.55–3.85 (m, 4H; thereof 3.79 (s, 2H)), 4.23 (d, 1H), 4.33–4.57 (m, 3H), 7.44 (d, 2H), 7.69 (d, 2H)

$^{13}$C-NMR (75 MHz, D$_2$O): amidine and carbonyl carbons: δ 166.9, 167.2, 169.1, 174.5

Example 4
HOOC—CH$_2$—CH$_2$—(R)Cgl-Pro-Pab×2 HCl
(i) BnOOC—CH$_2$—CH$_2$—(R)Cgl-Pro-Pab(Z)

0.406 g (0.782 mmole) of H—(R)Cgl-Pro-Pab(Z) (See Example 3) was dissolved in 3 ml ethanol and 132 μl (0.861 mmole) of bensylacrylate was added. The reaction mixture was stirred for three days at room temperature. The mixture was evaporated and the crude product purified by flash chromatography using a stepwise gradient of CH$_2$Cl$_2$:MeOH 95/5 and 90/10 as eluent to yield 0.399 g (75%) of the product.

$^1$H-NMR (300 MHz, CDCl$_3$):δ 0.8–1.0 (m, 1H), 1.0–1.3 (m, 4H), 1.35–2.2 (m, 9H), 2.3–2.6 (m, 4H), 2.65–2.78 (m, 1H), 3.05 (d, 1H), 3.4–3.6 (m, 2H), 4.25–4.52 (ABX-system central at d 4.40, 2H), 4.64 (dd, 1H), 5.05 (s, 2H), 5.20 (s, 2H), 7.2–7.38 (m, 10H), 7.43 (d, 2H), 7.78 (d, 2H)

$^{13}$C-NMR (75 MHz, CDCl$_3$): amidine and carbonyl carbons: δ 164.7, 167.9, 171.3, 172.7 and 175.4.

(ii) HOOC—CH$_2$—CH$_2$—(R)Cgl-Pro-Pab×2 HCl 0.261 g (0.383 mmole) of BnOOC—CH$_2$—CH$_2$—(R) Cgl-Pro-Pab(Z) was mixed with 0.075 g 5% Pd/C, 1 ml 1M HCl-solution and 10 ml ethanol. The mixture was hydrogenated at atmospheric pressure for two hours. After filtration through hyflo and evaporation of the solvent the product 0.196 g (96%) was obtained by freeze drying twice from water $^1$H—NMR (300 MHz, D$_2$O): δ 1.17–1.40 (m, 5H), 1.60–1.92 (m, 5H), 1.92–2.2 (m, 4H), 2.32–2.48 (m, 1H), 2.81 (t, 2H), 3.11–3.36 (ABX$_2$-system centered at δ 3.24, 2H), 3.63–3.90 (m, 2H), 4.25 (d, 1H), 4.42–4.63 (m, 3H), 7.54 (d, 2H), 7.78 (d, 2H)

$^{13}$C-NMR (75 MHz, D$_2$O): amidine and carbonyl carbons: δ 167.0, 167.30, 174.6 and 174.7.

Example 5

(HOOC—CH$_2$)$_2$—(R)Cgl-Pro-Pab×2 HCl 46 mg (0.056 mmole) of (BnOOC—CH$_2$)$_2$—(R)Cgl-Pro-Pab(Z) (See Example 3) was mixed with 25 mg 5% Pd/C, 0.7 ml 1M HCl-solution and 7 ml ethanol. The mixture was hydrogenated at atmospheric pressure for one hour. The catalyst was filtered off through hyflo and the solvent evaporated. The final product 25 mg (77%) was obtained by freeze drying twice from water.

$^1$H-NMR (300 MHz, D$_2$O): δ 1.0–1.4 (m, 5H), 1.45–2.2 (m, 9H), 2.25–2.45 (m, 1H), 3.53–3.84 (m, 2H), 3.84–4.22 (AB-system centered at δ 4.03, 4H), 4.26 (d, 1H), 4.35–4.6 (m, 3H), 7.53 (d, 2H), 7.77 (d, 2H)

$^{13}$C-NMR (75 MHz, D$_2$O): amidine and carbonyl carbons: δ 167.1, 167.3, 170.6 and 174.5

Example 6

H—(R)Cgl-Pic-Pab×2 HCl (i) Boc-(R)Cgl-Pic-Pab(Z)

0.478 g (2.49 mmol) EDC was added at −18° C. to a stirred solution of 0.875 g (2.37 mmol) Boc-(R)Cgl-Pic-OH (See preparation of starting materials), 1.22 g (9.97 mmol) DMAP, and 0.706 g (2.49 mmol) H-Pab(Z) (See preparation of starting materials) in a mixture of 30 ml acetonitrile and 1 ml DMF. The reaction mixture was allowed to reach room temperature during a couple of hours and stirring was continued for 48 h. The solvent was removed in vacuo and the residue was dissolved in 50 ml ethyl acetate. The solution was washed with 15 ml water, 3×15 ml 0.3 M KHSO$_4$, 2×15 ml Na$_2$CO$_3$ solution and water. Removal of the solvent gave a residue which was subjected to flash chromatography using ethyl acetate/heptane 9:1 as eluent. The yield was 0.96 g (64%).

(ii) H—(R)Cgl-Pic-Pab(Z)

Hydrogen chloride was bubbled through a solution of 0.56 g (0.88 mmol) Boc-(R)Cgl-Pic-Pab(Z) in 25 ml ethyl acetate. After a couple of minutes crystals precipitated from the solution. The solvent was removed in vacuo and 50 ml ethyl acetate was added. Washing with 2×15 ml 2 M sodium hydroxide solution and extraction of the aqueous phase with 25 ml ethyl acetate was followed by drying (sodium sulphate) of the combined extracts and removal of the solvent in vacuo to give 0.448 g (95%) of the desired product.

(iii) H—(R)Cgl-Pic-Pab×2 HCl

A solution of 98 mg (0.18 mmol) H-Cgl-Pic-Pab(Z) in 5 ml 95% ethanol and 1 ml water was stirred in an atmosphere of hydrogen for 4 hours in the presence of 5% Pd/C. The mixture was filtered and 0.3 ml 1 M hydrochloric acid was added. The ethanol was removed in vacuo and the residue was freeze dried to give 70 mg (81%) of the desired compound.

$^1$H-NMR (300 MHz, CD$_3$OD): δ 1.00–1.56 (m, 7H), 1.56–1.94 (m, 9H), 2.32 (bd, 1H), 3.32–3.45 (m, 1H), 3.90 (bd, 1H), 4.35 (d, 1H), 4.50 (s, 2H), 5.10–5.20 (m, 1H), 7.55 (d, 2H), 7.76 (d, 2H)

$^{13}$C-NMR (75 MHz, D$_2$O): amidine and carbonyl carbons: δ 167.2, 170.5 and 173.4.

Example 7

HOOC—CH$_2$—(R,S)CH(COOH)—(R)Cgl-Pic-Pab×2 HCl (i) BnOOC—CH$_2$—(R,S)CH(COOBn)—(R)Cgl-Pic-Pab(Z)

A mixture of 350 mg (0.66 mmol) H—(R)Cgl-Pic-Pab(Z) (See Example 6) and 233 mg dibenzyl maleate in 2.5 ml ethanol was kept at room temperature for 4 days. The ethanol was removed in vacuo and the residue was subjected to flash chromatography using ethyl acetate/heptane 9:1 as eluent to give 0.108 mg of the product.

(ii) HOOC—CH$_2$—(R,S)CH(COOH)—(R)Cgl-Pic-Pab×2 HCl 105 mg (0.13=mmol) BnOOC—CH$_2$—(R,S)CH(COOBn)—(R)Cgl-Pic-Pab(Z) dissolved in 5 ml 95% ethanol and 1 ml water was hydrogenated for 5 hours in the presence of 5% Pd/C. 0.3 ml 1 M hydrochloric acid was added and the mixture was filtered and the solvent was removed in vacuo. The residue was dissolved in water and freeze dryed to yield 54 mg (73%) of the desired substance.

$^1$H-NMR (300 MHz, CD$_3$OD, mixture of two diastereomers 5/4): δ 1.10–1.60 (m, 7H), 1.60–2.04 (m, 9H), 2.23–2.42 (m, 1H), 2.93–3.15 (m 2H), 3.30–3.42 (m, 1H, partially hidden by the MeOD-peak), 3.71–3.95 (m, 1H), 3.98–4.10 (m, 1H), 4.40–4.60 (m, 3H), 5.10–5.20 (m, 1H), 7.49–7.60 (m, 2H), 7.70–7.81 (m, 2H)

$^{13}$C-NMR (75 MHz D$_2$O): amidine and carbonyl carbons: δ 167.1, 168.95, 169.6 and 173.1.

MS m/z 516 (M$^+$+1)

Example 8

H—(R)Cha-Aze-Pab×2 HCl (i) Boc-(R)Cha-Aze-Pab(Z)

409 mg (2.13 mmol) EDC was added at −18° C. to a stirred mixture of 0.72 g (2.03 mmol) Boc-(R)Cha-Aze-OH (See preparation of starting materials), 1.04 g (8.53 mmol) DMAP, and 604 mg (2.13 mmol) H-Pab(Z) (See preparation of starting materials) in 20 ml acetonitrile. The reaction mixture was allowed to reach room temperature over night and the solvent was subsequently removed in vacuo. The residue was dissolved in 40 ml ethyl acetate and the organic phase was washed successively with 10 ml water, 3×10 ml 0.3M KHSO4, 2×10 ml Na$_2$CO$_3$—NaCl (aq), and finally 10 ml Brine. Drying (Na$_2$SO$_4$) and removal of the solvent in vacuo gave a residue which was subjected to flash chromatography using ethyl acetate/methanol 9:1 as eluent to yield 645 mg (51%) of the title compound.

(ii) H—(R)Cha-Aze-Pab(Z)

Hydrogen chloride was bubbled through a solution of 640 mg (1.03 mmol) Boc-(R)Cha-Aze-Pab(Z) in 25 ml of ethyl acetate. After a couple of minutes, TLC analysis indicated the completion of the reaction. Vacuum was applied to remove excess hydrogen chloride and the mixture was then diluted to 50 ml with ethyl acteate. Washing with 2×15 ml Na$_2$CO$_3$ (aq) was followed by extraction of the aqueous phase with 15 ml ethyl acetate. The combined organic extracts were washed with water and dried (Na$_2$CO$_3$) and the solvent was removed in vacuo to give 513 mg (96%) of H—(R)Cha-Aze-Pab(Z).

(iii) H—(R)Cha-Aze-Pab×2 HCl 76 mg (0.15 mmol) H—(R)Cha-Aze-Pab(Z) dissolved in 5 ml 95% ethanol and 1 ml water was hydrogenated at atmospheric pressure in the presence of 5% Pd/C for 4 h. Removal of the catalyst by filtration, addition of 0.4 ml 1M hydrochloric acid and evaporation of the solvent in vacuo gave a residue which was dissolved in 2 ml water. Freeze drying gave 57 mg (85%) of the product.

¹H-NMR (500 MHz, D$_2$O, 2 rotamers, 3:1 mixture): δ 1.02–1.20 (m, 2H), 1.22–1.92 (m, 11H), 2.40–2.50 (m, 1H), 2.80–2.90 (m, 1H), 4.25 (bt, 1H), 4.40 (dq, 1H), 4.53 (dq, 1H), 4.65 (s, 2H), 5.05–5.10 (m, 1H), 7.65 (d, 2H), 7.88 (d, 2H).

Chemical shifts of resolved signals of the minor rotamer: δ 0.57 (m), 0.85 (m), 2.95 (m), 4.06 (dq), 4.17 (dq), 4.63 (s), 5.33 (m), 7.70 (d), 7.93 (d).

¹³C-NMR (125 MHz D$_2$O): amidine and carbonyl carbons: δ 167.2, 170.4 and 172.8.

Example 9
HOOC—CH$_2$—(R)Cha-Aze-Pab×2 HCl
(i) BnOOC—CH$_2$—(R)Cha-Aze-Pab(Z)

0.119 g (0.52 mmol) benzyl bromoacetate was added to a mixture of 0.27 g (0.52 mmol) H—(R)Cha-Aze-Pab(Z) (See Example 8) and 0.158 g (1.14 mmol) K$_2$CO$_3$ in 5.2 ml acetonitrile and heated to 60° C. in an oilbath for 1 h. The solvent was removed and ethyl acetate and water was added. The phases were separated and the organic phase was washed with brine and dried (Na$_2$SO$_4$). Evaporation in vacuo gave 0.344 g of a residue which was subjected to flash chromatography using ethyl acetate as eluent, and then another time using ethylacetate:tetrahydrofuran: NH$_3$-saturated methanol (60:5:2) to give 0.163 g of the desired product.

¹H-NMR (300 MHz, CDCl$_3$); δ 0.7–1.0 (m, 2H). 1.05–2.05 (m, 11H), 2.35–2.55 (m, 1H), 2.55–2.75 (m, 1H), 3.15–3.32 (m, 3H), 3.95–4.05 (t, 2H), 4.4 and 4.5 (ABX-system, 2H), 4.8–4.95 (m, 1H), 5.05 (s, 2H), 5.2 (s, 2H), 7.2–7.5 (m, 12H), 7.7–7.85 (d, 2H), 8.3–8.45 (t, 1H).

¹³C-NMR (75 MHz, CDCl$_3$): amidine and carbonyl carbons: δ 164.5, 167.8, 170.7, 171.9 and 175.9.

(ii) HOOC—CH$_2$—(R)Cha-Aze-Pab×2 HCl 0.163 g (0.243 mmol) BnOOC—CH$_2$—(R)Cha-Aze-Pab (Z) dissolved in 5.5 ml ethanol (99.5%) and 0.7 ml hydrogen chloride (1 N) was hydrogenated in the presence of 0.17 g 5% Pd/C for 4 h. Removal of the catalyst by filtration and evaporation of the solvent followed by dissolving in water and freeze drying gave 107 mg (85%) of the title compound.

¹H-NMR (500 MHz, CD$_3$OD, mixture of two rotamers): major rotamer: δ 0.95–1.95 (m, 13H), 2.3–2.4 (m, 1H), 2.6–2.75 (m, 1H), 3.5–3.75 (m, 2H), 4.05–4.15 (m, 1H), 4.15–4.23 (m, 1H), 4.36–4.43 (m, 1H), 4.43–4.5 (m, 1H), 4.58–4.65 (m, 1H), 4.83–4.88 (m, 1H), 7.5–7.6 (m, 2H), 7.73–7.82 (m, 2H).

Resolved signals from the minor rotamer appears at δ 2.2–2.3 (m), 3.95–4.05 (m), 5.1–5.17 (m), 7.6–7.67 (m).

¹³C-NMR (75 MHz, CD$_3$OD): amidine and carbonyl carbons; δ 168.2, 169.8, 168.9 and 172.3.

Example 10
HOOC—CH$_2$—(R,S)CH(COOH)—(R)Cha-Aze-Pab×2 HCl
(i) BnOOC—CH$_2$—(R,S)CH(COOBn)—(R)Cha-Aze-Pab (Z)

A mixture of 230 mg (0.443 mmol) H—(R)Cha-Aze-Pab (Z) (See Example 8) and 144 mg (0.487 mmol) dibenzyl maleate in 1.5 ml 95% ethanol was stirred at ambient temperature for 5 days. After removal of the ethanol in vacuo, the residue was subjected to flash chomatography using ethyl acetate/methanol 95/5 as eluent to give 54 mg (15%) of the product.
(ii) HOOC—CH$_2$—(R,S)CH(COOH)—(R)Cha-Aze-Pab 49 mg (0.06 mmol) BnOOC—CH$_2$—(R,S)CH (COOBn)—(R)Cha-Aze-Pab(Z) dissolved in 5 ml 95% ethanol and 1 ml water was hydrogenated in the presence of 5% Pd/C for 4.5 h. Removal of the catalyst by filtration and evaporation of the solvent in vacuo gave a residue which was dissolved in 2 ml water and 0.2 ml 1M hydrochloric acid. Freeze drying gave 32 mg (93%) of the product.

The ¹H-NMR spectrum of the title compound in D$_2$O exhibits two sets of strongly overlapping signals arising from the two diastereomers. Additionally resolved resonances of a minor rotamer, integrating to approximatly 15% also appears in the spectrum.

¹H-NMR (300 MHz, D$_2$O): δ 1.03–2.00 (m, 13H), 2.32–2.53 (m, 1H), 2.72–2.96 (m 1H), 3.06–3.28 (m, 2H), 4.10–4.55 (m, 4H), 4.62 (bs, 2H), 5.00–5.10 (m, 1H), 7.55–7.68 (m, 2H), 7.80–7.94 (m, 2H)

Resolved signals from the minor rotamer appears at δ 0.65 (m), 0.80 (m), 4.00 (m), 5.24 (m), 5.35 (m).

¹³C-NMR (75 MHz D$_2$O): amidine and carbonyl carbons: δ 167.2, 169.0, 171.0, 172.3 and 174.1.

Example 11
HOOC—CH$_2$—(R or S)CH(COOH)-Cha-Aze-Pab/a×2 HCl
(i) BnOOC—CH$_2$—(R or S)CH(COOBn)—(R)Cha-Aze-Pab(Z)/a A mixture of 2.0 g (3.8491 mmol) H—(R)Cha-Aze-Pab (Z) (See Example 8) and 1.37 g dibenzyl maleate in 10 ml 95% ethanol was stirred at ambient temperature for 4 days. After removal of the ethanol in vacuo, the residue was subjected to flash chromatography using ethyl acetate/methanol 98/2 as eluent to give 1.024 g (32%) of BnOOC—CH$_2$—(R,S)CH(COOBn)-(R)Cha-Aze-Pab(Z). The two diastereomers were separated by RPLC using (CH$_3$CN/0.1 M NH$_4$OAc 65/35) as eluent. This diastereomer eluted first from the column. After removal of the acetonitrile in vacuo the water phase was extracted three times with ethyl acetate. The organic phase was washed once with water dried (Na$_2$SO$_4$), filtered and evaporated to yield 0.352 g of the title compound as a pure stereoisomer.

(ii) HOOC—CH2—(R or S)CH(COOH)—(R)Cha-Aze-Pab/a 2×HCl 350 mg (0.43 mmol) BnOOC—CH$_2$—(R or S)CH(COOBn)—(R)Cha-Aze-Pab(Z)/a (The diasteisomer from (i) above) dissolved in 15 ml 95% ethanol and 3 ml water was hydrogenated in the presence of 5% Pd/C for 4.5 h. Removal of the catalyst by filtration and evaporation of the solvent in vacuo gave a residue which was dissolved in 5 ml water and 1.0 ml 1M hydrochloric acid. Freeze drying gave 214 mg (87%) of the product as a pure stereoisomer.

¹H-NMR (300 MHz, MeOD, mixture of two rotamers): δ 0.85–1.93 (m, 13H), 2.25–2.38 (m, 1H), 2.60–2.75 (m, 1H), 2.88 (dd, 2H), 3.92 (t, 1H), 4.15–4.25 (m, 2H), 4.30–4.43 (m, 1H), 4.56 (AB-system, 2H), 4.76–4.86 (m, 1H, partially obscured by the solvent signal), 7.59 (d, 2H), 7.78 (d, 2H).

Resolved signals arising from the minor rotamer appears at δ 0.70, 2.95, 3.82, 4.00, 5.08 and 7.83

¹³C-NMR (75 MHz D$_2$O): amidine and carbonyl carbons: δ 166.9, 168.8, 171.7, 172.3 and 173.8.

Example 12
HOOC—CH$_2$—(RorS)CH(COOH)—(R)Cha-Aze-Pab/b×2 HCl
(i) BnOOC—CH$_2$—(R or S)CH(COOBn)—(R)Cha-Aze-Pab(Z)/b The title compound was obtained by using the same procedure as described in Example 11 above on BnOOC—CH$_2$—(R,S)CH(COOBn)—(R)Cha-Aze-Pab(Z). This diastereomer came out after the first one from the column. Yield 0.537 g.

(ii)HOOC—CH$_2$—(RorS)CH(COOH)—(R)Cha-Aze-Pab/b×2 HCl 530 mg (0.65 mmol) BnOOC—CH$_2$—(R or S)CH (COOBn)—(R)Cha-Aze-Pab(Z)/b dissolved in 15 ml 95% ethanol and 3 ml water was hydrogenated in the presence of 5% Pd/C for 5 h. Removal of the catalyst by filtration and evaporation of the solvent in vacuo gave a residue which was dissolved in 6 ml water and 1.0 ml 1M hydrochloric acid. Freeze drying gave 290 mg (78%) of the product.

$^1$H-NMR (300 MHz, MeOD, mixture of two rotamers): δ 0.86–1.90 (m, 13H), 2.30–2.42 (m, 1H), 2.60–2.75 (m,1H), 2.75–2.85 (m, 1H), 2.95–3.05 (m, 1H), 3.65–3.71 (m, 1H), 4.00–4.10 (m, 1H), 4.14–4.24 (m, 1H), 4.36–4.62 (m, 3H), 4.78–4.86 (m, 1H partially obscured by the solvent signal), 7.57 (d, 2H), 7.75 (d, 2H).

Resolved signals arising from a minor rotamer appears at δ 0.78, 2.92, 3.82, 5.36 and 7.80

$^{13}$C-NMR (75 MHz D$_2$O): amidine and carbonyl carbons: δ 166.8, 169.0, 172.0, 172.4 and 175.2.

Example 13

HOOC—CH$_2$—CH$_2$—(R)Cha-Aze-Pab×2 HCl (i) BnOOC—CH$_2$—CH$_2$—(R)Cha-Aze-Pab(Z)

A mixture of 182 mg (0.35 mmol) H—(R)Cha-Aze-Pab(Z) (See Example 8) and 62.5 mg (0.385 mmol) benzyl acrylate in 1.5 ml 95% ethanol was stirred at room temperature for 4 days. The solvent was removed in vacuo and the residue was subjected to flash chromatography using ethyl acetate/methanol 9:1 as eluent to give 200 mg (84%) of the title compound.

(ii) HOOC—CH$_2$—CH$_2$—(R)Cha-Aze-Pab×2 HCl 195 mg (0.29 mmol) BnOOC—CH$_2$—CH$_2$—(R)Cha-Aze-Pab(Z) dissolved in 10 ml 95% ethanol and 2 ml water was hydrogenated in the presence of 5% Pd/C for 4 h. Removal of the catalyst by filtration and evaporation of the solvent in vacuo gave a residue which was dissolved in 2 ml water and 0.4 ml 1M hydrochloric acid. Freeze drying gave 130 mg (86%) of the product.

$^1$H-NMR (500 MHz, CD$_3$OD): δ 0.98–1.27 (m, 2H), 1.30–1.90 (m, 11H), 2.27–2.35 (m, 1H), 2.65–2.74 (m, 1H), 2.77 (t, 2H), 3.32 (t, 2H), 4.10 (t, 1H), 4.17–4.25 (m, 1H), 4.40–4.49 (m, 1H), 4.55 (AB, 2H), 4.83–4.90 (m, 1H), 7.58 (d, 2H), 7.77 (d, 2H).

$^{13}$C-NMR (125 MHz D$_2$O): amidine and carbonyl carbons: δ 167.0, 168.9, 172.4 and 174.6.

Example 14

HOOC—CH$_2$—NH—CO—CH$_2$—(R)Cha-Aze-Pab×2 HCl (i) BnOOC—CH$_2$—NH—CO—CH$_2$—(R)Cha-Aze-Pab(Z)

A mixture of 0.212 g (0.408 mmole) H—(R)Cha-Aze-Pab(Z) (See Example 8), 0.124 g (0.89 mmole) K$_2$CO$_3$ and 0.128 g (0.449 mmole) BnOOC—CH$_2$—NH—CO—CH$_2$—Br (See preparation of starting materials) in 6 ml acetonitrile was stirred at 50° C. for two hours. After evaporation of the solvent the residue was dissolved in water and ethyl acetate. The water layer was extracted twice with ethyl acetate and the combined organic layer was dried (Na$_2$SO$_4$), filtered and evaporated. The product was purified by flash chromatography using a stepwise gradient of ethyl acetate/tetrahydrofurane (85/15, 4/1, 7/3) to yield 0.190 g (64%) of the title compound.

$^1$H-NMR (300 MHz, CDCl$_3$): δ 0.75–2.1 (m, 13H), 2.43 (m, 1H), 2.56 (d, 1H), 2.79 (m, 1H), 3.0–3.15 (m, 2H; thereof 3.05 (d, 1H)), 3.89–4.18 (m, 5H), 4.8–4.98 (m, 2H), 5.15 (s, 2H), 5.18 (s, 2H), 7.2–7.47 (m, 12H), 7.72 (t, NH), 7.86 (d, 2H), 8.14 (bs, NH), 8.31 (dd, NH), 9.42 (bs, NH)

$^{13}$C-NMR (75 MHz, CDCl$_3$): amidine and carbonyl carbons: δ 164.5, 168.7, 169.22, 169.83, 171.7, 175.5

(ii) HOOC—CH$_2$—NH—CO—CH$_2$—(R)Cha-Aze-Pab×2 HCl 0.19 g (0.26 mmole) of BnOOC-CH$_2$—NH—CO—CH$_2$—(R)Cha-Aze-Pab(Z) was mixed with 0.075 g 5 t Pd/C, 1.5 ml 1N HCl-solution, 3 ml water and 17 ml ethanol and the mixture was hydrogenated at atmospheric pressure for one hour. Filtration of the catalyst, evaporation of the solvent followed by freeze drying from water gave 144 mg (97%) of the title compound.

$^1$H-NMR (D$_2$O, 300 MHz, two rotamers 4:1): δ 0.88–1.88 (m, 13H), 2.25–2.42 (m, 1H), 2.63–2.89 (m, 1H), 3.94 (s, 2H), 3.99 (apparent doublet, 2H), 4.16 (t, 1H), 4.28 (q, 1H), 4.41 (q, 1H), 4.56 (s, 2H), 4.98 (dd, 1H), 7.53 (d, 2H), 7.77 (d, 2H), Resolved signals from the minor rotamer appears at δ 0.50 (bq), 0.77 (bq), 5.21 (dd), 7.56 (d) and 7.81 (d).

$^{13}$C-NMR (D$_2$O, 75 MHz): The carbonyls and amidine-carbon at δ 166.8, 166.9, 168.6, 172.3 and 173.4.

Resolved signals from the minor rotamer appears at δ: 166.6, 169.6 and 172.0

Example 15

H—(R)Cha-Pro-Pab×2 KCl (i) Boc-(R)Cha-Pro-Pab(Z)

0.135 ml (1.1 mmol) pivaloyl chloride was added at room temperature to a stirred mixture of 0.155 ml (1.1 mmol) triethyl amine and 405 mg (1.1 mmol) Boc-(R)Cha-Pro-OH (See preparation of starting materials) in 5 ml DMF. After 3 h 340 mg (1.1 mmol) H-Pab(Z)(See preparation of starting materials) in 5 ml DMF was added and stirring was continued over night. The reaction mixture was diluted with water and extracted with ethyl acetate/toluene 1:1. The organic phase was dried (MgSO$_4$) and the solvent was removed in vacuo to give a residue which was subjected to flash chromatography using ethyl acetate as eluent. The yield was 309 mg (49%).

(ii) H—(R)Cha-Pro-Pab(Z)

Hydrogen chloride was bubbled through a solution, until saturation, of 1.246 g (2 mmol) Boc-(R)Cha-Pro-Pab(Z) in 20 ml ethyl acetate at room temperature. After 30 minutes sodium carbonate solution (10%) was added and the organic phase which separated was dried (K$_2$CO$_3$). The drying agent was washed with methylene chloride and the solvent was evaporated from the combined organic phases to give 1.11 is g (100%) of the title compound.

(iii) H—(R)Cha-Pro-Pab×2 HCl 100 mg (0.19 mmol) H—(R)Cha-Pro-Pab(Z) dissolved in 15 ml ethanol was hydrogenated in the presence of 38 mg 10% Pd/C for 1.5 h. Dilution of the reaction mixture with distilled water and removal of the catalyst by filtration followed by removal of the ethanol in vacuo and freeze drying gave the title compound as a colorless powder. The peptide was finally converted to the dihydrochloride by dissolution in hydrochloric acid followed by freeze drying to give 90 mg (100%) of the title compound.

$^1$H-NMR (300 MHz, D2O); & 1.0–2.0 (m, 13H), 2.0–2.3 (m, 3H), 2.3–2.5 (m, 1H), 3.6–3.7 (m, 1H), 3.8–3.9 (m, 1H), 4.3–4.5 (t, 1H), 4.5–4.6 (m, 3H), 7.4–7.6 (m, 3H), 7.6–7.9 (m, 2H).

$^{13}$C-NMR (75 MHz, D2O): amidine and carbonyl carbons: δ 167.2, 170.0, 174.9.

Example 16

HOOC—CH$_2$—(R)Cha-Pro-Pab×2 HCl (i) BnOOC—CH$_2$—(R)Cha-Pro-Pab(Z)

A mixture of 268 mg (0.5 mmol) H—(R)Cha-Pro-Pab(Z) (See Example 15), 90 μl (0.55 mmol) benzyl bromoacetate and 181 mg (1.3 mmol) K$_2$CO$_3$ in 2 ml acetonitrile was sonicated at 40° C. for 2.5 h. The mixture was filtered through hyflo and the solvent was removed in vacuo to give a residue which was subjected to flash chromatography using ethyl acetate as eluent to give 194 mg (57%) of the title compound.

HOOC—CH$_2$—(R)Cha-Pro-Pab×2 HCl 194 mg (0.28 mmol) BnOOC—CH$_2$—(R)Cha-Pro-Pab(Z) dissolved in 10 ml ethanol was hydrogenated in the presence of 77 mg 10% Pd on charcoal for 3 h. The reaction mixture was diluted with water and the catalyst was removed by filtration. Evaporation of the ethanol in vacuo followed by freeze drying gave a white residue. Hydrochloric acid was added and the resulting solution was finally freeze dried to give 115 (68%) of the desired product.

$^1$H-NMR (300 MHz, D$_2$O); δ 1.0–1.2 (m, 2H), 1.2–1.5 (m, 3H), 1.5–2.0 (m, 5H), 2.0–2.3 (m, 3H), 2.3–2.5 (m, 1H), 3.6–3.8 (m, 1H), 3.8–4.0 (m, 3H), 4.4–4.7 (m, 4H), 7.5–7.7 (d, 2H), 7.7–7.9 (d, 2H).

$^{13}$C-NMR (75 MHz, D$_2$O): amidine and carbonyl carbons: δ 167.1, 168.2, 169.3, 174.6.

Example 17

HOOC—CH$_2$—(Me)(R)Cha-Pro-Pab (i) Boc-(Me)(R)Cha-Pro-Pab(Z)

To a solution of 0.8 g (1.67 mmol) of Boc-(Me)(R)Cha-Pro-OSu (See preparation of starting materials) in 3 ml DMF was added a solution of 0.562 g (1.85 mmol) of H-Pab(Z) (See preparation of starting materials) in 3 ml of DMF, and the pH of the resulting solution was adjusted to 8–9 with N-methylmorpholine, whereafter the solution was stirred at room temperature for 2 days.

The solution was poured onto water, and the resulting mixture was extracted with 3×25 ml of ethyl acetate. The organic solution was washed with 1M KHSO$_4$ solution, 10% NaHCO$_3$ solution, water and brine, and dried (Na$_2$SO$_4$). Evaporation of the solvent gave 0.65 g (60%) of the title compound as a yellowish white powder.

(ii) Me—(R)Cha-Pro-Pab(Z)

A solution of 0.60 g (0.92 mmol) of Boc-(Me)(R)Cha-Pro-Pab(Z) in 50 ml of EtOH was saturated with HCl at 0° C., and the solution was stored in refrigerator overnight. The resulting solution was evaporated to dryness, and the residue was dissolved in a Na$_2$CO$_3$ solution, extracted with 3×25 ml ethyl acetate. The extract was washed with brine and evaporated to give 0.4 g (791) of the compound as a white fluffy powder.

$^1$H-NMR (CDCl$_3$, 300 MHz): δ 0.8–1.0 (m, 2H), 1.1–1.4 (m, 5H), 1.4–1.55 (m, 1H), 1.6–1.9 (m, 10H), 1.9–2.05 (m, 2H), 2.05–2.2 (m, 2H), 2,19 (s,3H), 2.4–2.5 (m, 1H), 3.28 (dd, 1H), 3.41 (q, 1H), 3.62 (m, 1H), 4.42 (m, 2H), 4.61 (d, 1H), 5.2 (s, 2H), 7.2–7.45 (m, 7H), 7.72 (t, 1H), 7.79 (d, 2H).

(iii) BnOOC—CH$_2$-(Me)(R)Cha-Pro-Pab(Z)

A mixture of 0.40 g (0.73 mmol) of Me—(R)Cha-Pro-Pab(Z), 0.17 g BnOOC—CH$_2$Br and 0.20 g (2 equiv.) of K$_2$CO$_3$ (mortared) in 15 ml of CH$_3$CN was stirred at room temperature overnight. The resulting mixture was evaporated, ethyl acetate was added, and the mixture was washed with water and brine, dried (Na2SO4), and evaporated. The crude product (0.69 g) was subjected to flash chromatography (CH$_2$Cl$_2$/MeOH 10/1) yielding 0.39 g (77%) of a light yellow very viscous oil.

HOOC—CH$_2$-(Me)(R)Cha-Pro-Pab

To a solution of 0.39 g (0.56 mmol) of BnOOC—CH$_2$-(Me)(R)Cha-Pro-Pab(Z) in 30 ml of EtOH was added 0.1 g of Pd/C (10%), and the substance was hydrogenated at atmospheric pressure. The solution was filtered and evaporated, whereafter the remaining syrupy material was freeze dried to yield 0.25 g (95%) of the compund as a white crystalline powder.

$^1$H-NMR (300 MHz, CD$_3$OD): δ 0.85–1.1 (m, 2H), 1.1–1.4 (m, 6H), 1.5–1.85 (m, 9H), 1.9–2.05 (m, 3H), 2.05–2.15 (m, 1H), 2.15–2.3 (m, 1H), 2.57 (s, 3H), 3.32 (d, 1H), 3.55–3.75 (m, 2H), 3.95–4.1 (m, 2H), 4.35–4.5 (m, 3H), 7.55 (d, 2H), 7.72 (d, 2H).

$^{13}$C-NMR (75 MHz, CD$_3$OD): amidine and carbonyl carbons: δ 168.4, 171.5, 174.7, 175.1.

Example 18

HOOC—CH$_2$—CH$_2$—(R)Cha-Pro-Pab×2 HCl (i) BnOOC—CH$_2$—CH$_2$—(R)Cha-Pro-Pab(Z)

A mixture of 149 mg (0.28 mmol) H—(R)Cha-Pro-Pab(Z) (See Example 15) and 66 mg (0.4 mmol) benzyl acrylate in 1.5 ml ethanol was kept at room temperature for 36 h. The solvent was removed in vacuo and the residue was subjected to flash chromatography using ethyl acetate as eluent to give 124 mg (64%) of the desired product.

(ii) HOOC—CH$_2$—CH$_2$—(R)Cha-Pro-Pab×2 HCl 124 mg (0.18 mmol) BnOOC—CH$_2$—CH$_2$—(R)Cha-Pro-Pab(Z) dissolved in 10 ml ethanol was hydrogenated for 1 h in the presence of 55 mg 10% Pd/C. The catalyst was removed by filtration and the solvent was removed in vacuo. The residue was dissolved in hydrochloric acid and the resulting solution was freeze dried to give 87 mg (79%) of the title compound.

$^1$H-NMR (300 MHz, D$_2$O): δ 1.0–2.0 (m, 13H), 2.0–2.2 (m, 3H), 2.2–2.4 (m, 1H), 2.7–2.8 (t, 2H), 3.2–3.3 (m, 1H), 3.3–3.4 (m, 1H), 3.5–3.7 (m, 1H), 3.7–3.9 (m, 1H), 4.3–4.6 (m, 4H), 7.4–7.6 (m, 2H), 7.7.6–7.8 (m, 2H).

$^{13}$C-NMR (75 MHz, D$_2$O): amidine and carbonyl carbons: δ 167.0, 168.3 and 174.6 (Two carbons are overlapping).

Example 19

HOOC—CH$_2$—CH$_2$—(Me)(R)Cha-Pro-Pab×2 HCl (i) BnOOC—CH$_2$—CH$_2$-(Me)(R)Cha-Pro-Pab(Z)

To a solution of 274 mg (0.5 mmol) of Me—(R)Cha-Pro-Pab(Z) (See Example 17) in 5 ml of EtOH (99%) was added 97.3 mg (0.6 mmol) of benzyl acrylate and the reaction was stirred at room temperature. After 72 h an additional amount of 16.2 mg (0.1 mmol) of benzyl acrylate was added and the stirring continued for 24 h. The solvent was evaporated and the residue was subjected to flash chromatography (CH$_2$Cl$_2$/MeOH(NH$_3$-saturated), 95/5) to give 198 mg (56%) of the title compound.

$^1$H-NMR (500 MHz, CDCl$_3$): δ 0.8–2.0 (several m, 16H), 2.14 (s, 3H), 2.24–2.33 (m, 2H), 2.38–2.46 (m, 1H), 2.67 (t, 2H), 3.32–3.40 (m, 2H), 3.71 (m, 1H), 4.36–4.44 (m, 2H), 4.58 (m, 1H), 5.03 (apparent s, 2H), 5.20 (s, 2H), 7.25–7.37 (m, 10H), 7.43 (d, 2H), 7.64 (t, 1H(NH)), 7.81 (d, 2H).

$^{13}$C-NMR (125 MHz, CDCl$_3$): amidine and carbonyl carbons: δ 164.7, 167.9, 171.7, 172.3 and 172.6.

(ii) HOOC—CH$_2$—CH$_2$-(Me)(R)Cha-Pro-Pab×2 HCl

To a solution of 198 mg (0.27 mmol) BnOOC—CH$_2$—CH$_2$-(Me)(R)Cha-Pro-Pab(Z) in 10 ml EtOH and 1 ml 1M HCl was added 60 mg of 5% Pd/C (containg 50% H$_2$O by weight) and the mixture was hydrogenated at athmospheric pressure for 4 h. The catalyst was filtered off and the solvent was evaporated. The remaining oil was dissolved in water and freeze dried to give the title compound in a quantitative yield.

$^1$H-NMR (500 MHz, D$_2$O): δ 1.08–1.2 (m, 2H), 1.2–1.42 (m, 4H), 1.68–1.91 (m, 5H), 1.93–2.08 (m, 2H), 2.09–2.26 (m, 3H), 2.49 (m, 1H), 2.95 (m, 2H), 3.03 (s, 3H), 3.60 (apparent bs, 2H), 3.82 (m, 1H), 3.98 (m, 1H), 4.53 (m, 1H), 4.61 (bs, 2H), 4.64 (m, 1H), 7.63 (d, 2H), 7.97 (d, 2H).

$^{13}$C-NMR (75 MHz, D$_2$O): amidine and carbonyl carbons: δ 167.2, 167.8 and 174.5. Two peaks are probably overlapping.

Example 20
HOOC—CH$_2$—(R or S)CH(COOH)—(R)Cha-Pro-Pab/a×2 HCl (i) BnOOC—CH$_2$—(R,S)CH(COOBn)—(R)Cha-Pro-Pab(Z)

A mixture of 0.50 g (0.94 mmol) of H—(R)Cha-Pro-Pab(Z) (See Example 15) and 0.28 q (0.94=mol) of dibenzyl maleate in 20 ml of EtOH was kept at room temperature for 5 days. Evaporation of the solvent followed by flash chromatography using CH$_2$Cl$_2$/MeOH as eluent gave 0.15 g (19%) of the diastereomeric mixture.

$^1$H NMR (500 MHz, CDCl$_3$) δ 0.7–2.1 (m, 17H), 2.3–2.4 (m, 1H), 2.5–2.8 (m, 2H), 3.2–3.7 (in, 4H), 4.46 (d, 1H), 4.65 (bd, 1H), 4.81 (d, 1H), 4.9–5.1 (m, 3H), 5.20 (s, 2H), 7.1–7.4 (m, 15H), 7.4–7.5 (m, 2H), 7.6–7.8 (m, 3H).

(ii) HOOC—CH$_2$—(R or S)CH(COOH)—(R)Cha-Pro-Pab/a×2 HCl

A mixture of 0.15 g (0.18 mmol) of BnOOC—CH$_2$—(R,S)CH(COOBn)—(R)Cha-Pro-Pab(Z) was dissolved in 5 ml of ethanol and was hydrogenated over 5% Pd/C at atmospheric pressure for 1 h. to give HOOC—CH$_2$—(R,S)CH(COOH)—(R)Cha-Pro-Pab. The two diastereomers were separated by RPLC using (CH$_3$CN/0.1 M NH$_4$OAc 15/85) as eluent followed by freeze drying from HCl. This diastereomer eluted first from the column. Yield 19 mg (18%).

$^1$H-NMR (500 MHz, D$_2$O, mixture of two rotamers) major rotamer: δ 1.0–2.0 (m, 15H), 2.15 (m, 2H), 2.44 (m, 1H), 3.00 (bd, 1H), 3.05 (bd, 1H), 3.69 (m, 1H), 3.84 (m, 1H), 3.97 (bs, 1H), 4.5–4.7 (1,3H), 7.62 (d, 2H), 7.87 (d, 2H).

$^{13}$C-NMR (75 MHz, D$_2$O): amidine and carbonyl carbons: δ 167.2, 168.3, 173.8, 174.6 and 178.2.

Example 21
HOOC—C$_2$—(RorS)CH(COOH)—(R)Cha-Pro-Pab/b×2 HCl

The title compound was obtained by using the same procedure as described in Example 20 an HOOC—CH$_2$—(R,S)CH(COOH)—(R)Cha-Pro-Pab. This diastereomer came out after the first one from the column. Yield 19 mg (18%).

$^1$H-NM (500 MHz, D$_2$O, mixture of two rotamers) major rotamer: δ 1.0–2.0 (m, 14H), 2.15–2.25 (m, 3H), 2.44 (m, 1H), 3.11 (bd, 1H), 3.19 (bd, 1H), 3.71 (m, 1H), 3.92 (m, 1H), 4.03 (bs, 1H), 4.5–4.7 (m, 3H), 7.58 (d, 2H), 7.84 (d, 2H).

Resolved signals arising from the minor rotamer appears at: δ 7.66 (d) and 7.91 (d).

$^{13}$C-NMR (75 MHz, D$_2$O): amidine and carbonyl carbons: δ 167.3, 168.5 and 174.7. Two carbons are probably overlapping.

Example 22
HOOC—CH$_2$—NH—CO—CH$_2$—(R)Cha-Pro-Pab×2 KCl (i) BnOOC—CH$_2$—NH—CO—CH$_2$—(R)Cha-Pro-Pab(Z)

0.246 g (0.460 mmole) of H—(R)Cha-Pro-Pab(Z) (See Example 15), 0.140 g (1.01 mmole) K$_2$CO$_3$ and 0.145 g (0.506 mmole) BnOOC—CH$_2$—NH—CO—CH$_2$—Br (See preparation of starting materials) was mixed in 6 ml acetonitrile. The mixture was stirred at 50° C. for 2 h 30 minutes, the solvent was evaporated and the residue was partitioned between water and ethyl acetate. The layers were separated and the water layer was extracted one more time with ethyl acetate. The combined organic layer was dried (Na$_2$SO$_4$), filtered and evaporated to yield 0.350 g of an oil. The crude product was purified by flash chromatography using a stepwise gradient of CH$_2$Cl$_2$/MeOH 97/3, 95/5, 92.5/7.5 to yield 0.227 g (67%) of the title compound.

$^{13}$C-NMR (75 MHz, CDCl$_3$): δ 25.0, 26.0, 26.2, 26.4, 26.7, 32.4, 34.2, 34.4, 40.8, 40.9, 42.9, 46.7, 50.5, 58.4, 60.2, 67.0, 67.2, 127.5, 127.8, 128.2, 128.3, 128.4, 128.5, 128.6, 128.6, 134.1, 135.2, 137.0, 142.6, 164.7, 168.9, 169.3, 170.4, 172.2, 175.0

(ii) HOOC—CH$_2$—NH—CO—CH$_2$—(R)Cha-Pro-Pab×2 HCl 0.089 g (0.12 mmole) BnOOC—CH$_2$—NH—CO—CH$_2$—(R)Cha-Pro-Pab(Z) was mixed with 30 mg 5% Pd/C and dissolved in 10 ml acetic acid. The mixture was hydrogenated at athmospheric pressure for one and a half hour. Filtration of the catalyst through hyflo and freeze drying with 1 ml 1N hydrochloric acid gave 0.058 g (82%) of the desired product.

$^1$H—NMR (300 MHz, D$_2$O): δ 0.9–2.2 (m, 16H), 2.25–2.47 (m, 1H), 3.55–3.7 (m, 1H), 3.7–4.1 (m, 5H), 4.42 (t, 1H), 4.48–4.6 (m, 3H), 7.51 (d, 2H), 7.77 (d, 2H)

$^{13}$C-NMR (75 MHz, D$_2$O): amidine and carbonyl carbons: δ 166.8, 167.1, 168.2, 173.6 and 174.6

Example 23
EtOOC—CH$_2$—CH$_2$—CH$_2$—(R)Cha-Pro-Pab×HOAc (i) EtOOC—CH═CH—CH$_2$—(R)Cha-Pro-Pab(Z)

H—(R)Cha-Pro-Pab(Z) (See Example 15) (275 mg, 0.51 mmol) was treated with K$_2$CO$_3$ (141 mg, 1.02 mmol) and BrCH$_2$CH═CHCOOEt (108 mg, 0.56 mmol) in CH$_3$CN (10 ml) at 20° C. for 20 h. The solvent was evaporated and the residue was dissolved in EtOAc (5 ml)/H$_2$O (2 ml). The organic layer was separated, dried (Na$_2$SO$_4$), and concentrated yielding 397 mg of an oil which was purified by flash chromatography using EtOAc/Heptane, 1/4 as eluent to give 252 mg (77%) of the title compound.

$^1$H-NMR (500 MHz, CDCl$_3$): δ 0.8–1.05 (m, 2H), 1.1–1.45 (m, 3H), 1.3 (t, 3H), 1.5–1.9 (m, 8H), 1.95–2.05 (m, 1H), 2.1–2.15 (m, 1H), 2.45–2.55 (m, 1H), 3.0 and 3.15 (two d, 2H), 3.35–3.45 (m, 2H), 3.55–3.65 (m, 1H), 4.15 (q, 2H), 4.3 (d, 1H), 4.6–4.7 (m, 2H), 5.2 (s,2H), 5.85 (d, 1H), 6.75 (dt, 1H), 5.3–5.4 (m, 4H), 7.45 (d, 2H), 7.85 (d, 2H).

$^{13}$C-NMR (75.0 MHz, CDCl$_3$): amidine and carbonyl carbons: δ 165.7, 171.2 and 175.7 (two peaks are probably overlapping).

(ii) EtOOC—CH$_2$—CH$_2$—CH$_2$—(R)Cha-Pro-Pab×HOAc

EtOOCCH═CHCH$_2$—(R)Cha-Pro-Pab(Z) (250 mg, 0.38 mmol) was disolved in ethanol and hydrogenated in the presence of 5% Pd/C during approximately 2 h. Removal of the catalyst by filtration and evaporation of the solvent in vacuo gave after purification by RPLC using (CH$_3$CN/0.1 M NH$_4$OAc) as eluent 70 mg (36%) of the desired product.

$^1$H NMR (500 MHz, CD$_3$OD): δ 0.9–1.05 (m, 2H), 1.15–1.55 (m, 5H), 1.25 (t, 3H), 1.6–1.85 (m, 7H), 1.95–2.6 (m, 8H), 3.55–3.65 (m, 2H), 3.8 (m, 1H), 4.1 (q, 2H), 4.45 (m and d, 2H), 4.55 (d, 1H), 7.55 and 7.75 (two d, 4H).

$^{13}$C-NMR (75.0 MHz, CD$_3$OD): amidine and carbonyl carbons: δ 168.3, 173.2, 174.6 and 174.9.

Example 24
Ph(4-COOH)—SO$_2$—(R)Cha-Pro-Pab×HCl (i) Ph(4-COOH)—SO$_2$—(R)Cha-Pro-Pab(Z)

64 mg (0.32 mmol) 4-chlorosulfonyl-benzoic acid was added at ice bath temperature to a solution of 156 mg (0.29 mmol) H—(R)Cha-Pro-Pab(Z) (See Example 15) and 59 mg (0.58 mmol) triethyl amine in 4 ml methylene chloride. The mixture was slowly allowed to reach room temperature and after 24 hours it was washed with water and dried (Na$_2$SO$_4$). Removal of the solvent in vacuo and purification of the residue by flash chromatography using ethyl acetate/methanol 9:1 followed by methylene chloride/methanol 3:1 as eluents gave 82 mg (39%) of the product.

(ii) Ph(4-COOH)—SO2—(R)Cha-Pro-Pab×HCl 80 mg (0.11 mmol) Ph(4-COOH)—SO$_2$—(R)Cha-Pro-Pab(Z) was hydrogenated over 5% Pd/C in EtOH. The catalyst was filtered off, the solvent evaporated and the crude product was purified by RPLC using (CH$_3$CN/0.1 M NH$_4$OAc 1/4) as eluent and finally converted to the hydrochloride salt by freeze drying from HCl which gave 21 mg (29%) of the product.

$^1$H-NMR (300 MHz, CD$_3$OD, mixture of two rotamers): δ 0.45–1.82 (m, 13H), 1.90–2.30 (m, 4H), 2.95–4.16 (several m, total 3H), 4.35–4.68 (m, 3H), 7.54 (d, 2H), 7.74 (d, 1H), 7.80 (d, 1H), 7.90–8.00 (m, 2H), 8.05–8.22 (m, 2H)

$^{13}$C-NMR (75 KHz, CD$_3$OD): amidine and carbonyl carbons: δ 168.4, 173.4, 173.9 and 174.2

MS m/z 584 (M$^+$+1)

Example 25
H—(R)Cha-Pic-Pab×2 HCl (i) Boc-(R)Cha-Pic-Pab(Z)

3.57 g (18.6 mmol) EDC was added at −15° C. to a mixture of 7.11 g (18.6 mmol) Boc-(R)Cha-Pic-OH (See preparation of starting materials), 9.07 g (74.2 mmol) DMAP and 5.26 g (18.6 mmol) H-Pab(Z) (See preparation of starting materials) in 200 ml DMF. The temperature was allowed to rise to 20° C. over night. The solvent was removed in vacuo and toluene and water was added. The organic phase was washed with water, 1M KHSO$_4$, 10% Na$_2$CO$_3$ and brine. Drying (MgSO$_4$) and evaporation of the solvent in vacuo gave 13.63 g of a residue which was subjected to flash chromatography on silica gel using ethyl acetate/toluene 2:1 as eluent to give 9.5 g (79%) of the title compound.

$^1$H-NMR (300 MHz, CDCl$_3$): δ 0.7–1.0 (m, 2H), 1.0–2.2 (m, 25H), 2.3–2.5 (m, 1H), 2.9–3.1 (m, 1H), 3.8 (d, 1H), 4.3 (dd, 1H), 4.4–4.6 (m, 2H), 5.1 (s, 2H), 5.1–5.3 (m, 2H), 7.2–7.3 (m, 5H), 7.35 (d, 2H), 7.4–7.5 (m, 1H), 7.75 (d, 2H).

$^{13}$C-NMR (75 MHz, CDCl$_3$): amidine and carbonyl carbons: δ 156.8, 164.6, 168.2, 170.0 and 173.4.

(ii) H—(R)Cha-Pic-Pab(Z)

Hydrogen chloride was bubbled through a solution of 9.5 g (14.7 mmol) Boc-(R)Cha-Pic-Pab(Z) in 100 ml ethyl acetate at room temperature until saturation. After 10 minutes Na$_2$CO$_3$ solution (10%) was added and the organic phase which separated was dried (K$_2$CO$_3$) and the solvent was removed in vacuo to give the title compound in quantitative yield.

$^1$H-NMR (500 MHz, CD$_3$OD): δ 0.85–1.05 (m, 2H), 1.15–1.90 (m, 16H), 2.25–2.35 (m, 1H), 3.20–3.30 (m, 1H), 3.80–3.90 (d, 1H), 3.90–4.0 (m, 1H), 4.4–4.5 (two d, 2H), 4.7 (br s, 5H) 5.15 (s, 2H), 5.20 (m, 1H), 7.25–7.45 (m, 7H), 7.85 (d, 2H).

(iii) H—(R)Cha-Pic-Pab×2 HCl 55 mg (0.1 mmol) H—(R)Cha-Pic-Pab(Z) dissolved in a mixture of 5 ml ethanol and 0.45 ml 1M hydrochloric acid was hydrogenated in the presence of 33 mg 10% Pd/C for 1.5 h. Removal of the catalyst by filtration and evaporation of the solvent in vacuo gave a residue which was subjected to RPLC using 0.1 M NH$_4$OAc/CH$_3$CN as eluent. The purified peptide was finally converted to the dihydrochloride salt by dissolution in hydrochloric acid followed by freeze drying. The yield was 17 mg (35%) of the title compound $^1$H-NMR (300 MHz, D$_2$O, 2 rotamers, 3:1 mixture): δ 1.0–2.0 (m, 18H), 2.33 (d, 1H), 3.4–3.5 (m, 1H), 3.8–3.9 (m, 1H), 4.4–4.8 (m, 3H), 5.15.5.25 (m, 1H), 7.5–7.7 (m, 2H), 7.8–8.0 (m, 2H).

Resolved signals from the minor rotamer appears at δ: 0.5–0.7 (m) and 3.0–3.1 (m)

13C-NMR (75 MHz, D$_2$O): amidine and carbonyl carbons: δ 167.3, 171.6 and 173.6.

Resolved signals for the minor rotamer appears at δ 170.6 and 172.4.

Example 26
HOOC—CH$_2$—(R)Cha-Pic-Pab×2 HCl (i) BnOOC—CH$_2$—(R)Cha-Pic-Pab(z)

A mixture of 742 mg (1.35 mmol) H—(R)Cha-Pic-Pab(Z) (See Example 25), 230 ml (1.45 mmol) benzyl bromoacetate and 558 mg (4 mmol) K$_2$CO$_3$ in 4 ml acetonitrile was sonicated at 40° C. for 40 minutes. The solvent was removed and the residue was subjected to flash chromatography to give 720 mg (77%) of the desired product.

$^1$H-NMR (500 MHz, CDCl$_3$); δ 0.8–1.0 (m, 2H), 1.1–1.9 (m, 16H), 2.1–2.4 (br s, 1 or 2H), 2.4 (d, 1H), 3.0 (m, 1H), 3.25 (d, 1H), 3.45 (d, 1H), 3.55–3.65 (m, 1H), 3.7 (m, 1H), 4.35 (dd, 1H), 4.55 (dd, 1H), 4.80 (two d, 2H), 5.2 (s, 2H), 5.3 (m, 1H), 7.2–7.4 (m, 12H), 7.8 (d, 2H).

$^{13}$C-NMR (125 MHz, CDCl$_3$): amidine and carbonyl carbons: δ 164.5, 167.9, 170.5, 173.4 and 175.5.

(ii) HOOC—CH$_2$—(R)Cha-Pic-Pab×2 HCl 509 mg (0.73 mmol) BnOOC—CH$_2$—(R)Cha-Pic-Pab (Z) dissolved in 25 ml ethanol was hydrogenated in the presence of 259 mg 10% Pd/C for 4 h. Removal of the catalyst by filtration and evaporation of the solvent in vacuo gave a residue which was dissolved in distilled water. Hydrochloric acid was added and the solution was finally freeze dried to give 281 mg (79%) of the title compound.

$^1$H-NMR (500 MHz, D$_2$O, mixture of rotamers 4:1): major rotamer: δ 1.0–2.0 (m, 18H), 2.25–2.40 (m, 1H), 3.4–3.5 (m, 1H), 3.8–3.95 (m, 3H), 4.55–4.65 (two d, 2H), 5.15 (m, 1H), 7.55–7.75 (m, 2H), 7.8–8.0 (m, 2H).

$^{13}$C-NMR (125 MHz, D$_2$O): amidine and carbonyl carbons: δ 167.3, 169.9, 170.3 and 173.5.

Resolved signal for the minor rotamer appears at δ 166.9, 169.2 and 172.0

Example 27
HOOC—CH$_2$-(RorS)CE(COOH)—(R)Cha-Pic-Pab/a X 2 KCl (i) BnOOC—CH$_2$—(R,S)CH(COOBn)—(R)Cha-Pic-Pab (Z)

A mixture of 592 mg (1.1 mmol) H—(R)Cha-Pic-Pab(Z) (See Example 25) and 332 mg (1.1 mmol) dibenzyl maleate in 1 ml ethanol was kept at room temperature for 1 week. The solvent was removed in vacuo and the residue was subjected to flash chromatography using methanol/methylene chloride as eluent to give 275 mg (30%) the diastereomeric mixture.

(ii) HOOC—CH$_2$—(R or S)CH(COOH)—(R)Cha-Pic-Pab/a×2 HCl 275 mg BnOOC—CH$_2$—(R,S)CH(COOBn)—(R)Cha-Pic-Pab(Z) dissolved in 20 ml 951 ethanol was hydrogenated for 18 hours in the presence of 75 mg 10% Pd/C. The mixture was filtered through hyflo and the solvent was removed in vacuo. Addition of water followed by freeze drying gave 166 mg of HOOC—CH$_2$—(R,S)CH(COOH)—(R)Cha-Pic-Pab. The two diastereomers were separated by RPLC using (CH$_3$CN/0.1 M NH$_4$OAc 1/4) as eluent followed by freeze drying from HCl. This diastereomer eluted first from the column. Yield 9 mg.

$^1$H-NMR (300 MHz, D$_2$O, mixture of rotamers): δ 1.0–2.0 (m, 18H), 2.25–2.4 (m, 1H), 3.0–3.2 (m, 2H), 3.4 (t, 1H), 3.8 (d, 1H), 4.05 (t, 1H), 4.5–4.7 (m, 3H), 5.2 (s, 1H), 7.55 (d, 2H), 7.9 (d, 2H).

Resolved signals from the minor rotamer appears at δ 4.0 (t) and 7.7 (d).

Example 28
HOOC—CH$_2$—(RorS)CH(COOH)—(R)Cha-Pic-Pab/b×2 HCl

The title compound was obtained by using the same procedure as described in Example 27 on HOOC—CH$_2$—(R,S)CH(COOH)—(R)Cha-Pic-Pat. This diastereomer came out after the first one from the column.

1H—NMR (500 MHz, D2O, mixture of rotamers; δ 1.0–2.0 (m, 18H), 2.25–2.4 (m, 1H), 3.0–3.2 (m, 2H), 3.5 (t, 1H), 3.85 (d, 1H), 4.15 (s, 1H), 4.5–4.7 (m, 3H), 5.15 (s, 1H), 7.55 (d, 2H), 7.8 (d, 2H).

Resolved signals from the minor rotamer appear at δ 4.35 (s), 7.65 (d) and 7.9 (d).

Example 29
HOOC—CH$_2$—CH$_2$—(R)Cha-Pic-Pab×2 KCl (i) BnOOC—CH$_2$—CH$_2$—(R)Cha-Pic-Pab(Z)

A mixture of 851 mg (1.55 mmol) H—(R)Cha-Pic-Pab(Z) (See Example 25) and 269 mg (1.71 mmol) benzyl acrylate in 5 ml ethanol was kept at room temperature for 40 h. The solvent was removed in vacuo and the residue was subjected to flash chromatography using methylene chloride/methanol as eluent to give 812 mg (74%) of the product.

$^1$H-NMR (500 MHz, CDCl$_3$): δ 0.8–1.0 (m, 2H), 1.1–1.9 (m, 16H), 2.3–2.5 (m, 3H), 2.6–2.8 (m, 2H), 3.0 (m, 1H), 3.5 (m, 1H), 3.6–3.7 (m, 1H), 4.3 (dd, 1H), 4.6 (dd, 1H), 4.95–5.05 (two d, 2H), 5.2 (s, 2H), 5.3 (m, 1H), 6.5–6.9 (br s, 1H), 7.0–7.1 (m, 1H), 7.2–7.5 (m, 12H), 7.75–7.85 (d, 2H), 9.3–9.7 (br s, 1H).

(ii) HOOC—CH$_2$—CH$_2$—(R)Cha-Pic-Pab×2 HCl 780 mg (1.1 mmol) BnOOC—CH$_2$—CH$_2$—(R)Cha-Pic-Pab(Z) dissolved in 25 ml ethanol was hydrogenated for 4 h in the presence of 306 mg 15% Pd/C. The catalyst was removed by filtration and the solvent was removed in vacuo. The residue was dissolved in hydrochloric acid and the resulting solution was freeze dried to give 481 mg (78%) of the title compound.

$^1$H-NMR (500 MHz, D$_2$O): δ 0.95–1.1 (m, 2H), 1.15–1.9 (m, 16H), 2.2–2.3 (m, 1H), 2.7–2.8 (t, 2H), 3.2–3.3 (m, 3H), 3.4–3.5 (m, 1H), 3.75–3.85 (m, 1H), 4.4–4.6 (m, 3H), 5.15 (m 1H), 7.5–7.6 (m, 2H), 7.8–7.9 (m, 2H), 8.6–8.7 (m, $^{13}$C-NMR (125 MHz, CD$_3$OD): amidine and carbonyl carbons: δ 170.6, 175.9, 179.5 and 183.5.

Example 30
HOOC—CO—(R)Cha-Pic-Pab×HOAc (i) EtOOC—CO—(R)Cha-Pic-Pab(Z) 0.12 g ethyloxalyl chloride was added to a mixture of 0.42 g (0.77 mmol) H—(R)Cha-Pic-Pab(Z) (See Example 25) and 0.21 g (1.5 mmol) X$_2$CO$_3$ in 10 ml CH$_3$CN at room temperature. After 2 hours an additional amount of 0.07 g (0.5 mmol) ethyloxalyl chloride was added. The mixture was stirred at room temperature over night. The solvent was removed in vacuo. and the residue was dissolved in CH$_2$Cl$_2$ and washed with water. Evaporation and flash chromatography (toluene: ethyl acetate 1:2 followed by CH$_2$Cl$_2$: methanol) gave 0.21 g (42%) of the product.

(ii) HOOC—CO—(R)Cha-Pic-Pab(Z)

0.21 g (0.32 mmol) EtOOC—CO—(R)Cha-Pic-Pab(Z) was dissolved in 3 ml THF and 0.17 g (4.2 mmol) LiOH dissolved in 3 ml water was added. The mixture was stirred at room temperature over night and then poured onto ethyl acetate/water. The phases were separated and the organic phase was extracted with a KHCO$_3$-solution. The aqueous phase was acidified with 0.5M HCl (pH 1) and extracted with CH$_2$Cl$_2$, dried over Na$_2$SO$_4$ and evaporated to give 80 mg of the product.

(iii) HOOC—CO—(R)Cha-Pic-Pab×HOAc

HOOC—CO—(R)Cha-Pic-Pab(Z) was hydrogenated over 5% Pd/C in EtOH. The catalyst was filtered off and the solvent evaporated. The residue was subjected to purification by RPLC to give the title compound.

$^1$H NMR (500 MHz, DMSO-d$_6$); δ 0.8–1.0 (m, 2H), 1.1–1.75 (m, 15H), 1.86–1.94 (m, 1H), 2.13–2.2 (m, 1H), 3.75–3.81 (m, 1H), 4.32, 4.44 (AB, 2H), 4.71–4.77 (m, 1H), 4.98–5.02 (m, 1H), 7.41 (d, 2H), 7.75 (d, 2H), 8.1–8.15 (m, 1H), 8.22–8.27 (m, 1H), 9.32 (broad s), 9.90 (broad s). The signal of one of the protons (3.25) is partially obscured by the solvent signal.

MS m/z 486 (M$^+$+1)

Example 31
HOOC—CH$_2$—CO—(R)Cha-Pic-Pab (i) MeOOC—CH$_2$—CO—(R)Cha-Pic-Pab(Z)

0.39 g (0.72 mmol) H—(R)Cha-Pic-Pab(Z) (See Example 25) and 0.9 g (0.8 mmol) monomethylmalonate was dissolved in 40 ml CH$_2$Cl$_2$ and 0.16 g (0.8 mmol) DCC was added. The solution was stirred in room temperature over night. The precipitated DCU was removed by filtration and the filtrate was washed with 0.3M KHSO4 and KHCO$_3$-solution and dried (NaSO$_4$). Evaporation of the solvent followed by flash chromatography using toluen/ethyl acetate (1/3) as eluent gave 0.27 g (58%) of the desired product.

(ii) MeOOC—CH$_2$—CO—(R)Cha-Pic-Pab 90 mg (0.14 mmol) MeOOC—CH$_2$—CO—(R)Cha-Pic-Pab(Z) was dissolved in 10 ml ethanol and was hydrogenated in presence of 5% Pd/C for 5 hours. Removal of the catalyst by filtration and evaporation of the solvent gave 50 mg (70%) of the title product.

$^1$H NMR (300 MHz, CD$_3$OD): δ 0.85–1.1 (m, 2H), 1.1–1.9 (m, 16H), 2.35–2.45 (m, 1H), 3.2–3.4 (m, 3H), 3.7 (s, 3H), 3.95–4.05 (m, 1H), 4.4–4.55 (m, 3H), 5.15–5.25 (m, 1H), 7.4–7.55 (m, 2H), 7.7–7.85 (m, 2H).

$^{13}$C NMR (75 MHz, CD$_3$OD): amidine and carbonyl carbons: δ 168.2, 168.7, 170.0, 172.4 and 174.6.

MS m/z 514 (M$^+$+1)

(iii) HOOC—CH$_2$—CO—(R)Cha-Pic-Pab

To a solution of 0.14 g (0.27 mmol) of MeOOC—CH$_2$—CO—(R)Cha-Pic-Pab in 5 ml methanol was added 2 ml of 0.5 M NaOH at room temperature. After stirring for 5 hours water was added and the methanol was removed in vacuo. The aqueous phase was freeze dried. The soluble material was extracted out from the insoluble inorganic salts with absolute ethanol. The remaining solid after evaporation of the ethanol was suspended in water and 70 mg (52%) of the title compound was isolated by filtration.

$^1$H NMR (300 MHz, DMSO-d$_6$); δ 0.8–1.0 (m, 2H), 1.0–1.9 (m, 16H), 2.15–2.30 (m, 1H), 2.58, 2.86 (AB, 2H), 3.8–3.95 (m, 1H), 4.2–4.5 (m, 2H), 4.7–4.85 (m, 1H), 4.95–5.05 (m, 1H), 7.40 (d, 2H), 7.77 (d, 2H), 8.2–8.3 (m, 1H), 9.3–9.4 (m, 1H), 9.90 (broad s, 3H). The signal of one of the protons (3.21) is partially obscured by the solvent-signal.

$^{13}$C NMR (75 MHz, DMSO-d$_6$): amidine and carbonyl carbons: δ 165.8, 168.8, 169.9, 172.2 and 172.4.

MS m/z 500 (M$^+$+1)

Example 32
MeOOC—CH$_2$—CO—(R)Cha-Pic-Pab

See Example 31 (ii) above.

Example 33
H$_2$N—CO—CH$_2$—(R)Cha-Pic-Pab (i) H$_2$N—CO—CH$_2$—(R)Cha-Pic-Pab(Z)

Attempted alkylation of 455 mg (0.83 mmol) H—(R)Cha-Pic-Pab(Z) (See Example 25) with 80 mg (0.86 mmol)

chloroacetamide in 3 ml acetonitrile in the presence of 395 mg (2.86 mmol) potassium carbonate by sonication at 40° C. turned out to be an extremly sluggish reaction. Even the addition of 230 mg (2.6 mmol) lithium bromide did not seem to improve the reaction rate. However, addition of lithium iodide and heating/sonication gave small amounts of product, according to TLC. Workup by addition of water, extraction with ethyl acetate/toluene, drying of the organic phase (MgSO$_4$) and removal of the solvent in vacuo gave a residue which was subjected to flash chromatography using MeOH/CH$_2$Cl$_2$ as eluent to give 118 mg (24%) of the desired product.

(ii) H$_2$N—CO—CH$_2$—(R)Cha-Pic-Pab×2 HCl 118 mg (0.2 mmol) H$_2$N—CO—CH$_2$—(R)Cha-Pic-Pab (Z) dissolved in 10 ml 95% ethanol was hydrogenated in the presence of 143 mg 10% Pd/C for 2 h. The mixture was diluted with distilled water and hydrochloric acid and filtered through hyflo. Freeze drying gave 26 mg (24%) of the desired product.

$^1$H-NMR (300 MHz, CD$_3$OD): δ 0.9–1.1 (m, 2H), 1.1–1.9 (m, 16H), 2.3 (d, 1H), 3.4 (t, 1H), 3.6 (AB-system, 2H), 3.8 (d, 2H), 4.35 (t, 1H), 4.5 (s, 2H), 5.2 (s, 1H), 7.55 (d, 2H), 7.8 (d, 2H).

Example 34

Boc-(R)Cha-Pic-Pab 10 mg (0.015 mmol) Boc-(R)Cha-Pic-Pab(Z) (See Example 25) dissolved in 5 ml ethanol was hydrogenated in the presence of 38 mg 10% Pd/C for 4 h. Removal of the catalyst by filtration and evaporation of the solvent in vacuo followed by dissolution of the residue in water and freeze drying yielded 7.6 mg (95%) of the product.

$^1$H-NMR (300 MHz, CD$_3$OD): δ 0.9–1.1 (m, 2H), 1.1–1.9 (m, 16H), 2.4 (d, 1H), 3.25 (t, 1H), 4.0 (d, 1H), 4.5 (AB-system, 2H), 4.5–4.6 (m, 1H), 5.25 (s, 1H), 7.45 (d, 2H), 7.75 (d, 2H).

Example 35

Ac—(R)Cha-Pic-Pab×HCl (i) Ac—(R)Cha-Pic-Pab(Z)

Acetyl chloride 0.06 g (0.8 mmol) was added to a mixture of 0.37 q (0.68 mmol) H—(R)Cha-Pic-Pab(Z) (See Example 25) and 0.19 g (1.35 mmol) K$_2$CO$_3$ in 10 ml CH$_3$CN at room temperature. After stirring for an additional 30 minutes at room temperature the solvent was removed in vacuo. The residue was dissolved in CH$_2$Cl$_2$ and washed with water. Evaporation and flash chromatography using a stepwise gradient of CH$_2$Cl$_2$/MeOH (99.9/0.1, 99.8/0.2, 99.6/0.4, 99.2/0.8 and 98.4/1.6) gave 0.24 g (60%) of the product.

(ii) Ac—(R)Cha-Pic-Pab×HCl

Ac—(R)Cha-Pic-Pab(Z) was hydrogenated over 5% Pd/C at atmospheric pressure. After filtration of the catalyst and evaporation of the solvent the crude material was subjected to purification by RPLC using CH$_3$CN/0.1 M NH$_4$OAc (35/65) as eluent. Removal of the solvent and excess NH$_4$OAc followed by freeze drying from 1M HCl gave the title compound.

$^1$H-NMR (300 MHz, CD$_3$OD): δ 0.85–1.1 (m, 2H), 1.15–2.0 (m, 19H), 2.35–2.47 (m, 1H), 3.2–3.33 (m, 1H), 3.95–4.05 (m, 1H), 4.46,4.57 (ABX, 2H), 5.16–5.22 (m, 1H), 7.51 (d, 2H), 7.76 (d, 2H), 8.23 (m, 1H). The signal of one of the protons is totally obscured by the solvent-signal.

$^{13}$C-NMR (75 MHz, CD$_3$OD): amidine and carbonyl carbons: δ 168.3, 172.5, 173.8, 175.1

MS m/z 456 (M$^+$+1)

Example 36

Me—SO$_2$—(R)Cha-Pic-Pab×HCl (i) Me—SO$_2$—(R)Cha-Pic-Pab(Z)

A solution of 48 mg (0.42 mmol) methanesulfonyl chloride in 0.5 ml methylene chloride was added at 0° C. to a stirred solution of 209 mg (0.382 mmol) H—(R)Cha-Pic-Pab(Z) (See Example 25) and 0.11 ml (0.763 mmol) triethyl amine in 5 ml of methylene chloride. The reaction mixture was allowed to reach room temperature over night. Washing with water followed by drying (Na$_2$SO$_4$) and evaporation of the solvent in vacuo gave a residue which was subjected to flash chromatography using ethyl acetate/methanol (95/5) as eluent to give 159 mg (67%) of the product.

(ii) Me—SO$_2$—(R)Cha-Pic-Pab×HCl 150 mg (0.24 mmol) Me—SO$_2$—(R)Cha-Pic-Pab(z) dissolved in 5 ml 95% ethanol and 1 ml water was hydrogenated in the presence of 5% Pd/C for 4 h. Removal of the catalyst by filtration, addition of 0.2 ml 1M hydrochloric acid and evaporation of the solvent in vacuo gave a residue which was dissolved in 2 ml water and freeze dryed to give 116 mg (86%) of the product.

$^1$H-NMR (500 MHz, CD$_3$OD): δ 0.90–1.10 (m, 2H), 1.15–1.85 (m, 15H), 1.90 (bd, 1H), 2.30 (bd, 1H), 2.85 (s, 3H), 3.35 (dt, 1H), 3.90 (bd, 1H), 4.45 (AB-system, 2H) 4.50–4.55 (m, 1H), 5.13 (dd, 1H), 7.50 (d, 2H), 7.75 (d, 2H).

$^{13}$C-NMR (125 MHz D$_2$O): amidine and carbonyl carbons: δ 166.8, 173.0 and 174.6.

Example 37

H—(R)Cha-(R,S)betaPic-Pab×2 HCl (i) Boc-(R)Cha-(R,S)betaPic-Pab(Z)

EDC was added at −18° C. to a stirred solution of 1.0 g (2.6 mmol) Boc-(R)Cha-(R,S)betaPic-OH (See preparation of starting materials), 1.28 g (10.5 mmol) DMAP, 0.74 g (2.6 mmol) H-Pab-(Z) (See preparation of starting materials) in 35 ml DMF. The reaction mixture was allowed to reach room temperature over night and the solvent was subsequently removed in vacuo. The residue was dissolved in CH$_2$Cl$_2$ and the organic layer was washed succesively with 0.3M KHSO$_4$, KHCO$_3$-solution and brine. Drying (Na$_2$SO$_4$) and removal of the solvent gave a residue which was subjected to flash chromatography using heptane:ethyl acetate with 4% methanol as eluent to yield 0.74 g (44%) of the desired product.

(ii) H—(R)Cha-(R,S)betaPic-Pab(Z)

0.68 g (1.05 mmol) Boc-(R)Cha-(R,S)betaPic-Pab(Z) was dissolved in ethyl acetate saturated with HCl(g). The solution was stirred for 1 h at room temperature. Water was added and the mixture was made alkaline with K$_2$CO$_3$. The water phase was extracted with ethyl acetate. The organic phase was then washed with water and dried (Na$_2$SO$_4$). Evaporation gave 0.5 q (87%) of the desired product.

(iii) H—(R)Cha-(R,S)betaPic-Pab×2 HCl 65 mg (0.19 mmol) H—(R)Cha-betaPic(R,S)-Pab(Z) was dissolved in 7 ml ethanol and hydrogenated in presence of 5% Pd/C for 4 hours. Removal of the catalyst by filtration, evaporation of the solvent and freeze drying from 1M HCl and water gave 41 mg (71%) of the product.

$^1$H NMR (300 MHz, D$_2$O, 2 diastereomers 4/5, and rotamers); δ 0.8–2.16 (m, ), 2.5–2.77 (m, 3H), 3.13–3.43 (m, 3H), 3.68–3.94 (m, 1H), 4.18–4.41 (m, 1H), 4.41–4.52 (m, 3H), 7.46–7.57 (m, 2H), 7.72–7.83 (m, 2H).

Example 38

HOOC—CH$_2$—CH$_2$—(R)Cha-(R,S)betaPic-Pab×2 HCl (i) BnOOC—CH$_2$—CH$_2$—(R)Cha-(R,S)betaPic-Pab(Z)

0.21 g (0.38 mmol) H—(R)Cha-(R,S)betaPic-Pab(Z) (See Example 37) was dissolved in 2 ml ethanol. 0.68 g (0.42 mmol) benzyl acrylate was added and the solution was stirred for 5 days. Evaporation and flash chromatography with CH$_2$Cl$_2$/MeOH (95/5) as eluent gave 0.19 g (70%) of the desired product.

(ii) HOOC—CH$_2$—CH$_2$—(R)Cha-(R,S)betaPic-Pab×2 HCl 170 mg (0.24 mmol) BnOOC—CH$_2$—CH$_2$—(R)Cha-(R,S)betaPic-Pab(Z) was dissolved in 10 ml ethanol and hydrogenated in presence of 5% Pd/C for 4 hours. Removal of the catalyst by filtration, evaporation of the solvent and freeze drying from 1M HCl and water gave 103 mg (77%) of the product.

$^1$H NMR (300 MHz, D$_2$O, mixture of 2 diastereomers 4/5 and rotamers); δ 0.92–2.03 (m, H), 2.51–2.78 (m, 1H), 3.21–3.52 (m, 1H), 3.88–4.01 (m, 1H), 4.07–4.3. (m, 2H), 4.4–4.71 (m, 2H), 7.59 (d, 2H), 7.86 (d, 2H)

$^{13}$C NMR (300.13 MHz, 020, mixture of 2 diastereomers 4/5 and rotamers): amidine and carbonyl carbons: δ 167.0, 168.0, 168.1, 175.9, 176.0, 176.3, 176.4 and 178.2.

Example 39

HOOC—CH$_2$—(R)Cha-Val-Pab×2 HCl (i) Boc-(R)Cha-Val-Pab(Z)

1.77 g (9.2 mmol) EDC was added at −12° C. to a mixture of 3.41 g (9.2 mmol) Boc-(R)Cha-Val-OH(See preparation of starting materials), 2.61 g (9.2 mmol) H-Pab(Z)(See preparation of starting materials), and 4.5 g (36.8 mmol) DMAP in 50 ml DMF. The reaction mixture was allowed to reach room temperature over night and workup by dilution with water was followed by extraction with toluene, ether and ethyl acetate. Subsequent drying (MgSO$_4$) of the combined organic extracts, removal of the solvent in vacuo and flash chromatography using CH$_2$Cl$_2$/MeOH as eluent gave 2.77 g (47%) of the desired product.

(ii) H—(R)Cha-Val-Pab(Z)

Hydrogen chloride was bubbled through a solution of 2.77 g (4.4 mmol) Boc-(R)Cha-Val-Pab(Z) in 75 ml ethyl acetate. After 15 minutes sodium carbonate solution was added to pH 10 and the aqueous phase was extracted with ethyl acetate. Drying (potassium carbonate) and removal of the solvent in vacuo gave 1.8 g (77%) of H—(R)Cha-Val-Pab(Z).

(iii) BnOOC—CH$_2$—(R)Cha-Val-Pab(Z)

A mixture of 326 mg (0.61 mmol) H—(R)Cha-Val-Pab(Z), 105 ml (0.67 mmol) benzyl bromoacetate, and 252 mg (1.83 mmol) potassium carbonate in 2 ml acetonitrile was sonicated for 2.5 h at 40° C. More acetonitrile was added, in order to dissolve the product, and the mixture was filtered and the solvent was removed in vacuo. The residue was purified by flash chromatography using methanol/methylene chloride as eluent. The product was finally crystallised from ethyl acetate to give 124 mg (30%) of colourless crystals.

(iv) HOOC—CH$_2$—(R)Cha-Val-Pab×2 HCl 124 mg (0.18 mmol) BnOOC—CH$_2$—(R)Cha-Val-Pab(Z) in 20 ml ethanol was hydrogenated for 2 hours in the presence of 25 mg 10% Pd/C. 10 ml of THF was added and the hydrogenation was continued for another 2 hours at 0.50° C. The mixture was filtered through hyflo and the filtercake was washed with dilute hydrochloric acid. The organic solvents were removed from the combined filtrates in vacuo. Freeze drying of the remaining solution yielded 55 mg (50%) of the desired compound.

$^1$H-NMR (500 MHz, D$_2$O); δ 0.75–1.4 (m, 12H), 1.5–1.9 (m, 7H), 2.0–2.15 (bs, 1H), 3.45 (AB-system, 2H), 4.1 (m, 2H), 4.5 (m, 2H), 7.5 (s, 2H), 7.7 (s, 2H), 8.9 (s, 1H).

Example 40

HOOC—CH$_2$—CH$_2$—(R)Cha-Val-Pab×2 HCl (i) H—(R)Cha-(R,S)Val-Pab(Z)

The title compound was prepared by coupling Boc-(R)Cha-Val-OH with H-Pab(Z), using the pivaloyl coupling as described for Boc-(R)Cha-Pic-OMe (See preparation of starting materials). A total epimerization of the valine occured to give Boc-(R)Cha-(R,S)Val-Pab(Z). The Boc protecting group was removed in the same way as described for Boc-(R)Cha-Val-Pab(Z) (See Example 39) to give the title compound.

(ii) BnOOC—CH$_2$—CH$_2$—(R)Cha-(R,S)Val-Pab(Z)

A solution of 1.007 g (1.9 mmol) H—(R)Cha-(R,S)Val-Pab(Z) and 308 mg (1.9 mmol) benzyl acrylate in 3 ml of ethanol was kept at 40° C. over night. The solvent was removed in vacuo and the residue was purified by flash chromatography using methanol/methylene chloride (10/90) as eluent to give 1.086 g (82%) of the title compound.

(iii) HOOC—CH$_2$—CH$_2$—(R)Cha-Val-Pab×2 HCl 1.086 g (1.6 mmol) BnOOC—CH$_2$—CH$_2$—(R)Cha-(R,S)Val-Pab(Z) was hydrogenated in 25 ml THF and 14 ml 0.5 M hydrochloric acid in the presence of 223 mg 10% Pd/C for 2 hours. Removal of the catalyst by filtration through celite and removal of the THF in vacuo followed by freeze drying of the remaining aqueous solution gave a residue of which approximately 300 mg was subjected to HPLC using 25% acetonitrile in 0.1 M Ammonium acetate buffer as eluent. Two main fractions were isolated, of which the second fraction contained the title compound. 67 mg of title compound, as the dihydrochloride, was isolated.

$^1$H-NMR (500 MHz, D$_2$O); δ 1.0–1.15 (m, 12H), 1.2–1.4 (m, 7H), 1.65–1.9 (m, 7H), 2.15–2.25 (m, 1H), 2.85 (t, 2H), 3.15–3.2 (m, 1H), 3.3–3.35 (m, 1H), 4.15–4.2 (m, 1H), 4.25 (d, 1H), 4.55–4.65 (AB-system, 2H), 7.65 (d, 2H), 7.85 (d, 2H).

$^{13}$C-NMR (75 MHz, D$_2$O): amidine and carbonyl carbons: δ 167.0, 169.8, 173.96 and 174.04.

Example 41

H—(R)Hoc-Aze-Pab×2 HCl (i) Boc-(R)Hoc-Aze-Pab(Z)

Prepared in the same way as described for Boc-(R)Cha-Pic-Pab(Z) (See Example 25) by replacing Boc-(R)Cha-Pic-OH with Boc-(R)Hoc-Aze-OH (See preparation of starting materials). The crude product was subjected to flash chromatography (Toluene/EtOAc 116) to give 0.32 g (0.37%) of the desired product.

(ii) H—(R)Hoc-Aze-Pab(Z)

Boc-(R)Hoc-Aze-Pab(Z) was treated in the same way as describes for Boc-(R)Cha-Pic-Pab(Z) in Example 25 to to give 0.23 g (88%) of the title compound.

(iii) H—(R)Hoc-Aze-Pab×2 HCl 20 mg (0.037 mmol) of H—(R)Hoc-Aze-Pab(Z) was dissolved in 3 ml ethanol and hydrogenated in presence of 5% Pd/C for 4 hours at athmospheric pressure. Removal of the catalyst by filtration, evaporation of the solvent and freeze drying from 1M HCl gave 11 mg (63%) of the product.

$^1$H NMR (300.13 MHz, D$_2$O, mixture of two rotamers 3:1): major rotamer: δ 0.9–2.1 (m, 15H), 2.4–2.6 (m, 1H), 2.7–3.0 (m, 1H), 4.1–4.3 (m, 1H), 4.35–4.56 (m, 1H), 4.65 (s, 2H), 5.0–5.11 (m, 1H), 7.62 (d, 2H), 7.9 (d, 2H). The signal of one of the protons is totally obscured by the H-O-D-signal.

Example 42
HOOC—CH₂—CH₂—(R)Hoc-Aze-Pab×2 TFA
(i) BnOOC—CH₂—CH₂—(R)Hoc-Aze-Pab(Z)

0.067 g (0.41 mmol) benzylacrylate was added to a solution of 0.2 g (0.37 mmol) H—(R)Hoc-Aze-Pab(Z) (See Example 41) in 2 ml ethanol (95%) at room temperature.

The reaction was left at room temperature for 5 days. The solvent was removed in vacuo and the residue was purified with flash chromatography (CH₂Cl₂: MeOH, 96/4) to give 0.16 g (62%) of the desired product.

(ii) HOOC—CH₂—CH₂—(R)Hoc-Aze-Pab×2 TFA 160 mg (0.23 mmol) BnOOC—CH₂—CH₂—(R)Hoc-Aze-Pab(Z) was dissolved in 10 ml ethanol and subjected to hydrogenation at atmospheric pressure in presence of 5% Pd on charcoal for 3 hours. Removal of the catalyst by filtration evaporation of the solvent and freeze drying from water and TFA gave 120 mg (87%) of the product.

¹H NMR (300.13 MHz, D₂O 2 rotamers 3:1); major rotamer: δ 0.9–1.9 (m, 13H), 1.94–2.16 (m, 2H), 2.38–2.55 (m, 1H), 2.7–2.97 (m, 3H), 3.2–3.44 (m, 2H), 4.16 (m, 1M), 4.35–4.58 (m, 2H), 4.65 (s, 2H), 5.0–5.12 (m, 1M), 7.63 (d, 2H), 7.87 (d, 2H)

¹³C NMR (300.13 MHz, D₂O): amidine and carbonyl carbons: δ 167.3, 168.7, 172.5 and 176.6.

Example 43
HOOC—CH₂—(R,S)CR(COOH)—(R)Hoc-Pro-Pab×2 HCl
(i) Boc-(R)Hoc-Pro-Pab(Z)

Prepared from Boc-(R)Hoc-Pro-OH (See preparation of starting materials) in the same way as described for Boc-(R)Cha-Pic-Pab(Z) in Example 25. Flash chromatography using ethyl acetate as eluent gave 0.886 g (58%) of the title compound.

¹H-NMR. (300 MHz, CDCl₃); δ 0.7–0.95 (m, 2H), 0.95–2.1 (m, 27H (thereof 1.2 (s, 9H)), 2.1–2.4 (m, 1H), 3.3–3.5 (m, 1H), 3.65–3.95 (m, 1H), 4.0–4.2 (m, 1H), 4.2–4.45 (m, 2H), 4.45–4.6 (d, 1H), 5.15 (apparent bs, 2H), 5.2–5.3 (d, 1H), 7.1–7.4 (m, 7H), 7.65 (m, 1H), 7.7–7.8 (d, 2H), 9.4 (bs, 1H).

¹³C-NMR (75 MHz, CDCl₃): amidine and carbonyl carbons: δ 156.3, 164.6, 168.1, 171.4 and 172.4.

(ii) H—(R)Hoc-Pro-Pab(Z)

40 ml ethyl acetate saturated with hydrogen chloride was added to 0.82 g (1.266 mmol) Boc-(R)Hoc-Pro-Pab(Z) at 0° C. The temperature was allowed to rise to roomtemperature. The reaction was not completed after 1.5 h and therefore hydrogen chloride was bubbled through the reaction mixture during 5 minutes. The solvent was evaporated and ethyl acetate and saturated sodium carbonate was added and the phases were separated. The organic phase was washed with brine and dried (Na₂SO₄) and the solvent evaporated in vacuo to give the title compound in almost quantitative yield.

¹H-NMR (300 MHz, CDCl₃); δ 0.75–0.95 (m, 2H), 0.95–2.4 (m, 17H), 3.3–3.55 (m, 2H), 3.55–3.7 (m, 1H), 4.25–4.45 (m, 2H), 4.5–4.6 (m, 1H), 5.15 (s, 2H), 7.15–7.35 (m, 5H), 7.35–7.45 (m, 2H), 7.6–7.7 (m, 1H), 7.7–7.85 (d, 2H).

¹³C-NMR (75 MHz, CDCl₃): amidine and carbonyl carbons: δ 164.5, 167.8, 171.4 and 175.3.

(iii) BnOOC—CH₂—(R,S)CH(COOBn)—(R)Hoc-Pro-Pab(Z)

To 0.15 g (0.5 mmol) benzyl acrylate in 1.5 ml EtOH (99%) was added 0.273 g (0.498 mmol) H—(R)Hoc-Pro-Pab(Z) and the mixture was stirred at room temperature for 10 days.

The solvent was removed in vacuo and the residue was subjected to flash chromatography, using ethyl acetate as eluent to give 0.103 g (25%) of BnOOC—CH₂—(R,S)CH(COOBn)—(R)Hoc-Pro-Pab(Z).

¹H-NMR (300 MHz, CDCl₃); δ 0.75–2.05 (m, 18H), 2.3–2.45 (m, 1H), 2.45–2.8 (m, 3H), 3.15–3.45 (m, 3H), 3.5–3.65 (m, 1H), 4.3–4.5 (m, 2H), 4.55–4.7 (m, 1H), 4.8 (s, 1H), 4.9–5.1 (m, 3H), 5.2 (s, 2H), 7.1–7.2 (m, 1H), 7.2–7.4 (m, 13H), 7.4–7.45 (d, 2H), 7.6–7.8 (m, 3H).

(iv) HOOC—CH₂—(R,S)CH(COOH)—(R)Hoc-Pro-Pab×2 HCl 103 mg (0.122 mmol) BnOOC—CH₂—(R,S)CH(COOBn)—(R)Hoc-Pro-Pab(Z) dissolved in 4 ml ethanol (99.5%) and 0.3 ml chloroform was hydrogenated in the presence of 111 mg 5% Pd/C for 2 h. Removal of the catalyst by filtration and evaporation of the solvent followed by dissolving in water and freeze drying showed incomplete hydrogenation. The hydrogenation was continued in the presence of ethanol, 1 N HCl and 5% Pd/C for 5 hours.

Removal of the catalyst by filtration and evaporation of the solvent followed by dissolving in water and freeze drying gave the title compound.

¹H-NMR (500 MHz, CD₃OD, mixture of two diastereomers); δ 0.8–1.0 (m, 2H), 1.1–1.4 (m, 6H), 1.6–1.8 (m, 5H), 1.9–2.15 (m, 5H) 2.25–2.35 (m, 1H), 2.9–3.2 (m, 2H), 3.5–3.65 (m, 1H), 3.7–3.9 (2m, total 1H), 4.15–4.4 (2m, total 1H), 4.4–4.6 (m, 4H), 7.5–7.6 (m, 2H), 7.7–7.85 (m, 2H).

¹³C-NMR (75 MHz, CDCl₃): amidine and carbonyl carbons: δ 167.9, 168.2, 168.3, 172.8, 173.6, 174.3 and 174.4. The signals from the two diastereomers are partly overlapping.

Example 44
HOOC—CH₂-(R)Hoc-Pic-Pab×2 HCl
(i) Boc-(R)Hoc-Pic-Pab(Z)

Prepared from Boc-(R)Hoc-Pic-OH (See preparation of starting materials) and H-Pab(Z) (See preparation of starting materials) in the same way as described for Boc-(R)Cha-Pic-Pab(Z) (See Example 25). Flash chromatography using ethyl acetate as eluent gave 1.3 g (78%) of the title compound.

¹H-NMR (300 MHz, CDCl₃): δ 0.75–0.95 (m, 2H), 0.95–2.0 (m, 31H (thereof 1.3 (s, 9H)), 2.4–2.5 (n, 1H), 3.0–3.1 (m, 1H), 3.8 (m, 1H), 4.2–4.45 (m, 2H), 4.45–4.55 (m, 2H), 5.15 (apparent bs, 3H), 5.25–5.3 (m, 1H), 7.0 (bs, 1H), 7.15–7.5 (m, 7H), 7.7–7.85 (d, 2H), 9.45 (bs, 1H).

¹³C-NMR (75 MHz, CDCl₃): amidine and carbonyl carbons: δ 156.6, 164.7, 168.1, 170.0 and 173.0.

(ii) H—(R)Hoc-Pic-Pab(Z)

100 ml ethyl acetate saturated with hydrogen chloride was added to 1.3 g (1.96 mmol) Boc-(R)Hoc-Pic-Pab(Z) at 0° C. The temperature was allowed to rise to roomtemperature. The solvent was evaporated after 40 minutes and ethyl acetate and saturated sodium carbonate was added and the phases were separated. The organic phase was washed with brine and dried (Na₂SO₄) and the solvent evaporated in vacuo to give 0.85 g (77.5%) of the product.

¹H-NMR (300 MHz, CDCl₃): δ 0.75–0.95 (m, 2H), 1.05–2.3 (m, 25H), 3.0–3.15 (m, 1H), 3.6–3.75 (m, 2H), 4.25–4.4 (m, 2H), 5.15 (apparent bs, 3H), 7.05–7.2 (d, 2H), 7.2–7.35 (m, 4H), 7.35–7.4 (d, 1H), 7.6–7.8 (d, 2H).

¹³C-NMR (75 MHz, CDCl₃): amidine and carbonyl carbons: δ 164.5, 167.9, 170.8 and 175.7.

(iii) BnOOC—CH₂—(R)Hoc-Pic-Pab(Z)

0.171 g (0.748 mmol) benzyl bromoacetate was added to a mixture of 0.4 g (0.712 mmol) H—(R)Hoc-Pic-Pab(Z) and 0.217 g (1.57 mmol) K₂CO₃ in 7 ml acetonitrile. The mixture was heated to 60° C. in oilbath for 1 h. The solvent was removed and ethyl acetate and water was added. The phases were separated and the organic phase was washed with brine and dried (Na$_2$SO$_4$). Evaporation in vacuo gave 0.626 g of a residue which was subjected to flash chromatography using ethyl acetate as eluent, to give 2 products. The first compound eluated from the column was (BnOOC—CH$_2$)$_2$(R)Hoc-Pic-Pab(Z) (0.28 g) and the second compound eluated was the title compund (0.27 g).

BnOOC—CH$_2$—(R)Hoc-Pic-Pab(Z):

$^1$H-NMR (300 MHz, CDCl$_3$): δ 0.7–0.95 (m, 2H), 1.0–1.75 (m, 18H), 2.3–2.5 (m, 1 or 2H), 2.9–3.05 (m, 1H), 3.2–3.3 (m, 1H), 3.35–3.5 (m, 2H), 3.6–3.7 (m, 1H), 4.35, 4.55 (ABX-system, 2H), 4.75 (s, 2H), 5.15 (apperent s, 3H), 5.25–5.3 (m, 1H), 7.1–7.45 (m, 12H), 7.7–7.8 (d, 2H).

$^{13}$C-NMR (75 MHz, CDCl$_3$): amidine and carbonyl carbons: δ 164.6, 167.9, 170.5, 173.4 and 175.0.

(iv) HOOC—CH$_2$—(R)Hoc-Pic-Pab×2 HCl 259 mg (0.365 mmol) BnOOC—CH$_2$—(R)Hoc-Pic-Pab (Z) dissolved in 7.8 ml ethanol (99.5%) and 1.2 ml hydrogen chloride (1 N) was hydrogenated in the presence of 280 mg 5% Pd/C for 4 h. Removal of the catalyst by filtration and evaporation of the solvent followed by dissolving in water and freeze drying gave 170 mg (83%) of the title compound.

$^1$H-NMR (300 MHz, CDCl$_3$): δ 0.4–1.85 (m, 20H), 1.85–2.2 (m, 1H), 2.9–3.2 (m, 1H), 3.4–3.9 (m, 3H), 4.05–4.3 (m, 2H), 4.3–5.05 (m, 2H), 7.1–7.4 (m, 2H), 7.4–7.7 (m, 2H).

$^{13}$C-NMR (75 MHz, CDCl$_3$): amidine and carbonyl carbons: δ 167.8, 168.6, 169.6 and 172.3.

Example 45

(HOOC—CH$_2$)$_2$—(R)Hoc-Pic-Pab×2 HCl (i) (BnOOC—CH$_2$)$_2$(R)Hoc-Pic-Pab(Z)

The title compound was obtained in the alkylation of H—(R)Hoc-Pic-Pab(Z) as described in Example 44 above.

$^1$H-NMR (300 MHz, CDCl$_3$): δ 0.7–0.95 (m, 2H), 0.95–1.95 (m, 18H), 2.35–2.5 (m, 1H), 2.9–3.05 (m, 1H), 3.5–3.85 (m, 6H), 4.35–4.55 (m, 2H), 4.9 (2s, 4H), 5.2 (s, 2H), 5.25–5.35 (m, 1H), 7.1–7.45 (m, 16H), 7.5–7.65 (m, 1H), 7.7–7.85 (d, 2H).

$^{13}$C-NMR (75 MHz, CDCl$_3$): amidine and carbonyl carbons: δ 164.7, 167.9, 170.5, 172.0 and 172.4.

(ii) (HOOC—CH$_2$)$_2$—(R)Hoc-Pic-Pab×2 HCl 153 mg (0.178 mmol) (BnOOC—CH$_2$)$_2$—(R)Hoc-Pic-Pab(Z) dissolved in 4.5 ml ethanol (99.5%) and 0.5 ml hydrogen chloride (1 N) was hydrogenated in the presence of 150 mg 5% Pd/C for 3.5 h. Removal of the catalyst by filtration and evaporation of the solvent followed by dissolving in water and freeze drying gave 109 mg (99%) of (HOOC—CH$_2$)$_2$—(R)Hoc-Pic-Pab dihydrochloride. This crude material (80% purity) was subjected to putification by RPLC using CH3CN/0.1 M NH4OAc, 1:4 as eluent. Removal of the solvent and excess NH4OAc followed by freeze drying from 1 M HCl gave the title compound.

$^1$H-NMR (500 MHz, D$_2$O, mixture of two rotamers): major rotamer: & 0.95–2.15 (m, 20H), 2.25–2.35 (m, 1H), 3.45–3.55 (m, 1H), 3.95–4.25 (m, 5H), 4.6–4.65 (m, 2H), 4.92–5.01 (m, 1H) 5.15–5.20 (m, 1H), 7.58–7.63 (d, 2H), 7.84–7.89 (d, 2H).

Resolved signals arising from the minor rotamer appears at: δ 0.7–0.85 (m), 2.35–3.45 (m), 3.05–3.15 (m), 4.47–4.55 (m), 4.55–4.6 (m), 4.65–4.7 (m), 7.63–7.67 (d), 7.89–7.95 (d).

$^{13}$C-NMR (75 MHz, D$_2$O): amidine and carbonyl carbons: δ 168.20, 169.70, 170.20 and 172.71.

Example 46

HOOC—CH$_2$—(R)Pro(3-(S)Ph)-Pro-Pab×2 HCl (i) Boc-(R)Pro(3-(S)Ph)-Pro-Pab(Z)

To a solution of 570 mg (1.5 mmol) Boc-(R)Pro(3-(S) Ph)-Pro-OH (See preparation of starting materials), 425 mg (1.5 mmol) H-Pab(Z) (See preparation of starting materials) and 733 mg (6 mmol) DMAP in 25 ml CH$_3$CN/DMF (1.5/1) was added 310 mg (1.62 mmol) EDC and the mixture was stirred for 23 h at room temperature. Most of the solvent was evaporated and 50 ml water was added to the residue. The water phase was extracted with 1×75 and 2×50 ml EtOAc. The combined organic phase was washed with 1×20+1×10 ml 1M KHSO$_4$, 1×15 ml NaHCO$_3$(aq), 3×15 ml water, 1×15 ml brine and dried (MgSO$_4$). Filtration and evaporation of the solvent gave 670 mg of an oil which was purified by flash chromatography using EtOAc as eluent which gave 529 mg (55%) of the title compound.

$^1$H-NMR (300 MHz, CDCl$_3$): δ 1.26 (s, 9H), 1.53–1.88. (m, 3H), 2.1–2.31 (m, 3H), 2.52 (q, 1H), 3.58–3.77 (m, 4H), 4.31 (d, 1H), 4.35 and 4.47 (ABX-system, 2H), 4.65 (dd, 1H), 5.19 (s, 2H), 7.1–7.37 (m, 10H), 7.42 (d, 2H), 7.81 (d, 2H), 8.0 (t, 1H(NH)).

$^{13}$C-NMR (75 MHz, CDCl$_3$): amidine and carbonyl carbons: δ 154.6, 164.6, 168.1, 171.1 and 171.3.

(ii) H—(R)Pro(3-(S)Ph)-Pro-Pab(Z)

529 mg (0.81 mmol) of Boc-(R)Pro(3-(S)Ph)-Pro-Pab(Z) was dissolved in 15 ml EtOAc/HCl(g,saturated) at room temperature and stirred for 3 h. The solvent was evaporated and the residue was dissolved in 70 ml CH$_2$Cl$_2$. the organic phase was washed with 1×10 ml 2 M NaOH, 1×10 ml water, 1×10 ml brine and dried (MgSO$_4$). Filtration and evaporation of the solvent gave 403 mg (90%) of the title compound as a white powder.

$^1$H-NMR (300 MHz, CDCl$_3$): δ 1.44–1.57 (m, 1H), 1.62–1.86 (m, 2H), 1.96–2.35 (m, 3H), 2.45 (q, 1H), 3.05–3.35 (m, 4H), 3.83 (bd, 1H), 4.25–4.45 (m, 2H), 4.53 (m, 1H), 5.19 (s, 2H), 7.16–7.37 (m, 10H), 7.42 (d, 2H), 7.66 (t, 1H,(NH)), 7.77 (d, 2H).

$^{13}$C-NMR (75 MHz, CDCl$_3$): amidine and carbonyl carbons: δ 164.4, 167.9, 171.1 and 173.0.

(iii) BnOOC—CH$_2$—(R)Pro(3-(S)Ph)-Pro-Pab(Z)

A mixture of 200 mg (0.36 mmol) H—(R)Pro(3-(S)Ph)-Pro-Pab(Z), 105 mg (0.46 mmol) Br—CH$_2$—COOBn and 125 mg (0.90 mmol) K$_2$CO$_3$ in 10 ml CH$_3$CN was heated to 50° C. for 1 h and 30 minutes. The solvent was evaporated and the residue was dissolved in 70 ml EtOAc. The organic phase was washed with 10 ml water and dried (MgSO$_4$). Filtration and evaporation of the solvent gave 260 mg of an oil. The crude material was purified by flash chromatography using a stepwise gradient of CH$_2$Cl$_2$/MeOH(NH$_3$-saturated) (95/5 followed by 9/1) to give 182 mg (72%) of the title compound as a white solid.

$^1$H-NMR (300 MHz, CDCl$_3$): δ 1.43–1.82 (m, 3H), 1.96–2.13 (m, 1H), 2.14–2.22 (m, 1H), 2.26–2.43 (m, 2H), 3.02–3.14 (m, 2H), 3.24–3.51 (m, 4H), 3.83 (d, 1H), 4.29–4.46 (ABX-system centered at 4.37, 2H), 4.58 (dd, 1H), 4.97–5.1 (AB-system centered at 5.03, 2H), 5.19 (s, 2H), 7.16–7.38 (m, 15H), 7.43 (d, 2H), 7.5–7.8 (m, 3H, one NH).

$^{13}$C-NMR (75 MHz, CDCl$_3$): amidine and carbonyl carbons: δ 164.5, 167.9, 171.15, 171.2 and 172.7.

(iv) HOOC—CH$_2$—(R)Pro(3-(S)Ph)-Pro-Pab×2 HCl 0.18 g (0.26 mmole) of BnOOC—CH$_2$—(R)Pro(3-(S) Ph)-Pro-Pab(Z) was mixed with 0.075 g 5% Pd/C, 1.0 ml 1N HCl-solution, 1 ml water and 10 ml ethanol and the mixture was hydrogenated at atmospheric pressure for one hour.

Filtration of the catlyst through hyflo, evaporation of the solvent followed by freeze drying twice from water gave 129 mg of a crude product. The crude product was purified by RPLC using a stepwise gradient of 0.1 M NH$_4$OAc/CH$_3$CN 4/1 followed by 3/1. Evaporation followed by freeze drying from water and 1N HCl-solution gave 70 mg (50%) of the pure product.

$^1$H-NMR (300 MHz, D$_2$O): δ 1.42–1.60 (m, 1H), 1.65–1.83 (m, 1H), 1.83–1.98 (m, 1H), 2.03–2.20 (m, 2H), 2.63 (t, 2H), 3.28–3.40 (m, 1H), 3.55–3.78 (m, 2H), 3.81–3.96 (AB-system central at δ 3.88, 2H), 4.06–4.19 (m, 1H), 4.37–4.61 (AB-system central at δ 4.49, 2H), 4.48 (dd, 1H), 4.70 (d, 1H), 7.35–7.58 (m, 7H), 7.74 (d, 2H)

$^{13}$C-NMR (75 MHz, CDCl$_3$): amidine and carbonyl carbons: δ 167.02, 167.2, 169.3 and 174.4.

Example 47

HOOC—CH$_2$—CH$_2$—(R)Pro(3-(S)-Pro-Pab×2 HCl
(i) BnOOC—CH$_2$—CH$_2$—(R)Pro(3-(S)Ph)-Pro-Pab(Z)

To a solution of 190 mg (0.34 mmol) H—(R)Pro(3-(S)Ph)-Pro-Pab(Z) (See Example 46) in 7 ml EtOH (99%) was added 114 mg (0.70 mmol) of benzyl acrylate and the reaction mixture was stirred at room temperature for 24 h. Evaporation of the solvent followed by flash chromatography using a stepwise gradient of CH$_2$Cl$_2$/MeOH(NH$_3$-saturated) (95/5 followed by 9/1) gave 202 mg (83%) of the title compound.

$^1$H-NMR (300 MHz, CDCl$_3$): δ 1.5–1.71 (m, 2H), 1.74–1.9 (m, 1H), 1.9–2.05 (m, 1H), 2.2–2.64 (m, 5H), 2.69–2.82 (m, 2H), 2.84–2.96 (m, 1H), 3.18–3.48 (m, 4H), 4.28–4.44 (m, 2H), 4.61 (m, 1H), 4.48–5.08 (AB-system centered at 5.03, 2H), 5.19 (s, 2H), 7.15–7.37 (m, 15H), 7.44 (d, 2H), 7.75–7.85 (m, 3H, one NH).

$^{13}$C-NMR (75 MHz, CDCl$_3$): amidine and carbonyl carbons: δ 164.6, 168.0, 171.2, 172.5 and 172.9.

(ii) HOOC—CH$_2$—CH$_2$—(R)Pro(3-(S)Ph)-Pro-Pab×2 HCl 0.20 g (0.28 mmole) of BnOOC—CH$_2$—CH$_2$—(R)Pro(3-(S)Ph)-Pro-Pab(Z) was mixed with 0.075 g 5% Pd/C, 1.0 ml 1N HCl-solution, 1 ml water and 10 ml ethanol and the mixture was hydrogenated at atmospheric pressure for one hour. Filtration of the catalyst through hyflo, evaporation of the solvent followed by freeze drying twice from water gave 125 mg 79% of the title compound.

H-NMR (300 MHz, D$_2$O): δ 1.44 (m, 1H), 1.65–1.9 (m, 2H), 2.0–2.2 (m, 2H), 2.62 (q, 2H), 2.83 (t, 2H), 3.27–3.4 (m, 1H), 3.4–3.8 (m, 4H), 4.0–4.15 (m, 1H), 4.35–4.6 (m, 3H), 4.68 (d, 1H), 7.35–7.6 (m, 7H), 7.77 (d, 2H)

$^{13}$C-NMR (75 MHz, CDCl$_3$): amidine and carbonyl carbons: δ 166.2, 167.1, 174.1 and 174.2.

Example 48

HOOC—CH$_2$—CH$_2$—(R)Tic-Pro-Pab×2 HCl
(i) Boc-(R)Tic-Pro-Pab(Z)

Prepared in the same way as described for Boc-(R)Cha-Pic-Pab(Z) (See Example 25) using Boc-(R)Tic-Pro-OH (See preparation of starting materials) instead of Boc-(R)Cha-Pic-OH. Flash chromatography using heptane/EtOAc (4/1) followed by EtOAc as eluents gave 425 mg (37%) of the title compound.

$^1$H NMR (500 MHz, CDCl$_3$): δ 1.35 (s, 9H), 1.95–2.15 (m, 3H), 2.4 (m, 1H), 2.8 (m, 1H), 3.3 (m, 1H), 3.55 (m, 2H), 4.25–4.4 (two m, 2H)$_1$ 4.55–4.7 (two m, 2H), 7.15–7.5 (m, 10H), 7.85 (d,2H).

$^{13}$C-NMR (75.0 MHz, CDCl$_3$): amidine and carbonyl carbons: δ 164.6, 171.5 and 171.6. (two peaks are probably overlapping)

(ii) H—(R)Tic-Pro-Pab(Z)

Boc-(R)Tic-Pro-Pab(Z) (379 mg, 0.59 mmol) was dissolved in EtOAc saturated with HCl(g) and stirred at room temperature. Evaporation of the solvent gave 251 mg (79%) of the title compound as a white powder.

$^1$H NMR (500 MHz, CDCl$_3$): δ 1.65–2.15 (two m, 7H), 2.45 (m, 1H), 2.75 (n, 1H), 2.9 (m, 1H), 3.0 (m, 1H), 3.25 (m, 1H), 3.55 (m, 1H), 3.85 (m, 1H), 4.35–4.55 (m, 2H), 4.75 (d, 1H), 4.9 (s, 1H), 5.25 (s, 2H), 6.8–7.45 (several m, 8H), 7.5 and 7.85 (two d, 4H).

$^{13}$C-NMR (75.0 MHz, CDCl$_3$): amidine and carbonyl carbons: δ 164.5, 171.3 and 172.7 (two peaks are probably overlapping).

(iii) BnO$_2$C—CH$_2$—CH$_2$—(R)Tic-Pro-Pab(Z)

H—(R)Tic-Pro-Pab(Z) (140 mg, 0.26 mmol) was treated with benzyl acrylat (63 mg, 0.39 mmol) in EtOH (1.3 ml) at 20° C. during 48 h. Evaporation of the solvent and flash chromatography using (50% EtOAc/Heptan then 10% MeOH/EtOAc) as eluent afforded 133 mg (73%) of the desired product as a white solid material.

$^1$H NMR (500 MHz, CDCl$_3$): δ 1.75–2.0 (two m, 4H), 2.25 (m, 1H), 1.4–1.65 (m, 3H), 2.7–2.95 (two m, 4H), 3.05–3.2 (n, 2H), 3.9 (m, 1H), 4.45 (m, 2H), 4.65 (m, 1H), 5.1 (two d, 2H), 5.25 (s, 2H), 6.85–7.45 (several m, 12H), 7.5 and 7.9 (two d, 4H).

$^{13}$C-NMR (75.0 MHz, CDCl$_3$): amidine and carbonyl carbons: δ 171.5, 171.9 and 172.1 (two peaks are probably overlapping).

(iv) HOOC—CH$_2$—CH$_2$—(R)Tic-Pro-Pab×2 HCl

BnO$_2$C—CH$_2$—CH$_2$—(R)Tic-Pro-Pab(Z) (125 mg, 0,17 mmol) was hyrogenated over 5% Pd/C using EtOH/HCl as solvent. Filtration of the catlyst and freeze drying gave 73 mg (77%) of the title compound as a white powder.

$^1$H NMR (500 MHz, D$_2$O): δ 2.1–2.35 (two m, 3H), 2.6 (m, 1H), 2.95–3.1 (m, 2H), 3.25–3.5 (two m, 2H), 3.65 (m, 3H), 4.65 (s, 2H), 4.75 (m, 1H), 5.85 (s, 1H), 7.15–7.6 (three m, 4H), 7.6 and 7.85 (two d, 4H).

$^{13}$C-NMR (75.0 MHz, D$_2$O): amidine and carbonyl carbons: δ 166.9, 167.1 and 174.3 (two peaks are probably overlapping).

Example 49

HOOC—CH$_2$—CH$_2$—(R)Cgl-Aze-Pig×2 HCl
(i) Boc-(R)Cgl-Aze-Pig(z)$_2$

To a mixture of 0.623 g (1.83 mmole) Boc-(R)Cgl-Aze-OH(See preparation of starting materials), 0.816 g (1.92 mmole) H-Pig(Z)$_2$ (See preparation of starting materials) and 0.89 g (7.3 mmole) DMAP in 10 ml dichloromethane was added 0.368 g (1.92 mmole) of EDC and the mixture was stirred over night. The mixture was diluted and washed with 0.3 M KHSO$_4$ and once with brine. The organic layer was dried (Na$_2$SO$_4$), filtered and evaporated to yield 1.4 g of a crude product. Purification by flash chromatography using ethyl acetate as eluent gave 0.3 g (22%) of the pure product.

(ii) H—(R)Cgl-Aze-Pig(z)$_2$ 0.3 g (0.4 mmole) Boc-(R)Cgl-Aze-Pig(Z)$_2$ was mixed with 10 ml dichloromethane and 2.5 ml trifluoroacetic acid. The mixture was stirred for one and a half hour. After evaporation of the solvent the residue was dissolved in dichloromethane and washed twice with 0.2 M NaOH-solution. The combined water layer was extracted one more time with dichloromethane. The combined organic layer was dried (Na$_2$SO$_4$), filtered and evaporated to yield 0.24 g (93%) of the product.

$^1$H-NMR (300 MHz, CDCl$_3$, 339K): δ 0.9–1.9 (m, 15H), 1.94 (bd, 1N), 2.37–2.52 (m, 1H), 2.65–2.8 (m, 1H), 2.9–3.08 (m, 3H), 3.20 (t, 2H), 1.05–4.28 (m, 4H), 4.86 (dd, 1H), 5.16 (s, 4H), 7.2–7.42 (m, 10H), 7.98 (bs, NH).

(iii) BnOOC—CH$_2$—CH$_2$—(R)Cgl-Aze-Pig(Z)$_2$ 0.231 g (0.36 mmole) was dissolved in 2 ml ethanol and 61 μl (0.40 mmole) bensylacrylate was added. The reaction mixture was stirred for five days at room temperature. The mixture was evaporated and the crude product purified by flash chromatography using a stepwise gradient of CH$_2$Cl$_2$/MeOH (95/5, 90/10) as eluent to yield 0.218 g (75%) of the pure product.

$^1$H-NMR (300 MHz, CDCl$_3$, 335K): 0.93 (bq, 1H), 1.02–1.85 (m, 14H), 1.94 (bd, 1H), 2.33–2.5 Cm, 3H), 2.58–2.77 (m, 2H), 2.79–3.02 (m, 4H), 3.17 (t, 2H), 4.0–4.25 (m, 4H), 4.86 (dd, 1H), 5.11 (s, 2H), 5.12 (s, 4H), 7.2–7.4 (m, 15H), 8.03 (bs, NH), 10.35 (bs, NH)

(iv) HOOC—CH$_2$—CH$_2$—(R)Cgl-Aze-Pig×2 HCl 0.218 g (0.27 mmole) of BnOOC—CH$_2$—CH$_2$—(R)Cgl-Aze-Pig(Z)$_2$ was mixed with 0.10 g 5% Pd/C, 1 ml 1M HCl-solution, 1 ml water and 10 ml ethanol and the mixture was hydrogenated at atmospheric pressure for one hour. Filtration of the catalyst through hyflo, evaporation of the solvent followed by freeze drying twice from water gave 134 mg (95%) of the title compound.

$^1$H-NMR (300 MHz, D$_2$O): δ 1.0–1.4 (m, 7H), 1.55–2.05 (m, 9H), 2.22–2.34 (m, 1H), 2.61–2.76 (m, 1H), 2.88 (t, 2H), 3.08 (bt, 2H), 3.19 (d, 2H), 3.34 (m, 2H), 3.83 (bd, 2H), 3.95 (d, 1H), 4.29–4.49 (m, 2H), 4.90 (dd, 1H)

$^{13}$C-NMR (75 MHz, D$_2$O): amidine and carbonyl carbons: δ 156.4, 167.6, 172.1 and 174.7

Example 50
HOOC—CH$_2$—(R)Cgl-Pro-Pig×2 HCl
(i) Boc-(R)Cgl-Pro-Pig(Z)$_2$ 0.568 g (2.96 mmol) EDC was added at −15° C. to a mixture of 1 g (2.82 mmol) Boc-(R)Cgl-Pro-OH (See preparation of starting materials), 1.197 g (2.82 mmol) H-Pig(Z)$_2$ (See preparation of starting materials) and 1.38 g (11.28 mmol) DMAP in acetonitrile. The temperature was allowed to rise to roomtemperature over night. The solvent was evaporated in vacuo and methylenchloride and 1 M KHSO$_4$ was added. The phases were separated and the organic phase was washed with saturated NaHCO$_3$, water and brine, drying (Na$_2$SO$_4$) and evaporation of the solvents gave 2.033 g of a residue wich was subjected to flash chromatography using ethylacetate as eluent. This gave two products; 720 mg (34%) of the title compound which eluted first from the column followed by 775 mg (44%) of Boc-(R)Cgl-Pro-Pig (Z) formed by loss of one of the Z-protecting groups.

$^1$H-NMR (300 MHz, CDCl$_3$); Some signals, especially in the piperidin ring, are selectively broader due to an intramolecular exchange process. This is especially pronounced for the 2- and 6-CH$_2$ groups of the piperidin ring, wich exhibit a broad peak ranging from 3.5 to 4.5 ppm.

δ 0.85–2.1 (m, 19H), 2.3–2.45 (m, 1H), 2.8–3.2 (m, 4H), 3.45–3.55 (m, 1H), 3.55–3.65 (m, minor rotamer), 3.8–3.93 (m, 1H), 3.97–4.1 (m, 1H), 4.52–4.62 (d, 1H), 5.1 (apparent bs, 5H), 7.12–7.41 (m, 10H).

$^{13}$C-NMR (75 MHz, CDCl$_3$): amidine and carbonyl carbons: δ 155.2, 156.3, 171.0 and 172.1.

(ii) H—(R)Cgl-Pro-Pig(Z)$_2$ 720 mg (0.946 mmol) of Boc-(R)Cgl-Pro-Pig(Z)$_2$ was dissolved in 35 ml of TFA/CH$_2$Cl$_2$, 1/4 and stirred for 30 minutes. The solvent was removed in vacuo and ethylacetate and 2M NaOH was added. The organic layer was washed with water and brine, dried (Na$_2$SO$_4$) and the solvent was evaporated in vacuo to give the title compound in quantitative yield.

$^1$H-NMR (300 MHz, CDCl$_3$); Some signals, especially in the piperidin ring, are selectively broader due to an intramolecular exchange process. This is especially pronounced for the 2- and 6-CH$_2$ groups of the piperidin ring, wich exhibit a broad peak ranging from 3.5 to 4.5 ppm.

δ 0.8–2.15 (m, 19H), 2.22–2.4 (m, 1H), 2.75–2.98 (m, 2H), 2.98–3.18 (m, 2H), 3.18–3.35 (m, 1H), 3.35–3.5 (qvart., 1H), 3.5–3.7 (m, 1H), 4.42–4.58 (d, 1H), 5.1 (s, 4H), 7.1–7.5 (m, 10H).

$^{13}$C-NMR (75 MHz, CDCl$_3$): amidine and carbonyl carbons; δ 154.96, 171.31, 174.82.

(iii) BnOOC—CH$_2$—(R)Cgl-Pro-Pig(Z)$_2$ 0.298 g (0.999 mmol) BnOOC—CH$_2$—OTf (see preparation of startingmaterials was added to a mixture of 0.64 g (0.999 mmol) H—(R)Cgl-Pro-Pig(Z)$_2$ and 0.531 g (2.996 mmol) K$_2$CO$_3$ in 6.4 ml acetonitrile and heated to reflux. After 1 h 20 min the mixture was washed with water, dried (Na$_2$SO$_4$) and the solvent evaporated in vacuo to give 729 mg of a residue which was subjected to flash chromatography using ethylacetate as eluent. This gave two products: 120 mg of (BnOOC—CH$_2$)$_2$—(R)Cgl-Pro-Pig(Z)$_2$ which eluted first from the column and 142 mg (18%) of the title compound.

$^1$H-NMR (300 MHz, CDCl$_3$); Some signals, especially in the piperidin ring, are selectively broader due to an intramolecular exchange process. This is especially pronounced for the 2- and 6-CH$_2$ groups of the piperidin ring, wich exhibit a broad peak ranging from 3.5 to 4.6 ppm.

δ 0.94–2.27 (m, 19H), 2.28–2.43 (m, 1H), 2.8–2.98 (m, 2H), 2.98–3.06 (m, 1H), 3.06–3.15 (d, 1H), 3.15–3.25 (m, 1H), 3.3–3.5 (m, 4H), 4.5–4.61 (d, 1H), 5.1 (s, 6H), 7.1–7.6 (m, 15H), 10.52 (bs, 1H).

(iv) HOOC—CH$_2$—(R)Cgl-Pro-Pig×2 HCl 142 mg (0.176 mmol) BnOOC—CH$_2$—(R)Cgl-Pro-Pig (Z)$_2$ was hydrogenated in the presence of 0.88 ml 1 M hydrochloric acid, 10 ml ethanol (99.5%) and 180 mg 5% Pd/C for 2 h. Removal of the catalyst by filtration on hyflo and millipore filter followed by evaporation of the solvent in vacuo and freeze drying gave 95 mg of HOOC—CH$_2$—(R)Cgl-Pro-Pig×2 HCl. This crude material (79% purity) was purified on RPLC using CH$_3$CN/0.1H NH$_4$OAc 15/85 as eluent. Removal of the solvent and excess NH$_4$OAc by freeze drying, conversion to hydrochloric acid salt by dissolving in 1 M hydrochloric acid followed by freeze drying gave the title compound.

$^1$H-NMR (500 MHz, D$_2$O); δ 1.1–1.35 (m, 6H), 1.63–2.14 (m 13H), 2.26–2.36 (m, 1H), 3.01–3.23 (m, 4H), 3.49–3.62 (qvart., 2H), 3.62–3.77 (m, 2H), 3.77–3.88 (apparent d, 2H), 4.18–4.32 (d, 1H), 4.37–4.5 (m, 1H).

Example 51
H—(R)Cha-Aze-Pig×2 HCl
(i) Boc-(R)Cha-Aze-Pig(Z)$_2$

To a well stirred mixture of 86 mg (0.243 mmol) Boc-(R)Cha-Aze-OH (See preparation of starting materials), 100 mg (0.236 mmol) H-Pig(Z)$_2$ (See preparation of starting materials) and 115 mg (0.944 mmol) DMAP in 5 ml CH$_3$CN was added 50 mg (0.260 mmol) EDC and the reaction was stirred for 20 h at room temperature. The solvent was evaporated and the residue was dissolved in 70 ml EtOAc and the organic phase was washed with 3×5 ml 1 M KHSO$_4$, 1×5 ml NaHCO$_3$, 3×5 ml H$_2$O, 1×5 ml brine and dried (MgSO$_4$). Filtration and evaporation of the solvent gave 141 mg of an oil. The crude product was purified by flash chromatography (36 g SiO$_2$) using a stepwise gradient of CH$_2$Cl$_2$/MeOH (97/3 followed by 95/5) to yield 43 mg (24%) of the title compound.

(ii) H—(R)Cha-Aze-Pig(z)$_2$

Hydrogen chloride was bubbled through a mixture of 43 mg (0.0565 mmol) Boc-(R)Cha-Aze-Pig(Z)$_2$ in 10 ml of ethylacetate during 5 minutes. The solvent was evaporated in vacuo and ethyl acetate and 0.1 M NaOH-solution was added. The phases were separated and the organic phase was washed with water and brine and dried (Na$_2$SO$_4$). The solvent was evaporated to give 38 mg, wich was subjected to flash chromatography using 10% NH3-saturated methanol in ethyl acetate as eluent to give 28 mg of the desired product.

$^1$H-NMR (300 MHz, CDCl$_3$); Some signals, especially in the piperidin ring, are selectively broader due to an intramolecular exchange process. This is especially pronounced for the 2- and 6-CH$_2$ groups of the piperidin ring, wich exhibit a broad peak ranging from 3.7 to 4.5 ppm.

δ 0.75–1.85 (m, 18H), 2.35–2.53 (m, 1H), 2.62–2.78 (m, 1H), 2.8–3.0 (m, 2H), 3.0–3.28 (m, 2H), 3.28–3.3.7 (m, 1H), 3.97–4.18 (m, 2H), 4.8–4.9 (m, 1H), 5.1 (s, 4H), 7.2–7.45 (m, 9H), 8.05–8.15 (m, 1H).

(iii) H—(R)Cha-Aze-Pig×2 HCl 28 mg (0.042 mmol) H—(R)Cha-Aze-Pig(Z)$_2$ dissolved in 2 ml ethanol (99.5%) and 0.13 ml hydrogen chloride (1 N) was hydrogenated in the presence of 35 mg 5% Pd/C for 4 h. Removal of the catalyst by filtration and evaporation in vacuo of the solvent followed by dissolving in water and freeze drying gave 12 mg (60. %) of H—(R)Cha-Aze-Pig dihydrochloride.

$^1$H-NMR (500 MHz, 300 K, CD$_3$OD); Some signals, especially in the piperidin ring, are selectively broader due to an intramolecular exchange process. This is especially pronounced for the 2- and 6-CH$_2$ groups of the piperidin ring, wich exhibit a broad peak ranging from 3.7 to 4.5 ppm.

δ 0.75–2.1 (m, 18H), 2.2–2.35 (m, 1H), 2.62–2.75 (in, 1H), 3.0–3.12 (t, 2H), 3.12–3.23 (d, 2H), 3.85–3.95 (d, 2H), 3.95–4.0 (dd, 1H), 4.15–4.23 (m, 1H), 4.35–4.42 (m, 1H), 4.72–4.78 (m, 1H).

$^{13}$C-NMR (75 MHz, CD$_3$OD): guanidine: δ 157.6; carbonyl carbons: δ 170.0 and 172.6.

Example 52

HOOC—CH$_2$—(R)Cgl-Aze-Pac×2 HCl (i) Boc-(R)Cgl-Aze-Pac(Z)

To a solution of 0.47 g (1.4 mmol) of Boc-(R)Cgl-Aze-OH (See preparation of starting materials), 0.40 g (1.4 mol) of H-Pac(Z)(See preparation of starting materials) and 0.67 g (5.5 mmol) of DMAP in 5 ml of acetonitril was added 0.27 g of EDC at 0° C. The mixture was stirred at room temperature over night and subsequently diluted with ethyl acetate. The solution was washed with KHSO$_4$ (aq) and NaHCO$_3$ (aq), dried (Na$_2$SO$_4$), filtered and evaporated. Flash chromatography using ethyl acetate followed by ethyl acetate/methanol 98/2 as eluents gave 0.25 g (301) of the title compound as a mixture of 1,4-cis- and trans-products with respect to the Pac part of the molecule.

$^1$H-NMR (500 MHz, CDCl$_3$): δ 0.8–2.0 (m, 29H; thereof 1.45 (s, 9H)), 2.15 and 2.34 (m, 1H, isomers), 2.45–2.7 (m, 2H), 3.0–3.4 (m, 2H), 3.85 (m, 1H), 4.14 (m, 1H), 4.33 (m, 1H), 4.85 (m, 1H), 4.98 (m, 1H), 5.04 (s, 2H), 7.25–7.45 (m, 5H), 7.8–7.9 (m, 1H), 9.2–9.5 (m, 1H).

(ii) H—(R)Cgl-Aze-Pac(Z)×HCl

Boc-(R)Cgl-Aze-Pac(Z), 0.25 g (0.41 mmol), was dissolved in 100 ml of ethyl acetate and cooled in an ice bath. HCl (g) was bubbled through for 5 min and the solvent was evaporated.

$^1$H-NMR (300 MHz, MeOD): δ 0.8–2.0 (m, 22H), 2.05–2.35 (m, 1H), 2.4–2.55 (m, 1H), 2.6–2.75 (M, 1H), 3.00 (d, 1H), 3.05 and 3.37 (multiplets, 0.6H and 0.4H respectively, isomers), 3.15–3.3 (m, 1H), 4.05–4.2 (m, 2H), 4.88 (dd, 1H), 5.11 (s, 2H), 7.2–7.45 (m, 5H), 8.0–8.15 (m, 1H).

(iii) BnO$_2$C—CH$_2$—(R)Cgl-Aze-Pac(Z)

A mixture of 0.17 g (0.33 mmol) of H—(R)Cgl-Aze-Pac(Z)×HCl, 0.11 g (0.37 mmol) of benzyl triflyloxyacetate and 0.14 g (1.0 mmol) of K$_2$CO$_3$ in 5 ml of acetonitrile was stirred at room temperature for 3 days. The crude material was flash chromatographed with EtOAc/CH$_2$Cl$_2$/MeOH 95/20/5. Yield: 70 mg (32%)

$^1$H-NMR (500 MHz, CDCl$_3$): δ 0.85–2.3 (m, 20H), 2.48 (m, 1H), 2.63 (m, 1H), 2.87 (m, 1H), 3.05–3.25 (m, 1H), 3.25–3.35 (m, 2H), 3.38 (dd, 1H), 3.95 (m, 1H), 4.08 (m, 1H), 4.88 (m, 1H), 5.1–5.2 (m, 4H), 5.9–6.3 (m, 1H), 7.25–7.5 (m, 10H), 8.00 and 8.08 (broad triplets, 1H, isomers).

(iv) HO$_2$C—CH$_2$—(R)Cgl-Aze-Pac×2 HCl

BnO$_2$C—CH$_2$—(R)Cgl-Aze-Pac(Z), 70 mg (0.11 mmol), was dissolved in 5 ml of ethanol, and 5% Pd/C and 0.1 ml of conc. HCl were added. The mixture was hydrogenated at atmospheric pressure for 1 h. After filtration and evaporation the product was purified through preparative RPLC using 0.1 M NH$_4$OAc/CH$_3$CN 4/1 as eluent. After change of salt to the hydrochloride and freeze drying the title compound was obtained as a 45/55 mixture of 1,4-cis- and trans-isomers with respect to the Pac part of the molecule. Yield: 40 mg (74%).

$^1$H-NMR (500 MHz, D$_2$O) δ 1.1–2.1 (m, 20H), 2.32 (m, 1H), 2.52 (m, 1H), 2.63 (m, 1H), 2.72 (m, 1H), 3.1–3.3 (m, 1H), 3.40 (m, 1H), 3.8–3.95 (m, 2H), 4.04 (d, 1H), 4.39 (m, 1H), 4.93 (m, 1H).

$^{13}$C-NMR (125 MHz, D$_2$O) amidine and carbonyl carbons: δ 167.7, 172.0, 174.9 and 175.2.

Example 53

H—(R)Cha-Pro-Pac×2 HCl (i) Boc-(R)Cha-Pro-Pac(Z)

211 mg (1.1 μmmol) EDC was added at 0° C. to a stirred solution of 0.4 g (1.1 mmol) H-Pac(Z)×2 HCl (See preparation of starting materials), 0.4 g (1.1 mmol) Boc-(R)Cha-Pro-OH(See preparation of starting materials), and 0.55 g DMAP in 7 ml acetonitrile. The reaction mixture was stirred at 0° C. for 1 h and at room temperature for 2 h. The solvent was removed in vacuo and the residue was diluted with ethyl acetate and water. The organic phase was washed with acetic acid, water, and sodium hydrogen carbonate solution and dried (MgSO$_4$). Removal of the solvent in vacuo gave a residue which was purified by flash chromatography using ethyl acetate as eluent to give 196 mg (27%) of the title compound.

(ii) H—(R)Cha-Pro-Pac(Z)

Hydrogen chloride was bubbled through a solution of 196 mg Boc-(R)Cha-Pro-Pac(Z) in 25 ml ethyl acetate. After 10 minutes the reaction mixture was diluted with methylene chloride and sodium hydroxide solution was added. The aqueous phase was extracted several times with methylene chloride and the combined organic phases were dried (K$_2$CO$_3$) and the solvent was removed in vacuo to give 86 mg (52%) of the title compound.

(iii) H—(R)Cha-Pro-Pac×2 HCl

The title compound was prepared by hydrogenation of H—(R)Cha-Pro-Pac(Z) in ethanol in the presence of 10% Pd/C.

H-NMR (300 MHz, D2O; A ca: 1:1 mixture of 1,4-cis- and 1,4-trans isomers in the Pac part of the molecule); δ 1.15–1.3 (q), 1.6–1.85 (m), 1.9–2.0 (m), 2.0–2.1 (d), 2.1–2.15 (m), 2.15–2.2 (m), 2.65–2.7 (m), 2.7–2.8 (m), 2.95–3.0 (d), 3.15–3.2 (d), 5.4 (s), 7.45–7.55 (m).

Example 54

N—(R)Cgl-Ile-Pab×2 HCl (i) Boc-(R)Cgl-Ile-Pab(Z)

To a stirred mixture of 1.33 g (3.6 mmol) Boc-(R)Cgl-Ile-OH (See Preparation of starting materials), 1.12 g (3.9 mmol) H-Pab(Z) (See Preparation of starting materials) and 1.76 g (14.4 mmol) DMAP in 50 ml CH$_3$CN/DMF (1/1) was added 0.75 g (3.9 mmol) EDC at +5° C. The reaction mixture was allowed to reach room temperature and left for 60 h. The CH₃CN was removed by evaporation and the residue was poured out in 100 ml water (a yellow precipitate was formed). The mixture was extracted with 2×50 ml EtOAc and the combined organic phase was washed with 2×30 ml NaHCO₃(saturated), 2×50 ml 0.2 M HCl, 1×50 ml Brine and dried (MgSO₄). Evaporation followed by flash chromatography using CH₂Cl₂/THF (85/15) as eluent gave 510 mg (24%) of the title compound.

(ii) H—(R)Cgl-Ile-Pab(Z)

530 mg Boc-(R)Cgl-Ile-Pab(Z) was dissolved in 14 ml CH₂Cl₂/TFA (2.5/1) and stirred for 2 h at room temperature. Evaporation of the solvent followed by flash chromatography using CH₂Cl₂/MeOH(NH₃-saturated) (95/5) as eluent gave the title compound.

(iii) H—(R)Cgl-Ile-Pab×2 HCl 75 mg (0.14 mmol) H—(R)Cgl-Ile-Pab(Z) was hydrogenated over 10% Pd/C in 5 ml EtOH, which contained an excess HCl(g) to give the dihydrochloride, at atmospheric pressure for 6 h. Addition of 2 g activated charcoal and 20 ml EtOH followed by filtration through celite, evaporation of the solvent and freeze drying from water gave 50 mg (89%) of the title compound as a white powder.

¹H-NMR(500 MHz, MeOD): δ 0.90 (t, 3H), 0.94 (d, 3H), 1.1–2.0 (m, 14H), 3.83 (bs, 1H), 4.26 (d, 1H), 4.50 (m, 2H), 7.57 (bd, 2H), 7.78 (bd, 2H).

Example 55

H—(R)Cgl-Aze-Pab

Hydrogenation of 257 mg (5.08 μmmol) H—(R)Cgl-Aze-Pab(Z) (See Example 1 (ii)) over 5% Pd/C in 6 ml EtOH/H₂O at atmospheric pressure for 6 h followed by filtration of the catalyst, evaporation of the solvent and freeze drying from water gave 200 mg (89%) of the title compound.

¹H-NMR (500 MHz, D₂O): δ 1.0–2.0 (m, 11H), 2.25 (m, 1H), 2.70 (m, 1H), 3.30 (m, 1H), 3.75 (m, 1H), 4.30 (m, 1H), 4.45 (m, 1H), 4.55 (m, 2H), 7.60 (m, 2H), 7.77 (m, 2H).

MS m/z 372 (M⁺+1).

Example 56

HOOC—(R,S)CH(Me)—(R)Cha-Pro-Pab×HOAc (i) BnOOC—(R,S)CH(Me)—(R)Cha-Pro-Pab(Z)

0.250 g (0.47 mmol) H—(R)Cha-Pro-Pab(Z) (See Example 15) dissolved in 5 ml CH₂Cl₂ was cooled to −10° C. and 150 mg (0.48 mmol) of TfOCH₂COOBn (See Preparation of Startingmaterials) dissolved in 3 ml CH₂Cl₂ was added slowly. 200 mg (1.45 mmol) of potassium carbonate was added and the mixture was stirred at roomtemperature for 20 h. The mixture was diluted with CH₂Cl₂, extracted with water and dried (MgSO₄). Evaporation of the solvent followed by flash chromtography using CH₂Cl₂/MeOH 9/1 as eluent gave 150 mg (46%) of the title compound.

(ii) HOOC—(R,S)CH(Me)—(R)Cha-Pro-Pab×HOAc 150 mg (0.2 mmol) BnOOC—(R,S)CH(Me)—(R)Cha-Pro-Pab(Z) was hydrogenated over 50 mg 5% Pd/C in 20 ml EtOH at athmospheric pressure for 4 h. Filtration of the catalyst, evaporation of the solvent followed by purification by RPLC, using CH₃CN/0.1 M NH₄OAc 1/4 as eluent, gave 35 mg (37%) of the title compound.

¹H-NMR (500 MHz, MeOD): δ 1.00 (m, 1H), 1.20–1.45 (m, 5H), 1.5 (m, 1H), 1.6–1.8 (m, 6H), 1.9–2.1 (m, 6H), 2.25 (m, 1H), 3.25 (m, 1H), 3.5 (m, 1H), 3.85 (m, 1H), 4.15 (m, 1H), 4.35–4.6 (m, 3H), 4.9 (m, partially hidden by the HOD line, 6H), 7.55 (d, 2H), 7.75 (d, 2H).

Example 57

MeOOC—CH₂—(R)Cgl-Aze-Pab×2 HCl (i) MeOOC—CH₂—(R)Cgl-Aze-Pab(Z)

0.186 g (0.841 mmol) TfO-CH₂—COOMe (See preparation of starting materials) was dissolved in CH₂Cl₂ and slowly added to a mixture of 0.425 g (0.841 mmol) H—(R)Cgl-Aze-Pab(Z) (See Example 1), 0.894 g (5.04 mmol) K₂CO₃ in CH₂Cl₂ (totally 4.3 ml) at roomtemperature, and stirred over night. More CH₂Cl₂ was added and the mixture was washed with water and brine, dried, filtered and the solvent was evaporated in vacuo to give 0.51 g of a residue that was three times subjected to flash chromatography on silica gel using, first CH₂Cl₂/THF/MeOH (16/4/1), then CH₂Cl₂/THF(2% NH₃) (8/2) and the last time diethylether/MeOH(NH₃-saturated) (95/5) as eluent. This gave 0.324 g (67%) of the title compound.

(ii) MeOOC—CH₂—(R)Cgl-Aze-Pab×2 HCl 220 mg (0.38 mmol) MeOOC—CH₂—(R)Cgl-Aze-Pab(Z) was hydrogenated in the presence of 1.14 ml 1 N HCl, 6.5 ml MeOH and 300 mg Pd/C for 2 h. Removal of the catalyst by filtration on cellite and millipore filter followed by evaporation of the solvent in vacuo and freeze drying twice gave 178 mg (91%) of the title compound.

¹H-NMR (500 MHz, D₂O); δ 1.12–1.4 (m, 5H), 1.68–1.81 (m, 2H), 1.81–1.9 (m, 3H), 1.97–2.1 (m, 1H), 2.29–2.4 (m, 1H), 2.68–2.8 (m, 1H), 3.86 (s, 3H), 4.1 (s, 2H), 4.1–4.5 (d, 1H), 4.36–4.42 (t, 2H), 4.59 (s, 2H), 4.99–5.04 (m, 1H), 7.65–7.7 (d, 2H), 7.8–7.85 (d, 2H).

¹³C-NMR (75 MHz, MeOD): amidine and carbonyl carbons; δ 146.78, 167.68, 168.15, 172.29.

Example 58

EtOOC—CH₂—(R)Cgl-Aze-Pab×2 HCl (i) EtOOC—CH₂—(R)Cgl-Aze-Pab(Z)

0.208 g (0.876 mmol) TfO-CH₂—COOEt (See preparation of starting materials) was dissolved in CH₂Cl₂ and slowly added to a mixture of 0.443 g (0.876 mmol) H—(R)Cgl-Aze-Pab(Z) (See Example 1) and 0.931 g (5.26 mmol) K₂CO₃ in CH₂Cl₂ (totally 4 ml) cooled on an ice-bath. After 2 h the ice-bath was removed and stirring was continued at roomtemperature for 2 hours. More CH₂Cl₂ was added and the mixture was washed with water and brine, dried, filtered and the solvent was evaporated in vacuo to give 0.51 g of a residue that was subjected to flash chromatography using diethylether/MeOH(NH₃-saturated) (95/5) as eluent. This gave 0.387 g (75%) of the title compound.

(ii) EtOOC—CH₂—(R)Cgl-Aze-Pab×2 HCl 395 mg (0.668 mmol) EtOOC—CH₂—(R)Cgl-Aze-Pab(Z) was hydrogenated in the presence of 12 ml EtOH (99.5%) and 390 mg Pd/C for 5 h. Removal of the catalyst by filtration on cellite and millipore filter, followed by evaporation of the solvent in vacuo and freeze drying twice, gave 281 mg (88%) of EtOOC—CH₂—(R)Cgl-Aze-Pab. 2 eqvivalents of 1 N HCl was added, and freeze drying three times gave 288 mg (81%) of the title compound.

¹H-NMR (500 MHz, D₂O); δ 1.05–1.48 (m, 8H), 1.6–2.05 (m, 6H), 2.15–2.33 (m, 1H), 2.58–2.79 (m, 1H), 3.89–4.0 (m, 3H), 4.2–4.33 (m, 3H), 4.33–4.44 (m, 1H), 4.44–4.66 (m, 2H), 4.91 (m, 1H (partially hidden by the H-O-D signal)), 7.54–7.63 (d, 2H), 7.72–7.84 (d, 2H).

Example 59

"BuOOC—CH₂—(R)Cgl-Aze-Pab×HOAc (i) "BuOOC—CH₂—(R)Cgl-Aze-Pab(z)

Prepared in the same way as described for "HexOOC—CH₂—(R)Cgl-Aze-Pab(Z) (See Example 60 (i)) using TfO-CH₂—COO"Bu as alkylating agent. The crude product was purified by flash chromatography twice, first using CH₂Cl₂/

MeOH (95/1) as eluent and then $CH_2Cl_2$/i-propylalcohol (90/7) to give 324 mg (47%) of the title compound.

(ii) "BuOOC—$CH_2$—(R)Cgl-Aze-Pab×HOAc

The deprotection was done according to the procedure described in Example 57 (ii). The crude material was purified on RPLC using $CH_3CN$ (30%) in 0.05 M $NH_4OAc$ and 0.05 M HOAc as eluent to give 100 mg (53%) of the title compound.

$^1$H-NMR (300 MHz, MeOD); δ 0.85–2.1 (m, 18H), 2.15–2.37 (m, 1H), 2.58–2.8 (m, 1H), 3.7–5.0 (m, 10H), 4.88–5.0 (partially hidden by the H-O-D signal)), 7.46–7.65 (d, 2H), 7.71–7.88 (d, 2H).

$^{13}$C-NMR (75 MHz, MeOD): amidine and carbonyl carbons; δ 146.8, 168.12, 168.2, 172.2.

Example 60

"HexOOC—$CH_2$—(R)Cgl-Aze-Pab×2 HCl (i) "HexOOC—$CH_2$—(R)Cgl-Aze-Pab(Z)

0.402 g (1.375 mmol) TfO-$CH_2$—COO"Hex (See Preparation of starting materials) was dissolved in $CH_2Cl_2$ and slowly added to a mixture of 0.695 g (1.375 mmol) H—(R) Cgl-Aze-Pab(Z) (See Example 1), 1.463 g (8.25 mmol) $K_2CO_3$ in $CH_2Cl_2$ (totally 4 ml) at <–10° C. After 1 h the $CO_2$-ice-bath was removed and stirring was continued at room temperature for 45 minutes. More $CH_2Cl_2$ was added and the mixture was washed with water and brine, dried, filtered and the solvent was evaporated in vacuo to give 0.828 g of a residue, wich was twice subjected to flash chromatography, first using diethylether/MeOH($NH_3$-saturated) (95/5), and then $CH_2Cl_2$/MeOH($NH_3$-saturated) (95/5) as eluent. This gave 0.42 g (47%) of the title compound.

(ii)"HexOOC—$CH_2$—(R)Cgl-Aze-Pab×2 HCl

Hydrogenation of 400 mg (0.617 mmol)"HexOOC—$CH_2$—(R)Cgl-Aze-Pab(Z) in the presence of 12 ml THF and 400 mg Pd/C for 1.5 h did not give complete de-protection. The hydrogenation was completed in 4 h in the presence of 1.7 ml 1 N HCl, 12 ml MeOH and 340 mg Pd/C. Removal of the catalyst by filtration on cellite and millipore filter, followed by evaporation of the solvent in vacuo and freeze drying twice, gave 287 mg (79%) of the title compound.

$^1$H-NMR (300 MHz, MeOD); δ 0.8–2.13 (m, 22H), 2.13–2.31 (m, 1H), 2.61–2.81 (m, 1H), 3.93–4.15 (m, 3H), 4.15–4.37 (m, 3H), 4.37–4.7 (m, 3H), 4.88–5.0 (m, 1H (partialyy hidden by the H-O-D signal)), 7.52–7.69 (d, 2H), 7.75–7.9 (d, 2H).

$^{13}$C-NMR (75 MHz, MeOD): amidine and carbonyl carbons; δ 146.84, 167.67, 167.84, 172.17.

Example 61

H—(R)Cgl-Pro-Pac×2 HCl (i) Boc-(R)Cgl-Pro-Pac(Z)

377 mg (1.97 mmol) EDC was added at 0° C. to a stirred solution of 708 mg (1.95 mmol) of Boc-(R)Cgl-Pro-OH (See Preparation of startingmaterial), 714 mg (2.0 mmol) H-Pac(Z)×2 HCl (See Preparation of startingmaterial) and 1.078 g (8.8 mmol) DMAP in 12.5 ml acetonitrile. The reaction mixture was allowed to reach room temperature over night. The solvent was removed in vacuo and the residue was first purified by flash chromatography, using 10% methanol in methylene chloride as eluent, and subsequently by RPLC. Two fractions (51 mg and 150 mg) giving MS m/z=626 (M+1) were isolated.

(ii) H—(R)Cgl-Pro-Pac(Z)

Hydrogen chloride was bubbled into a solution of 141 mg (0.22 mmol) Boc-(R)Cgl-Pro-Pac(Z) in 50 ml ethyl acetate. After 15 minutes 10% sodium carbonate solution was added and the organic phase was separated and dried ($K_2C_3$).

Evaporation of the solvent gave 71 mg (61%) of the product.

(iii) H—(R)Cgl-Pro-Pac×2 HCl

A mixture of 71 mg (0.14 mmol) H—(R)Cgl-Pro-Pac(Z) and a small spatula of 10% Pd/C in 10 ml of ethanol was hydrogenated at room temperature and atmospheric pressure for 2 h. The catalyst was removed by filtration and the solvent was removed in vacuo. The residue was dissolved in 50 ml water and 0.6 g 1M hydrochloric acid. Freeze drying yielded 38 mg (58%) of the title compound.

MS m/z 392 (M+1)

Example 62

HOOC—$CH_2$—(R)Cha-Pro-Pac×HOAc (i) BnOOC—$CH_2$—(R)Cha-Pro-Pac(Z)

A mixture of 84 mg (0.15 mmol) H—(R)Cha-Pro-Pac(Z) (See Example 53 (ii)), one spatula of potassium carbonate, and 47 mg of TfO$CH_2$—COOBn (See Preparation of starting materials) in 3 ml of methylene chloride was stirred at room temperature over night. The reaction mixture was filtered and the solvent was removed in vacuo to give a residue which was subjected to flash chromatography using ethyl acetate/methylene chloride/methanol 95:20:5 as eluent. 29 mg of the desired product was isolated.

(ii) HOOC—$CH_2$—(R)Cha-Pro-Pac×HOAc

A mixture of 29 mg BnOOC—$CH_2$—(R)Cha-Pro-Pac(Z) and 37 mg of 10% Pd—C in 5 ml etanol was stirred for 4 h at room temperature and atmospheric pressure. Filtration of the catalyst followed by removal of the solvent and purification by RPLC gave the desired compound.

MS m/z 464 (M+1).

Example 63

HOOC—$CH_2$—$CH_2$—(R)Cgl-Pro-Pac (i) BnOOC—$CH_2$—$CH_2$—(R)Cgl-Pro-Pac(Z)

A solution of 0.35 g (0.64 mmol) H—(R)Cgl-Pro-Pac(Z) (See Example 61 (ii)), 124 mg (0.76 mmol) benzyl acrylate, and 280 μl (2 mmol) triethyl amine in 1 ml ethanol was kept at room temperature for 3 days. Removal of the solvent followed by purification by HPLC gave 18 mg (4%) of the title compound.

(ii) HOOC—$CH_2$—$CH_2$—(R)Cgl-Pro-Pac

A mixture of 18 mg BnOOC—$CH_2$—$CH_2$—(R)Cgl-Pro-Pac(Z) and a small spatula of 10% Pd/C was hydrogenated for 2 h at room temperature and atmospheric pressure in EtOH. Filtration followed by removal of the solvent in vacuo and dissolution in water and freeze drying gave 7 mg (78%) of the title compound. MS m/z 464 (M+1).

Example 64

HOOC—$CH_2$—$CH_2$—(R)Cha-Aze-Pac (i) Boc-(R)Cha-Aze-Pac(Z)

A solution of 0.4 g (1.38 mmol) H-Pac(Z) (See Preparation of startingmaterial of H-Pac(Z)×2 HCl), 0.5 g (1.41 mmol) Boc-(R)Cha-Aze-OH(See Preparation of startingmaterial), and 0.67 g (5.5 mmol) DMAP in 20 ml acetonitrile was mixed at 0° C. with a solution of 0.26 g (1.4 mmol) EDC in 15 ml acetonitrile. The reaction mixture was kept at room temperature over night and the solvent was subsequently removed in vacuo. The residue was partitioned between ethyl acetate and water. The aqueous phase was extracted once more with ethyl acetate and the combined organic phases were washed with sodium hydrogen sulphate solution, sodium carbonate solution, and brine and then dried (sodium sulphate). Evaporation of the solvent gave 0.54 g (63%) of the title compound.

(ii) H—(R)Cha-Aze-Pac(Z)

Hydrogen chloride was bubbled into a solution of 0.54 g (0.9 mmol) Boc-(R)Cha-Aze-Pac(Z) in ethyl acetate. The solution was kept in the refrigerator over night and the solvent was then removed in vacuo and the residue was dissolved in ethyl acetate. The solution was washed with aqueous sodium hydrogen carbonate solution, water and brine and dried (sodium sulphate). Removal of the solvent gave 0.35 g (77%) of the product.

(iii) BnOOC—$CH_2$—$CH_2$—(R)Cha-Aze-Pac(Z)

A solution of 180 mg (0.33 mmol) H—(R)Cha-Aze-Pac (Z) and 53 mg (0.33 mmol) benzyl acrylate in ethanol was kept at room temperature for 60 h. The solvent was removed in vacuo and the residue was dissolved in ethyl acetate. The solution was washed with potassium hydrogen sulphate solution and sodium hydrogen carbonate solution and brine. Drying (sodium sulphate) and removal of the solvent in vacuo gave a residue which was purified by flash chromatography, using 10% methanol in methylene chloride as eluent to yield 150 mg (66%) of the title compound (iv) HOOC—$CH_2$—$CH_2$—(R)Cha-Aze-Pac×2 HCl A mixture of 115 mg BnOOC—$CH_2$—$CH_2$—(R)Cha-Aze-Pac(Z) and 67 mg of 10% Pd—C in 10 ml ethanol was hydrogenated for 1.5 h at room temperature and atmospheric pressure. Filtration followed by removal of the solvent in vacuo and dissolution of the residue in water and 1.5 ml of 1M hydrochloric acid gave a solution which was freeze dried to give 30 mg (33%) of the title compound.

MS m/z 464 (M+1).

Example 65

HOOC—$CH_2$—(R)cha-Aze-Pig×2 HCl (i) BOC-(R)cha-Aze-Pig(z)

0.249 g (1.298 mmol) EDC was added at <−15° C. to a mixture of 0.473 g (1.236 mmol) Boc-(R)Cha-Aze-OH (See Preparation of starting materials), 0.404 g (1.236 mmol) H-Pig(Z)×HCl (See Preparation of starting materials) and 0.604 g (4.94 mmol) DMAP in 13.5 ml DMF. The temperature was allowed to rise to roomtemperature over night. The solvent was evaporated in vacuo and EtOAc and 2 M $KHSO_4$ was added. The phases were separated and the organic phase was washed with saturated $Na_2CO_3$ and brine. Repeting the extractive procedure, drying ($Na_2SO_4$), filtration and evaporation of the solvents gave 0.612 g of a residue which was subjected to flash chromatography using EtOAc/MeOH 9/1 as eluent. This gave 407 mg (53%) of the title compound.

(ii) H—(R)cha-Aze-Pig(z)

0.4 g (0.638 mmol) of Boc-(R)Cha-Aze-Pig(Z) was dissolved in 24.4 ml of TFA/$CH_2Cl_2$ 1/4, stirred for 30 minutes on an ice-bath, and for 30 minutes at roomtemperature. The solvent was removed in vacuo and EtOAc and saturated $Na_2CO_3$ was added. The phases were seperated and the organic layer was washed with water and brine, dried ($Na_2SO_4$), filtered and the solvent was evaporated in vacuo to give 336 mg (100%) of the title compound.

(iii) BnOOC—$CH_2$—(R)Cha-Aze-Pig(Z)

89 ml (0.562 mmol) BnOOC—$CH_2$—Br was slowly added to a mixture of 0.296 g (0.562 mmol) H—(R)Cha-Aze-Pig(Z) and 0.171 g (1.236 mmol) $K_2CO_3$ in 6 ml $CH_3CN$ heated to 60° C. on an oilbath. After 1 h 45 minutes the solvent was evaporated, EtOAc was added, and the mixture was washed with water, dried ($Na_2SO_4$), filtered and the solvent was evaporated in vacuo to give 346 mg of a residue which was subjected to flash chromatography using $CH_2Cl_2$/THF/MeOH (8/2/1) as eluent. This gave 297 mg (78%) of the title compound.

(iv) HOOC—$CH_2$—(R)Cha-Aze-Pig×2 HCl 243 mg (0.36 mmol) BnOOC—$CH_2$—(R)Cha-Aze-Pig (z) was hydrogenated in the presence of 1.7 ml 1 N HCl, 10 ml EtOH (99.5%) and 300 mg Pd/C for 2 h. Removal of the catalyst by filtration on cellite and millipore filter followed by evaporation of the solvent in vacuo and freeze drying twice gave 166 mg (88%) of the title compound.

$^1$H-NMR (500 MHz, $D_2O$); δ 0.6–1.9 (m, 18H), 2.1–2.27 (m, 1H), 2.52–2.76 (m, 1H), 2.82–3.2 (m, 4H), 3.46–3.61 (m, 1H), 3.61–3.81 (m, 2H), 3.81–4.0 (m, 2H), 4.0–4.24 (m, 2H), 4.24–4.4 (m, 1H).

Example 66

HOOC—$CH_2$—(R)Cha-Pro-Pig×2 HCl (i) Boc-(R)Cha-Pro-Pig(Z)

To a mixture of 0.3495 g (0.95 mmole) Boc-(R)Cha-Pro-OH (see Preparation of starting materials), 0.464 g (3.8 mmole) DMAP, 0.310 g (0.95 mmole) H-Pig(Z)×HCl (See Preparation of starting materials) in 5 ml $CH_2Cl_2$ was added 0.192 g (1 mmole) of EDC and the mixture was stirred over night at room temperature. The mixture was evaporated and the residue was dissolved in ethyl acetate. The organic phase was washed twice with 0.3 M $KHSO_4$ and once with brine. The organic layer was dried ($Na_2SO_4$), filtered and evaporated. The crude product was purified by flash chromatography using a stepwise gradient of $CH_2Cl_2$/MeOH (100/0, 97/3, 95/5, 90/10) as eluent to yield 307 mg of the title compound.

(ii) H—(R)Cha-Pro-Pig(Z)

0.306 g (0.48 mmole) Boc-(R)Cha-Pro-Pig(Z) was dissolved in 30 ml HCl saturated ethyl acetate. The mixture was allowed to stand for half an hour. The solvent was evaporated and the residue was dissolved in $CH_2Cl_2$. The organic layer was washed twice with 0.2 M NaOH. The combined water layer was extracted once with $CH_2Cl_2$ and the combined organic layer was dried ($Na_2SO_4$), filtered and evaporated to yield 257 mg (99%) of the title compound.

(iii) BnOOC—$CH_2$—(R)cha-Pro-Pig(z)

A mixture of 0.256 g (0.473 mmole) H—(R)Cha-Pro-Pig (Z), 0.144 g (1.04 mmole) $K_2CO_3$ and 82 μl (0.521 mmole) of bensylbromoacetate in 6 ml acetonitrile was heated to 60° C. for two hours under stirring. The solvent was evaporated and the residue was dissolved in $CH_2Cl_2$, washed once with water and once with brine, dried ($Na_2SO_4$), filtered and the solvent evaporated. The crude product was purified by flash chromatography using a stepwise gradient of $CH_2Cl_2$/MeOH (97/3, 95/5, 90/10) as eluent to yield 0.2 g product (90% pure according to RPLC). The final purification was made on a chromatotron (Harrison research, model 7924T) on a 2 mm silica plate in $CH_2Cl_2$/MeOH 95/5 yielding 0.158 q (48%) of the pure product.

(iv) HOOC—$CH_2$—(R)Cha-Pro-Pig×2 HCl 0.158 g (0.227 mmole) of BnOOC—$CH_2$—(R)Cha-Pre-Pig(Z) was mixed with 0.075 g Pd/C (5%), 1.0 ml 1N HCl-solution and 10 ml ethanol. The mixture was hydrogenated at atmospheric for one hour. Filtration through cellite and evaporation of the solvent followed by freeze drying twice from water gave 119 mg (97%) of the product.

$^1$H-NMR (D2O, 300 MHz): δ 0.95–1.44 (m, 7H), 1.52 (m, 1H), 1.60–2.20 (m, 13H), 2.39 (m, 1H), 3.07–3.32 (m, 4H), 3.68 (m, 1H), 3.77–4.02 (m, 5H; thereof 3.98 (s, 2H), 4.44–4.58 (m, 2H)

$^{13}$C-NMR ($D_2O$, 75 MHz): carbonyl- and guanidine carbons: δ 156.5, 168.3, 169.6, 174.5

Example 67

HOOC—$CH_2$—$CH_2$—(R)Cha-Pro-Pig×2 HCl (i) BnOOC—$CH_2$—$CH_2$—(R)Cha-Pro-Pig(Z)

0.297 g (0.55 mmole) H—(R)Cha-Pro-Pig(Z) (See Example 66 (ii)) was dissolved in 2 ml ethanol and 90 μl (0.59 mmole) bensylacrylate was added. The reaction mixture was stirred for four days at room temperature. The solvent was evaporated and the crude product chromatographed on a chromatotron (Harrison research, model 7924T) using a 2 mm silica plate with a stepwise gradient of $CH_2Cl_2$/MeOH (95/5, 90/10) as eluent to yield 0.338 g (87%) of the title compound.

(ii) HOOC—$CH_2$—$CH_2$—(R)Cha-Pro-Pig×2 HCl 0.238 g (0.227 mmole) of BnOOC—$CH_2$—$CH_2$—(R)Cha-Pro-Pig(Z) was mixed with 0.120 g Pd/c (5%), 1.2 ml 1N HCl-solution and 15 ml ethanol. The mixture was hydrogenated at atmospheric pressure for one hour. Filtration of the catalyst through cellite, evaporation of the solvent followed by freeze drying twice from water gave 178 mg (95%) of the title compound.

$^1$H-NMR ($D_2O$, 300 MHz): δ 0.82–1.45 (m, 5H), 1.45–2.15 (m, 13H), 2.29 (m, 1H), 2.83 (t, 2H), 2.9–3.4 (m, 6H), 3.57 (bq, 1H), 3.67–3.87 (m, 3H), 4.25–4.43 (m, 2H)

$^{13}$C-NMR ($D_2O$, 75 MHz): carbonyl- and guanidine carbons: δ 156.3, 168.2, 174.3, 174.6

MS m/z 479 ($M^+$+1)

Example 68
(HOOC—$CH_2$)$_2$—(R)Cgl-Pro-Pig×2 HCl 120 mg (0.126) mmol (BnOOC—$CH_2$)$_2$—(R)Cgl-Pro-Pig(Z)$_2$ (See Example 50 (iii)) was hydrogenated in the presence of 0.75 ml 1 N HCl, 7 ml EtOH (99.5%) and 150 mg Pd/C for 4 h. Removal of the catalyst by filtration on cellite and millipore filter and evaporation of the solvent in vacuo followed by freeze drying gave 66 mg (90%) of the title compound.

$^1$-NMR (500 MHz, $D_2O$); δ 1.05–1.38 (m, 7H), 1.53–1.64 (d, 1H), 1.64–2.14 (m, 11H), 2.27–2.39 (m, 1H), 3.03–3.28 (m, 4H), 3.58–3.70 (m, 1H), 3.7–3.8 (m, 1H), 3.8–3.9 (d, 2H), 4.07–4.22 (m, 2H), 4.22–4.35 (m, 1H), 4.38–4.5 (m, 1H).

$^{13}$C-NMR (75 MHz, $D_2O$): amidine and carbonyl carbons; δ 156.28, 166.73, 170.14, 174.01.

Example 69
HOOC—$CH_2$—$CH_2$—(HOOC—$CH_2$)—(R)Cha-Pro-Pig×2 HCl (i) BnOOC—$CH_2$—$CH_2$-(BnOOC—$CH_2$)—(R)Cha-Pro-Pig(Z)

To a cold (ice-bath temperature) mixture of 100 mg (0.14 mmol) BnOOC—$CH_2$—$CH_2$—(R)Cha-Pro-Pig(Z) (See Example 67 (i)) and 80 mg (0.57 mmol) potassium carbonate in 4 ml of $CH_2Cl_2$ was carfully added a solution of 64 mg (0.21 mmol) TfO-$CH_2$—COOBn dissolved in 1 ml $CH_2Cl_2$. The reaction mixture was left at 0° C. for 30 minutes and then allowed to reach room temperature for 2 h after which it was heated to reflux for 30 minutes and finally left over night at room temperature. Evaporation of the solvent followed by flash chromatography using $CH_2Cl_2$/MeOH (97/3) as eluent afforded 65 mg (54%) of the title compound.

(ii) HOOC—$CH_2$—$CH_2$—(HOOC—$CH_2$)—(R)Cha-Pro-Pig×2 HCl 65 mg (0.08 mmol) of BnOOC—$CH_2$—$CH_2$-(BnOOC—$CH_2$)—(R)Cha-Pro-Pig(Z) was dissolved in 10 ml of EtOH/1M HCl (9/1) and hydrogenated over 10% Pd/C for 3 h at athmospheric pressure. Filtration of the catalyst evaporation of the solvent followed by freeze drying from water gave 40 mg (97%) of the title compound as a white powder.

$^{13}$C-NMR (125 MHz, MeOD): amidine and carbonyl carbons: δ 157.5, 167.2, 169.1, 173.7 and 174.1.

Example 70
HOOC—$CH_2$—(R)Cgl-Aza-(R,S)Itp×2 HCl
(i) Boc-(R)Cgl-Aze-(R,S)Itp(Ts)

Boc-(R)Cgl-Aze-OH (See Preparation of starting materials) (400 mg, 1.17 mmol), H—(R,S)Itp(Ts) (See Preparation of starting materials) (366 mg, 1.23 mmol) and DMAP (286 mg, 2.34 mmol) was dissolved in $CH_3CN$ (6 ml) and cooled to 5° C. EDC (236 mg, 1.23 mmol) was added and the resulting mixture was stirred at room temperature over night. The $CH_3CN$ was removed and the residue was disolved in MeOH/EtOAc/$H_2O$. The separated organic layer was washed with $K_2CO_3$(sat), 2 M KHSO4, brine and dried($Na_2SO_4$). Evaporation of the solvent resulted in a white solid, 688 mg (85%).

MS m/z 620 ($M^+$+1)

(ii) H—(R)Cgl-Aze-(R,S)Itp(Ts)

Boc-(R)Cgl-Aze-(R,S)Itp(Ts) (500 mg, 0.8 mmol) was dissolved in $CH_2Cl_2$ (50 ml) and HCl(g) was bubbled through the solution for ca 4 min. After 45 min the solvent was removed by evaporation and the resulting product was dissolved in EtOAc/MeOH/$H_2O$ and the acidic solution was treated with 2 N NaOH(aq) to pH=8–9. The organic layer was separated and dried($Na_2SO_4$). Evaporation of the solvent afforded 425 mg (100%) of the title compound as a white solid.

MS m/z 520 ($M^+$+1)

(iii) BnOOC—$CH_2$—(R)Cgl-Aze-(R,S)Itp(Ts)

H—(R)Cgl-Aze-(R,S)Itp(Ts) (400 mg, 0.77 mmol), Benzyl-2-(para-nitrobenzenesulfonyloxy)acetate (See Preparation of starting materials) (325 mg, 0.92 mmol) and $K_2CO_3$ (235 mg, 1.7 mmol) was stirred in $CH_3CN$ (5 ml) at 45° C. After a few hours the conversion was only 25% and therefore the temperature was increased to 60° C. and an additional amount of Benzyl-2-(para-nitrobenzenesulfonyloxy)acetate was added.

The reaction was stirred for 48 h, (startingm.:product/25:63), and then worked up. The solvent was evaporated and EtOAc/$H_2O$ was added to the residue. The phases were separated and the water-phase was washed twice with EtOAc and then the combined organic phase was washed with $K_2CO_3$(sat), 2 M KHSO4, $H_2O$ and dried $Na_2SO_4$). This aforded, after back-extraction of the acidic KHSO$_4$, some 340 mg which was purified by RPLC. This gave 34 mg (7%) of the title compound.

MS m/z 668 ($M^+$+1).

(iv) HOOC—$CH_2$—(R)Cgl-Aze-(R,S)Itp×2 HCl

BnOOC—$CH_2$—(R)Cgl-Aze-(R,S)Itp(Ts) (34 mg, 0.05 mmol) was dissolved in THF (5 ml) and $NH_3$(g) was destined (40 ml) into the reaction flask with a dry-ice cooler. Na(s) was added and a deep blue color appeared. The reaction was stirred for 5 min before it was quenched with HOAc (50 μl). The dry-ice cooler was removed and the $NH_3$(l) was allowed to evaporate. To the residue $H_2O$ and HOAc was added to pH=7. Freeze-drying and preparative RPLC gave several fractions which were analyzed with FAB-MS. Two fractions contained the desired compound, 3 mg (10%) after freeze-drying with 2.2 eq of 1 M HCl:

MS m/z 424 ($M^+$+1).

Example 71
HOOC—$CH_2$—(R)Cha-Aze-(R,S)Itp
(i) Boc-(R)Cha-Aze-(R,S)Itp(Ts)

Boc-(R)Cha-Aze-OH (See Preparation of starting materials) (169 mg, 0.5 mmol), H—(R,S)Itp(Ts) (See Preparation of starting materials) (155 mg, 0.52 mmol), DMAP (122 mg, 1 mmol) was dissolved in $CH_3CN$ (2.5 ml) and cooled to 5° C. EDC×HCl (115 mg, 0.6 mmol) was added and the resulting mixture was stirred at room temperature over night. Extra (0.5 eq) H—(R,S)Itp(Ts) and EDC was added after stirring over nigth. The reaction mixture was stirred an additional night and worked up as described in the Boc-(R)Cgl-Aze-(R,S)Itp(Ts) (See Example 70) case above. This gave 260 mg of crude product. Purification by RPLC gave 180 mg (57%) of the title compound.

MS m/z 634 (M$^+$+1).

(ii) H—(R)Cha-Aze-(R,S)Itp(Ts)

Boc-(R)Cha-Aze-(R,S)Itp(Ts) (180 mg, 0.28 mmol) was dissolved in CH$_2$Cl$_2$ (20 ml) and HCl(g) was bubbled through the solution for ca 4 min. After 45 min the solvent was removed by evaporation and the resulting product was dissolved in CH$_2$Cl$_2$ and washed with 2 M NaOH to pH=8–9. The phases were separated and the organic phase was dried(Na$_2$SO$_4$) and evaporated to yield 163 mg (ca 100%):

MS m/z 534 (M$^+$+1).

(iii) BnOOC—CH$_2$—(R)Cha-Aze-(R,S)Itp(Ts)

H—(R)Cha-Aze-(R,S)Itp(Ts) (80 mg, 0.15 mmol), K$_2$CO$_3$ (45 mg, 0.33 mmol) and Br—CH$_2$COOBn (39 mg, 0.17 mmol) was stirred in CH$_3$CN (1.5 ml) at 60° C. for 2.5 h. The solvent was evaporated and the residue was dissolved in EtOAc/H$_2$O. The phases were separated and organic phase was washed with 10% citric acid and dried (Na$_2$SO$_4$). Evaporation of the solvent gave a 171 mg of crude product, which was purified by RPLC yielding 53 mg (52%) of the title compound.

MS M/z 681 (M$^+$+1).

(iv) HOOC—CH$_2$—(R)Cha-Aze-(R,S)Itp

BnOOC—CH$_2$—(R)Cha-Aze-(R,S)Itp(Ts) (50 mg, 0.07 mmol) was treated as described for BnOOC—CH$_2$—(R)Cgl-Aze-(R,S)Itp(Ts) (See Example 70 (iv)). This gave a product mixture which was purified on a RPLC yielding 12 mg of a 1:1 mixture of the title compound together with a reduced form which appear at mass 439 (m/z).

MS m/z 438 (M$^+$+1)

Example 72

H—(R)Cha-Pic-(R,S)Itp×2 HCl (i) Boc-(R)Cha-Pic-(R,S)Itp(Ts)

At roomtemperature 2.1 g (5.5 mmol) Boc-(R)Cha-Pic-OH (See Preparation of starting materials), 1.0 g (8.2 mmol) DMAP and 1.7 g (5.8 mmol) H—(R,S)Itp(Ts) (See Preparation of starting materials) was dissolved in 40 mL acetonitrile. After a few minutes of stirring 1.1 g (5.8 mmol) EDC was added and the stirring was continued for 60 hours. The solvent was removed in vacuo and the residue was dissolved in CH$_2$Cl$_2$, washed with water, 0.3M KHSO$_4$ and KHCO3 (aq) and dried(Na$_2$SO$_4$). Evaporation of the solvent and filtration through Silica gel gave 2.43 g (67%) of the product.

MS m/z 661 (M$^+$+1)

(ii) Boc-(R)Cha-Pic-(R,S)Itp 2.4 g (3.6 mmol) Boc-(R)Cha-Pic-(R,S)Itp(Ts) was dissolved in 15 mL THF and NH$_3$ (g) was condensed into the flask followed by addition of Na. The reaction was quenched after 5 min with acetic acid and the NH$_3$ and the THF was evaporated. The residue was freezedried from water and purified by RPLC (CH$_3$CN/0.1M NH$_4$OAc, 6/4) to give 0.93 g (51%) of the desired product.

MS m/z 507 (M$^+$+1)

(iii) H—(R)Cha-Pic-(R,S)Itp×2 HCl

At roomtemperature 50 mg (0.099 mmol) Boc-(R)Cha-Pic-(R,S)Itp was dissolved in ethylacetate saturated with HCl (g). After stirring 2 h the solvent was removed in vacuo. The residue was freezedried from water three times to give 35 mg (74%) of the desired product.

MS m/z 407 (M$^+$+1)

Example 73

HOOC—CH$_2$—(R)Cha-Pic-(R,S)Itp×2 HCl (i) Boc-(R)Cha-Pic-(R,S)Itp(Z)

At roomtemperature 0.84 g (1.66 mmol) Boc-(R)Cha-Pic-(R,S)Itp (See Example 72) was dissolved in 10 mL CH$_2$Cl$_2$ and 10 mL 0.5M NaOH. 0.29 µL (1.82 mmol) Z-Cl was added dropwise. After stirring for 3 h the phases were separated and the organic phase was washed with water and dried over Na$_2$SO$_4$. Evaporation and flash chromatography (ethylacetate/heptane 9/1) gave 0.5 g (47%) of the desired product.

MS m/z 641 (M$^+$+1)

(ii) H—(R)Cha-Pic-(R,S)Itp(Z)

At roomtemperature 0.5 g (0.78 mmol) Boc-(R)Cha-Pic-(R,S)Itp(Z) was dissolved in ethylacetate saturated with HCl. Water was added and the mixture was made basic with K$_2$CO$_3$. The phasees was separated. The waterphase was extracted with CH$_2$Cl$_2$ and the organic phase was washed with water. The combined organic phase was then dried (Na$_2$SO$_4$). Evaporation of the solvent gave 0.3 g (71%) of the desired product.

MS m/z 541 (M$^+$+1)

(iii) BnOOC—CH$_2$—(R)Cha-Pic-(R,S)Itp(Z)

0.29 g (0.5 mmol) H—(R)Cha-Pic-(R,S)Itp(Z), 0.15 g (1 mmol) K$_2$CO$_3$ was taken up in 25 mL acetonitrile. 154 mg (0.6 mmol) benzylbromoacetate was added and the mixture was stirred at 50° C. for 4 h. evaporation and purification by RPLC (acetonitrile:0.1M NH$_4$OAc 70:30) gave about 200 mg of the desired product.

(iv) HOOC—CH$_2$—(R)Cha-Pic-(R,S)Itp×2 HCl 200 mg BnOOC—CH$_2$—(R)Cha-Pic-(R,S)Itp(Z) was dissolved in ethanol. A small spoon of lot Pd on charcoal was added and the mixture was hydrogenated for 4 h. Filtration through hyflo, evaporation of the solvent followed by freezedrying from water gave 53 mg of the desired product.

$^1$H NMR (300.13 MHz, D$_2$O); δ 1.0–2.35 (overlapping m, 22H), 3.28–3.51 (M, 5H), 3.51–3.64 (m, 1H), 3.75–4-03 (m, 3H), 5.03–5.14 (s broad, 1H). The signal of one of the protons is partially obscured by the H-O-D-signal.

MS m/z 465 (M$^+$+1)

Example 74

H—(R)Cgl-Pro-(R,S)Hig×2 HCl (i) Boc-(R)Cgl-Pro-(R,S)Hig(Z)

To a mixture of 1.0 g (2.95 mmole) Boc-(R)Cgl-Pro-OH (See Preparation of startingmaterials), 1.44 g (11.8 mmole) DMAP, 1.12 g (3.25 mmole) H—(R,S)Hig(Z) (See Preparation of startingmaterials) in 15 ml CH$_2$Cl$_2$ was added 0.62 g (3.2 mmole) of EDC and the mixture was stirred at room temperature over night. The solvent was evaporated and the residue was dissolved in ethyl acetate. When the organic layer was washed twice with a 0.3 M KHSO$_4$-solution an oil separated from the organic layer. The ethyl acetate layer was dried (Na$_2$SO$_4$) and filtered. The oil and the water layer was then extracted with CH$_2$Cl$_2$ The organic layer was dried (Na$_2$SO$_4$), filtered and combined with the EtOAc phase from above. Evaporation and purification of the crude product on a chromatotron (Harrison research, model 7924T) using a 2 mm silica plate with a stepwise gradient of CH$_2$Cl$_2$/MeOH (97/3, 95/5, 90/10 as eluent to yielded 1.1 g (59%) of the title compound.

(ii) H—(R)Cgl-Pro-(R,S)Hig×2 HCl 81 mg (0.13 mmole) of Boc-(R)Cgl-Pro-(R,S)Hig(Z) was dissolved in 50 ml ethyl acetate saturated with HCl.

The mixture was allowed to stand for one hour, evaporated and the residue was dissolved in 10 ml ethanol. 40 mg Pd/C (5%), 1 ml water and 0.5 ml 1 M HCl-solution was added and the mixture was hydrogenated at atmospheric pressure over night. Filtration of the catalyst through cellite and evaporation of the solvent followed by freeze drying 3 times from water gave the title compound in 75% yield.

$^1$H-NMR (D$_2$O, 300 MHz): δ 0.95–1.35 (m, 5H), 1.50–2.45 (m, 15H), 3.02 (bt, 1H), 3.1–3.8 (m, 7H), 4.13 (d, 1H), 4.38 (bd, 1H)

¹³C-NMR (D₂O" 75 MHz): carbonyl and guanidinecarbons: δ 154.8, 168.9, 174.4

MS m/z 393 (M⁺+1)

Example 75

HOOC—CH₂—(R)Cgl-Pro-(R,S)Hig×2 HCl (i) H—(R)Cgl-Pro-(R,S)Hig(Z)

1 g (1.6 mmole) Boc-(R)Cgl-Pro-(R,S)Hig(Z) (See Example 74 (i)) was dissolved in 100 ml ethyl acetate saturated with HCl, and the mixture was allowed to stand for one hour. The mixture was evaporated and the residue was dissolved in CH₂Cl₂. The organic layer was washed twice with 0.2 M NaOH-solution, dried (Na₂SO₄), filtered and evaporated to yield 0.825 g (98%) of title compound.

(ii) BnOOC—CH₂—(R)Cgl-Pro-(R,S)Hig(Z)

0.442 g (0.839 mmole) H—(R)Cgl-Pro-(R,S)Hig(z), 0.256 g (1.85 mmole) K₂CO₃ and 145 μl (0.521 mmole) of bensylbromoacetate was mixed in 12 ml THF. The mixture was stirred at 40° C. for one hour and at room temperature over night. After evaporation of the solvent the residue was dissolved in CH₂Cl₂ and washed once with water and once with brine. The organic layer was dried (Na₂SO₄), filtered and evaporated and the crude product was purified on a chromatotron (Harrison research, model 7924T) using a 2 mm silica plate with a stepwise gradient of CH₂Cl₂/MeOH (97/3, 95/5, 90/10) as eluent to yield 0.165 g (29%) of the title compound.

(iii) HOOC—CH₂—(R)Cgl-Pro-(R,S)Hig×2 HCl 0.165 g (0.25 mmole) of BnOOC—CH₂—(R)Cgl-Pro-(R,S)Hig(Z) was mixed with 0.050 g Pd/C (5%), 0.7 ml 1 M HCl-solution and 10 ml ethanol. The mixture was hydrogenated at atmospheric pressure for four hours. Filtration of the catalyst through cellite and evaporation of the solvent followed by freeze drying twice from water gave 0.1 g (75%) of the product.

¹H-NMR (D₂O, 300 MHz): δ 1.05–1.45 (m, 5H), 1.55–2.5 (m, 15H), 3.08 (bt, 1H), 3.2–4.05 (m, 9H), 4.30 (d, 1H), 4.44 (m, 1H)

¹³C-NMR (D₂O, 75 MHz): carbonyl and guanidinecarbons: δ 154.9, 167.2, 169.4, 174.1

Example 76

H—(R)Cha-Pro-(R,S)Hig×2 HCl (i) Boc-(R)Cha-Pro-(R,S)Hig(Z)

0.72 g (1.95 mmole) Boc-(R)Cha-Pro-OH (See Preparation of starting materials), 0.95 g (7.8 mmole) DMAP, 0.74 g (2.14 mmole) 82% pure H—(R,S)Hig(Z) (see Preparation of starting materials) in 10 ml CH₂Cl₂ was added 0.486 g (2.54 mmole) of EDC and the mixture was stirred at room temperature for 3 days. The mixture was diluted with CH₂Cl₂ and washed with water, twice with 0.3M KHSO₄-solution and once with brine The organic layer was dried (Na₂SO₄), filtered and evaporated and the crude product was purified by flash chromatography using CH₂Cl₂/MeOH 95/5 as eluent to yield 0.450 g (33%) of the product.

(ii) H—(R)Cha-Pro-(R,S)Hig×2 HCl 50 mg (0.078 mmole) of Boc-(R)Cha-Pro-(R,S)Hig(Z) was dissolved in 20 ml ethyl acetate saturated with HCl. The mixture was allowed to stand for one hour, evaporated and the residue was dissolved in 10 ml ethanol. 20 mg Pd/C (5%) and 0.3 ml 1 M HCl-solution was added and the mixture was hydrogenated at atmospheric pressure for two hours. Filtration of the catalyst through through cellite and evaporation of the solvent followed by freeze drying twice from water gave 28 mg (76%) of the title compound.

¹H-NMR (D₂O 300 MHz): δ 0.9–1.6 (m, 6H), 1.6–2.5 (m, 16H), 3.09 (t, 1H), 3.31 (t, 1H), 3.37–3.74 (m, 4H), 3.81 (m, 1H), 4.35–4.47 (m, 2H)

¹³C-NMR (D₂O, 75 MHz): carbonyl and guanidinecarbons: δ 154.9, 169.8, 174.5

Example 77

H—(R)Cgl-Aze-Rig×2 HCl (i) Boc-(R)Cgl-Aze-Rig(Z)

To a solution of 0.50 g (1.6 mmol) of H—Rig(Z) (See Preparation of starting materials), 0.59 g (1.6 mmol) of Boc-(R)Cha-Aze-OH(See preparation of starting materials), 0.84 g (6.9 mmol) of dimethylaminopyridine in 30 ml of acetonitrile and 5 ml of dimethylformamide was added 0.33 g (1.7 mmol) of N-(3-dimethylaminopropyl)-N'-ethylcarbodiimide hydrochloride. The reaction was allowed to stir for 3 days then evaporated and partitioned between aqueous potassium hydrogen sulfate and methylene chloride. The methylene chloride layer was washed with aqueous sodium bicarbonate and water, dried (Na₂SO₄) and evaporated. The crude material was suction filtered through a pad of silica gel with methylene chloride/methanol 9/1 to give 0.78 g (76%) of the desired compound after evaporation.

¹H NMR (300 MHz, CDCl₃): δ 0.8–1.9 (m, 27H), 2.4–2.6 (m, 2H), 2.78 (bt, 2H), 3.15–3.4 (m, 2H), 3.80 (bt, 1H), 4.0–4.4 (m, 4H), 4.75 (bt, 1H), 4.97 (bd, 1H), 5.08 (s, 2H), 7.1–7.4 (m, 7H), 7.74 (b, 1H).

(ii) H—(R)Cgl-Aze-Rig(Z)×2 HCl

A flask containing Boc-(R)Cgl-Aze-Rig(Z), 0.76 g (1.2 mmol), in 50 ml of ethyl acetate was cooled in an ice bath. Dry HCl was bubbled through for 5 min and the solution was evaporated to give 0.74 g (100%) of the dihydrochloride as a white powder.

¹H-NMR (300 MHz, MeOD): δ 1.1–2.0 (m, 18H), 2.23 (m, 1H), 2.68 (m, 1H), 3.15–3.45 (m, 4H), 3.72 (bd, 1H), 3.9–4.0 (bd, 2H), 4.27 (m, 1H), 4.39 (m, 1H), 4.78 (m, 1H), 5.30 (s, 2H), 7.3–7.5 (m, 5H).

(iii) H—(R)Cgl-Aze-Rig×2 HCl

A flask containing a solution of 20 mg of H—(R)Cgl-Aze-Rig(Z) and a small amount of 5% Pd/C was hydrogenated at atmospheric pressure for 1 h. The mixture was filtered through celite and evaporated. The residue was lyophilized with a few drops of conc. HCl added to give the product. Yield: 8 mg (52%).

¹H-NMR (300 MHz, D₂O): δ 1.1–2.0 (m, 18H), 2.37 (m, 1H), 2.75 (m, 1H), 3.08 (bt, 2H), 3.39 (bt, 2H), 3.8–4.0 (m, 3H), 4.35–4.5 (m, 2H), 4.90 (m, 1H).

¹³C-NMR (75.5 MHz, D₂O): guanidine and carbonyl carbons: δ 172.2, 169.4, 156.4.

Example 78

HOOC—CH₂—(R)Cgl-Aze-Rig×2 HCl (i) BnOOC—CH₂—(R)Cgl-Aze-Rig(Z)

A mixture of 0.20 g (0.33 mmol) of H—(R)Cgl-Aze-Rig(Z) (See Example 77), 0.13 g of potassium carbonate, 80 mg of sodium iodide, 10 ml of tetrahydro-furane and 10 ml of acetonitrile was heated at 60° C. for 10 h. The solvents were evaporated and the crude material was flash chromatographed on silica gel using methylene chloride/methanol 92/8 as eluent. Yield: 0.13 g (58%).

¹H-NMR (300 MHz, CDCl₃) δ 0.9–2.1 (m, 18H), 2.45 (m, 1H), 2.61 (m,1H), 2.81 (m, 2H), 2.88 (d, 1H), 3.2–3.5 (m, 4H), 3.94 (m, 1H), 4.0–4.25 (m, 3H), 4.85 (m, 1H), 5.12 (s, 2H), 5.14 (s, 2H), 6.9–7.2 (b. 2H), 7.2–7.5 (m, 10H), 7.95 (m, 1H).

(ii) HOOC—CH₂—(R)Cgl-Aze-Rig×2 HCl

A mixture of 0.12 g (0.18 mmol) of BnOOC—CH₂—(R)Cgl-Aze-Rig(Z), 5 ml of ethanol, 3 drops of conc. HCl and a small amount of 5% Pd/C was hydrogenated at atmospheric pressure for 1 h. The mixture was filtered through celite and evaporated. The residue was lyophilized in water to give 91 mg (98%) of the product.

¹H-NMR (500 MHz, D₂O): δ 1.1–1.9 (M, 17H), 2.00 (m, 1H), 2.29 (m, 1H), 2.70 (m, 1H), 3.10 (m, 2H), 3.34 (t, 2H), 3.83 (bd, 2H), 3.89 (dd, 2H), 4.00 (d, 1H), 4.35 (m, 2H), 4.87 (m, 1H).

¹³C NMR (125.8 MHz, D₂O): guanidine and carbonyl carbons: δ 171.8, 169.6, 167.7, 156.3.

Example 79
HOOC—CH₂—CR)Cha-Pro-Rig×2 HCl
(i) Boc-(R)Cha-Pro-Rig(Z)

To a solution of 0.25 g (0.82 mmol) of 4-aminoethyl-1-benzyloxycarbonylamidino piperidine(H—Rig(Z)), (See preparation of starting materials), 0.32 g (0.82 mmol) of Boc-(R)Cha-Pro-OH (See Preparation of starting materials), 0.40 g (3.3 mmol) of dimethylaminopyridine in 10 ml of acetonitrile and 2 ml of dimethylformamide was added 0.165 g (0.86 mmol) of N-(3-dimethylaminopropyl)-N'-ethylcarbodiimide hydrochloride. The reaction was allowed to stir for 3 days then evaporated and partitioned between aqueous potassium hydrogen sulfate and methylene chloride. The methylene chloride layer was washed with aqueous sodium bicarbonate and water, dried (Na₂SO₄) and evaporated. The NMR spectrum of the crude product was satisfactory and the product which contained some dimethylformamide was used in the next step without further purification.

¹H-NMR (500 MHz, CDCl₃) δ 0.8–2.2 (m, 32H; thereof 1.41 (s, 9H)), 2.34 (m, 1H), 2.77 (bt, 2H), 3.10 (m, 1H), 3.29 (m, 1H), 3.40 (m, 1H), 3.83 (m, 1H), 4.17 (m, 2H), 4.30 (m, 1H), 4.54 (m, 1H), 5.07 (m, 1H), 5.08 (s, 2H), 7.03 (m, 1H), 7.05–7.4 (m, 7H).

(ii) H—(R)Cha-Pro-Rig(Z)

A flask containing the crude product of Boc-(R)Cha-Pro-Rig(Z) in 100 ml of ethyl acetate was cooled in an ice bath. Dry HCl was bubbled through for 5 min and the solution was evaporated to get rid of the excess of HCl. The product was dissolved in water and the extracted twice with ethyl acetate to remove the dimethylform-amide from the previous step. The aqueous phase was made alkaline with NaHCO₃ (ag) and extracted twice with methylene chloride. The combined organic phase was washed with water, dried (Na₂SO₄) and evaporated. Yield: 0.37 g (81%) over two steps.

¹H-NMR (300 MHz, CDCl₃) δ 0.8–2.4 (m, 24H), 2.82 (bt, 2H), 3.26 (m, 2H), 3.42 (bq, 1H), 3.70 (m, 2H), 4.19 (m, 2H), 4.49 (bd, 1H), 5.11 (s, 2H), 6.9–7.5 (m, 8H).

(iii) BnOOC—CH₂—(R)Cha-Pro-Rig(Z)

A mixture of 0.18 g (0.32 mmol) of H—(R)Cha-Pro-Rig (Z), an excess of potassium carbonate and 10 ml of acetonitrile was heated at 60° C. for 2 h. The solvents were evaporated and the crude material was flash chromatographed on silica gel using methylene chloride/methanol 95/5 as eluent. Yield: 0.20 g (88%).

¹H-NMR (300 MHz, CDCl₃) δ 0.8–2.1 (m, 23H), 2.37 (m, 1H), 3.1–3.5 (m, 7H), 4.0–4.2 (m, 2H), 4.54 (m, 1H), 5.1 (m, 4H), 6.9–7.5 (m, 13H).

(iv) HOOC—CH₂—(R)Cha-Pro-Rig×2 HCl

A mixture of 0.15 g (0.21 mmol) of BnOOC—CH₂—(R)Cha-Pro-Rig(z), 10 ml of ethanol, 4 drops of conc. HCl and a small amount of 5% Pd/C was hydrogenated at atmospheric pressure for 1 h. The mixture was filtered through celite and evaporated. The residue was lyophilized in water to give 95 mg (64%) of the product.

¹H-NMR (500 MHz, MeOD) δ 0.85–2.1 (m, 23H), 2.30 (m, 1H), 3.10 (m, 2H), 3.25 (m, 1H), 3.35 (m, 1H), 3.54 (m, 1H), 3.85–4.0 (m, 3H), 4.03 (d, 1H), 4.41 (m, 1H), 4.50 (m, 1H).

¹³C-NMR (125.8 MHz, D₂O): guanidine and carbonyl carbons: δ 174.0, 168.9, 168.1, 157.5.

Example 80
HOOC—CH₂—CH₂—(R)Cha-Aze-Rig×2 HCl
(i) Boc-(R)Cha-Aze-Rig(Z)

To a solution of 0.25 g (0.82 mmol) of 4-aminoethyl-1-benzyloxy-cabonylamidino piperidine (H—Rig(Z)), (See preparation of starting materials), 0.31 g (0.86 mmol) of Boc-(R)Cha-Aze-OH (See preparation of starting materials), 0.40 g (3.3 mmol) of dimethylaminopyridine in 10 ml of acetonitrile and 2 ml of dimethylformamide was added 0.17 g (0.86 mmol) of N-(3-dimethylaminopropyl)-N'-ethylcarbodiimide hydrochloride. The reaction was allowed to stir for 3 days then evaporated and partitioned between aqueous potassium hydrogen sulfate and methylene chloride. The methylene chloride layer was washed with aqueous sodium bicarbonate and water, dried (Na₂SO₄) and evaporated. The crude product which contained some dimethylformamide was used in the next step without further purification.

¹H-NMR (500 MHz, CDCl₃) δ 0.85 (m, 1H), 0.97 (m, 1H), 1.1–1.75 (m, 26H; thereof 1.41 (s, 9H)), 1.82 (bd, 1H), 2.53 (m, 2H), 2.77 (bt, 2H), 3.25 (m, 2H), 4.03 (q, 1H), 4.08 (m, 1H), 4.18 (m, 2H), 4.29 (m, 1H), 4.78 (m, 1H), 4.97 (m, 1H), 5.09 (s, 2H), 7.1–7.4 (m, 7H), 7.65 (m, 1H).

(ii) H—(R)Cha-Aze-Rig(Z)

A flask containing the crude product of Boc-(R)Cha-Aze-Rig(Z) in 100 ml of ethyl acetate was cooled in an ice bath. Dry HCl was bubbled through for 5 min and the solution was evaporated to get rid of the excess of HCl. The product was dissolved in water and the extracted twice with ethyl acetate to remove the dimethylformamide from the previous step. The aqueous phase was made alkaline with NaHCO₃ (aq) and extracted twice with methylene chloride. The combined organic phase was washed with water, dried (Na₂SO₄) and evaporated. Yield: 0.31 g (70%) over two steps.

¹H-NMR (300 MHz, CDCl₃) δ 0.8–1.9 (m, 20H), 2.48 (m, 1H), 2.73 (m, 1H), 2.85 (bt, 2H), 3.25 (m, 1H), 3.35 (m, 2H), 4.05 (q, 1H), 4.1–4.25 (m, 3H), 4.86 (m, 1H), 5.12 (s, 2H), 6.9–7.2 (m, 2H), 7.2–7.45 (m, 5H), 7.93 (m, 1 h).

(iii) BnOOC—CH₂—CH₂—(R)Cha-Aze-Rig(Z)

A solution of 0.31 g (0.57 mmol) of H—(R)Cha-Aze-Rig (Z) and 93 mg (0.57 mmol) of benzyl acrylate in 5 ml of ethanol was allowed to stand at room temperature for one week. It was evaporated and flash chromatographed on silica gel using methylene chloride/methanol 94/6 as eluent. Yield: 0.20 g (49%).

¹H NMR (500 MHz, CDCl₃) δ 0.8–1.0 (m, 2H), 1.1–1.8 (m, 18H), 2.48 (m, 1H), 2.54 (bt, 2H), 2.68 (m, 2H), 2.81 (bt, 2H), 2.87 (m, 1H), 3.20 (m, 1H), 3.25 (m, 1H), 3.31 (m, 1H), 4.04 (q, 1H), 4.1–4.2 (m, 3H), 4.84 (dd, 1H), 5.05–5.15 (m, 4H), 7.0–7.5 (m, 12H), 8.03 (m, 1H).

(iv) HOOC—CH₂—CH₂—(R)Cha-Aze-Rig×2 HCl

The title compound was made and purified in the same way as described in Example 80 from 0.20 g (0.28 mmol) of BnOOC—CH₂—CH₂—(R)Cha-Aze-Rig-(Z). Yield: 30 mg (19%) of the dihydrochloride salt.

¹H-NMR (500 MHz, CDCl₃) δ 1.0–1.9 (m, 20H), 2.33 (m, 1H), 2.70 (m, 1H), 2.83 (m, 2H), 3.10 (m, 2H), 3.3–3.4 (m, 4H), 3.85 (bd, 2H), 3.92 (m, rotamer), 4.14 (t, 1H), 4.17 (m, rotamer)₁ 4.31 (m, 1H), 4.46 (m, 1H), 4.89 (m, 1H), 5.18 (m, rotamer).

¹³C NMR (125.8 MHz, D₂O) guanidine and carbonyl carbons: δ 175.4, 171.8, 168.8, 156.3.

Example 81
HOOC—CH₂—(R)cha-Pro-(S)Itp×2 HCl
(i) Boc-(R)Cha-Pro-(S)Itp(Ts)

At roomtemperature 0.87 g (2.36 mmol) Boc-(R)Cha-Pro-OH (See preparation of startingmaterials), 0.78 g (4.72 mmol) DMAP and 0.70 g (2.36 mmol) H—(S)Itp(Ts) (See preparation of starting materials) was dissolved in 12 mL acetonitrile. After stirring 20 minutes 0.59 g (3.07 mmol) EDC was added. After 18 hours the solvent was removed in vacuo and the residue was dissolved in $CH_2Cl_2$, washed with water, citric acid (10%), $KHCO_3$ (aq), water and dried with $Na_2SO_4$. Evaporation gave 1.74 g (>100% yiled (purity of about 60%)) of the desired product. Which was used in the next step without further purification.

FAB-MS: m/z 647 ($M^+$+1)

(ii) H—(R)Cha-Pro-(S)Itp(Ts)

The Boc-protecting group was removed in the same way as described for Boc-(R)Cha-Pic-(R,S)Itp(Z) (See Example 72 (ii)) to give 0.75 g (81) of the title compound.

FAB-MS: m/z=547 ($M^+$+1)

(iii) BnOOC—$CH_2$—(R)Cha-Pro-(S)Itp(Ts)

0.75 g (1.37 mmol) H—(R)Cha-Pro-(S)Itp(Ts), 0.38 g (2.74 mmol) $K_2CO_3$ was taken up in 15 mL acetonitrile. 0.39 g (1.65 mmol) benzylbromoacetate was added and the mixture was stirred at 50° C. for 2 h. Evaporation of the solvent followed by flash chromatography using ethylacetate/methanol 95/5 as eluent gave about 530 mg of the desired product.

FAB-MS: m/z=695 ($M^+$+1)

(iv) HOOC—$CH_2$—(R)Cha-Pro-(S)Itp×2 HCl 0.53 g (0.76=mmol) BnOOC—$CH_2$—(R)Cha-Pro-(S)Itp (Ts) was dissolved in 15 mL THF. $NH_3$ (g) was condensed into the flask and Na (m) was added. The reaction was quenched after 30 min with acetic acid and the $NH_3$ and the THF was evaporated. The residue was freeze dried from water and the crude product was purified by RPLC (acetonitrile/0.1M HOAc 15/85) gave 0.25 g (61%) of the desired product after freeze-drying from aqueous HCl.

$^1$H-NMR (500.13 MHz, $D_2O$); δ 0.9–2.09 (overlapping m, 20H), 2.22–2.35 (m, 1H), 3.2–3.36 (m, 4H), 3.44–3.62 (overlapping m, 2H), 3.7–3.8 (m, 1H), 3.87–3.99 (m, 2H), 4.33–4.48 (overlapping m, 2H).

$^{13}$C-NMR (500.13 MHz, $D_2O$); carbonyl- and guanidinecarbons: δ 154.3, 168.1, 169.0 and 174.2

Example 82
H—(R)Cha-Pro-(R,S)Nig×2 HCl (i) Boc-(R)Cha-Pro-(R,S)Nig(Z)

174 mg (0.471 mmole) Boc-(R)Cha-Pro-OH (See preparation of starting materials), 229 mg (1.87 mmole) DMAP, 130 mg (0.471 mmole) H—(R,S)Nig(Z) (See Preparation of starting materials) was mixed in 2 ml $CH_2Cl_2$ and 117 mg (0.61 mmole) of EDC was added and the mixture was stirred for four days. The mixture was diluted with $CH_2Cl_2$ and washed with water, twice with 0.3 M $KHSO_4$-solution and once with brine The organic layer was dried ($Na_2SO_4$), filtered and evaporated and the crude product was purified twice by flash chromatography using $CH_2Cl_2$/MeOH 95/5 as eluent the first time and $CH_2Cl_2$/MeOH 97/3 as eluent the second time to yield 0.104 g (35%) of the title compound.

MS m/z 627 (M++1)

(ii) H—(R)Cha-Pro-(R,S)Nig×2 HCl 10 mg (0.016 mmole) of Boc-(R)Cha-Pro-(R,S)Nig(Z) was dissolved in 15 ml ethyl acetate saturated with HCl. The mixture was allowed to stand for half an hour. The mixture was evaporated and the residue was dissolved in 6 ml ethanol and 8 mg 51 Pd/C (5%) and 0.1 ml 1 M HCl-solution was added and the mixture was thydrogenated at atmospheric pressure for one and a half hour. After filtration through hyflo and evaporation of the solvent gave 4 mg of the title compound the product.

$^1$H-NMR (300 MHz, $D_2O$): δ 0.9–1.58 (m, 6H), 1.58–2.45 (m, 13H), 2.65 (m, 1H), 3.19 (m, 1H), 3.34 (d, 2H), 3.4–3.73 (m, 4H), 3.82 (m, 1H), 4.34–4.49 (m, 2H).

$^{13}$C-NMR(75 MHz, D2O): carbonyl and guanidinecarbons: δ 155.1, 169.9 and 174.8.

Example 83
H—(R)Pro-Phe-Pab×2 HCl (i) Boc-(R)Pro-Phe-Pab(Z)

To a mixture of 1.2 g (3.31 mmol) Boc-(R)Pro-Phe-OH (See preparation of starting materials) and 1.70 g (13.91 mmol) DMAP in 40 ml $CH_3CN$ at room temperature was added 0.98 g (3.35 mmol) H-Pab(Z) (See preparation of starting materials) dissolved in 1 ml DMF. After stirring for 2 h the reaction mixture was cooled to −18° C. and 0.66 g (3.48 mmol) EDC was added portion wise and the reaction was left at room temperature over night. The solvent was evaporated and the residue was dissolved in 100 ml EtOAc and washed with 1×30 ml water, 3×30 ml 0.3 M $KHSO_4$, 1×30 ml $Na_2CO_3$, 1×30 ml water and dried. Evaporation of the solvent followed by flash chromatography using $CH_2Cl_2$/MeOH (95/5) as eluent gave 0.691 g (38%) of the title compound.

(ii) H—(R)Pro-Phe-Pab(Z)

0.673 g Boc-(R)Pro-Phe-Pab(Z) was dissolved in 30 ml EtOAc and the solution was saturated with HCl(g) for a few minutes (a white solid precipitated out from the solution). The solvent and excess HCl was evaporated and 60 ml EtOAc was added to the residue and the organic phase was washed with 2×20 ml 2 M NaOH. The washing water was extracted with 1×25 ml EtOAc which was combined with the other EtOAc-phase and the combined organic phase was washed with water, dried and evaporated to give 560 mg (98%) of the desired product.

$^1$H-NMR (500 MHz, $CDCl_3$): & 1.5–1.74 (m, 3H), 1.98–2.05 (m, 1H), 2.78–2.85 (m, 1H), 2.90–2.96 (m, 1H), 3.0–3.2 (ABX-system centered at 3.1, 2H), 3.62 (dd, 1H), 4.3–4.45 (ABX-system centered at 4.37, 2H), 4.58 (q, 1H), 5.22 (s, 2H), 6.96 (bt, 1H), 7.1–7.4 (m, 10H), 7.46 (d, 2H), 7.76 (d, 2H), 8.12 (d, 1H).

(iii) H—(R)Pro-Phe-Pab×2 HCl 200 mg H—(R)Pro-Phe-Pab(Z) was dissolved in 10 ml 95% EtOH and 2 ml of water and the mixture was hydrogenated over 5% Pd/C at atmospheric pressure for 5 h. Filtration of the catalyst and addition of 1 ml 1 M HCl followed by evaporation and freeze drying from water gave the title compound in 88% yield.

$^1$H-NMR (500 MHz, $CD_3OD$): δ 1.51–1.59 (m, 1H), 1.69–1.80 (m, 1H), 1.87–1.97 (m, 1H), 2.19–2.29 (m, 1H), 2.90 (dd, 1H), 3.20–3.33 (m, 3H, partially hidden by the solvent peak), 4.27 (m, 1H), 4.43–4.54 (AB-system centered at 4.48, 2H), 4.75–4.81 (m, 1H), 4.87 (s, 2H), 7.2–7.3 (m, 5H), 7.45 (d, 2H), 7.75 (d, 2H).

$^{13}$C-NMR (125 MHz, $D_2O$): amidine and carbonyl carbons: δ 166.7, 170.1 and 173.4.

Example 84
HOOC—$CH_2$—(R)Pro-Phe-Pab×2 HCl (i) BnOOC—$CH_2$—(R)Pro-Phe-Pab(Z)

To a slurry of 244 mg (0.463 mmol) H—(R)Pro-Phe-Pab (Z) (See Example 83) and 159.9 mg (1.157 mmol) $K_2CO_3$ in 8 ml DMF/$CH_3CN$ (5/3) was added 127.2 mg (0.555 mmol) benzylbromo acetate dissolved in 2 ml DMF and the mixture was stirred at 60° C. for 1.5 h and at room temperature over night. The solvent was evaporated and the residue was dissolved in 50 ml EtOAc, washed with 2×20 ml water and dried ($Na_2SO_4$). Evaporation of the solvent followed by flash chromatography using $CH_2Cl_2$/MeOH (9/1) as eluent gave 176 mg (56%) of the title compound as a white solid.

$^1$H-NMR (300 MHz), $CDCl_3$): δ 1.45–1.80 (m, 3H), 2.06 (m, 1H), 2.54 (m, 1H), 2.92–3.28 (m, 6H), 4.3–4.5 (ABX-system centered at δ=4.4, 2H), 4.60 (dd, 1H), 5.10 (apparent s, 2H), 5.2 (apparent s, 2H), 7.1–7.4 (m, 15H), 7.43 (d, 2H), 7.75 (d, 2H), 7.932 (d, 1H).

(ii) HOOC—CH$_2$—(R)Pro-Phe-Pab×2HCl 170 mg (0.252 mmol) of BnOOC—CH$_2$—(R)Pro-Phe-Pab(Z) was dissolved in 12 ml EtOH/water (5/1) and hydrogenerated over 5% Pd/C at atmospheric for 4.5 h. The catalyst was filtered off, the solvent evaporated and the residue freeze dried from HCl(aq) to give the title compound.

$^1$H-NMR (500 MHz, CD$_3$OD): δ 1.62 (m, 1H), 1.82 (m, 1H), 2.08 (m, 1H), 2.38 (m, 1H), 2.90 (dd, 1H), 3.25–3.35 (m, 2H), partially hidden by the solvent peak), 3.80 (m, 1H), 4.08–4.19 (AB-system centered at 6=4.19, 2H), 4.39 (m, 1H), 4.45–4.58 (AB-system centered at 6=4.50, 2H), 4.80 (m, 1H), 7.20–7.35 (m, 5H), 7.45 (d, 2H), 7.75 (D, 2H).

$^{13}$C-NMR (125 MHz, D$_2$O): amidine and carbonyl carbons: δ 166.8, 169.1, 169.5 and 173.2.

Example 85
H—(R)Phe-Phe-Pab (i) Boc-(R)Phe-Phe-Pab(Z)

Boc-(R)Phe-Phe-OH (16.4 mmol) (see preparation of starting materials), Pab(Z)-HCl (18.0 mmol) and 4-dimetylaminopyridine (24.6 mmol) were dissolved in 50 mL of acetonitrile. The solution was cooled to ice-water temperature and 1-(3-dimetylaminopropyl)-3-ethylcarbodiimide hydrochloride (21.3 mmol) was added. The cooling bath was removed and the reaction mixture was stirred over night. The solvent was then evaporated under reduced pressure, the residue dissolved in 50 mL of ethylacetate and the resulting solution extracted with 50 mL of water. Boc-(R)Phe-Phe-Pab(Z) precipitating from the two-phase mixture was filtered and washed with water yielding 8.7 g (78%) after drying under vacuum at 45° C. for 24 h. $^1$H NMR (200 MHz, d-CHCl$_3$ and d4-CH$_3$OH); δ 8.35–7.00 (m, 19H), 4.63 (t. 1H), 4.3–4.1 (m, 1H), 3.40–2.70 (m, 6H), 1.30 (s, 9H).

(ii) H—(R)Phe-Phe-Pab(Z)

Boc-(R)Phe-Phe-Pab(Z) (10.3 mmol) was slurried in 70 mL of ethylacetate and 31 mL of 3.3 M ethylacetate/HCl was added. The slurry was stirred for 4 h after which the hydrochloride salt of H—(R)Phe-Phe-Pab(Z) was filtered off and washed with serveral portions of ethylacetate. The salt was dissolved in a mixture of 50 mL of methylenechloride, 50 mL of 1 M potassiumcarbonate and ca 5 μL of ethanol. The organic layer was collected and the solvent was removed under reduced pressure yielding 5.0 g of H—(R)Phe-Phe-Pab(Z) (84%). $^1$H NMR (200 MHz, d$_6$-DMSO); δ 9.1 (s, 2H), 8.59 (m, 1H), 8.1 (m, 1H), 7.90 (d, 2H), 7.4–7.0 (m, 17H), 5.09 (s, 2H), 4.58 (m, 1H), 4.31 (m, 2H), 3.1–2.7 (m, 4H).

(iii) H—(R)Phe-Phe-Pab(Z) (0.42 mmol) was dissolved in 10 mL of tetrahydrofuran and 1 mL of water. Palladium on charocoal (42 mg) was charged to the solution and the mixture was hydrogenated at 45 psi hydrogen pressure in a Parr shaking apparatus for 2 days. After complete hydrogenolysis the mixture was diluted with methanol and the catalyst was filtered off. Evaporation of the solvents gave crude H—(R)Phe-Phe-Pab which was purified by chromatography on neutral alumina (70–230 Mesh) eluting with methylenechloride-methanol-ammoniumhydroxide (80:20:2). Yield 76 mg of the title compound (41%). $^1$H NMR (200 MHz, d$_6$-DMSO); δ 7.61 (d, 2H)$_1$ 7.4–7.0 (m, 12H), 4.64 (m, 1H), 4.44 (m, 2H), 4.13 (t, 1H), 3.1–2.8 (m, 4H).

Example 86
HOOC—CO—(R)Phe-Phe-Pab (i) MeOOC—CO—(R)Phe-Phe-Pab(Z)

H—(R)Phe-Phe-Pab(Z) (0.87 mmol) (see Example 85 (iii)) was dissolved in 10 mL of tetrahydrofuran. The solution was cooled on an icewater bath and triethylamine (1.73 mmol) followed by methyloxalylchloride (0.95 mmol) were added. The cooling bath was removed and the reaction mixture stirred for 18 h at ambient temperature. The reaction mixture was diluted with ethylacetate and extracted with water. The organic phase was collected and the solvent was removed under reduced pressure yielding 0.45 g of MeOOC—CO—(R)Phe-Phe-Pab(Z) (78%) which was used in the next step without further purification. TSP-MS found m/z 664 (calculated for MH$^+$ (C$_{37}$H$_{38}$N$_5$O$_7$) 664).

(ii) HOOC—CO—(R)Phe-Phe-Pab(Z)

MeOOC—CO—(R)Phe-Phe-Pab(Z) (0.68 mmol) was dissolved in 4 mL of tetrahydrofuran and 2 mL of water. Lithiumhydroxide (2.6 mmol) was added and the reaction mixture was stirred at room temperature for 1.5 h. After complete hydrolysis the reaction mixture was diluted with 25 mL of water and acidified by addition of 0.5 mL of acetic acid. The precipitate was filtered and washed with several portions of water yielding 0.40 g of crude HOOC—CO—(R)Phe-Phe-Pab(Z) after drying under vacuum at 45° C. for 24 h. The crude product was slurried in 10 mL of ethanol and 1 mL of water. The Solution was brought to reflux and the insoluble title compound was filtered off, yielding 0.23 g of HOOC—CO—(R)Phe-Phe-Pab(Z) (41% over two steps). $^1$H NMR (200 MHz, d$_6$-DMSO); δ 8.62 (m, 2H), 8.41 (d, 1H), 7.89 (d, 2H), 7.4–6.9 (m, 17H), 5.10 (s, 2H), 4.54 (m, 2H), 4,34 (m, 2H), 3.2–2.6 (m, 4H).

(iii) HOOC—CO—(R)Phe-Phe-Pab

HOOC—CO—(R)Phe-Phe-Pab(Z) (0.20 mmol) was slurried in 20 mL of tetrahydrofuran and 5 mL of water. Palladium on charcoal (52 mg) was charged to the solution and the mixture was hydrogenated at 45 psi hydrogen pressure in a Parr shaking apparatus for 2 days. After complete hydrogenolysis the mixture was diluted with 40 mL of methanol and the catalyst was filtered off. Evaporation of the solvents yielded 50 mg of the title compound (49%). $^1$H NMR (200 MHz, d$_6$-DMSO); δ 9.2 (s), 8.78 (d), 8.60 (m), 7.91 (m), 7.79 (d, 2H), 7.35–6.8 (m,12H), 4.6–4.0 (m, 4H), 3.0–2.6 (m, 4H).

Example 87
HOOC—CH$_2$—(R)Phe-Phe-Pab (i) BnOOC—CH$_2$—(R)Phe-Phe-Pab(Z)

H—(R)Phe-Phe-Pab(Z) (0.87 mmol) (see Example 85 (ii)) and potassium carbonate (2.6 mmol) were slurried in 10 mL of acetonitrile. Iodobenzylacetate (0.95 mmol) was added to the mixture and the solution was heated to 30° C. and stirred at that temperature for 2 days. After complete alkylation the solvent was removed and the residue dissolved in 10 mL of ethylacetate. The solution was rapidly extracted with 10 mL of water and from the collected organic phase the title compound precipitates. BnOOC—CH$_2$(R)Phe-Phe-Pab(Z) was filtered off and dried under vacuum at 45° C. for 24 h yielding 177 mg BnOOC—CH$_2$—(R)Phe-Phe-Pab(Z) (28%). $^1$H NMR (200 MHz, CDCl$_3$); δ 7.79 (d, 2H), 7.5–7.1 (m, 22H), 6.55 (t, 1H), 5.21 (s, 2H), 5.03 (s, 2H), 4.64 (m, 1H), 4.41 (m 2H), 3.3–2.6 (m, 7H).

(ii) BnOOC—CH$_2$—(R)Phe-Phe-Pab(Z)

BnOOC—CH$_2$—(R)Phe-Phe-Pab(Z) (0.32 mmol) was slurried in 30 mL of tetrahydrofuran and 3 mL of water. Palladium on charcoal (41 mg) was charged to the solution and the mixture was hydrogenated at 45 psi hydrogen pressure in a Parr shaking apparatus for 2 days. After complete hydrogenolysis the mixture was diluted with 40 mL of water and the catalyst was filtered off. Evaporation of the solvents yielded 95 mg of the title compound (59%). TSP-MS found m/z 502 (calculated for $MH^+(C_{28}H_{32}N_5O_4)$ 502).

Example 88
H—(R)Cha-Pro-Mig
(i) Boc-(R)Cha-Pro-Mig(Z)

To a stirred mixture of 0.344 g (0.93 mmol) Boc-(R)Cha-Pro-OH (see preparation of starting materials), 0.245 g (0.93 mmol) of H-Mig(Z) (see preparation of starting materials) and 0.227 g (1.86 mmol) of DMAP in 10 mL $CH_3CN$ was added 0.232 g (1.21 mmol) of EDC at −10° C. The reaction mixture was allowed to reach roomtemperature and left for 5 days. The $CH_3CN$ was evaporated and the residue was dissolved in EtOAc and washed with $H_2O$, $NaHCO_3$ (aq) and brine. The organic layer was dried with $Na_2SO_4$ and evaporated. The crude product was purified by flash chromatography using a gradient of EtOAc/MeOH, 95/5 to 90/10, as eluent to yield 0.340 g (60%) of the title compund.

(ii) H—(R)Cha-Pro-Mig(Z)

0.34 g (0.55 mmol) Boc-(R)Cha-Pro-Mig(Z) was dissolved in 8 mL of EtOAc saturated with HCl(g) and stirred for 10 min. at roomtemperature. 10 mL of a saturated solution of KOH(aq) was added dropwise. The layers were separated and the aqueous phase was extracted with 3×8 mL EtOAc. The organic layers were combined, washed with brine, dried with $Na_2SO_4$ and evaporated to yield 0.286 g (100%) of the title compound.

(iii) H—(R)Cha-Pro-Mig 0.050 g (0.132 mmol) of H—(R)Cha-Pro-Mig(Z) was dissolved in 3 mL MeOH and hydrogenated over 10% Pd/C at atmospheric pressure over night. The solution was filtered through celite and the solvent evaporated to yield 0.040 g (80%) of the title compound.

$^1$H-NMR (500 MHz, MeOD): δ 0.92–1.02 (m, 2H), 1.18–1.47 (m, 6H), 1.66–1.73 (m, 4H), 1.85–2.04 (m, 4H), 2.17–2.22 (m, 1H), 2.95–2.98 (m, 1H), 3.12–3.16 (m, 1H), 3.47–3.55 (m, 2H), 3.62–3.66 (m, 1H), 3.75–3.78 (m, 1H), 3.85–3.89 (m, 1H), 4.05–4.12 (m, 3H), 4.34–4.37 (m, 1H).

Signals from a minor rotamer appear at: δ 3.4, 3.7, 4.13–4.16, 4.3.

MS m/z 379 ($M^+$+1)

Example 89
H—(R)Cha-Pro-Dig
(i) Boc-(R)Cha-Pro-Dig(Z)

To a stirred mixture of 0.280 g (0.76 mmol) Boc-(R)Cha-Pro-OH (see preparation of starting materials), 0.210 g (0.76 mmol) of H-Dig(Z) (see preparation of starting materials) and 0.186 g (1.52 mmol) of DMAP in 8 mL $CH_3CN$ was added 0.189 g (0.99 mmol) of EDC at −10° C. The reaction mixture was allowed to reach roomtemperature and left for 4 days. The $CH_3CN$ was evaporated and the residue was dissolved in EtOAc and washed with $H_2O$, $NaHCO_3$ (aq) and brine. The organic layer was dried with $Na_2SO_4$ and evaporated. The crude product was purified by flash chromatography using a gradient of EtOAc/MeOH, 95/5 to 90/10, as eluent to yield 0.210 g (44%) of the title compund.

(ii) H—(R)Cha-Pro-Dig(Z)

0.210 g (0.33 mmol) Boc-(R)Cha-Pro-Dig(Z) was dissolved in 8=L of EtOAc saturated with HCl(g) and stirred for 10 min. at roomtemperature. 8 mL of a saturated solution of KOH(aq) was added dropwise. The layers were separated and the aqueous phase was extracted with 3×8 mL EtOAc. The organic layers were combined, washed with brine, dried with $Na_2SO_4$ and evaporated to yield 0.146 g (83%) of the title compound.

(iii) H—(R)Cha-Pro-Dig 0.046 g (0.087 mmol) of H—(R)Cha-Pro-Dig(Z) was dissolved in 3 mL MeOH and hydrogenated over 10% Pd/C at atmospheric pressure over night. The solution was filtered through celite and the solvent evaporated to yield 0.040 g (110%) of the title compound.

$^1$H-NMR (500 MHz, MeOD): δ 0.90–1.04 (m, 2H), 1.10–1.47 (m, 6H), 1.66–1.74 (m, 4H), 1.78–2.05 (m, 4H), 2.13–2.21 (m, 1H), 2.74–2.83 (m, 1H), 2.94–2.99 (m, 1H), 3.15–3.29 (m, 1H), 3.44–3.57 (m, 2H), 3.65–3.87 (m, 3H), 4.07–4.25 (m, 3H), 4.35–4.39 (m, 2H).

Signals from a minor rotamer appear at: δ 4.29–4.32.

MS m/z 393 ($M^+$+1)

Example 90
H—(R)Cha-Aze-Dig
(i) Boc-(R)Cha-Aze-Dig(Z)

The title compound was prepared from Boc-(R)Cha-Aze-OH and H-Dig(Z) (see preparation of starting material) according to the procedure for Boc-(R)Cha-Pro-Dig(Z) in a yield of 0.253 g (54%).

(ii) H—(R)Cha-Aze-Dig(Z)

The title compound was prepared from Boc-(R)Cha-Aze-Dig(Z) according the procedure for Boc-(R)Cha-Pro-Dig(Z) in a yield of 0.210 g (100%).

(iii) H—(R)Cha-Aze-Dig 0.060 g (0.117 mmol) of H—(R)Cha-Aze-Dig(Z) was dissolved in 3 mL MeOH and hydrogenated over 10% Pd/C at atmospheric pressure over night. The solution was filtered through celite and the solvent evaporated to yield 0.042 g (95%) of the title compound.

$^1$H-NMR (500 MHz, MeOD): δ 0.91–1.02 (m, 2H), 1.18–1.48 (m, 6H), 1.66–1.90 (m, 8H), 2.15–2.17 (m, 1H), 2.66–2.68 (m, 1H), 2.80–2.83 (m, 1H), 3.14–3.29 (m, 1H), 3.39–3.44 (m, 1H), 3.72–3.80 (m, 2H), 4.01–4.04 (m, 1H), 4.14–4.23 (m, 2H), 4.48–4.49 (m, 1H), 4.60–4.64 (m, 1H).

Signals from a minor rotamer appear at: δ 2.25, 2.6, 4.3, 4.67.

MS m/z 379 ($M^+$+1).

EXAMPLES OF PHARMACEUTICAL PREPARATIONS

The compound according to the invention can be formulated in solid dosage forms for oral administration such as plain tablets, coated tablets or modified release tablets. Liquid or solid-semisolid dosage forms for rectal administration. Lyophilized substance or liquids as emulsion or suspension for parenteral use. Liquid solid or semisolid dosage forms for topical administration.

In pressurized aerosols or in dry powder inhalers for oral or nasal inhalation.

Example P1
Tablets for Oral Administration 1000 tablets are prepared from the following ingredients:

| | |
|---|---|
| Active compound | 100 g |
| Lactose | 200 g |
| Polyvinyl pyrrolidone | 30 g |
| Microcrystalline cellulose | 30 g |
| Magnesium stearate | 6 g |

The active constituent and lactose are mixed with an aqueous solution of polyvinyl pyrrolidone. The mixture is dried and milled to form granules. The microcrystalline cellulose and then the magnesium stearate are then admixed.

The mixture is then compressed in a tablet machine giving 1000 tablets, each containing 100 mg of active constituent.

Example P2

Solution for Parenteral Administration

A solution is prepared from the following ingredients:

| Active compound | 5 g |
|---|---|
| Sodium chloride for injection | 6 g |

Sodium hydroxide for pH adjustment ad pH 5–7 Water for inj. up to 1000 ml

The active constituent and the sodium chloride are dissolved in the water. The pH is adjusted with 2 M NaOH to pH 3–9 and the solution is filled into sterile ampoules.

Example P3

Tablets for Oral Administration

| 1. Active compound | 150 g |
|---|---|
| 2. Sodium aluminium silicate | 20 g |
| 3. Paraffin | 120 g |
| 4. Microcrystalline cellulose | 20 g |
| 5. Hydroxy propyl cellulose | 5 g |
| 6. Sodium stearyl fumarate | 3 g |

1–4 are mixed and an aqueous solution of 5 is added. The mixture is dried and milled and 6 is admixed. The mix is then compressed in a tablet machine.

Example B6

Inhaler Powder

The active compound is micronized in a jet mill to a particle size suitable for inhalation (mass diameter<4 µm).

100 mg of the micronized powder is filled into a powder multidose inhaler (Turbohaler®). The inhaler is equipped with a dosing unit which delivers a dose of 1 mg.

Biology

Determination of Thrombin Clotting Time (TT):

Human thrombin (T 6769, Sigma Chem Co) in buffer solution, pH 7.4, 100 µl, and inhibitor solution, 100 µl, were incubated for one min. Pooled normal citrated human plasma, 100 µl, was then added and the clotting time measured in an automatic device (KC 10, Amelung).

The clotting time in seconds was plotted against the inhibitor concentration, and the $IC_{50}TT$ was determined by interpolation.

$IC_{50}TT$ is the concentration of inhibitor that doubles the thrombin clotting time for human plasma.

Determination of Activated Partial Thromboplastin Time (APTT)

APTT was determined in pooled normal human citrated plasma with the reagent PTT Automated 5 manufactured by Stago. The inhibitors were added to the plasma (10 µl inhibitor solution to 90 µl plasma) and APTT was determined in the mixture by use of the coagulation analyser KC10 (Amelung) according to the instructions of the reagent producer. The clotting time in seconds was plotted against the inhibitor concentration in plasma and the $IC_{50}APTT$ was determined by interpolation.

$IC_{50}APTT$ is defined as the concentration of inhibitor in plasma that doubled the Activated Partial Thromboplastin Time.

Determination of Thrombin Time Ex Vivo

The inhibition of thrombin after oral administration of the compounds were examined in conscious rats that two days prior to the experiment were equipped with a catheter for blood sampling from the carotid artery. On the experimental day blood samples were withdrawn at fixed times after the administration of the compound into plastic tubes containing 1 part sodium citrate solution (0.13 mol per L.) and 9 parts of blood. The tubes were centrifuged to obtain platelet poor plasma. The plasma was used for determination of thrombin time as described below.

The citrated rat plasma, 100 µl, was diluted with a saline solution, 0.9%, 100 µl, and plasma coagulation was started by the addition of human thrombin (T 6769, Sigma Chem Co, USA) in a buffer solution, pH 7.4, 100 µl. The clotting time was measured in an automatic device (KC 10, Amelumg, Germany).

Determinaton of the Inhibition Constant $K_I$ for Plasma Kallikrein $K_i$ determinations were made with a chromogenic substrate method, and performed on a Cobas Bio centrifugal analyzer manufactured by Roche (Basel, Switzerland). Residual enzyme activity after incubation of human plasma kallikrein with various concentrations of test compound was determined at three different substrate concentrations, and measured as change in optical absorbance at 405 nm and 37° C.

Human plasma kallikrein (E.C.3.4.21.34, Chromogenix AB, Mölndal, Sweden), 250 µl of 0.4 nkat/ml in buffer (0.05 mol/l Tris-HCl, pH 7.4, 1 0.15 adjusted with NaCl) with bovine albumin 5 g/l (cat no 810033, ICI Biochemicals Ltd, High Wycombe, Bucks, GB), was incubated for 300 s with 80 µl of test compound solution in 0.15 mol/l NaCl containing albumin 10 g/l. An additional 10 µl of water was supplied in this step. Then 40 µl of kallikrein substrate (S-2302, Chromogenix AB, 1.25, 2.0 or 4.0 mmol/l in water) was added together with another 20 µl of water, and the absorbance change monitored.

$K_i$ was evaluated from Dixon plots, i.e. diagrams of inhibitor concentration versus $1/(\Delta A/min)$, where the data for the different substrate concentrations form straight lines which intercept at $x = -K_i$.

Abbreviations

| ABBREVIATIONS | |
|---|---|
| Ac = | acetyl |
| aq = | aqueous |
| Aze = | Azetidine-2-carboxylic acid |
| betaPic = | Piperidine-3-carboxylic acid |
| Boc = | tert-butyloxycarbonyl |
| Boc-Dig(Z) = | 3-(N-tert-butyloxycarbonyl-aminoethyl)-1-(N-benzyloxy-carbonylamidino) azetidine |
| Boc-Mig(Z) = | 3-(N-ter-butyloxycarbonyl-aminomethyl)-1-(N-benzyloxy-carbonylamidino) azetidine |
| Boc-Pig(Z) = | 4-(N-tert-butyloxycarbonyl-aminomethyl)-1-(N-benzyloxy-carbonylamidino) piperidine |
| Boc-Pig(Z)$_2$ = | 4-(N-tert-butyloxycarbonyl-aminomethyl)-1-(N,N'-dibenzyloxy-carbonylamidino) piperidine |
| Brine = | saturated water/NaCl solution |
| Bn = | benzyl |
| Bu = | butyl |

ABBREVIATIONS (continued)

| | |
|---|---|
| Cgl = | Cyclohexyl glycine |
| Cha = | β-cyclohexyl alanine |
| CME-CDI = | 1-Cyclohexyl-3-(2-morpholinoethyl) carbodiimide metho-p-toluenesulfonate |
| DBU = | 1,8-diazabicyclo[5.4.0]undec-7-ene |
| DCC = | dicyclohexyl carbodiimide |
| DCU = | dicyclohexyl urea |
| DMAP = | N,N-dimethyl amino pyridine |
| DMF = | dimethyl formamide |
| DMSO = | dimethyl sulphoxide |
| EDC = | 1-(3-Dimetylaminopropyl)-3-ethylcarbodiimide hydrochloride |
| Et = | ethyl |
| EtOAc = | ethyl acetate |
| EtOH = | ethanol |
| Gly = | glycine |
| h = | hours |
| HCl = | hydrochloric acid |
| Hex = | hexyl |
| HOAc = | acetic acid |
| HOBt = | N-hydroxy benzotriazole |
| Hoc = | Homocyclohexyl alanine |
| Hop = | Homophenyl alanine |
| HOSu = | N-hydroxysuccinimide |
| H-Dig(Z) = | 3-aminoethyl-1-(N-benzyloxycarbonyl-amidino) azetidine |
| H-Dig = | 3-aminoethyl-1-amidino azetidine |
| H-(R,S)Hig(Z) = | (3RS)-1-(N-benzyloxycarbonylamidino)-3-aminoethyl pyrrolidine |
| H-(R,S)Hig = | (3RS)-1-amidino-3-aminoethyl pyrrolidine |
| H-Hig = | 1-amidino-3-aminoethyl pyrrolidine |
| H-(R,S)Itp(Ts) = | (4RS)-1,3-diaza-2-tosylimino-4-aminoethylcyclohexane |
| H-(R,S)Itp = | (4RS)-1,3-diaza-2-imino-4-aminoethylcyclohexane |
| H-(S)Itp(Ts) = | (4S)-1,3-diaza-2-tosylimino-4-aminoethylcyclohexane |
| H-(S)Itp = | (4S)-1,3-diaza-2-imino-4-aminoethyl-cyclohexane |
| H-Itp = | 1,3-diaza-2-imino-4-aminoethyl cyclohexane |
| H-Mig(Z) = | 3-aminomethyl-1-(N-benzyloxycarbonylamidino) azetidine |
| H-Mig = | 3-aminomethyl-1-amidino azetidine |
| H-(R,S)Nig(Z) = | (3RS)-1-(N-benzyloxycarbonylamidino)-3-aminomethyl pyrrolidine |
| H-(R,S)Nig = | (3RS)-1-amidino-3-aminomethyl pyrrolidine |
| H-Nig = | 1-amidino-3-aminomethyl pyrrolidine |
| H-Pab = | 1-amidino-4-aminomethyl benzene |
| H-Pab(Z) = | 4-aminomethyl-1-(N-benzyloxy carbonylamidino) benzene |
| H-Pac = | 1-amidino-4-aminomethyl cyclohexane |
| H-Pac(Z) = | 4-aminomethyl-1-(N-benzyloxy carbonylamidino) cyclohexane |
| H-Pig = | 4-aminomethyl-1-amidino piperidine |
| H-Pig(Z) = | 4-aminometyl-1-(N-benzyloxycarbonyl-amidino)-piperidine |
| H-Pig(Z)$_2$ = | 4-aminomethyl-1-(N,N'-dibenzyloxy carbonylamidino) piperidine |
| H-Rig(Z) = | 4-aminoethyl-1-(N-benzyloxy-carbonylamidino) piperidine |
| H-Rig = | 4-aminoethyl-1-N-amidino piperidine |
| Me = | methyl |
| MeOH = | methanol |
| Mpa = | mega pascal |
| Ms = | mesyl |
| NMM = | N-methyl morpholine |
| Pd/C = | palladium on charcoal |
| Pgl = | phenyl glycine |
| Phe = | phenyl alanine |
| Pic = | pipecolinic acid |
| Pro = | proline |
| RPLC = | Reverse phase high performace liquid chromathography |
| Tf = | trifluoromethylsulfonyl |
| TFA = | trifluoroacetic acid |
| THF = | tetrahydrofuran |
| Tic = | 1-carboxy-1,2,3,4-tetrahydro-isoquinoline |
| Ts = | tosyl |
| Val = | valine |
| Z = | benzyloxy carbonyl |

Prefixes n, s, i and t have their usual meanings: normal, iso, sec and tertiary. The stereochemistry for the amino acids is by default (S) if not otherwise stated.

ABBREVIATIONS (continued, the wavy lines on the nitrogen atoms in the structural formulas below signify the bond position of the fragment.)

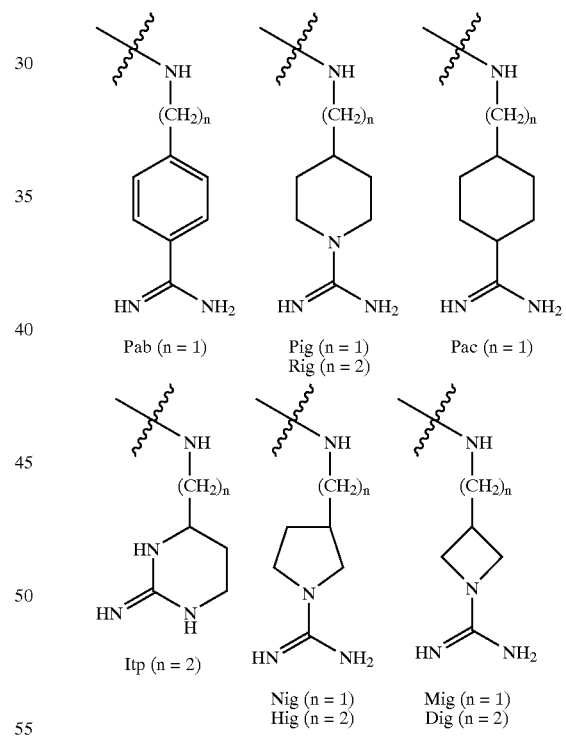

Pab (n = 1)
Pig (n = 1)
Rig (n = 2)
Pac (n = 1)

Itp (n = 2)

Nig (n = 1)
Hig (n = 2)

Mig (n = 1)
Dig (n = 2)

What is claimed is:

1. A pharmaceutical preparation comprising an effective amount of acetylsalicylic acid and a compound of the formula I $$A^1—A^2—NH—(CH_2)_n—B$$

Formula I wherein:

$A^1$ represents a structure of Formula IIa;

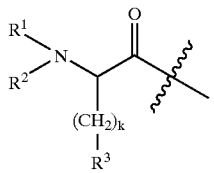

IIa wherein:

k is an integer 0, 1, 2, 3 or 4;

$R^1$ represents H, an alkyl group having 1 to 4 carbon atoms, or $R^{11}OOC$-alkyl- where the alkyl group has 1 to 4 carbon atoms and is optionally substituted in the position which is alpha to the carbonyl group, and the alpha substituent is a group $R^{17}—(CH_2)_p—$, wherein p is 0, 1 or 2 and $R^{17}$ is methyl, phenyl, OH, $COOR^{12}$, $CONHR^{12}$, where $R^{12}$ is H or an alkyl group having 1 to 4 carbon atoms, and $R^{11}$ is H or an alkyl group having 1 to 4 carbon atoms, or $R^1$ represents $Ph(4-COOR^{12})—CH_2—$, where $R^{12}$ is as defined above, or $R^1$ represents $R^{13}—NH—CO$-alkyl-, where the alkyl group has 1 to 4 carbon atoms and is optionally substituted alpha to the carbonyl with an alkyl group having 1 to 4 carbon atoms and where $R^{13}$ is H or an alkyl group having 1 to 4 carbon atoms or $—CH_2COOR^{12}$, where $R^{12}$ is as defined above, or $R^1$ represents $R^{12}OOC—CH_2—OOC$-alkyl-, where the alkyl group has 1 to 4 carbon atoms and is optionally substituted alpha to the carbonyl with an alkyl group having 1 to 4 carbon atoms and where $R^{12}$ is as defined above, or $R^1$ represents $R^{14}SO_2—$, $Ph(4-COOR^{12})—SO_2—$, $Ph(3-COOR^{12})—SO_2—$, $Ph(2-COOR^{12})—SO_2—$ where $R^{12}$ is as defined above and $R^{14}$ is an alkyl group having 1–4 carbon atoms, or $R^1$ represents $—CO—R^{15}$, wherein $R^{15}$ is an alkyl group having 1–4 carbon atoms, or $R^1$ represents $—COOR^{15}$, where $R^{15}$ is as defined above, or $R^1$ represent $—CO—(CH_2)_p—COOR^2$, where $R^{12}$ is as defined above and p is an integer 0, 1 or 2, or $R^1$ represents $—CH_2PO(OR^{16})_2$, $—CH_2SO_3H$ or $—CH_2$-(5-(1H)-tetrazolyl) where $R^{18}$ is, individually at each occurrence, H, methyl or ethyl;

$R^2$ represents H or an alkyl group having 1 to 4 carbon atoms or $R^{21}OOC$-alkyl-, where the alkyl group has 1 to 4 carbon atoms and where $R^{21}$ is H or an alkyl group having 1 to 4 carbon atoms;

$R^3$ represents an alkyl group having 1–4 carbon atoms, and the alkyl group may be optionally substituted by one or more fluorine atoms, or $R^3$ represents a cyclopentyl, cyclohexyl- or a phenyl group which may be optionally substituted with an alkyl group having 1 to 4 carbon atoms, or $R^3$ represents a phenyl group substituted with a $OR^{31}$ group, where $R^{31}$ is H or an alkyl group having 1 to 4 carbon atoms and k is 0, 1, or $R^3$ represents a 1-naphthyl or 2-naphthyl group and k is 0, 1, or $R^3$ represent a cis- or trans-decalin group and k is 0, 1, or $R^3$ represents 4-pyridyl, 3-pyrrolidyl or 3-indolyl which may be optionally substituted with a $OR^{31}$ group, where $R^{31}$ is as defined above and k is 0, 1, or $R^3$ represents $Si(Me)_3$ or $CH(R^{32})_2$ wherein $R^{32}$ is a cyclohexyl- or a phenyl group;

$A^2$ represents a structure of formula IIIa,

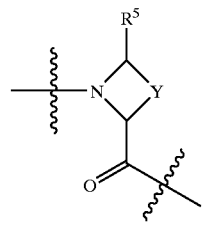

IIIa wherein:

Y represents a methylene group, or

Y represents an ethylene group and the resulting 5-membered ring may be optionally substituted by one or two fluorine atoms, a hydroxy group or an oxo group in position 4, or may be optionally unsaturated, or Y represents $—CH_2—O—$, $—CH_2—S—$, $—CH_2—SO—$, with the heteroatom functionality in position 4, or Y represents a n-propylene group and the resulting 6-membered ring may be optionally substituted in position 5 by one fluorine atom, a hydroxy group or an oxo group, may be optionally substituted by two fluorine atoms in one of positions 4 or 5 or may be optionally unsaturated in position 4 and 5, or may be optionally substituted in position 4 by an alkyl group with 1 to 4 carbon atoms, or Y represents $—CH_2—O—CH_2—$, $—CH_2—S—CH_2—$, $—CH_2—SO—CH_2—$, or Y represent $—CH_2—CH_2—CH_2—CH_2—$;

$R^5$ represents H or an alkyl group having 1 to 4 carbon atoms, or $R^5$ represents $—(CH_2)P—COOR^{51}$, where p is 0, 1 or 2 and $R^{51}$ is H or an alkyl group having 1 to 4 carbon atoms;

n is an integer 0, 1, 2, 3 or 4;

B represents a group of Formula IVb,

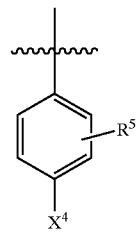

IVb wherein:

$X^5$ represents $C(NH)—NH_2$;

$R^6$ is H or an alkyl group having 1–4 carbon atoms;

either the compound as such or stereoisomers thereof or in the form of a physiologically acceptable salt, in association with a pharmaceutical carrier.

2. A pharmaceutical preparation comprising an effective amount of acetylsalicylic acid and a compound of the formula

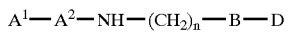  Formula V wherein:

$A^1$ represents a structure of Formula IIa;

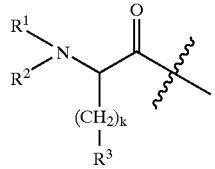  IIa wherein:
- k is an integer 0, 1, 2, 3 or 4;
- $R^1$ represents $R^{11}OOC$-alkyl-, where the alkyl group has 1 to 4 carbon atoms and is optionally substituted in the position which is alpha to the carbonyl group, and the alpha substituent is a group $R^{17}$—$(CH_2)_p$—, wherein p is 0, 1 or 2 and $R^{17}$ is $COOR^{12}$, $CONHR^{12}$, where $R^{12}$ is H, an alkyl group having 1 to 4 carbon atoms or a benzyl group, and $R^{11}$ is H or an alkyl group having 1 to 4 carbon atoms, or a benzyl group, or
- $R^1$ represents $Ph(4-COOR^{12})$—$CH_2$—, where $R^{12}$ is as defined above, or
- $R^1$ represents $R^{13}$—NH—CO-alkyl-, where the alkyl group has 1 to 4 carbon atoms and is optionally substituted alpha to the carbonyl with an alkyl group having 1 to 4 carbon atoms and where $R^{13}$ is H or an alkyl group having 1 to 4 carbon atoms or —$CH_2COOR^{12}$, where $R^{12}$ is as defined above, or
- $R^1$ represents $R^{12}OOC$—$CH_2$—$OOC$-alkyl-, where the alkyl group has 1 to 4 carbon atoms and is optionally substituted alpha to the carbonyl with an alkyl group having 1 to 4 carbon atoms and where $R^{12}$ is as defined above, or
- $R^1$ represents $R^{14}SO_2$—, $Ph(4-COOR^{12})$—$SO_2$—, $Ph(3-COOR^{12})$—$SO_2$—, $Ph(2-COOR^{12})$—$SO_2$—where $R^{12}$ is as defined above and $R^{14}$ is an alkyl group having 1–4 carbon atoms, or
- $R^1$ represents —CO—$R^5$, wherein $R^{15}$ is an alkyl group having 1–4 carbon atoms, or
- $R^1$ represents —CO—$OR^{15}$, where $R^{15}$ is as defined above, or
- $R^1$ represent —CO—$(CH_2)_p$—$COOR^2$, where $R^{12}$ is as defined above and p is an integer 0, 1 or 2, or
- $R^2$ represents H or an alkyl group having 1 to 4 carbon atoms or $R^{21}OOC$-alkyl-, where the alkyl group has 1 to 4 carbon atoms and where $R^{21}$ is H or an alkyl group having 1 to 4 carbon atoms or a benzyl group;
- $R^3$ represents an alkyl group having 1–4 carbon atoms, and the alkyl group may be optionally substituted by one or more fluorine atoms, or
- $R^3$ represents a cyclopentyl, cyclohexyl- or a phenyl group which may be optionally substituted with an alkyl group having 1 to 4 carbon atoms, or
- $R^3$ represents a phenyl group substituted with a $OR^{31}$ group, where $R^{31}$ is H or an alkyl group having 1 to 4 carbon atoms and k is 0, 1, or
- $R^3$ represents a 1-naphthyl or 2-naphthyl group and k is 0, 1, or
- $R^3$ represent a cis- or trans-decalin group and k is 0, 1, or
- $R^3$ represents 4-pyridyl, 3-pyrrolidyl or 3-indolyl which be optionally substituted with a $OR^{31}$ group, where $R^{31}$ is as defined above and k is 0, 1, or
- $R^3$ represents $Si(Me)_3$ or $CH(R^{32})_2$, wherein $R^{32}$ is a cyclohexyl- or a phenyl group;

$A^2$ represents a structure of Formula IIIa

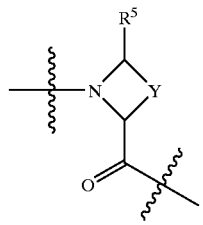  IIIa wherein:
- Y represents a methylene group, or
- Y represents an ethylene group and the resulting 5-membered ring may be optionally substituted by one or two fluorine atoms, a hydroxy group or an oxo group in position 4, or may be optionally unsaturated, or
- Y represents —$CH_2$—O—, —$CH_2$—S—, —$CH_2$—SO—, with the heteroatom functionality in position 4, or
- Y represents a n-propylene group and the resulting 6-membered ring may be optionally substituted in position 5 by one fluorine atom, a hydroxy group or an oxo group, may be optionally substituted by two fluorine atoms in one of positions 4 or 5 or may be optionally unsaturated in position 4 and 5, or may be optionally substituted in position 4 by an alkyl group with 1 to 4 carbon atoms, or
- Y represents —$CH_2$—O—$CH_2$—, —$CH_2$—S—$CH_2$—, —$CH_2$—SO—$CH_2$—, or
- Y represent —$CH_2$—$CH_2$—$CH_2$—$CH_2$—;
- $R^5$ represents H or an alkyl group having 1 to 4 carbon atoms, or
- $R^5$ represents —$(CH_2)_p$—$COOR^{51}$, where p is 0, 1 or 2 and $R^{51}$ is H or an alkyl group having 1 to 4 carbon atoms;
- n is an integer 0, 1, 2, 3 or 4;
- B represents a group of Formula IVb

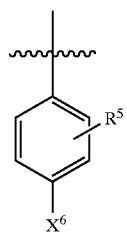  IVb wherein:
- $X^5$ represents $C(NH)$—$NH_2$;
- $R^6$ is H or an alkyl group having 1–4 carbon atoms;
- D is Z or $(Z)_2$;

Z is a benzyloxy carbonyl group;
either the compound as such or stereoisomers thereof or in the form of a physiologically acceptable salt, in association with a pharmaceutical carrier.

3. A pharmaceutical preparation according to claim 1 or 1 wherein $R^1$ represents $R^{11}$OOC-alkyl-, where the alkyl group has 1 to 4 carbon atoms and $R^{11}$ is H.

4. A pharmaceutical preparation according to claim 1 or 2 wherein B is a structure of formula IVb, wherein $X^5$ is C(NH)—$NH_2$ and $R^6$ is H and n is 1.

5. A pharmaceutical preparation according to claim 1 or 2 in which n is 1, $A^1$ is a structure of formula IIa wherein k is 0 or 1, $R^1$ represents $R^{11}$OOC-alkyl-, where the alkyl group has 1 to 4 carbon atoms, $R^2$ represents H, $R^3$ represents a cyclohexyl group, $A^2$ represents a structure of formula lla wherein Y represents a methylene group, an ethylene group, or a n-propylene group and the resulting 6-membered ring may be optionally substituted in position 4 by an alkyl group with 1 to 4 carbon atoms, $R^5$ represents H, B represents a structure of formula IVb wherein $X^5$ represents C(NH)—$NH_2$ and $R^6$ is H.

6. A pharmaceutical preparation comprising an effective amount of acetylsalicylic acid and a compound selected from HOOC—$CH_2$—(R)Cgl-Aze-Pab
HOOC—$CH_2$—$CH_2$—(R)Cgl-Aze-Pab
HOOC—$CH_2$—(R)Cgl-Pro-Pab
HOOC—$CH_2$—$CH_2$—(R)Cgl-Pro-Pab
(HOOC—$CH_2$)$_2$—(R)Cgl-Pro-Pab
H—(R)Cgl-Pic-Pab
HOOC—$CH_2$—(R,S)CH(COOH)—(R)Cgl-Pic-Pab
H—(R)Cha-Aze-Pab
HOOC—$CH_2$—(R)Cha-Aze-Pab
HOOC—$CH_2$—(R,S)CH(COOH)—(R)Cha-Aze-Pab
HOOC—$CH_2$—(R or S)CH(COOH)—(R)Cha-Aze-Pab/a
HOOC—$CH_2$—(R or S)CH(COOH)—(R)Cha-Aze-Pab/b
HOOC—$CH_2$—$CH_2$—(R)Cha-Aze-Pab
HOOC—$CH_2$—NH—CO—$CH_2$—(R)Cha-Aze-Pab
H—(R)Cha-Pro-Pab
HOOC—$CH_2$—(R)Cha-Pro-Pab
HOOC—$CH_2$-(Me)(R)Cha-Pro-Pab
HOOC—$CH_2$—$CH_2$—(R)Cha-Pro-Pab
HOOC—$CH_2$—$CH_2$—(Me)(R)Cha-Pro-Pab
HOOC—$CH_2$—(R or S)CH(COOH)—(R)Cha-Pro-Pab/a
HOOC—$CH_2$—(R or S)CH(COOH)—(R)Cha-Pro-Pab/b
HOOC—$CH_2$—NH—CO—$CH_2$—(R)Cha-Pro-Pab
EtOOC—$CH_2$—$CH_2$—$CH_2$—(R)Cha-Pro-Pab
Ph(4-COOH)—$SO_2$—(R)Cha-Pro-Pab
H—(R)Cha-Pic-Pab
HOOC—$CH_2$—(R)Cha-Pic-Pab
HOOC—$CH_2$—(R or S)CH(COOH)—(R)Cha-Pic-Pab/a
HOOC—$CH_2$—(R or S)CH(COOH)—(R)Cha-Pic-Pab/b
HOOC—$CH_2$—$CH_2$—(R)Cha-Pic-Pab
HOOC—CO—(R)Cha-Pic-Pab
HOOC—$CH_2$—CO—(R)Cha-Pic-Pab
Me—OOC—$CH_2$—CO—(R)Cha-Pic-Pab
$H_2$N—CO—$CH_2$—(R)Cha-Pic-Pab
Boc-(R)Cha-Pic-Pab
Ac—(R)Cha-Pic-Pab
Me—$SO_2$—(R)Cha-Pic-Pab
H—(R)Hoc-Aze-Pab
HOOC—$CH_2$—$CH_2$—(R)Hoc-Aze-Pab
HOOC—$CH_2$—(R,S)CH(COOH)—(R)Hoc-Pro-Pab
HOOC—$CH_2$—(R)Hoc-Pic-Pab
(HOOC—$CH_2$)$_2$—(R)Hoc-Pic-Pab
H—(R)Cgl-Aze-Pab
HOOC—(R,S)CH(Me)—(R)Cha-Pro-Pab
MeOOC—$CH_2$—(R)Cgl-Aze-Pab
EtOOC—$CH_2$—(R)Cgl-Aze-Pab
"BuOOC—$CH_2$—(R)Cgl-Aze-Pab
"HexOOC—$CH_2$—(R)Cgl-Aze-Pab
either as such or a stereoisomer thereof or in the form of a physiologically acceptable salt, in association with a pharmaceutical carrier.

7. A pharmaceutical preparation comprising an effective amount of acetylsalicylic acid and a compound selected from HOOC—$CH_2$—(R)Cgl-Aze-Pab
HOOC—$CH_2$—$CH_2$—(R)Cha-Aze-Pab
HOOC—$CH_2$—(R)Cha-Pro-Pab
HOOC—$CH_2$—$CH_2$—(R)Cha-Pro-Pab
HOOC—$CH_2$—(R)Cha-Pic-Pab
EtOOC—$CH_2$—(R)Cgl-Aze-Pab either as such or a stereoisomer thereof or in the form of a physiologically acceptable salt, in association with a pharmaceutical carrier.

8. A pharmaceutical preparation comprising an effective amount of acetylsalicylic acid and a compound selected from BnOOC—$CH_2$—(R)Cgl-Aze-Pab(Z)
BnOOC—$CH_2$—$CH_2$—(R)Cgl-Aze-Pab (Z)
BnOOC—$CH_2$—(R)Cgl-Pro-Pab(Z)
BnOOC—$CH_2$—$CH_2$—(R)Cgl-Pro-Pab(Z)
(BnOOC—$CH_2$)$_2$—(R)Cgl-Pro-Pab(Z)
BnOOC—$CH_2$—(R,S)CH(COOBn)—(R)Cgl-Pic-Pab (Z)
BnOOC—$CH_2$—(R)Cha-Aze-Pab (Z)
BnOOC—$CH_2$—(R,S)CH(COOBn)—(R)Cha-Aze-Pab (Z)
BnOOC—$CH_2$—(R or S)CH(COOBn)—(R)Cha-Aze-Pab(Z)/a
BnOOC—$CH_2$—(R or S)CH(COOBn)—(R)Cha-Aze-Pab(Z)/b
BnOOC—$CH_2$—$CH_2$—(R)Cha-Aze-Pab(Z)
BnOOC—$CH_2$—NH—CO—$CH_2$—(R)Cha-Aze-Pab(Z)
BnOOC—$CH_2$—(R)Cha-Pro-Pab(Z)
BnOOC—$CH_2$-(Me)(R)Cha-Pro-Pab(Z)
BnOOC—$CH_2$—$CH_2$—(R)Cha-Pro-Pab(Z)
BnOOC—$CH_2$—$CH_2$-(Me)(R)Cha-Pro-Pab(Z)
BnOOC—$CH_2$—(R,S)CH(COOBn)—(R)Cha-Pro-Pab (Z)
BnOOC—$CH_2$—NH—CO—$CH_2$—(R)Cha-Pro-Pab (Z)
Ph(4-COOH)—$SO_2$—(R)Cha-Pro-Pab(Z)
Boc-(R)Cha-Pic-Pab(Z)
BnOOC—$CH_2$—(R)Cha-Pic-Pab(Z)
BnOOC—$CH_2$—(R,S)CH(COOBn)—(R)Cha-Pic-Pab (Z)

BnOOC—CH$_2$—CH$_2$—(R)Cha-Pic-Pab(Z)
EtOOC—CO—(R)Cha-Pic-Pab(Z)
MeOOC—CH$_2$—CO—(R)Cha-Pic-Pab(Z)
H$_2$N—CO—CH$_2$—(R)Cha-Pic-Pab (Z)
Ac—(R)Cha-Pic-Pab (Z)
Me—SO$_2$—(R)Cha-Pic-Pab(Z)
BnOOC—CH$_2$—CH$_2$—(R)Hoc-Aze-Pab(Z)
BnOOC—CH$_2$—(R,S)CH(COOBn)—(R)Hoc-Pro-Pab (Z)
BnOOC—CH$_2$—(R)Hoc-Pic-Pab(Z)
(BnOOC—CH$_2$)$_2$—(R)Hoc-Pic-Pab(Z)
BnOOC—(R,S)CH (Me)—(R)Cha-Pro-Pab(Z)
MeOOC—CH$_2$—(R)Cgl-Aze-Pab(Z)
EtOOC—CH$_2$—(R)Cgl-Aze-Pab(Z)
″BuOOC—CH$_2$—(R)Cgl-Aze-Pab(Z)
″HexOOC—CH$_2$—(R)Cgl-Aze-Pab(Z)

either as such or a stereoisomer thereof or in the form of a physiologically acceptable salt, in association with a pharmaceutical carrier.

9. A pharmaceutical preparation comprising an effective amount of acetylsalicylic acid and a compound selected from BnOOC—CH$_2$—(R)Cgl-Aze-Pab(Z)
BnOOC—CH$_2$—(R)Cha-Pro-Pab(Z)
BnOOC—CH$_2$—(R)Cha-Pic-Pab(Z)
EtOOC—CH$_2$—(R)Cgl-Aze-Pab(Z)

either as such or a stereoisomer thereof or in the form of a physiologically acceptable salt, in association with a pharmaceutical carrier.

10. A pharmaceutical preparation comprising an effective amount of acetylsalicylic acid and the compound HOOC—CH$_2$—(R)Cgl-Aze-Pab or a stereoisomer thereof or a physiologically acceptable salt thereof, in association with a pharmaceutical carrier.

11. A pharmaceutical preparation comprising an effective amount of acetylsalicylic acid and the compound EtOOC—CH$_2$—(R)Cgl-Aze-Pab or a stereoisomer thereof or a physiologically acceptable salt thereof, in association with a pharmaceutical carrier.

12. A pharmaceutical preparation comprising an effective amount of acetylsalicylic acid and the compound HOOC—CH$_2$—(R)Cgl-Aze-Pab, in association with a pharmaceutical carrier.

13. A pharmaceutical preparation comprising an effective amount of acetylsalicylic acid and the compound EtOOC—CH$_2$—(R)Cgl-Aze-Pab, in association with a pharmaceutical carrier.

14. A method for inhibiting thrombin in a mammal in need of such inhibition, which comprises administering to the mammal an effective amount of a pharmaceutical preparation as claimed in claim 1.

15. A method for inhibiting thrombin in a mammal in need of such inhibition, which comprises administering to the mammal an effective amount of a pharmaceutical preparation as claimed in claim 2.

16. A method for inhibiting thrombin in a mammal in need of such inhibition, which comprises administering to the mammal an effective amount of a pharmaceutical preparation as claimed in claim 10.

17. A method for inhibiting thrombin in a mammal in need of such inhibition, which comprises administering to the mammal an effective amount of a pharmaceutical preparation as claimed in claim 11.

18. A method for inhibiting thrombin in a mammal in need of such inhibition, which comprises administering to the mammal an effective amount of a pharmaceutical preparation as claimed in claim 12.

19. A method for inhibiting thrombin in a mammal in need of such inhibition, which comprises administering to the mammal an effective amount of a pharmaceutical preparation as claimed in claim 13.

20. A method of treatment or prophylaxis of thrombosis and of hypercoagulability in blood and tissues in a mammal in need of such treatment or prophylaxis, which comprises administering to the mammal an effective amount of a pharmaceutical preparation as claimed in claim 1.

21. A method of treatment or prophylaxis of thrombosis and of hypercoagulability in blood and tissues in a mammal in need of such treatment or prophylaxis, which comprises administering to the mammal an effective amount of a pharmaceutical preparation as claimed in claim 2.

22. A method of treatment or prophylaxis of thrombosis and of hypercoagulability in blood and tissues in a mammal in need of such treatment or prophylaxis, which comprises administering to the mammal an effective amount of a pharmaceutical preparation as claimed in claim 10.

23. A method of treatment or prophylaxis of thrombosis and of hypercoagulability in blood and tissues in a mammal in need of such treatment or prophylaxis, which comprises administering to the mammal an effective amount of a pharmaceutical preparation as claimed in claim 11.

24. A method of treatment or prophylaxis of thrombosis and of hypercoagulability in blood and tissues in a mammal in need of such treatment or prophylaxis, which comprises administering to the mammal an effective amount of a pharmaceutical preparation as claimed in claim 12.

25. A method of treatment or prophylaxis of thrombosis and of hypercoagulability in blood and tissues in a mammal in need of such treatment or prophylaxis, which comprises administering to the mammal an effective amount of a pharmaceutical preparation as claimed in claim 13.

26. A method for inhibiting kininogenases in a mammal in need of such inhibition, which comprises administering to the mammal an effective amount of a pharmaceutical preparation as claimed in claim 1.

27. A method for inhibiting kininogenases in a mammal in need of such inhibition, which comprises administering to the mammal an effective amount of a pharmaceutical preparation as claimed in claim 2.

28. A method for inhibiting kininogenases in a mammal in need of such inhibition, which comprises administering to the mammal an effective amount of a pharmaceutical preparation as claimed in claim 10.

29. A method for inhibiting kininogenases in a mammal in need of such inhibition, which comprises administering to the mammal an effective amount of a pharmaceutical preparation as claimed in claim 11.

30. A method for inhibiting kininogenases in a mammal in need of such inhibition, which comprises administering to the mammal an effective amount of a pharmaceutical preparation as claimed in claim 12.

31. A method for inhibiting kininogenases in a mammal in need of such inhibition, which comprises administering to the mammal an effective amount of a pharmaceutical preparation as claimed in claim 13.

32. A combination comprising (a) acetylsalicylic acid and (b) a compound of the formula I Formula I

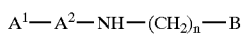

wherein:
A$^1$ represents a group of Formula IIa;

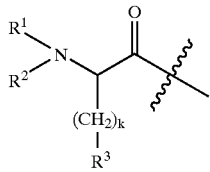

IIa wherein:
k is an integer 0, 1, 2, 3 or 4;
R$^1$ represents H, an alkyl group having 1 to 4 carbon atoms, or R$^{11}$OOC-alkyl- where the alkyl group has 1 to 4 carbon atoms and is possibly substituted in the position which is alpha to the carbonyl group, and the alpha substituent is a group R$^{17}$—(CH$_2$)$_p$—, wherein p is 0, 1 or 2 and R$^{17}$ is methyl, phenyl, OH, COOR$^{12}$, CONHR$^{12}$, where R$^{12}$ is H or an alkyl group having 1 to 4 carbon atoms, and R$^{11}$ is H or an alkyl group having 1 to 4 carbon atoms, or
R$^1$ represents Ph(4-COOR$^{12}$)—CH$_2$—, where R$^{12}$ is as defined above, or
R$^1$ represents R$^{13}$—NH—CO-alkyl-, where the alkyl group has 1 to 4 carbon atoms and is possibly substituted alpha to the carbonyl with an alkyl group having 1 to 4 carbon atoms and where R$^{13}$ is H or an alkyl group having 1 to 4 carbon atoms or —CH$_2$COOR$^{12}$, where R$^{12}$ is as defined above, or
R$^1$ represents R$^{12}$OOC—CH$_2$—OOC-alkyl-, where the alkyl group has 1 to 4 carbon atoms and is possibly substituted alpha to the carbonyl with an alkyl group having 1 to 4 carbon atoms and where R$^{12}$ is as defined above, or
R$^1$ represents R$^{14}$SO$_2$—, Ph(4-COOR$^{12}$)—SO$_2$—, Ph(3-COOR$^{12}$)—SO$_2$—, Ph(2-COOR$^{12}$)—SO$_2$— where R$^{12}$ is as defined above and R$^{14}$ is an alkyl group having 1–4 carbon atoms, or
R$^1$ represents —CO—R$^{15}$, wherein R$^{15}$ is an alkyl group having 1–4 carbon atoms, or
R$^1$ represents —COOR$^{15}$, where R$^{15}$ is as defined above, or
R$^1$ represent —CO—(CH$_2$)$_p$—COOR$^2$, where R$^{12}$ is as defined above and p is an integer 0, 1 or 2, or
R$^1$ represents —CH$_2$PO(OR$^{16}$)$_2$, —CH$_2$SO$_3$H or —CH$_2$-(5-(1H)-tetrazolyl) where R$^{16}$ is, individually at each occurrence, H, methyl or ethyl;
R$^2$ represents H or an alkyl group having 1 to 4 carbon atoms or R$^{21}$OOC-alkyl-, where the alkyl group has 1 to 4 carbon atoms and where R$^{21}$ is H or an alkyl group having 1 to 4 carbon atoms;
R$^3$ represents an alkyl group having 1–4 carbon atoms, and the alkyl group may or may not carry one or more fluorine atoms, or
R$^3$ represents a cyclopentyl, cyclohexyl- or a phenyl group which may or may not be substituted with an alkyl group having 1 to 4 carbon atoms, or
R$^3$ represents a phenyl group substituted with a OR$^{31}$ group, where R$^{3'}$ is H or an alkyl group having 1 to 4 carbon atoms and k is 0, 1, or R$^3$ represents a 1-naphthyl or 2-naphthyl group and k is 0, 1, or
R$^3$ represent a cis- or trans-decalin group and k is 0, 1, or
R$^3$ represents 4-pyridyl, 3-pyrrolidyl or 3-indolyl which may or may not be substituted with a OR$^{31}$ group, where R$^{31}$ is as defined above and k is 0, 1, or
R$^3$ represents Si(Me)$_3$ or CH(R$^{32}$)$_2$ wherein R$^{32}$ is a cyclohexyl- or a phenyl group;
A$^2$ represents a group of formula IIIa

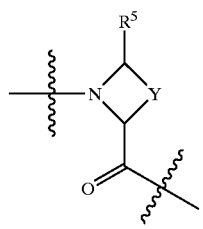

IIIa wherein:
Y represents a methylene group, or
Y represents an ethylene group and the resulting 5-membered ring may or may not carry one or two fluorine atoms, a hydroxy group or an oxo group in position 4, or may or may not be unsaturated, or
Y represents —CH$_2$—O—, —CH$_2$—S—, —CH$_2$—SO—, with the heteroatom functionality in position 4, or
Y represents a n-propylene group and the resulting 6-membered ring may or may not carry in position 5 one fluorine atom, a hydroxy group or an oxo group, carry two fluorine atoms in one of positions 4 or 5 or be unsaturated in position 4 and 5, or carry in position 4 an alkyl group with 1 to 4 carbon atoms, or
Y represents —CH$_2$—O—CH$_2$—, —CH$_2$—S—CH$_2$—, —CH$_2$—SO—CH$_2$—, or
Y represent —CH$_2$—CH$_2$—CH$_2$—CH$_2$—;
R$^5$ represents H or an alkyl group having 1 to 4 carbon atoms, or
R$^5$ represents —(CH$_2$)$_p$—COOR$^5$, where p is 0, 1 or 2 and R$^{51}$ is H or an alkyl group having 1 to 4 carbon atoms;
n is an integer 0, 1, 2, 3 or 4;
B represents a group of Formula IVb

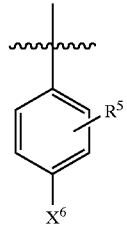

IVb wherein:
X$^5$ represents C(NH)—NH$_2$;
R$^6$ is H or an alkyl group having 1–4 carbon atoms;
either the compound as such or stereoisomers thereof or in the form of a physiologically acceptable salt.

33. A combination comprising (a) acetylsalicylic acid and (b) the compound HOOC—CH$_2$—(R)Cgl-Aze-Pab or a stereoisomer thereof or a physiologically acceptable salt thereof.

34. A combination comprising (a) acetylsalicylic acid and (b) the compound EtOOC—CH$_2$—(R)Cgl-Aze-Pab or a stereoisomer thereof or a physiologically acceptable salt thereof.

35. A combination comprising (a) acetylsalicylic acid and (b) the compound HOOC—CH$_2$—(R)Cgl-Aze-Pab.

36. A combination comprising (a) acetylsalicylic acid and (b) the compound EtOOC—CH$_2$—(R)Cgl-Aze-Pab.

37. A combination as claimed in claim 32 which comprises a kit of parts comprising components (a) and (b).

38. A combination product as claimed in claim 32, in which components (a) and (b) are suitable for sequential, separate and/or simultaneous use in the treatment of a condition where inhibition of thrombin is required.

39. A combination product as claimed in claim 38 wherein component (a) is combined with component (b).

40. A method for inhibiting thrombin in a mammal in need of such inhibition, which comprises administering to the mammal an effective amount of a combination as claimed in claim 32.

41. A method for inhibiting thrombin in a mammal in need of such inhibition, which comprises administering to the mammal an effective amount of a combination as claimed in claim 33.

42. A method for inhibiting thrombin in a mammal in need of such inhibition, which comprises administering to the mammal an effective amount of a combination preparation as claimed in claim 34.

43. A method for inhibiting thrombin in a mammal in need of such inhibition, which comprises administering to the mammal an effective amount of a combination as claimed in claim 35.

44. A method for inhibiting thrombin in a mammal in need of such inhibition, which comprises administering to the mammal an effective amount of a combination as claimed in claim 36.

45. A method for inhibiting thrombin in a mammal in need of such inhibition, which comprises administering an effective amount of components (a) and (b) of a combination as claimed in claim 32 separately, sequentially or simultaneously to the mammal.

46. A method of treatment or prophylaxis of thrombosis and of hypercoagulability in blood and tissues in a mammal in need of such treatment or prophylaxis, which comprises administering to the mammal an effective amount of a combination as claimed in claim 32.

47. A method of treatment or prophylaxis of thrombosis and of hypercoagulability in blood and tissues in a mammal in need of such treatment or prophylaxis, which comprises administering to the mammal an effective amount of a combination as claimed in claim 33.

48. A method of treatment or prophylaxis of thrombosis and of hypercoagulability in blood and tissues in a mammal in need of such treatment or prophylaxis, which comprises administering to the mammal an effective amount of a combination as claimed in claim 34.

49. A method of treatment or prophylaxis of thrombosis and of hypercoagulability in blood and tissues in a mammal in need of such treatment or prophylaxis, which comprises administering to the mammal an effective amount of a combination as claimed in claim 35.

50. A method of treatment or prophylaxis of thrombosis and of hypercoagulability in blood and tissues in a mammal in need of such treatment or prophylaxis, which comprises administering to the mammal an effective amount of a combination as claimed in claim 36.

51. A method of treatment or prophylaxis of thrombosis and of hypercoagulability in blood and tissues in a mammal in need of such treatment or prophylaxis, which comprises administering an effective amount of components (a) and (b) of a combination as claimed in claim 22 separately, sequentially or simultaneously to the mammal.

52. A method for inhibiting kininogenases in a mammal in need of such inhibition, which comprises administering to the mammal an effective amount of a combination as claimed in claim 32.

53. A method for inhibiting kininogenases in a mammal in need of such inhibition, which comprises administering to the mammal an effective amount of a combination as claimed in claim 33.

54. A method for inhibiting kininogenases in a mammal in need of such inhibition, which comprises administering to the mammal an effective amount of a combination as claimed in claim 34.

55. A method for inhibiting kininogenases in a mammal in need of such inhibition, which comprises administering to the mammal an effective amount of a combination as claimed in claim 35.

56. A method for inhibiting kininogenases in a mammal in need of such inhibition, which comprises administering to the mammal an effective amount of a combination as claimed in claim 36.

57. A method for inhibiting kininogenases in a mammal in need of such inhibition, which comprises administering an effective amount of components (a) and (b) of a combination as claimed in claim 32 separately, sequentially or simultaneously to the mammal.

\* \* \* \* \*